(12) United States Patent
Farrell

(10) Patent No.: US 12,024,529 B2
(45) Date of Patent: Jul. 2, 2024

(54) COMPOUNDS THAT INHIBIT MCL-1 PROTEIN

(71) Applicant: AMGEN INC., Thousand Oaks, CA (US)

(72) Inventor: Robert Farrell, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 18/313,703

(22) Filed: May 8, 2023

(65) Prior Publication Data

US 2023/0271981 A1  Aug. 31, 2023

Related U.S. Application Data

(63) Continuation of application No. 17/075,864, filed on Oct. 21, 2020, now Pat. No. 11,685,747, which is a continuation of application No. 16/569,927, filed on Sep. 13, 2019, now Pat. No. 11,001,598, which is a continuation of application No. 16/123,030, filed on Sep. 6, 2018, now Pat. No. 10,494,381, which is a continuation of application No. 15/376,456, filed on Dec. 12, 2016, now Pat. No. 10,100,063, which is a continuation of application No. 14/839,149, filed on Aug. 28, 2015, now Pat. No. 9,562,061.

(60) Provisional application No. 62/043,929, filed on Aug. 29, 2014.

(51) Int. Cl.

| | | |
|---|---|---|
| *C07D 249/18* | (2006.01) | |
| *C07C 59/56* | (2006.01) | |
| *C07C 59/68* | (2006.01) | |
| *C07C 311/11* | (2006.01) | |
| *C07D 498/00* | (2006.01) | |
| *C07D 513/08* | (2006.01) | |
| *C07D 513/10* | (2006.01) | |

(52) U.S. Cl.
CPC ............ *C07D 513/10* (2013.01); *C07C 59/56* (2013.01); *C07C 59/68* (2013.01); *C07C 311/11* (2013.01); *C07D 249/18* (2013.01); *C07D 498/00* (2013.01); *C07D 513/08* (2013.01)

(58) Field of Classification Search
CPC .................................................. C07D 249/18
See application file for complete search history.

(56) References Cited

U.S. PATENT DOCUMENTS

| | | |
|---|---|---|
| 4,522,811 A | 6/1985 | Eppstein et al. |
| 6,468,798 B1 | 10/2002 | Deb et al. |
| 6,471,996 B1 | 10/2002 | Sokoll et al. |
| 6,472,375 B1 | 10/2002 | Hoon et al. |
| 9,562,061 B2 | 2/2017 | Brown et al. |
| 2009/0054402 A1 | 2/2009 | Wang et al. |
| 2014/0051683 A1 | 2/2014 | Wang et al. |
| 2015/0045357 A1 | 2/2015 | Nikolovska-Coleska et al. |
| 2015/0284328 A1 | 10/2015 | Wang et al. |
| 2017/0088560 A1 | 3/2017 | Brown et al. |
| 2019/0016736 A1 | 1/2019 | Brown et al. |
| 2020/0062780 A1 | 2/2020 | Brown et al. |

FOREIGN PATENT DOCUMENTS

| | | |
|---|---|---|
| WO | 2008/131000 A2 | 10/2008 |
| WO | 2011/022312 A1 | 2/2011 |
| WO | 2011/094708 A2 | 8/2011 |
| WO | 2013/052943 A2 | 4/2013 |
| WO | 2013/149124 A1 | 10/2013 |

OTHER PUBLICATIONS

International Search Report for analogous PCT Application No. PCT/US2015/047472, mailed on Oct. 30, 2015.
Written Opinion of the International Searching Authority for analogous PCT Application No. PCT/US2015/047472, mailed on Oct. 30, 2015.
Beroukhim,R., et al., "The landscape of somatic copy-number alteration across human cancers," Nature 463, 899-905 (2010).

(Continued)

*Primary Examiner* — Timothy P Thomas
(74) *Attorney, Agent, or Firm* — Kimberly L. Berkowski

(57) ABSTRACT

Provided herein are compounds that are useful intermediates that may used to synthesize myeloid cell leukemia 1 protein (Mcl-1) inhibitors. Also provided are Mcl-1 inhibitors, methods of their preparation, related pharmaceutical compositions, and methods of using the same. For example, provided herein are compounds of Formula I,

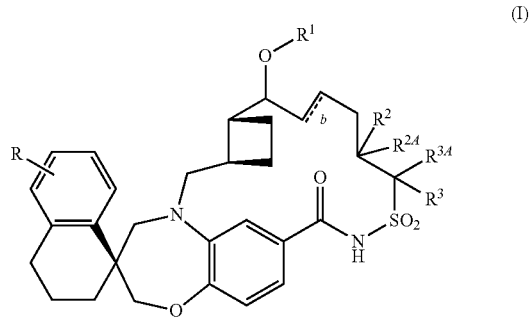

and pharmaceutically acceptable salts thereof and pharmaceutical compositions containing the compounds. The compounds and compositions provided herein may be used, for example, in the treatment of diseases or conditions, such as cancer.

1 Claim, 3 Drawing Sheets

(56) References Cited

OTHER PUBLICATIONS

Lessene, G., et al., "BCL-2 family antagonists for cancer therapy," Nat. Rev. Drug. Discov., vol. 7, 989-1000 (2008).
Akgul, C., "Mcl-1 is a potential therapeutic target in multiple types of cancer," Cell. Mol. Life Sci. vol. 66 1326-1336 (2009).
Mandelin II, A. M. et al., "Myeloid cell leukemia-1 as a therapeutic target," Expert Opin. Ther. Targets, 11(3):363-373 (2007).
Rowe, R. C., et al., Handbook of Pharmaceutical Excipients, 5$^{th}$ Edition (2005).
Berge, S. M. et al. "Pharmaceutical Salts", J. Pharm. Sci. 66: 1-19 (1977).
Hamajima, K. et al., "Intranasal Administration of HIV-DNA Vaccine Formulated with a Polymer, Carboxymethylcellulose, Augments Mucosal Antibody Production and Cell-Mediated Immune Response," Clin. Immunol. Immunopathol., 88(2), 205-210 (1998).
Higuchi, T. et al., "Pro-drugs as Novel Delivery Systems," vol. 14 of the A.C.S. Symposium Series (1975).
Roche, E.B., "Bioreversible Carriers in Drug Design", ed. Edward B. Roche, American Pharmaceutical Association and Pergamon Press, (1987).
Brubaker, J. D., et al., "A Practical, Enantioselective Synthetic Route to a Key Precursor to the Tetracycline Antibiotics," Org. Lett., 9, 3523-3525 (2007).
Krasovskiy, A et al., "Convenient Titration Method for Organometallic Zinc, Magnesium, and Lanthanide Reagents," Synthesis, 890-891 (2006).
Sigman, M. S. et al., "Palladium-Catalyzed Allylic Cross-Coupling Reactions of Primary and Secondary Homoallylic Electrophiles," J. Am. Chem. Soc., 134(28), 11408-11411 (2012).
Intellectual Property Office of Singapore Search Report dated Jan. 9, 2018 for analogous Singapore Patent Application.
Intellectual Property Office of Singapore Written Opinion dated Jan. 15, 2018 for analogous Singapore Patent Application.
Johnson, M.G. et al. Convenient Route to Secondary Sulfinates : Application to the Stereospecific Synthesis of α-C-Chiral Sulfonamides, Organic Letters, 16, pp. 6248-6251 (2014).
SciFinder Structure Search with Substances for Sulfonamides Performed May 30, 2018.
SciFinder Structure Search with References for Sulfonamides Performed May 30, 2018.
SciFinder Structure Search with Substances for Benzotriazoles Performed Jun. 1, 2018.
SciFinder Structure Search with References for Benzotriazoles Performed Jun. 1, 2018.
SciFinder Structure Search with Substances for Spirocyclic Bicyclic Performed May 30, 2018.
SciFinder Structure Search with References for Spirocyclic Bicyclic Performed May 30, 2018.
SciFinder Structure Search with Substances for CyclobutylCH$_2$O Performed Jul. 30, 2018.
SciFinder Structure Search with References for CyclobutylCH$_2$O Performed Jul. 30, 2018.
Communication and Extended European Search Report for analogous European Patent Application No. EP 18187957 dated Jan. 22, 2019 and Jan. 15, 2019.
SciFinder Structure Search with Substances for Aldehyde Phenoxy Compounds Performed May 16, 2019.
SciFinder Structure Search with References for Aldehyde Phenoxy Cmpounds Performed May 16, 2019.
SciFinder Structure Search with Substances for Diol Compounds Performed May 16, 2019.
SciFinder Structure Search with References for Diol Compounds Performed May 16, 2019.
SciFinder Structure Search with Substances for Hydroxy Phenoxy Compounds Performed May 16, 2019.
SciFinder Structure Search with References for Hydroxy Phenoxy Compounds Performed May 16, 2019.

COMPOUNDS THAT INHIBIT MCL-1 PROTEIN

CROSS REFERENCE TO RELATED APPLICATIONS

This application is a continuation of U.S. patent application Ser. No. 17/075,864, filed Oct. 21, 2020, pending, which is a continuation of U.S. patent application Ser. No. 16/569,927, filed Sep. 13, 2019, now U.S. Pat. No. 11,001,598, which is a continuation of U.S. patent application Ser. No. 16/123,030, filed Sep. 6, 2018, now U.S. Pat. No. 10,494,381, which is a continuation of U.S. patent application Ser. No. 15/376,456, filed Dec. 12, 2016, now U.S. Pat. No. 10,100,063, which is a continuation of U.S. patent application Ser. No. 14/839,149, filed Aug. 28, 2015, now U.S. Pat. No. 9,562,061, which claims the benefit of U.S. Provisional Patent Application No. 62/043,929, filed Aug. 29, 2014, each of which is hereby incorporated by reference in its entirety and for all purposes as if fully set forth herein.

FIELD OF THE INVENTION

The present invention relates to compounds that inhibit myeloid cell leukemia 1 protein (Mcl-1, also abbreviated as MCL-1 or MCLI); methods of treating diseases or conditions, such as cancer, using the compounds; and pharmaceutical compositions containing the compounds.

BACKGROUND OF THE INVENTION

One common characteristic of human cancer is overexpression of Mcl-1. Mcl-1 overexpression prevents cancer cells from undergoing programmed cell death (apoptosis), allowing the cells to survive despite widespread genetic damage.

Mcl-1 is a member of the Bcl-2 family of proteins. The Bcl-2 family includes pro-apoptotic members (such as BAX and BAK) which, upon activation, form a homo-oligomer in the outer mitochondrial membrane that leads to pore formation and the escape of mitochondrial contents, a step in triggering apoptosis. Antiapoptotic members of the Bcl-2 family (such as Bcl-2, Bcl-XL, and Mcl-1) block the activity of BAX and BAK. Other proteins (such as BID, BIM, BIK, and BAD) exhibit additional regulatory functions.

Research has shown that Mcl-1 inhibitors can be useful for the treatment of cancers. MCl-1 is overexpressed in numerous cancers. See Beroukhim et al. (2010) Nature 463, 899-905. Cancer cells containing amplifications surrounding the Mcl-1 and Bcl-2-1-1 anti-apoptotic genes depend on the expression of these genes for survival. Beroukhim et al. Mcl-1 is a relevant target for the re-initiation of apoptosis in numerous cancer cells. See G. Lessene. P. Czabotar and P. Colman, Nat. Rev. Drug. Discov., 2008, 7, 989-1000; C. Akgul Cell. Mol. Life Sci. Vol. 66, 2009; and Arthur M. Mandelin II, Richard M. Pope, Expert Opin. Ther. Targets (2007) 11(3):363-373.

New compositions and methods for preparing and formulating Mcl-1 inhibitors would be useful.

SUMMARY OF THE INVENTION

Figure 1:
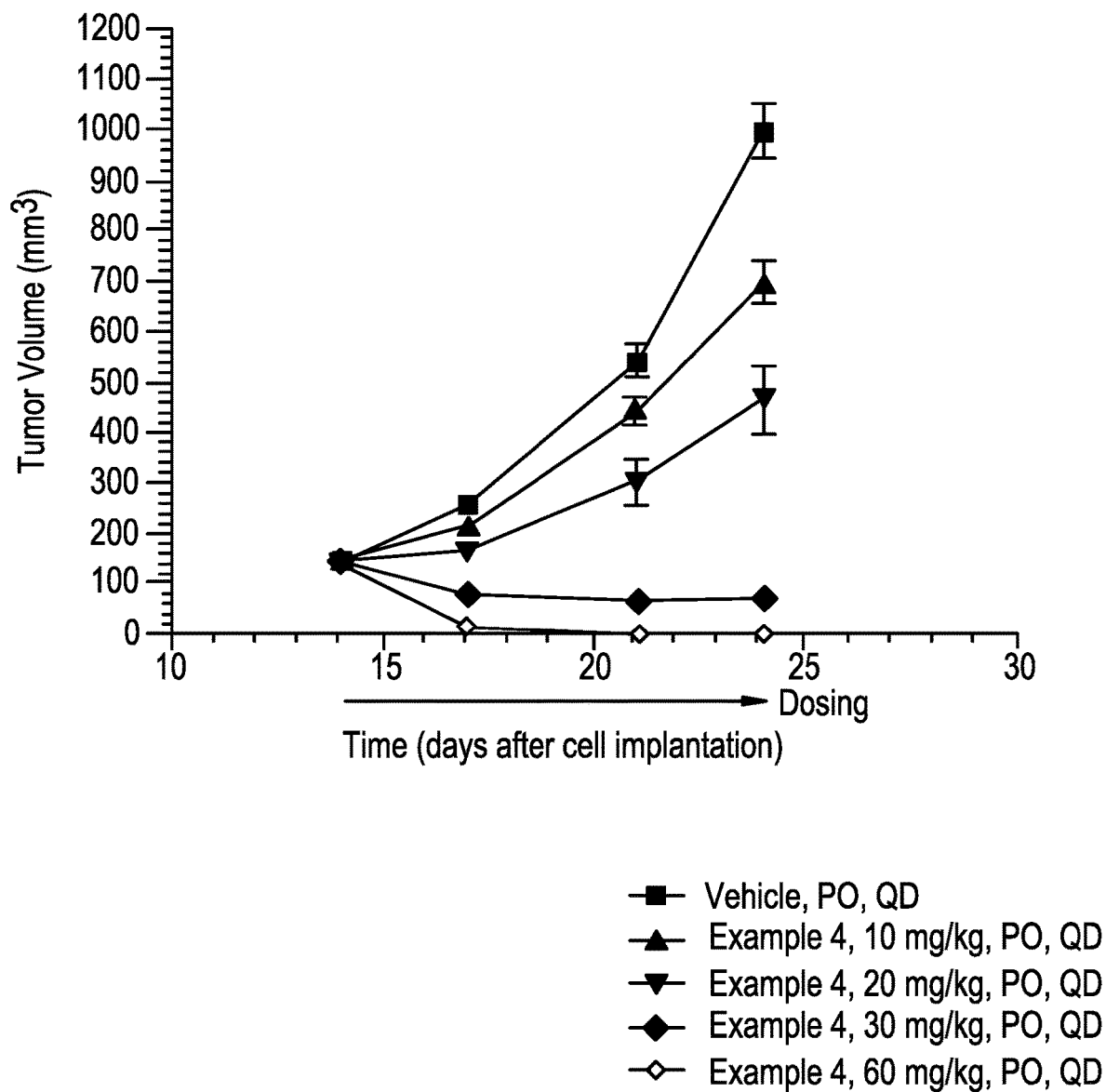
FIG. 1 illustrates the Mcl-1 inhibitor in-vivo efficacy of the compound of Example 4.

In one embodiment, the present invention provides compounds of Formula I,

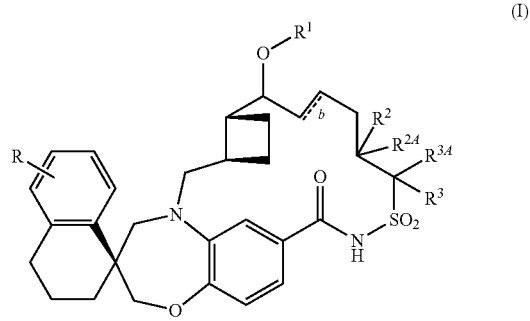

(I)

wherein, b, represented by the symbol ======= is a single or double chemical bond which may be cis or trans; R is a halo; $R^1$ is H, $C_{1-6}$alkyl, and $(CH_2CH_2O)_n$–$CH_3$, wherein n is an integer from 1 to 4; $R^2$ is H or $C_{1-6}$alkyl; $R^{2A}$ is H or $C_{1-6}$alkyl; $R^3$ is H or $C_{1-6}$ alkyl; and $R^{3A}$ is H, $C_{1-6}$ alkyl, $C_{3-6}$ cycloalkyl, or $(CH_2)_m$–$C_{3-6}$ cycloalkyl, wherein m is an integer from 1 to 4. In one embodiment, R is Cl. In one embodiment, $R^1$ is $C_{1-6}$ alkyl. In another embodiment, $R^1$ is $CH_3$. In one embodiment, $R^2$ is H and $R^{2A}$ is $C_{1-6}$ alkyl. In one embodiment, $R^3$ is H and $R^{3A}$ is $C_{1-6}$ alkyl. In another embodiment, b indicates a double bond.

In some embodiments of the invention the compound of Formula I is a compound of Formula II,

(II)

wherein $R^1$, $R^2$, $R^{2A}$, $R^3$ and $R^{3A}$ are defined above.

In some embodiments of the invention, the present invention provides compounds having the following structures:

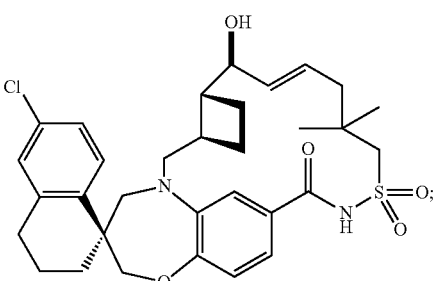

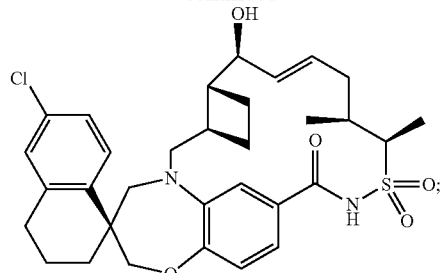
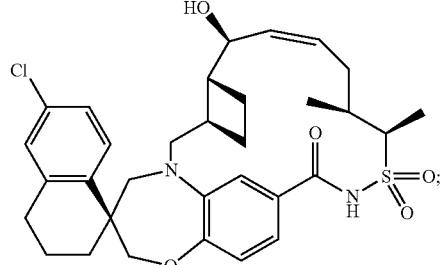
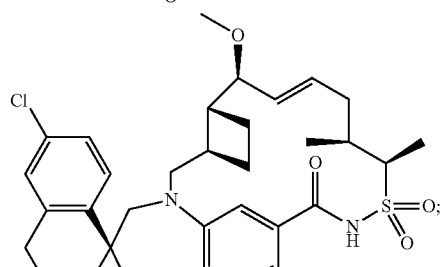
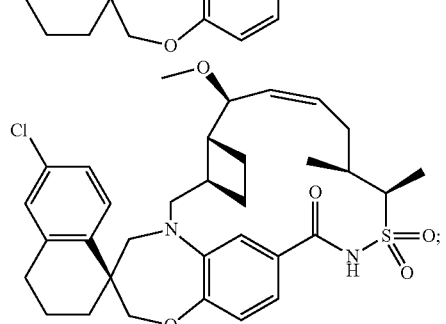
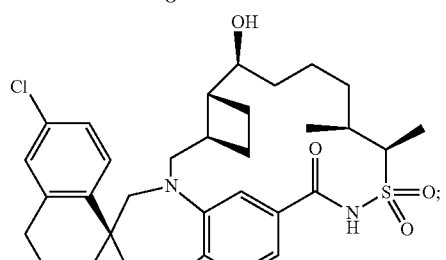
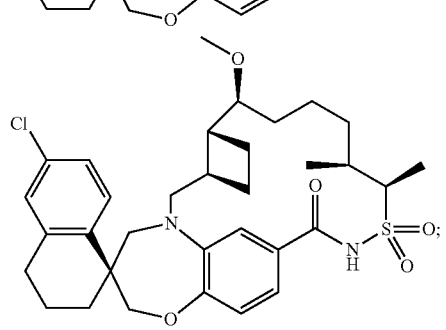
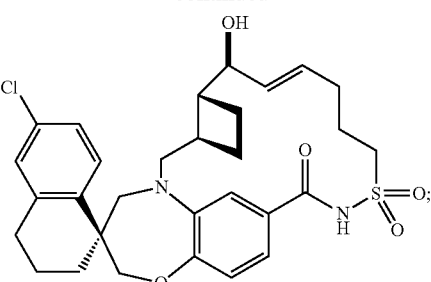
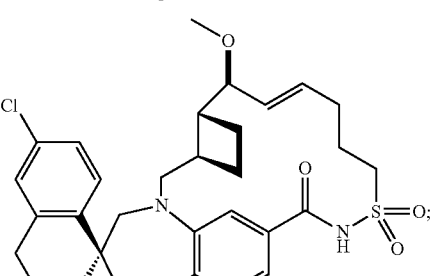
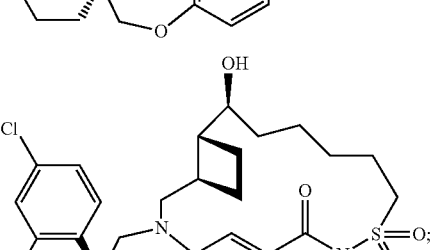
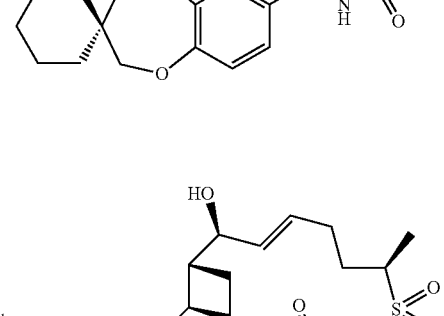
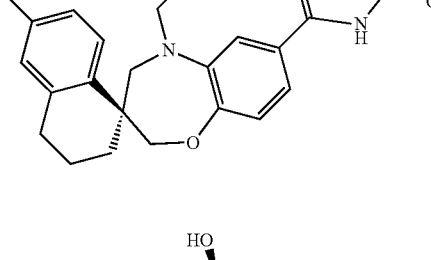
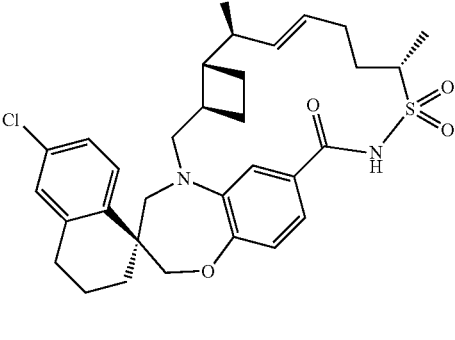

-continued
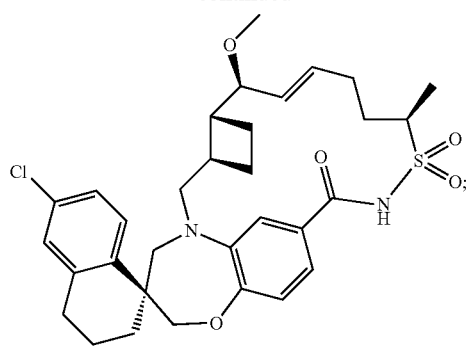
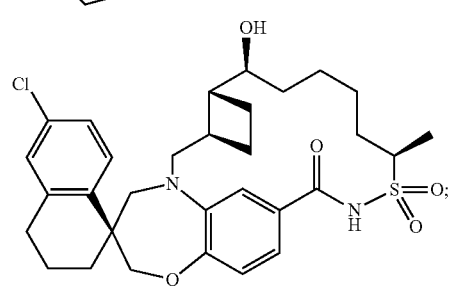
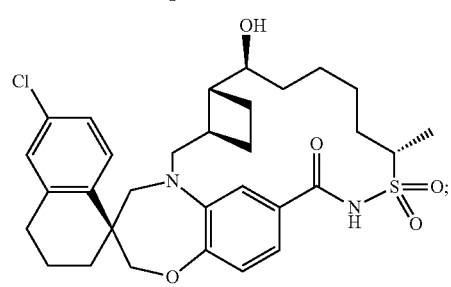
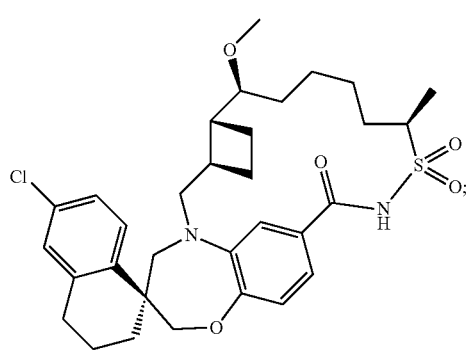
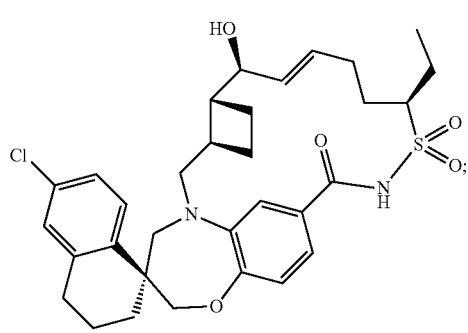
-continued
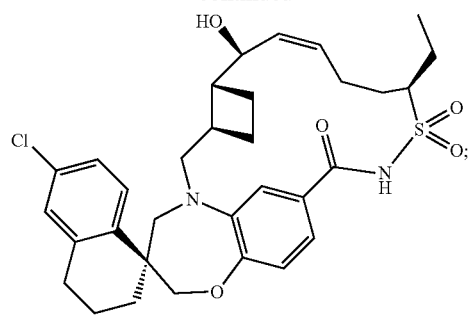
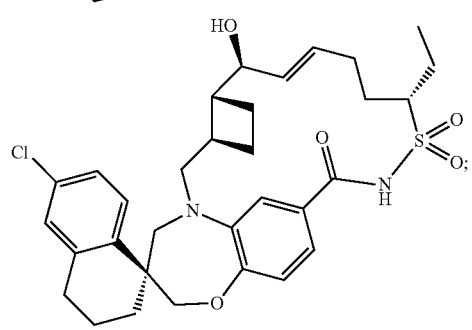
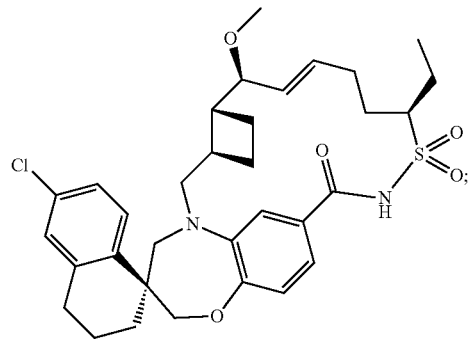
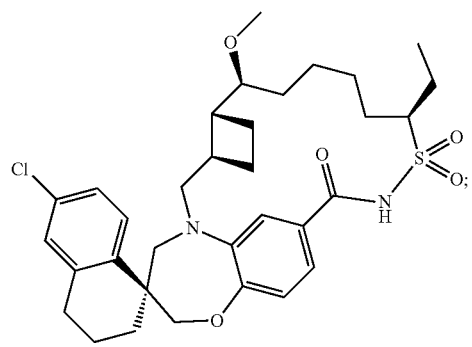
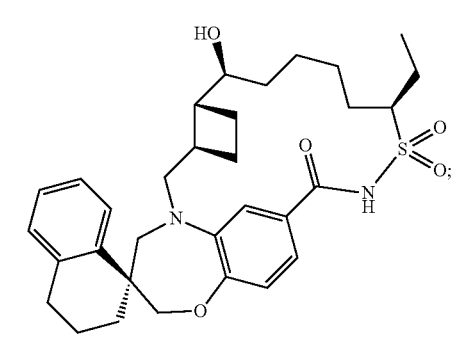

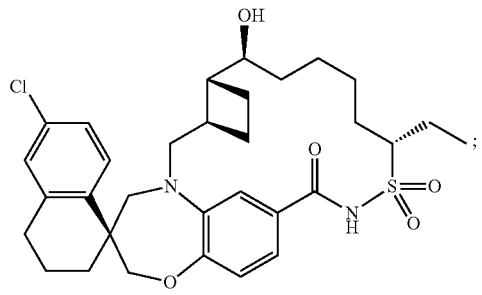
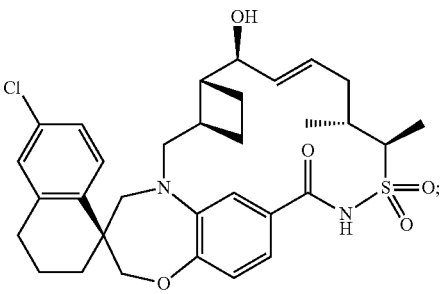
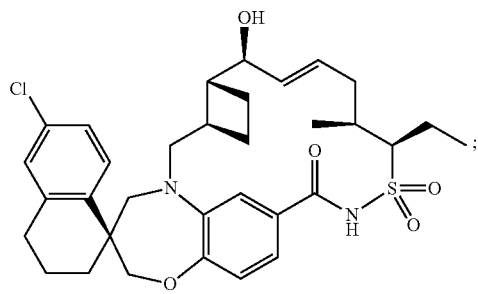
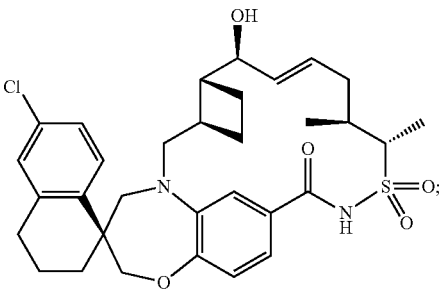
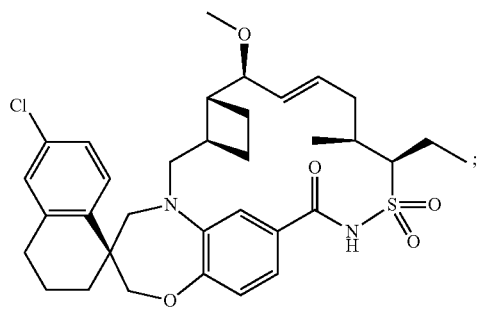
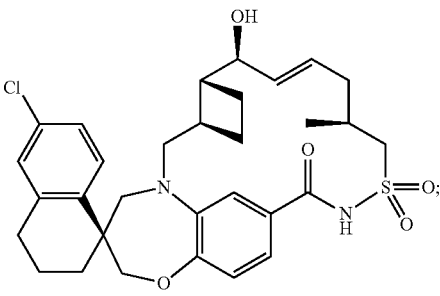
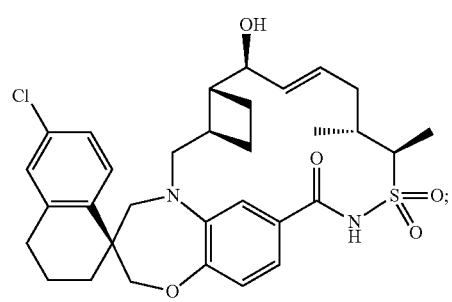
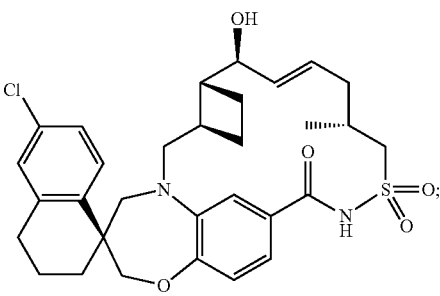
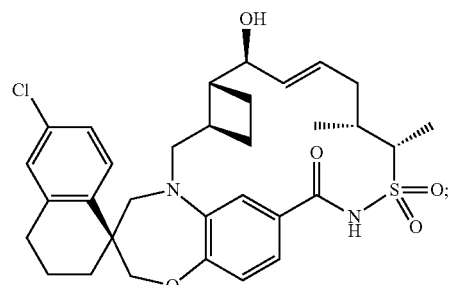
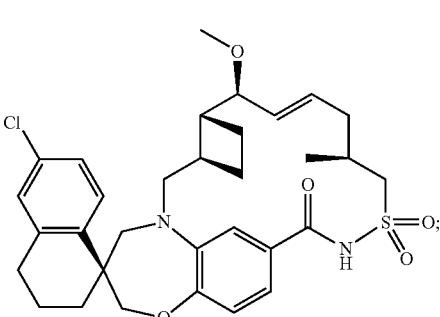

-continued
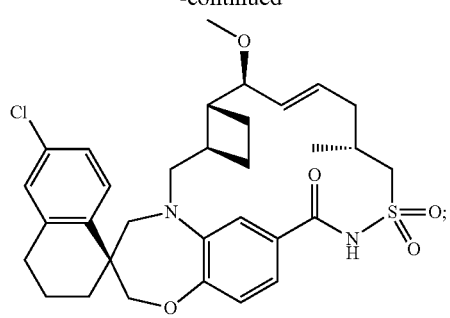
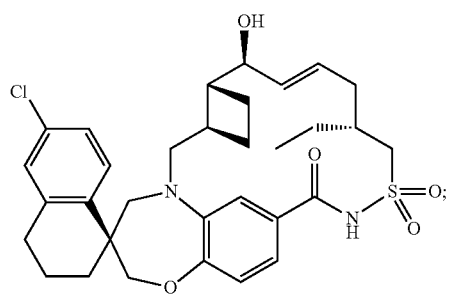
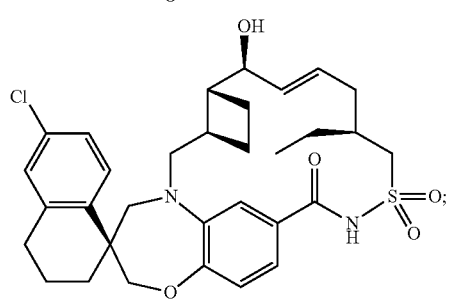
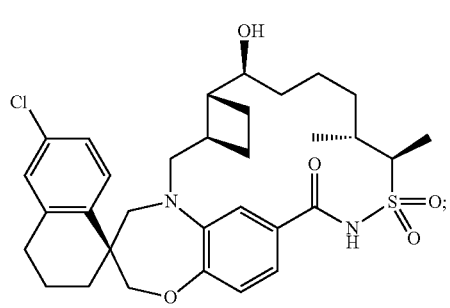
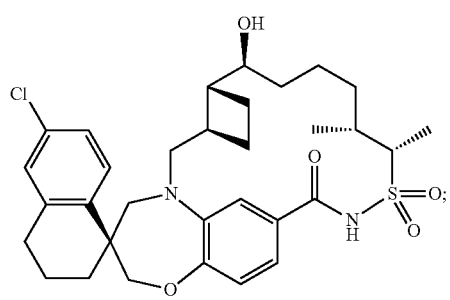
-continued
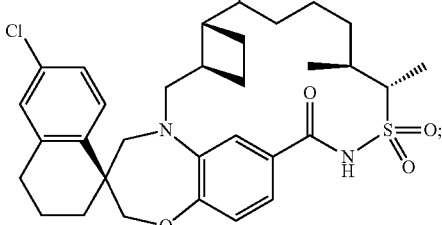
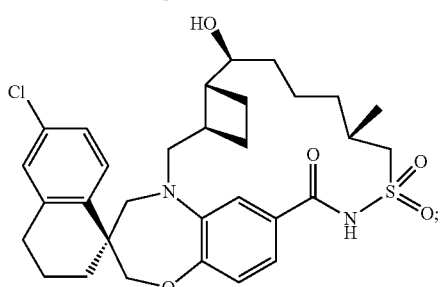
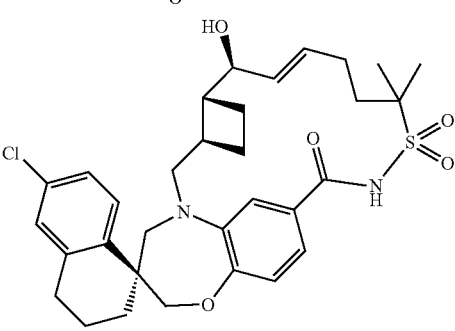
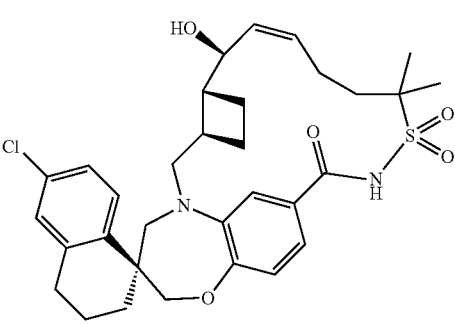
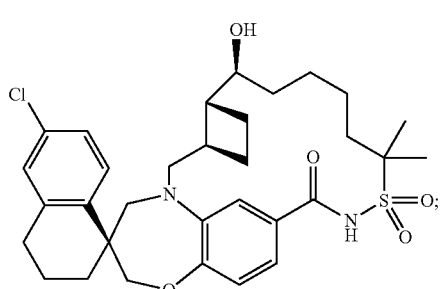

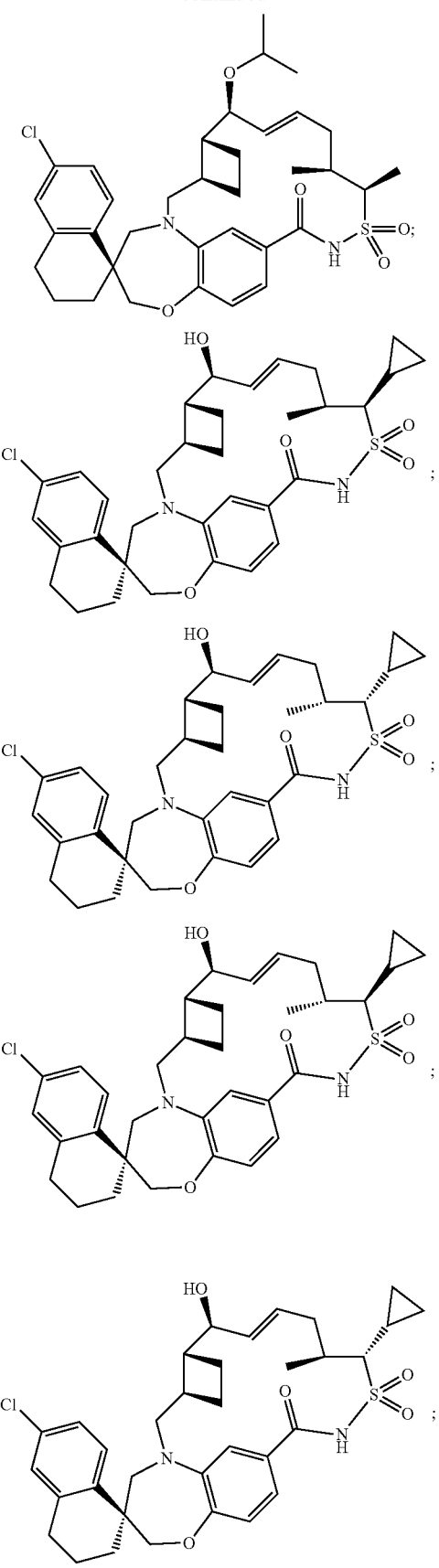

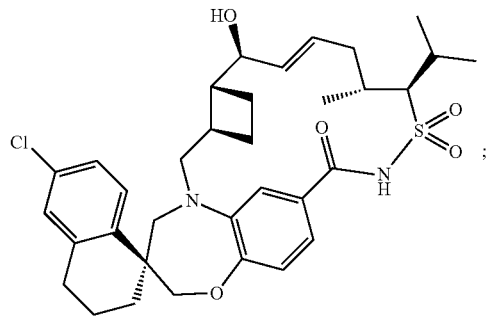
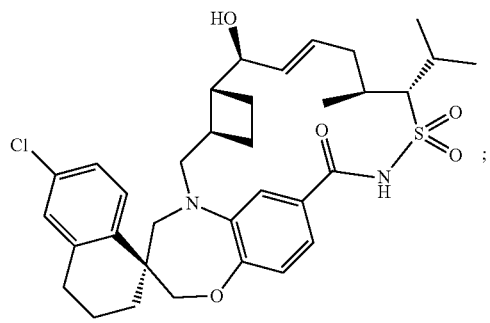
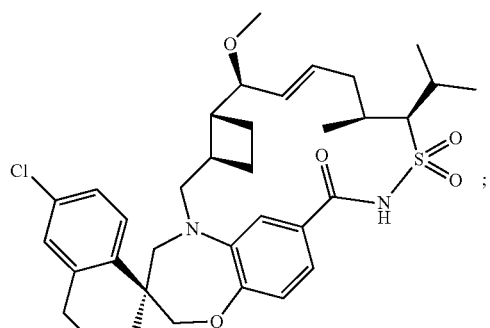
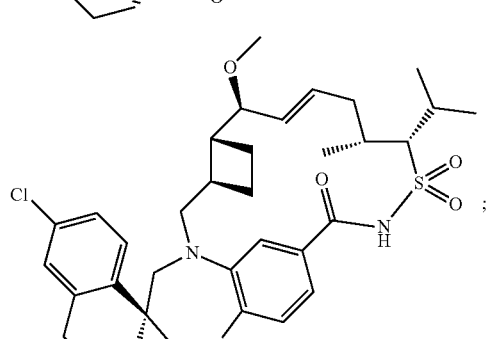
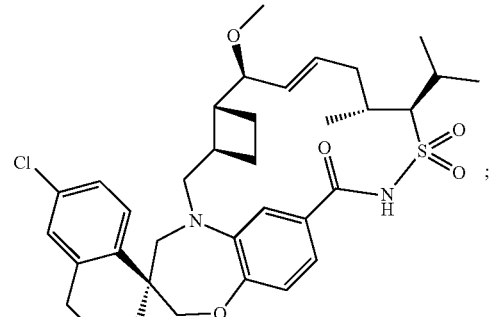
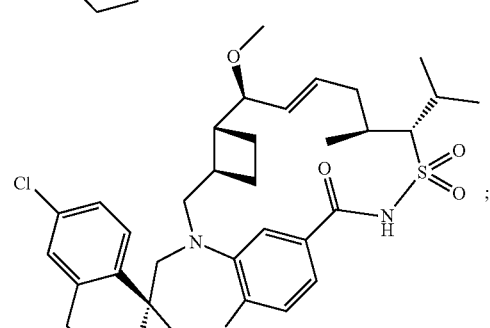
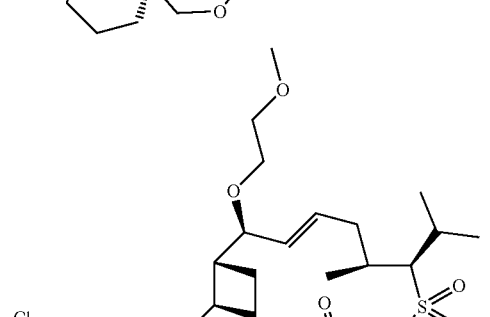
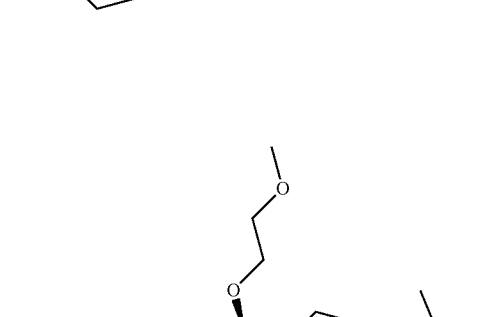
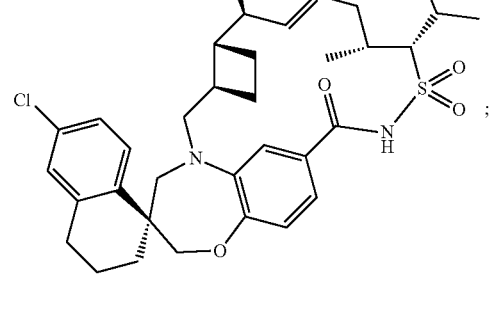

-continued
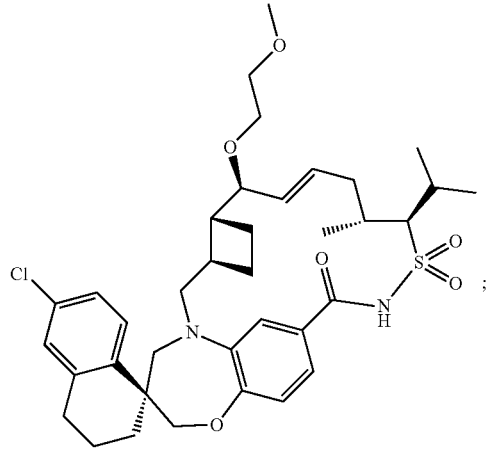
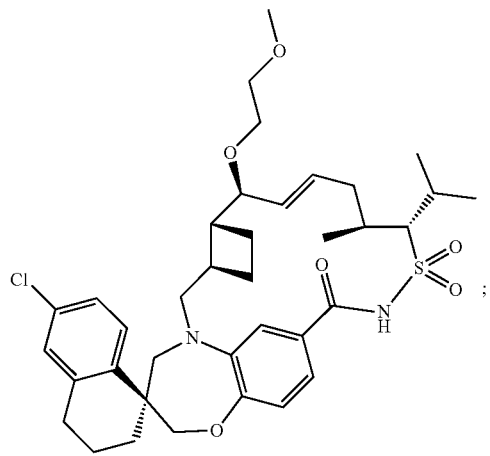
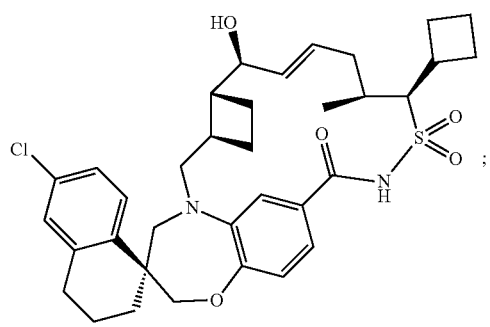
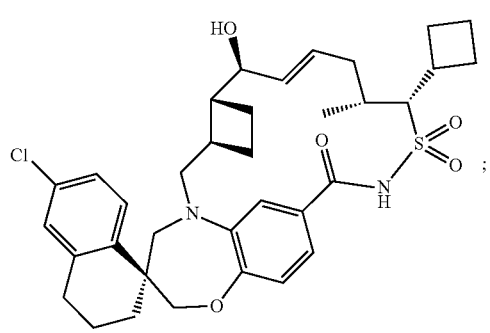
-continued
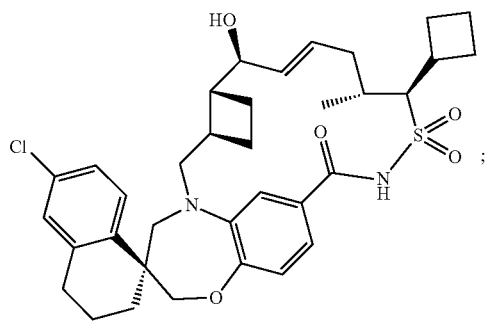
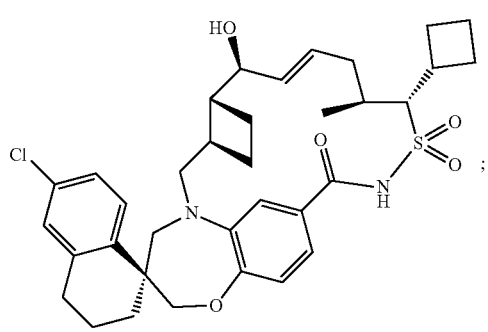
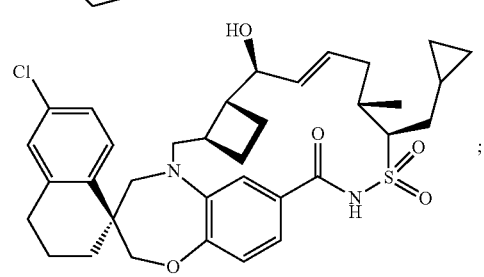
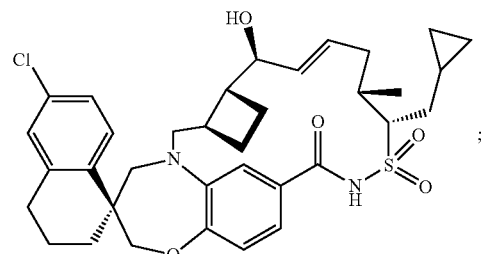
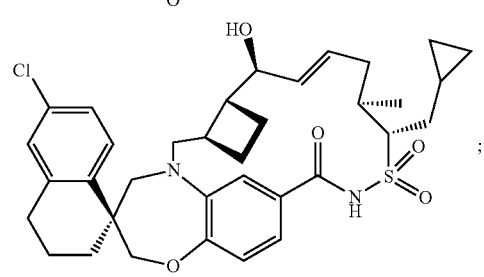
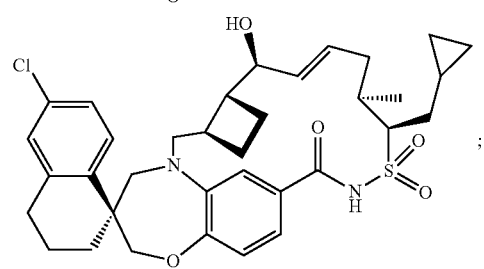

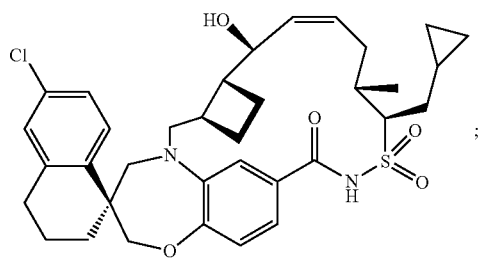
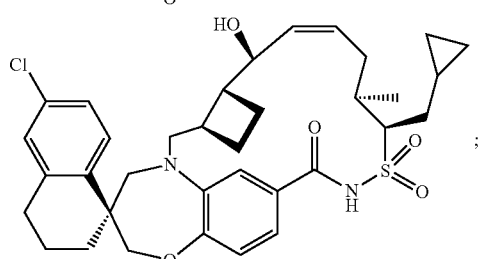
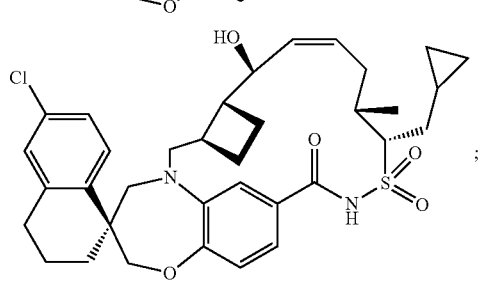
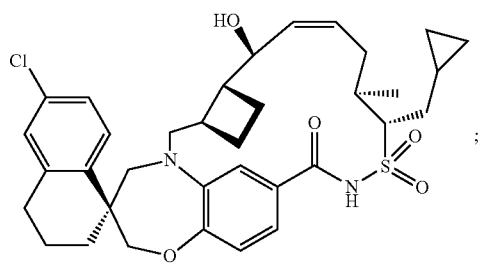
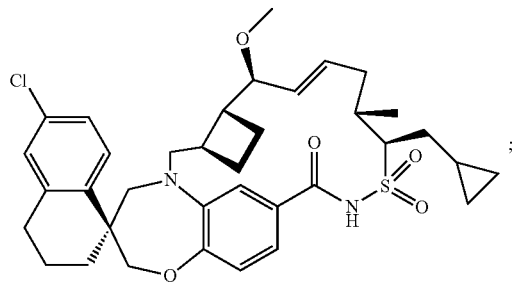
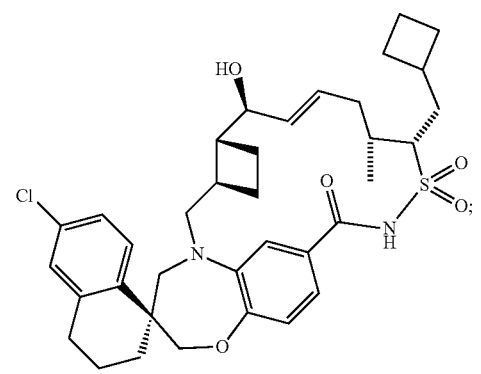
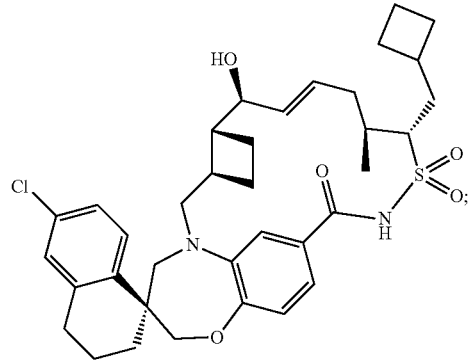
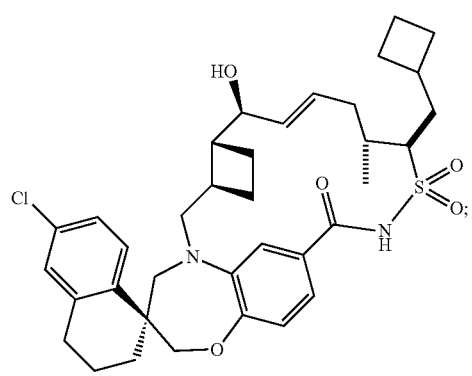
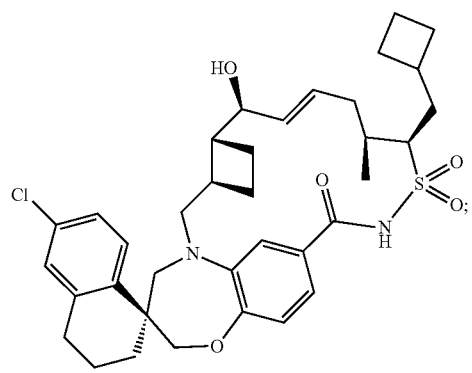
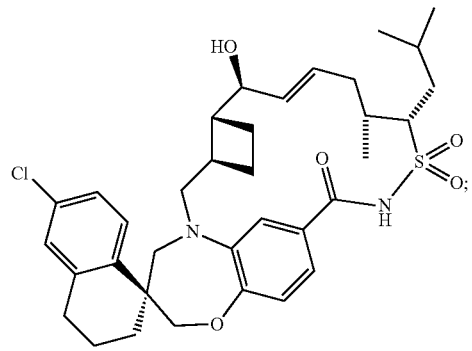

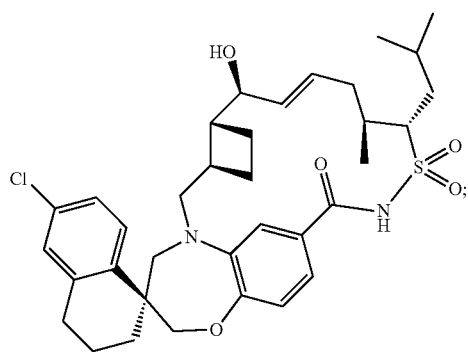
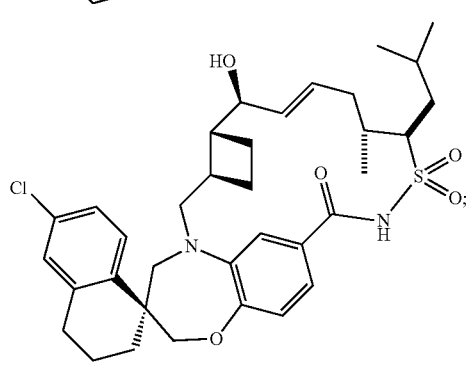
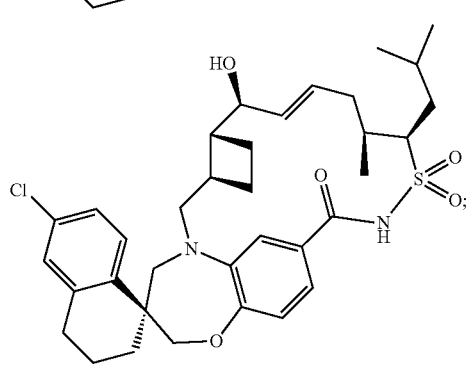
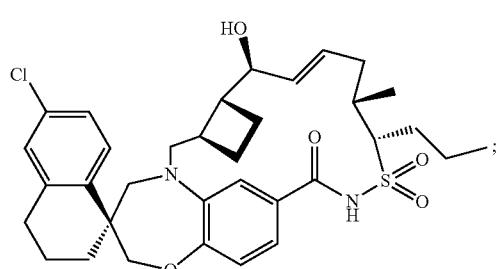
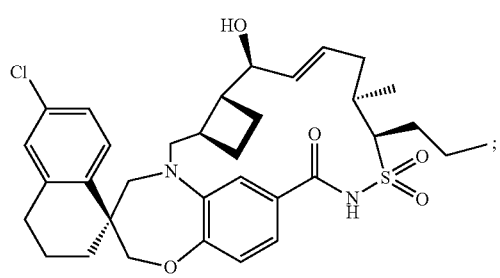
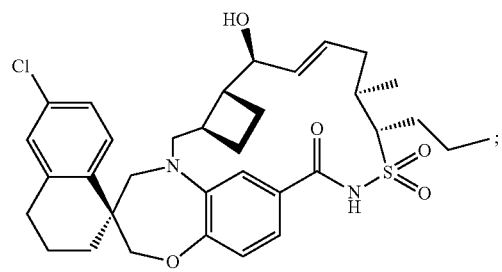
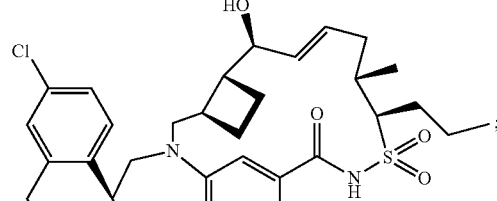
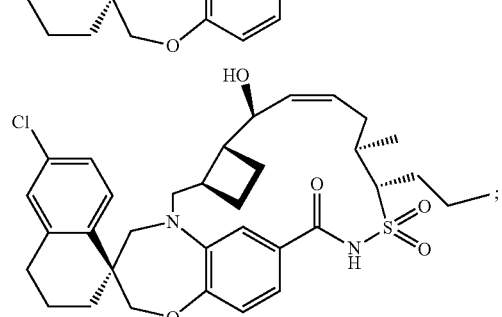
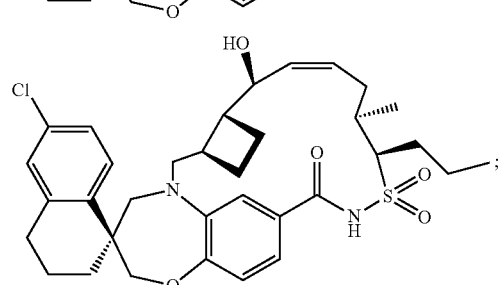
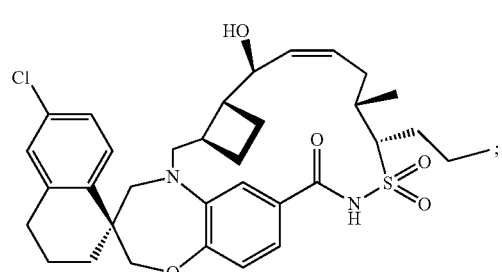
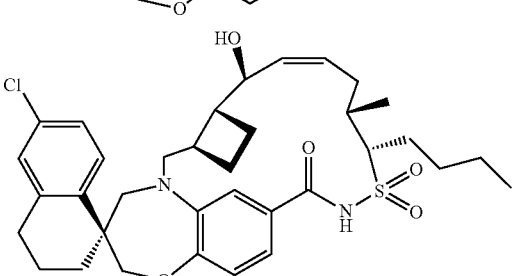

-continued
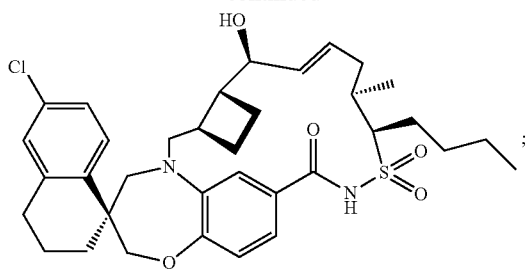
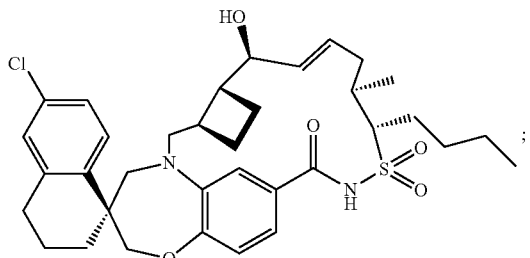
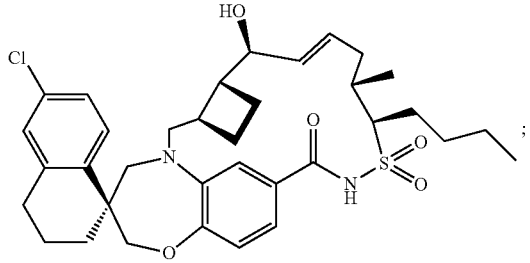
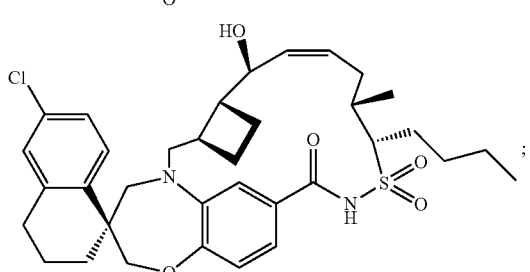
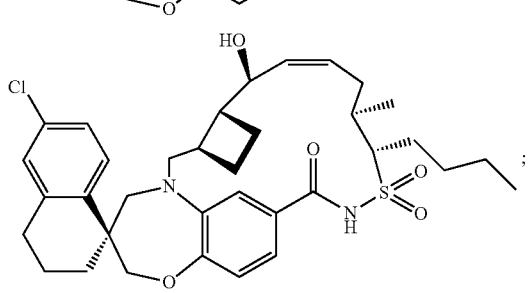
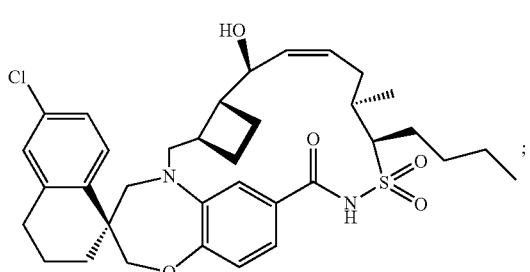
-continued
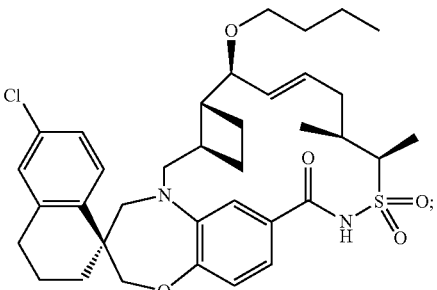
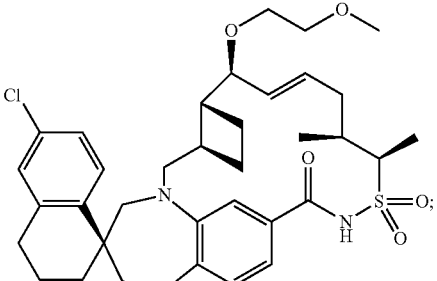
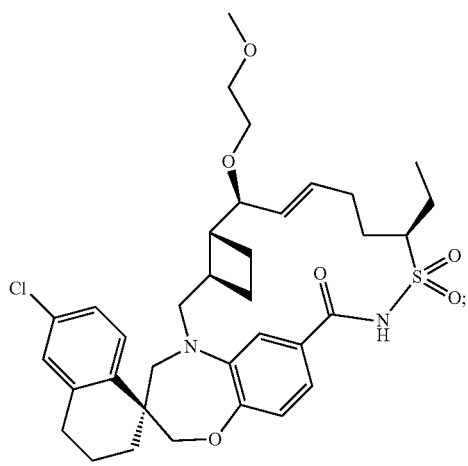
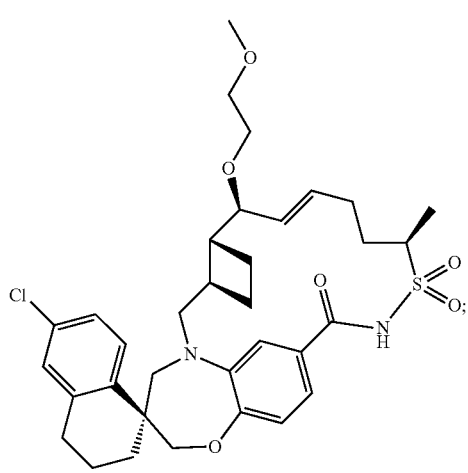

23
-continued
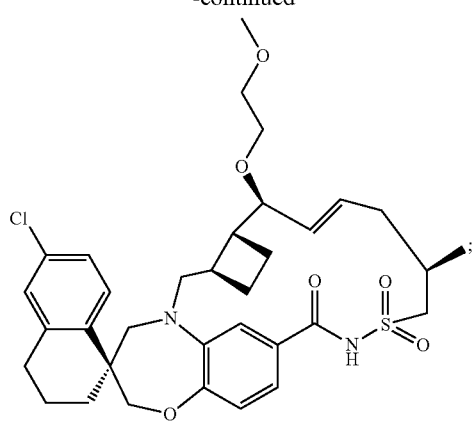
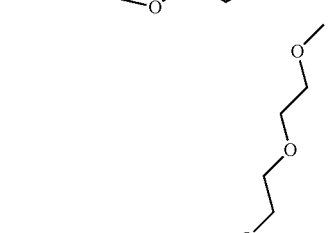
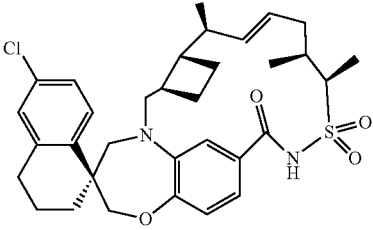
24
-continued
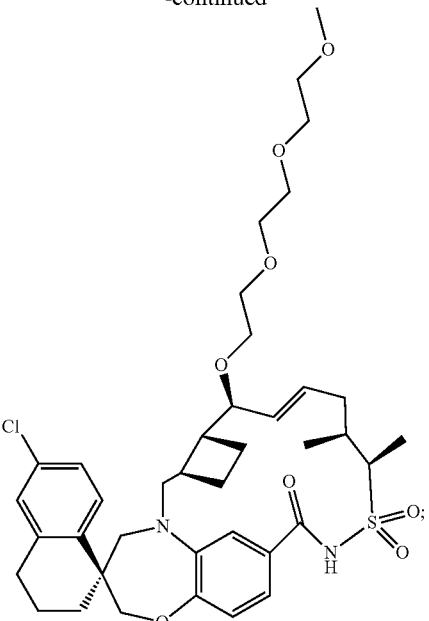
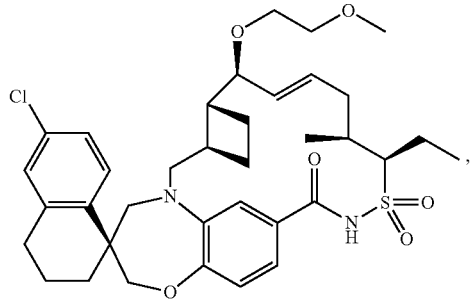
or a pharmaceutically acceptable salt thereof, and a pharmaceutically acceptable excipient, in conjunction with any of the above or below embodiments.

1. One embodiment of the present invention is directed to a compound, wherein the compound has a structure selected from:
2.
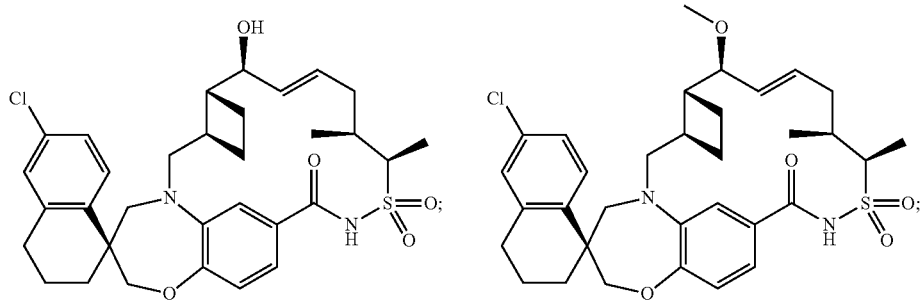
3.
4.
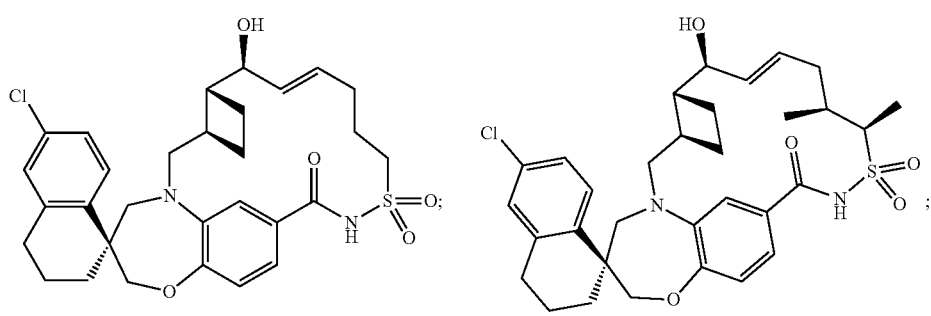
5.
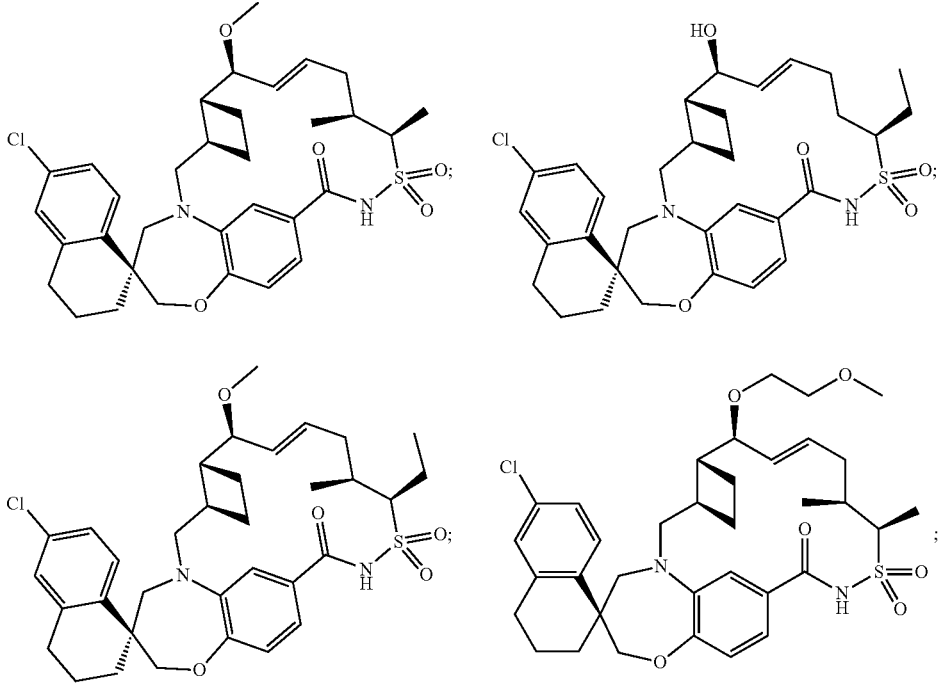

6.

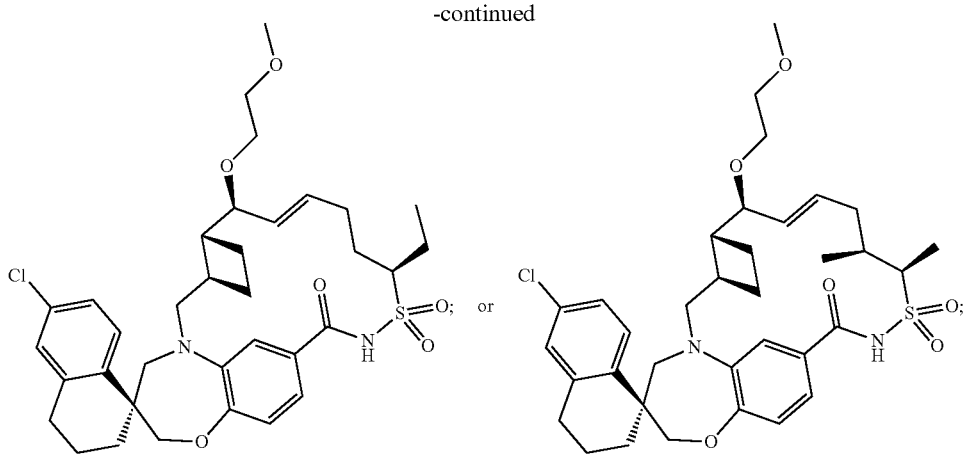

7. or a pharmaceutically acceptable salt thereof, and a pharmaceutically acceptable excipient, in conjunction with any of the above or below embodiments.

One embodiment of the present invention is directed to a compound having the structure

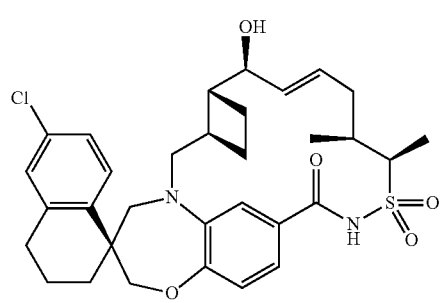 [SMILES: C[C@@H]1[C@@H](C)C/C=C/[C@H](O)[C@@H]2CC[C@H]2CN2C[C@@]3(CCCc4cc(Cl)ccc43)COc3ccc(cc32)C(=O)NS1(=O)=O]

or a pharmaceutically acceptable salt thereof, and a pharmaceutically acceptable excipient, in conjunction with any of the above or below embodiments.

Another embodiment of the present invention is directed to a compound having the structure

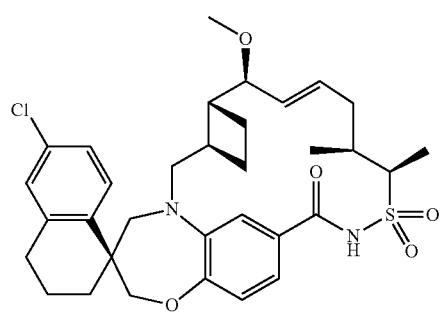 [SMILES: CO[C@H]1/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]

or a pharmaceutically acceptable salt thereof, and a pharmaceutically acceptable excipient, in conjunction with any of the above or below embodiments.

Another embodiment of the present invention is directed to a compound having the structure

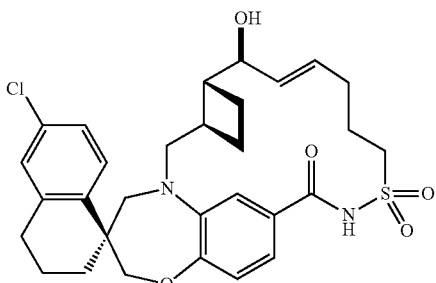

or a pharmaceutically acceptable salt thereof, and a pharmaceutically acceptable excipient, in conjunction with any of the above or below embodiments.

Another embodiment of the present invention is directed to a compound having the structure

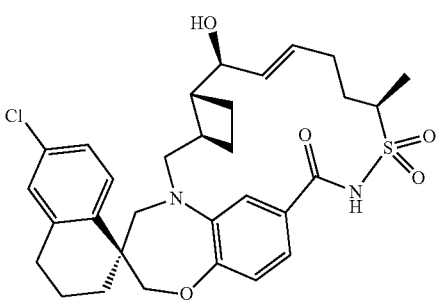 [SMILES: C[C@@H]1CC/C=C/[C@H](O)[C@@H]2CC[C@H]2CN2C[C@@]3(CCCc4cc(Cl)ccc43)COc3ccc(cc32)C(=O)NS1(=O)=O]

or a pharmaceutically acceptable salt thereof, and a pharmaceutically acceptable excipient, in conjunction with any of the above or below embodiments.

Another embodiment of the present invention is directed to a compound having the structure

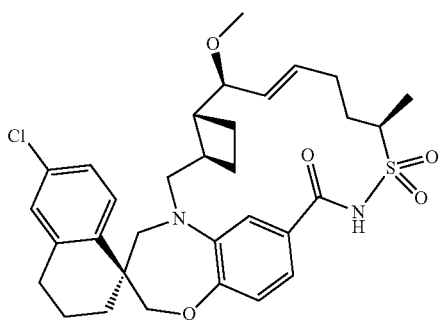 [SMILES: CO[C@H]1/C=C/CC[C@@H](C)S(=O)(=O)NC(=O)c2ccc3c(c2)N(C[C@@H]2CC[C@H]21)C[C@@]1(CCCc2cc(Cl)ccc21)CO3]

or a pharmaceutically acceptable salt thereof, and a pharmaceutically acceptable excipient, in in conjunction with any of the above or below embodiments.

Another embodiment of the present invention is directed to a compound having the structure

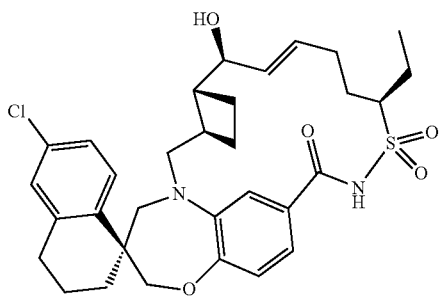 [SMILES: CC[C@@H]1CC/C=C/[C@H](O)[C@@H]2CC[C@H]2CN2C[C@@]3(CCCc4cc(Cl)ccc43)COc3ccc(cc32)C(=O)NS1(=O)=O]

or a pharmaceutically acceptable salt thereof, and a pharmaceutically acceptable excipient, in in conjunction with any of the above or below embodiments.

Another embodiment of the present invention is directed to a compound having the structure

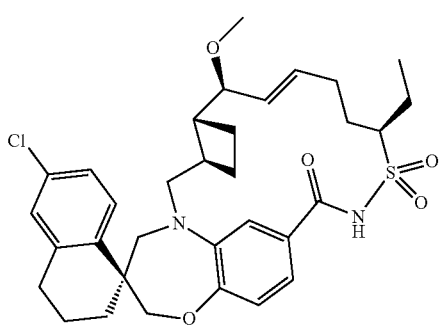 [SMILES: CC[C@@H]1CC/C=C/[C@H](OC)[C@@H]2CC[C@H]2CN2C[C@@]3(CCCc4cc(Cl)ccc43)COc3ccc(cc32)C(=O)NS1(=O)=O]

a pharmaceutically acceptable salt thereof, and a pharmaceutically acceptable excipient, in in conjunction with any of the above or below embodiments.

Another embodiment of the present invention is directed to a compound having the structure or a pharmaceutically acceptable salt thereof, and a pharmaceutically acceptable excipient, in in conjunction with any of the above or below embodiments.

Another embodiment of the present invention is directed to a compound having the structure or a pharmaceutically acceptable salt thereof, and a pharmaceutically acceptable excipient, in in conjunction with any of the above or below embodiments.

Another embodiment of the present invention is directed to a compound having the structure or a pharmaceutically acceptable salt thereof, and a pharmaceutically acceptable excipient, in in conjunction with any of the above or below embodiments.

One embodiment of the present invention is directed to a pharmaceutical composition comprising the compound of Formula I, or pharmaceutically acceptable salt thereof, and a pharmaceutically acceptable excipient.

Another embodiment of the present invention is directed to a method of inhibiting myeloid cell leukemia 1 protein (Mcl-1) of a cell comprising contacting the cell with the compound of Formula I in an effective amount to inhibit the Mcl-1, in conjunction with any of the above or below embodiments. In one embodiment, the contacting is in vitro. In another embodiment, the contacting is in vivo. In one embodiment, the contacting comprises administering the compound to a subject. In one embodiment, the administering is oral, parenteral, via injection, via inhalation, transdermal, or transmucosal. In one embodiment, the subject suffers from cancer.

One embodiment of the present invention is directed to a method of the treatment of cancer, comprising administering to a patient in need thereof a therapeutically effective amount of the compound of Formula I or a pharmaceutical composition comprising the compound of Formula I, or pharmaceutically acceptable salt thereof, and a pharmaceutically acceptable excipient, in conjunction with any of the above or below embodiments. In one embodiment, the cancer is a hematologic malignancy. In one embodiment, the cancer is selected from the group consisting of breast cancer, colorectal cancer, skin cancer, melanoma, ovarian cancer, kidney cancer, lung cancer, non-small cell lung cancer, lymphoma, non-Hodgkin's lymphoma, myeloma, multiple myeloma, leukemia, and acute myelogenous leukemia. In one embodiment, the cancer is multiple myeloma. In another embodiment, the method further comprises the step of administering to the patient in need thereof a therapeutically effective amount of at least one additional pharmaceutically active compound. In one embodiment, the additional pharmaceutically active compound is carfilzomib, in conjunction with any of the above embodiments.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the disclosure will be apparent from the following detailed description and figures, and from the claims.

DETAILED DESCRIPTION

The symbol "-" represents a covalent bond and can also be used in a radical group to indicate the point of attachment to another group. In chemical structures, the symbol - is commonly used to represent a methyl group in a molecule.

As used herein, chemical structures which contain one or more stereocenters depicted with dashed and bold bonds (i.e., ⋯⋯ and ▬▬) are meant to indicate absolute stereochemistry of the stereocenter(s) present in the chemical structure. As used herein, bonds symbolized by a simple line do not indicate a stereo-preference. Unless otherwise indicated to the contrary, chemical structures that include one or more stereocenters which are illustrated herein without indicating absolute or relative stereochemistry encompass all possible stereoisomeric forms of the compound (e.g., diastereomers, enantiomers) and mixtures thereof. Structures with a single bold or dashed line, and at least one additional simple line, encompass a single enantiomeric series of all possible diastereomers.

As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

The term "alkyl" means a straight or branched chain hydrocarbon. Representative examples of alkyl groups include methyl, ethyl, propyl, isopropyl, butyl, isobutyl, tert-butyl, sec-butyl, pentyl and hexyl. Typical alkyl groups are alkyl groups having from 1 to 8 carbon atoms, which groups are commonly represented as $C_{1-8}$ alkyl.

The term "compound", as used herein is meant to include all stereoisomers, geometric isomers, tautomers, and isotopes of the structures depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g., hydrates and solvates).

The term "cycloalkyl" means a cyclic, nonaromatic hydrocarbon. Representative examples of cycloalkyl groups include cyclopropyl, cyclobutyl, cyclopentyl, cyclohexyl and cycloheptyl. A cycloalkyl group can contain one or more double bonds. Representative examples of cycloalkyl groups that contain double bonds include cyclopentenyl, cyclohexenyl, cyclohexadienyl and cyclobutadienyl. Common cycloalkyl groups are $C_{3-8}$ cycloalkyl groups.

The term "excipient", as used herein, means any pharmaceutically acceptable additive, carrier, diluent, adjuvant or other ingredient, other than the active pharmaceutical ingredient (API), which is typically included for formulation and/or administration to a patient. Handbook of Pharmaceutical Excipients, 5$^{th}$ Edition, R. C. Rowe, P. J. Sheskey, and S. C. Owen, editors, Pharmaceutical Press, 2005, Hardback, 928, 0853696187.

For the terms "for example" and "such as" and grammatical equivalences thereof, the phrase "and without limitation" is understood to follow unless explicitly stated otherwise.

The term "halogen" or "halo" means F, Cl, Br or I.

The term "patient" means subjects including animals, such as dogs, cats, cows, horses, sheep and humans. Particular patients are mammals. The term patient includes males and females.

The term "patient in need" means a patient having, or at risk of having, one or more diseases or conditions where the Mcl-1 protein is involved, such as cancers. Identifying a patient in need can be in the judgment of a subject or a health care professional and can be subjective (e.g., opinion) or objective (e.g., measurable by a test or diagnostic method).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrastemal injection, and infusion.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

The term "pharmaceutically acceptable" is employed herein to refer to those ligands, materials, compositions, and/or dosage forms which are, within the scope of sound medical judgment, suitable for administration to a patient, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. As used herein the language "pharmaceutically acceptable carrier" includes buffer, sterile water for injection, solvents, dispersion media, coatings, antibacterial and antifungal agents, isotonic and absorption delaying agents, and the like, compatible with pharmaceutical administration. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted D-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions provided herein are non-pyrogenic, i.e., do not induce significant temperature elevations when administered to a patient.

The term "pharmaceutically acceptable salt" refers to the relatively non-toxic, inorganic and organic acid addition salts of a compound provided herein. These salts can be prepared in situ during the final isolation and purification of a compound provided herein, or by separately reacting the compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", *J. Pharm. Sci.* 66: 1-19.)

The phrases "systemic administration", "administered systemically", "peripheral administration", and "administered peripherally" as used herein mean the administration of a ligand, drug, or other material via route other than directly into the central nervous system, such that it enters the patient's system and thus, is subject to metabolism and other like processes, for example, subcutaneous administration.

The term "therapeutically effective amount" means an amount of a compound that ameliorates, attenuates or eliminates one or more symptom of a particular disease or condition, or prevents or delays the onset of one of more symptom of a particular disease or condition.

The terms "treating", "treat" or "treatment" and the like include preventative (e.g., prophylactic) and palliative treatment.

The methods provided herein include the manufacture and use of pharmaceutical compositions, which include one or more of the compounds provided herein. Also included are the pharmaceutical compositions themselves.

In some embodiments, a compound provided herein may contain one or more acidic functional groups and, thus, is capable of forming pharmaceutically acceptable salts with pharmaceutically acceptable bases. The term "pharmaceutically acceptable salts" in these instances refers to the relatively non-toxic inorganic and organic base addition salts of a compound provided herein. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxida Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

A pharmaceutical composition may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars and the like into the compositions. In addition, prolonged absorption of the injectable pharmaceutical form may be brought about by the inclusion of agents which delay absorption such as aluminum monostearate and gelatin.

In some cases, in order to prolong the effect of one or more compounds provided herein, it is desirable to slow the absorption of the compound from subcutaneous or intramuscular injection. For example, delayed absorption of a parenterally administered compound can be accomplished by dissolving or suspending the compound in an oil vehicle.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. The dose of the compound or composition can be varied over time. All combinations, delivery methods and administration sequences are contemplated.

The compounds of the present invention and in some embodiments, other additional pharmaceutically active compounds, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions prepared as described herein can be administered in various forms, depending on the disorder to be treated and the age, condition, and body weight of the patient, as is well known in the art. For example, where the compositions are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments.

These formulations can be prepared by conventional means in conjunction with the methods described herein, and, if desired, the active ingredient may be mixed with any conventional additive or excipient, such as a binder, a disintegrating agent, a lubricant, a corrigent, a solubilizing agent, a suspension aid, an emulsifying agent, or a coating agent.

Formulations suitable for oral administration may be in the form of capsules (e.g., gelatin capsules), cachets, pills, tablets, lozenges (using a flavored basis, usually sucrose and acacia or tragacanth), powders, troches, granules, or as a solution or a suspension in an aqueous or non-aqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of a compound provided herein as an active ingredient. A composition may also be administered as a bolus, electuary, or paste. Oral compositions generally include an inert diluent or an edible carrier.

Pharmaceutically compatible binding agents, and/or adjuvant materials can be included as part of an oral composition. In solid dosage forms for oral administration (capsules, tablets, pills, dragees, powders, granules, and the like), the active ingredient can be mixed with one or more pharmaceutically acceptable carriers, such as sodium citrate or dicalcium phosphate, and/or any of the following: (1) fillers or extenders, such as starches, cyclodextrins, lactose, sucrose, saccharin, glucose, mannitol, and/or silicic acid; (2) binders, such as, for example, carboxymethylcellulose, microcrystalline cellulose, gum tragacanth, alginates, gelatin, polyvinyl pyrrolidone, sucrose, and/or acacia; (3) humectants, such as glycerol; (4) disintegrating agents, such as agar-agar, calcium carbonate, potato, corn, or tapioca starch, alginic acid, Primogel, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, Sterotes, solid polyethylene glycols, sodium lauryl sulfate, and mixtures thereof; (10) a glidant, such as colloidal silicon dioxide; (11) coloring agents, and (12) a flavoring agent such as peppermint, methyl salicylate, or orange flavoring. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of a powdered compound moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, microspheres, and/or nanoparticles. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active compound(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions suitable for parenteral administration can include one or more compounds provided herein in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In one embodiment, the IV formulation consists of a composition containing hydroxypropyl beta cyclodextrin within a pH range between 8-10 as a buffered or unbuffered solution. The IV formulation can be formulated as a sterile solution ready for injection, a sterile solution ready for dilution into an IV admixture or a sterile solid for reconstitution. The API in the IV formulation may exist as a free acid/base or an in situ salt.

Examples of suitable aqueous and nonaqueous carriers which may be employed in the pharmaceutical compositions provided herein include water for injection (e.g., sterile water for injection), bacteriostatic water, ethanol, polyols (such as glycerol, propylene glycol, polyethylene glycol such as liquid polyethylene glycol, and the like), sterile buffer (such as citrate buffer), and suitable mixtures thereof, vegetable oils, such as olive oil, injectable organic esters, such as ethyl oleate, and Cremophor EL™ (BASF, Parsippany, NJ). In all cases, the composition must be sterile and should be fluid to the extent that easy syringability exists. Proper fluidity can be maintained, for example, by the use of coating materials, such as lecithin, by the maintenance of the required particle size in the case of dispersions, and by the use of surfactants.

The composition should be stable under the conditions of manufacture and storage and must be preserved against the contaminating action of microorganisms such as bacteria and fungi. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the methods of preparation are freeze-drying (lyophilization), which yields a powder of the active ingredient plus any additional desired ingredient from a previously sterile-filtered solution thereof.

Injectable depot forms can be made by forming microencapsule or nanoencapsule matrices of a compound provided herein in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes, microemulsions or nanoemulsions, which are compatible with body tissue.

For administration by inhalation, the compounds can be delivered in the form of an aerosol spray from a pressured container or dispenser that contains a suitable propellant (e.g., a gas such as carbon dioxide) or a nebulizer. Such methods include those described in U.S. Pat. No. 6,468,798. Additionally, intranasal delivery can be accomplished, as described in, inter alia, Hamajima et al., *Clin. Immunol. Immunopathol.*, 88(2), 205-10 (1998). Liposomes (e.g., as described in U.S. Pat. No. 6,472,375, which is incorporated herein by reference in its entirety), microencapsulation and nanoencapsulation can also be used. Biodegradable targetable microparticle delivery systems or biodegradable targetable nanoparticle delivery systems can also be used (e.g., as described in U.S. Pat. No. 6,471,996, which is incorporated herein by reference in its entirety).

Systemic administration of a therapeutic compound as described herein can also be by transmucosal or transdermal means. Dosage forms for the topical or transdermal administration of a compound provided herein include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The ointments, pastes, creams, and gels may contain, in addition to one or more compounds provided herein, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to a compound provided herein, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

A compound provided herein can be administered by aerosol. This is accomplished by preparing an aqueous aerosol, liposomal preparation, or solid particles containing a compound or composition provided herein. A nonaqueous (e.g., fluorocarbon propellant) suspension could be used. In some embodiments, sonic nebulizers are used because they minimize exposing the agent to shear, which can result in degradation of the compound.

Ordinarily, an aqueous aerosol can be made by formulating an aqueous solution or suspension of the agent together with conventional pharmaceutically acceptable carriers and stabilizers. The carriers and stabilizers vary with the requirements of the particular composition, but typically include nonionic surfactants (TWEEN® (polysorbates), PLURONIC® (poloxamers), sorbitan esters, lecithin, CREMOPHOR® (polyethoxylates)), pharmaceutically acceptable co-solvents such as polyethylene glycol, innocuous proteins like serum albumin, sorbitan esters, oleic acid, lecithin, amino acids such as glycine, buffers, salts, sugars, or sugar alcohols. Aerosols generally are prepared from isotonic solutions.

Transdermal patches have the added advantage of providing controlled delivery of a compound provided herein to the body. Such dosage forms can be made by dissolving or dispersing the agent in the proper medium. Absorption enhancers can also be used to increase the flux of the compound across the skin. The rate of such flux can be controlled by either providing a rate controlling membrane or dispersing the compound in a polymer matrix or gel.

The pharmaceutical compositions can also be prepared in the form of suppositories or retention enemas for rectal and/or vaginal delivery. Formulations presented as a suppository can be prepared by mixing one or more compounds provided herein with one or more suitable nonirritating excipients or carriers comprising, for example, cocoa butter, glycerides, polyethylene glycol, a suppository wax or a salicylate, which is solid at room temperature, but liquid at body temperature and, therefore, will melt in the rectum or vaginal cavity and release the active agent. Formulations which are suitable for vaginal administration also include pessaries, tampons, creams, gels, pastes, foams, or spray formulations containing such carriers as are known in the art to be appropriate.

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially (e.g., from Alza Corporation and Nova Pharmaceuticals, Inc). Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811, which is incorporated herein by reference in its entirety for all purposes.

The compounds of the present invention are used in the treatment of diseases, disorders or symptoms mediated by Mcl-1 inhibition. Examples of diseases, disorders or symptoms mediated by Mcl-1 inhibition include, but are not limited to, cancers. Non-limiting examples of cancers include breast cancer, colorectal cancer, skin cancer, melanoma, ovarian cancer, kidney cancer, lung cancer, non-small cell lung cancer, lymphoma, non-Hodgkin's lymphoma, myeloma, multiple myeloma, leukemia, and acute myelogenous leukemia.

The cancers can include carcinomas (originating in the outer layer of cells of the skin and internal membranes, e.g., breasts, kidneys, lungs, skin); sarcomas (arising from connective tissue such as bone, muscle, cartilage, and blood vessels), and hematologic malignancies (e.g., lymphomas and leukemias, which arise in the blood or blood-forming organs such as the spleen, lymph nodes, and bone marrow). Cancer cells can include, for example, tumor cells, neoplastic cells, malignant cells, metastatic cells, and hyperplastic cells.

In an embodiment, the disease, disorder or symptom is a hyperproliferative disorder, e.g., a lymphoma, leukemia, carcinoma (e.g., renal, breast, lung, skin), multiple myeloma, or a sarcoma. In one embodiment, the leukemia is acute myeloid leukemia. In one embodiment, the hyperproliferative disorder is a relapsed or refractory cancer.

Actual dosage levels of the active ingredients in the pharmaceutical compositions provided herein may be varied so as to obtain an amount of the active ingredient which is effective to achieve the desired therapeutic response for a particular patient, composition, and mode of administration, without being toxic to the patient.

The specific dosage and dosage range depends on a number of factors, including the requirements of the patient, the severity of the condition or disease being treated, the pharmacokinetic characteristics of the compound(s) employed, and the route of administration. In some embodiments, the compositions provided herein can be provided in an aqueous solution containing about 0.1-10% w/v of a compound disclosed herein, among other substances, for parenteral administration. Typical dose ranges can include from about 0.01 to about 50 mg/kg of body weight per day, given in 1-4 divided doses. Each divided dose may contain the same or different compounds. The dosage will be a therapeutically effective amount depending on several factors including the overall health of a patient, and the formulation and route of administration of the selected compound(s).

Dosage forms or compositions containing a compound as described herein in the range of 0.005% to 100% with the balance made up from non-toxic carrier may be prepared. Methods for preparation of these compositions are known to those skilled in the art. The contemplated compositions may contain about 0.001%-100% active ingredient, in one embodiment from about 0.1 to about 95%, in another embodiment from about 75 to about 85%. Although the dosage will vary depending on the symptoms, age and body weight of the patient, the nature and severity of the disorder to be treated or prevented, the route of administration and the form of the drug, in general, a daily dosage of from about 0.01 to about 3,000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the patient and adjusting the dosage and/or timing The compounds of the present invention can be administered alone, in combination with other compounds of the present invention, or with other pharmaceutically active compounds or agents. The other pharmaceutically active compounds/agents can be intended to treat the same disease or condition as the compounds of the present invention or a different disease or condition. If the patient is to receive or is receiving multiple pharmaceutically active compounds or agents, the compounds can be administered simultaneously, or sequentially.

The compounds of the present invention, or pharmaceutically acceptable salts thereof, may be used in combination with one or more additional pharmaceutically active compounds/agents.

One or more additional pharmaceutically active compounds or agents may be administered separately, as part of a multiple dose regimen, from the compound of Formula I (e.g., sequentially, e.g., on different overlapping schedules with the administration of one or more compounds of Formula I (including any subgenera or specific compounds thereof). In other embodiments, the one or more additional compounds/agents may be part of a single dosage form, mixed together with the compound of Formula I in a single composition. In still another embodiment, the one or more additional compounds/agents can be given as a separate dose that is administered at about the same time that one or more compounds of Formula I are administered (e.g., simultaneously with the administration of one or more compounds of Formula I (including any subgenera or specific compounds thereof). Both the compound of Formula I and the one or more additional compounds/agents can be present at dosage levels of between about 1 to 100%, and more preferably between about 5 to 95% of the dosage normally administered in a monotherapy regimen.

In a particular embodiment, the additional pharmaceutically active compound/agent is a compound or agent that can be used to treat a cancer. For example, the additional pharmaceutically active compound/agent can be selected from antineoplastic agents, anti-angiogenic agents, chemotherapeutic agents, and peptidal cancer therapy agents. In another embodiment, the antineoplastic agents are selected from antibiotic-type agents, alkylating agents, antimetabolite agents, hormonal agents, immunological agents, interferon-type agents, kinase inhibitors, proteasome inhibitors, and combinations thereof. It is noted that the additional pharmaceutically active compound/agent may be a traditional small organic chemical molecule or can be a macromolecule such as a protein, antibody, peptibody, DNA, RNA or a fragment of such macromolecules.

Examples of additional pharmaceutically active compounds/agents that can be used in the treatment of cancers and that can be used in combination with one or more compounds of the present invention include: acemannan; aclarubicin; aldesleukin; alitretinoin; amifostine; amrubicin; amsacrine; anagrelide; arglabin; arsenic trioxide; BAM 002 (Novelos); bicalutamide; broxuridine; celmoleukin; cetrorelix; cladribine; clotrimazole; DA 3030 (Dong-A); daclizumab; denileukin diftitox; deslorelin; dilazep; docosanol; doxercalciferol; doxifluridine; bromocriptine; cytarabine; HIT diclofenac; interferon alfa; tretinoin; edelfosine; edrecolomab; eflornithine; emitefur; epirubicin; epoetin beta; etoposide phosphate; exisulind; fadrozole; finasteride; fludarabine phosphate; formestane; fotemustine; gallium nitrate; gemtuzumab zogamicin; gimeracil/oteracil/tegafur combination; glycopine; goserelin; heptaplatin; human chorionic gonadotropin; human fetal alpha fetoprotein; ibandronic acid; interferon alfa; interferon alfa natural; interferon alfa-2; interferon alfa-2a; interferon alfa-2b; interferon alfa-N1; interferon alfa-n3; interferon alfacon-1; interferon alpha natural; interferon beta; interferon beta-1a; interferon beta-1b; interferon gamma natural; interferon gamma-1a; interferon gamma-1b; interleukin-1 beta; iobenguane; irsogladine; lanreotide; LC 9018 (Yakult); leflunomide; lenograstim; lentinan sulfate; letrozole; leukocyte alpha interferon; leuprorelin; levamisole+fluorouracil; liarozole; lobaplatin; lonidamine; lovastatin; masoprocol; melarsoprol; metoclopramide; mifepristone; miltefosine; mirimostim; mismatched double stranded RNA; mitoguazone; mitolactol; mitoxantrone; molgramostim; nafarelin; naloxone+pentazocine; nartograstim; nedaplatin; nilutamide; noscapine; novel erythropoiesis stimulating protein; NSC 631570 octreotide; oprelvekin; osaterone; paclitaxel; pamidronic acid; peginterferon alfa-2b; pentosan polysulfate sodium; pentostatin; picibanil; pirarubicin; rabbit antithymocyte polyclonal antibody; polyethylene glycol interferon alfa-2a; porfimer sodium; raltitrexed; rasburicase; rhenium Re 186 etidronate; RII retinamide; romurtide; samarium (153 Sm) lexidronam; sargramostim; sizofuran; sobuzoxane; sonermin; strontium-89 chloride; suramin; tasonermin; tazarotene; tegafur; temoporfin; teniposide; tetrachlorodecaoxide; thymalfasin; thyrotropin alfa; toremifene; tositumomab-iodine 131; treosulfan; tretinoin; trilostane; trimetrexate; triptorelin; tumor necrosis factor alpha natural; ubenimex; bladder cancer vaccine; Maruyama vaccine; melanoma lysate vaccine; valrubicin; verteporfin; virulizin; zinostatin stimalamer; abarelix; AE 941 (Aetema); ambamustine; antisense oligonucleotide; bcl-2 (Genta); APC 8015 (Dendreon); dexaminoglutethimide; diaziquone; EL 532 (Elan); EM 800 (Endorecherche); eniluracil; etanidazole; fenretinide; galocitabine; gastrin 17 immunogen; HLA-B7 gene therapy (Vical); granulocyte macrophage colony stimulating factor; histamine dihydrochloride; ibritumomab tiuxetan; ilomastat; IM 862 (Cytran); interleukin-2; iproxifene; LDI 200 (Milkhaus); leridistim; lintuzumab; CA 125 monoclonal antibody (MAb) (Biomira); cancer MAb (Japan Pharmaceutical Development); HER-2 and Fc MAb (Medarex); idiotypic 105AD7 MAb (CRC Technology); idiotypic CEA MAb (Trilex); LYM-1-iodine 131 MAb (Techniclone); polymorphic epithelial mucin-yttrium 90 MAb (Antisoma); marimastat; menogaril; mitumomab; motexafin gadolinium; MX 6 (Galderma); nolatrexed; P 30 protein; pegvisomant; porfiromycin; prinomastat; RL 0903 (Shire); rubitecan; satraplatin; sodium phenylacetate; sparfosic acid; SRL 172 (SR Pharma); SU 5416 (SUGEN); TA 077 (Tanabe); tetrathiomolybdate; thaliblastine; thrombopoietin; tin ethyl etiopurpurin; tirapazamine; cancer vaccine (Biomira); melanoma vaccine; melanoma oncolysate vaccine; viral melanoma cell lysates vaccine; valspodarl; fluorouracil; 5-fluorouracil; pacitaxel; imatinib; altretamine; cladibrine; cyclophosphamine; decarazine; irinotecan; mitosmycin; mitoxane; topotecan; vinorelbine; adriamycin; mithram; imiquimod; alemtuzmab; exemestane; bevacizumab; cetuximab; azacitidine; clofarabine; decitabine; desatinib; dexrazoxane; docetaxel; epirubicin; oxaliplatin; erlotinib; raloxifene; fulvestrant; letrozole; gefitinib; gemtuzumab; trastuzumab; gefitinib; ixabepilone; lapatinib;

lenalidomide; aminolevulinic acid; temozolomide; nelarabine; sorafenib; nilotinib; pegaspargase; pemetrexed; rituximab; dasatinib; thalidomide; bexarotene; temsirolimus; bortezomib; carfilozmib; oprozomib; vorinostat; capecitabine; zoledronic acid; anastrozole; sunitinib; aprepitant and nelarabine, or a pharmaceutically acceptable salt thereof.

Additional pharmaceutically active compounds/agents that can be used in the treatment of cancers and that can be used in combination with one or more compound of the present invention include: epoetin alfa; darbepoetin alfa; panitumumab; pegfilgrastim; palifermin; filgrastim; denosumab; ancestim; AMG 102; AMG 386; AMG 479; AMG 655; AMG 745; AMG 951; and AMG 706, or a pharmaceutically acceptable salt thereof.

In certain embodiments, a composition provided herein is conjointly administered with a chemotherapeutic agent. Suitable chemotherapeutic agents may include, natural products such as vinca alkaloids (e.g., vinblastine, vincristine, and vinorelbine), paclitaxel, epidipodophyllotoxins (e.g., etoposide and teniposide), antibiotics (e.g., dactinomycin (actinomycin D), daunorubicin, doxorubicin, and idarubicin), anthracyclines, mitoxantrone, bleomycins, plicamycin (mithramycin), mitomycin, enzymes (e.g., L-asparaginase which systemically metabolizes L-asparagine and deprives cells which do not have the capacity to synthesize their own asparagine), antiplatelet agents, antiproliferative/antimitotic alkylating agents such as nitrogen mustards (e.g., mechlorethanune, cyclophosphanide and analogs, melphalan, and chlorambucil), ethylenimines and methylmelamines (e.g., hexaamethylmelaamine and thiotepa), CDK inhibitors (e.g., seliciclib, UCN-01, P1446A-05, PD-0332991, dinaciclib. P27-00, AT-7519, RGB286638, and SCH727965), alkyl sulfonates (e.g., busulfan), nitrosoureas (e.g., carmustine (BCNU) and analogs, and streptozocin), trazenes-dacarbazinine (DTIC), antiproliferative/antimitotic antimetabolites such as folic acid analogs (e.g., methotrexate), pyrimidine analogs (e.g., fluorouracil, floxuridine, and cytarabine), purine analogs and related inhibitors (e.g., mercaptopurine, thioguanine, pentostatin and 2-chlorodeoxyadenosine), aromatase inhibitors (e.g., anastrozole, exemestane, and letrozole), and platinum coordination complexes (e.g., cisplatin and carboplatin), procarbazine, hydroxyurea, mitotane, aminoglutethimide, histone deacetylase (HDAC) inhibitors (e.g., trichostatin, sodium butyrate, apicidan, suberoyl anilide hydroamic acid, vorinostat, LBH 589, romidepsin, ACY-1215, and panobinostat), mTor inhibitors (e.g., temsirolimus, everolimus, ridaforolimus, and sirolimus), KSP (Eg5) inhibitors (e.g., Array 520), DNA binding agents (e.g., Zalypsis), PI3K delta inhibitor (e.g., GS-1101 and TGR-1202), PI3K delta and gamma inhibitor (e.g., CAL-130), multi-kinase inhibitor (e.g., TG02 and sorafenib), hormones (e.g., estrogen) and hormone agonists such as leutinizing hormone releasing hormone (LHRH) agonists (e.g., goserelin, leuprolide and triptorelin), BAFF-neutralizing antibody (e.g., LY2127399), IKK inhibitors, p38MAPK inhibitors, anti-IL-6 (e.g., CNT0328), telomerase inhibitors (e.g., GRN 163L), aurora kinase inhibitors (e.g., MLN8237), cell surface monoclonal antibodies (e.g., anti-CD38 (HUMAX-CD38), anti-CS1 (e.g., elotuzumab), HSP90 inhibitors (e.g., 17 AAG and KOS 953), PI3K/Akt inhibitors (e.g., perifosine), Akt inhibitor (e.g., GSK-2141795), PKC inhibitors (e.g., enzastaurin), FTIs (e.g., Zarnestra™), anti-CD138 (e.g., BT062), Torc½ specific kinase inhibitor (e.g., INK128), kinase inhibitor (e.g., GS-1101), ER/UPR targeting agent (e.g., MKC-3946), cFMS inhibitor (e.g., ARRY-382), JAK½ inhibitor (e.g., CYT387), PARP inhibitor (e.g., olaparib and veliparib (ABT-888)), BCL-2 antagonist. Other chemotherapeutic agents may include mechlorethamine, camptothecin, ifosfamide, tamoxifen, raloxifene, gemcitabine, navelbine, sorafenib, or any analog or derivative variant of the foregoing.

The compounds of the present invention may also be used in combination with radiation therapy, hormone therapy, surgery and immunotherapy, which therapies are well known to those skilled in the art.

In certain embodiments, a pharmaceutical composition provided herein is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof. In a particular embodiment, the compounds of the present invention can also be used in combination with additional pharmaceutically active agents that treat nausea. Examples of agents that can be used to treat nausea include: dronabinol; granisetron; metoclopramide; ondansetron; and prochlorperazine; or a pharmaceutically acceptable salt thereof.

As one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes, and bags. In some embodiments, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing health care professional.

The compounds of the present invention can be administered as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic acid functional group, a prodrug can comprise an ester formed by the replacement of the hydrogen atom of the acid group with a group such as ($C_1$-$C_8$) alkyl, ($C_2$-$C_{12}$) alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as 0-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_{2-3}$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as Z and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can also be separated by converting the enantiomeric mixture into a diastereomeric mixture by reaction with an appropriate optically active compound (e.g., an alcohol), separating the diastereomers and converting (e.g., hydrolyzing) the individual diastereomers to the corresponding pure enantiomers.

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The compounds of the present invention may exist in various solid states including crystalline states and as an amorphous state. The different crystalline states, also called polymorphs, and the amorphous states of the present compounds are contemplated as part of this invention.

EXAMPLES

The examples presented below illustrate specific embodiments of the present invention. These examples are meant to be representative and are not intended to limit the scope of the claims in any manner.

The following abbreviations may be used herein:
~ about
Ac$_2$O acetic anhydride
AcOH acetic acid
Al$_2$O$_3$ aluminum oxide
Calcd Calculated
CO$_2$ carbon dioxide
CSA 10-camphorsulfonic acid
DBU 1,8-diazabicyclo[5.4.0]undec-7-ene
DCE Dichloroethane
DCM Dichloromethane
DEA Diethylamine
Dess-Martin 1,1,1-triacetoxy-1,1-dihydro-1,2-benziodoxol-3-periodinane; (1H)-one
DIEA or DIPEA Diisopropylethylamine
DMAP 4-dimethylaminopyridine
DMF N,N-dimethylformamide
DMSO dimethyl sulfoxide
EDC N-ethyl-N'-(3-dimethylaminopropyl)carbodiimide
ee or e.e. enantiomeric excess
eq Equivalent
ESI or ES electrospray ionization
Et Ethyl
Et$_2$O diethyl ether
EtOAc ethyl acetate
Et$_3$N triethylamine
EtOH ethyl alcohol
g gram(s)
GC gas chromatography
h hour(s)

¹H NMR proton nuclear magnetic resonance spectroscopy
H₂ hydrogen gas
H₂O Water
H₂SO₄ sulfuric acid
HATU 1-[Bis(dimethylamino)methylene]-1H-1,2,3-triazolo[4,5-b]pyridinium 3-oxid hexafluorophosphate
HCl hydrochloric acid
Hex hexane(s)
HPLC high performance liquid chromatography
IP intraperitoneal
IPA isopropyl alcohol
IPAc isopropyl acetate
K₂CO₃ potassium carbonate
K₃PO₄ potassium phosphate
KF Karl Fischer titration
KHMDS potassium hexamethyldisilazide
KOAc potassium acetate
KOH potassium hydroxide
L liter(s)
LAH lithium aluminium hydride
LCMS, LC-MS or
LC/MS liquid chromatography mass spectrometry
LiHMDS lithium hexamethyldisilazide
LiOH lithium hydroxide
M molar (mol L⁻¹)
Me methyl
MeCN acetonitrile
MeI iodomethane
MeOH methyl alcohol
MeTHF methyltetrahydrofuran
mg milligram(s)
MgSO₄ magnesium sulphate
min minute(s)
mL milliliter(s)
MS mass spectrometry
MSA methanesulfonic acid
MsCl methanesulfonyl chloride
MTBE methyl tert-butyl ether
m/z mass-to-charge ratio
N Normality (Eq/L)
N₂ nitrogen gas
NaCl sodium chloride
Na₂CO₃ sodium carbonate
NaHCO₃ sodium bicarbonate
NaH₂PO₄ sodium dihydrogen phosphate
NaNO₂ sodium nitrite
NaOH sodium hydroxide
NaOtBu sodium tert-butoxide
Na₂SO₄ sodium sulfate
Na₂S₂O₃ sodium thiosulfate
NH₃ ammonia, azane
NH₄Cl ammonium chloride
NH₄OH ammonium hydroxide
NMP 1-methyl-2-pyrrolidinone
NMR nuclear magnetic resonance spectroscopy
PO per oral
POCl₃ phosphoryl chloride
PhMe toluene
ppm parts per million
QD once daily
QNMR quantitative NMR
RBF round-bottomed flask
RT or rt or r.t. room temperature
sat. or sat'd or satd Saturated
SFC supercritical fluid chromatography
SiO₂ silicon dioxide, silica
SOCl₂ thionyl chloride
TEMPO (2,2,6,6-tetramethylpiperidin-1-yl)oxidanyl
TFA trifluoroacetic acid
THF Tetrahydrofuran
TLC thin layer chromatography
TsOH toluene sulfonic acid
v/v volume per volume It is noted that when a percent (%) is used with regard to a liquid, it is a percent by volume with respect to the solution. When used with a solid, it is the percent with regard to the solid composition.

Biological Assays

Cell Free Mcl-1:Bim Affinity Assay (Mcl-1 HTRF)

The inhibition of the Mcl-1/Bim interaction was measured using a time-resolved fluorescence resonance energy transfer (TR-FRET) assay. The recombinant human Mcl-1 (C-terminally 6×His tagged Mcl-1 containing residues 171-327) was generated at Amgen Inc (Thousand Oaks, CA). A biotinylated peptide derived from human Bim (residues 51-76) was purchased from CPC Scientific (San Jose, CA). The TR-FRET assay was conducted in a 384-well white OptiPlate™ (PerkinElmer, Waltham, MA) in a total volume of 40 µL. The reaction mixture contained 0.1 nM Mcl-1 (171-327), 0.05 nM biotin-Bim(51-76), 0.05 nM LANCE® Eu-W1024 Anti-6×His (PerkinElmer), 0.072 nM Streptavidin-XLent (Cisbio, Bedford, MA), and serially diluted test compounds in the binding buffer of 20 mM Hepes, pH 7.5, 150 mM NaCl, 0.016 mM Brij®35, and 1 mM dithiothreitol. Test compounds were pre-incubated with Mcl-1(171-327) and biotin-Bim (51-76) for 60 min before addition of the detection mixture (LANCE® Eu-W1024 Anti-6×His and Streptavidin-XLent). The reaction plates were further incubated overnight and then were read on an Envisiont multimode reader (PerkinElmer). Fluorescence signals were measured at 620 nm (40-nm bandwidth) and 665 nm (7.5-nm bandwidth) with a 60 µs delay after excitation at 320 nm (75-nm bandwidth). The signal ratio at 665/620 nm corresponded to the Mcl-1/Bim interaction and was used in all data analyses. The $IC_{50}$ values of test compounds were determined from duplicate data by analyzing competition curves using a four-parameter sigmoidal model in GraphPad Prism (GraphPad Software, San Diego, CA) or in Genedata Screener® (Genedata, Basel, Switzerland).

Cell-Based Assay (Split Luciferase)

A split luciferase complementation assay was developed to determine the inhibition of Mcl-1/Bak protein-protein interactions in cells. A pcDNA-Luc(1-298)-BAK expression vector encoding amino acids (1-298) of Firefly luciferase fused to human Bak was generated along with a pcDNA-Luc(395-550)-Mcl-1 expression vector encoding amino acids (395-550) of Firefly luciferase fused to the human Mcl-1 gene. Human embryonic kidney (HEK) 293 M cells were transiently transfected with pcDNA-Luc(1-298)-BAK and pcDNA-Luc(395-550)-Mcl-1 at a 3:1 DNA mix ratio. Transient transfection was performed using Lipofectamine® LTX/Plus™ reagent (Life Technologies, Grand Island, NY). 24 h after transfection, cells were collected using non-enzyme based cell dissociation buffer StemPron Accutase® (Life Technologies), and resuspended in serum-free Opti-MEM® (Life Technologies). Cells were then seeded into assay plates with serially diluted test compounds in 0.3% DMSO at density of a 5000 cells/well. Cells were then incubated for 4 h at 37° C. in a cell culture incubator supplement with 5% $CO_2$. Test plates were equilibrated to room temperate for 30 min before addition of 30 µL Steady- Glo® Luciferase assay reagent (Promega, Madison, WI) into each test well. Luminescence was determined using an EnVision® Multilabel plate reader 25 min after the addition of detection reagent. $IC_{50}$ values were then calculated with Xlfit using a logistical 4-parameter fit model in GraphPad Prism (GraphPad Software, San Diego, CA) or in Genedata Screener® (Genedata, Basel, Switzerland).

Cell Viability Assay (OPM-2 10 FBS)

The human multiple myeloma cell line, OPM-2P as cultured in complete growth medium containing RPMI 1640 and 10% fetal bovine serum (FBS). Cells were seeded into 384-well plates at 3000 cells/well density in complete growth medium containing 10% FBS, and incubated for 16 h with serially diluted test compounds in a 37° C. incubator with 5% $CO_2$. Cell viability was tested using CellTiter-Glo®, assay (Promega, Madison, WI) according to the manufacturer recommendations. Luminescence was determined using an EnVision® Multilabel plate reader 25 min after the addition of detection reagent. $IC_{50}$ values were then calculated with Xlfit using a logistical 4-parameter fit model in GraphPad Prism (GraphPad Software San Diego, CA) or in Genedata Screener® (Genedata, Basel, Switzerland).

Results for compounds tested in these biological assays are set forth below.

| Example # | Mcl-1 HTRF (nM) | Split Luciferase (μM) | OPM-2 10% FBS (μM) |
|---|---|---|---|
| 1 | 0.85225 | 0.16327 | 1.88 |
| 2 | 0.21889 | 0.016948 | 0.10469 |
| 3 | 0.18143 | 0.032275 | 0.4845 |
| 4 | 0.36286 | 0.030808 | 0.23574 |
| 5 | 0.5115 | 0.0645 | 1.135 |
| 6 | 0.4465 | 0.05745 | 0.3945 |
| 7 | 1.175 | 0.147 | 1.06 |
| 8 | 0.977 | 0.211 | 1.68 |
| 9 | 1.2445 | 0.12655 | 1.1975 |
| 10 | 1.1846 | 0.2322 | 9.41 |
| 11 | 0.27715 | 0.042346 | 0.3225 |
| 12 | 9.48 | 1.0163 | 22.2 |
| 13 | 0.44069 | 0.034118 | 0.353 |
| 14 | 0.7012 | 0.090865 | 2.0977 |
| 15 | 64.42 | 0.951 | 12.6 |
| 16 | 2.08 | 0.107 | 4.335 |
| 17 | 0.24701 | 0.031189 | 0.25999 |
| 18 | 0.37167 | 0.042467 | 0.69433 |
| 19 | 2.875 | 0.529 | 3.99 |
| 20 | 0.64711 | 0.050429 | 0.3905 |
| 21 | 2.78 | 0.1925 | 4.17 |
| 22 | 0.70423 | 0.11712 | 1.254 |
| 23 | 3.68 | 0.3715 | — |
| 24 | 0.153 | 0.020067 | 0.1246 |
| 25 | 0.5425 | 0.0779 | 0.4045 |
| 26 | 2.6433 | 0.40167 | 3.46 |
| 27 | 19.85 | 1.14 | — |
| 28 | 0.8955 | 0.14387 | 1.54 |
| 29 | 9.435 | 0.458 | 5.575 |
| 30 | 0.38025 | 0.02645 | 0.16075 |
| 31 | 5.8 | 0.543 | 3.56 |
| 32 | 0.8105 | 0.0495 | 0.24167 |
| 33 | 7.02 | 0.872 | 14.9 |
| 34 | 0.437 | 0.037675 | 0.253 |
| 35 | 0.9545 | 0.08435 | 0.723 |
| 36 | 44.45 | 1.5 | — |
| 37 | 0.6.08 | 0.667 | 5.74 |
| 38 | 0.3.3 | 1.04 | — |
| 39 | 10.678 | — | — |
| 40 | 7.68 | 0.297 | 7.295 |
| 41 | 4.415 | 0.1285 | 4.75 |
| 42 | 7.55 | 0.8495 | — |
| 43 | 1.75 | 0.1295 | 0.9015 |
| 44 | 0.297 | 0.0215 | 0.2075 |
| 45 | 5.505 | 0.455 | 20 |
| 46 | 0.728 | 0.0783 | 0.334 |
| 47 | 0.2485 | 0.06005 | 0.2835 |
| 48 | 3.89 | 0.477 | 5.58 |
| 49 | 0.3165 | 0.0462 | 0.1845 |
| 50 | 1.014 | 0.2325 | 1.3245 |
| 51 | 24.3 | 0.792 | 14.4 |
| 52 | 0.882 | 0.14 | 1.114 |
| 53 | 1.39 | 0.05145 | 0.3285 |
| 54 | 0.15275 | 0.02915 | 0.13115 |
| 55 | 15.25 | 0.863 | 8.69 |
| 56 | 0.2895 | 0.03195 | 0.2075 |
| 57 | 2.155 | 0.3745 | 2.395 |
| 58 | 0.9175 | 0.0482 | 0.496 |
| 59 | 0.492 | 0.06155 | 0.247 |
| 60 | 0.51367 | 0.023433 | 0.15798 |
| 61 | 2.675 | 0.06865 | 1.32 |
| 62 | 10.265 | 0.166 | 6.7 |
| 63 | 0.42325 | 0.030684 | 0.18329 |
| 64 | 13.65 | 0.318 | 8.63 |
| 65 | 5.305 | 0.376 | 3.28 |
| 66 | 2.115 | 0.224 | 2.33 |
| 67 | 1.0845 | 0.08485 | 0.6 |
| 68 | 0.501 | 0.0164 | 0.17885 |
| 69 | 8.66 | 0.425 | 2.71 |
| 70 | 0.6385 | 0.034675 | 0.23825 |
| 71 | 5.415 | 0.354 | 2.22 |
| 72 | 2.705 | 0.16905 | 1.555 |
| 73 | 0.367 | 0.0344 | 0.174 |
| 74 | 2.225 | 0.273 | 1.74 |
| 75 | 2.835 | 0.159 | 2.56 |
| 76 | 1.1245 | 0.07735 | 0.6685 |
| 77 | 6.125 | 0.26 | 3.16 |
| 78 | 2.665 | 0.42 | 2.74 |

OPM2 Multiple Myeloma Xenograft Model

Figure 2:
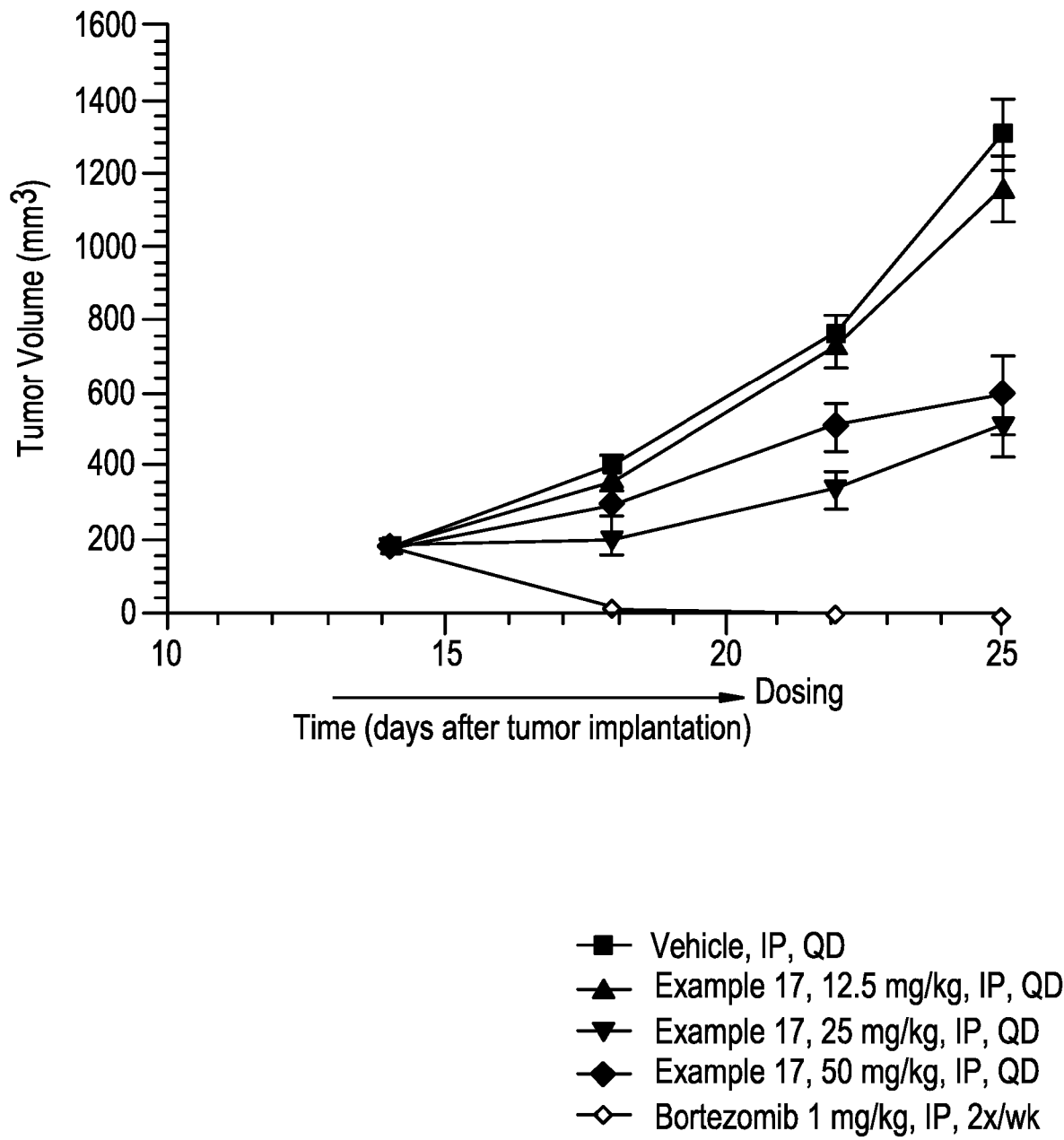
FIG. 2 illustrates the Mcl-1 inhibitor in-vivo efficacy of the compound of Example 17.
Figure 3:
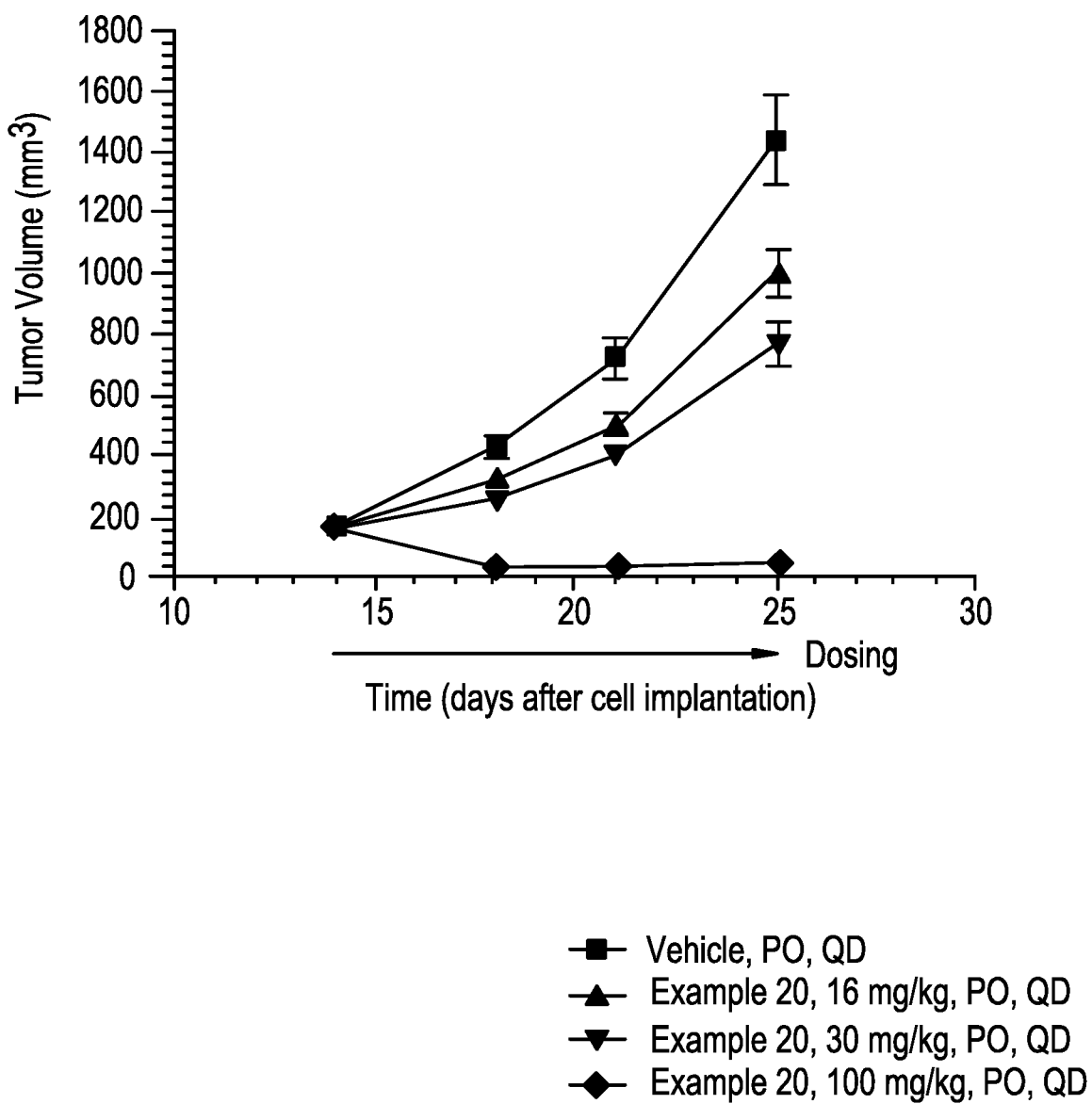
FIG. 3 illustrates the Mcl-1 inhibitor in-vivo efficacy of the compound of Example 20.

Female Athymic nude (Harlan, Inc., Indianapolis, IN) mice were inoculated subcutaneously with 5 million OPM-2 cells. FIGS. 1, 2 and 3 illustrate the results of the treatment with test compounds in various concentrations, compared to the vehicle, defined as the excipient(s) without an active compound, and in FIG. 2 additionally compared to Bortezomib™, a compound commercially available from Millennium Pharmaceuticals, Inc. (Cambridge, MA). The treatment was initiated 14 days later when the tumors had reached an average volume of 100-200 $mm^3$ and continued for an additional 10 days. Tumor volumes and body weights were recorded using electronic calipers and an analytical scale, respectively, twice per week. Statistical analysis was performed using Repeated Measures ANOVA (RMANOVA) followed by Dunnett's post-hoc analysis.

The following synthetic schemes show generally how to make intermediates and compounds of the present invention.

General Synthetic Schemes

General Procedure 1

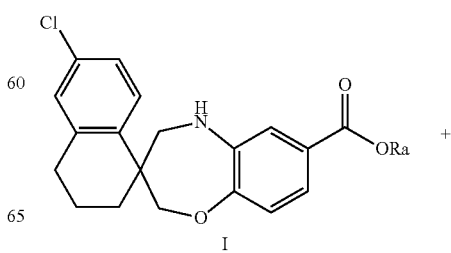

I

-continued

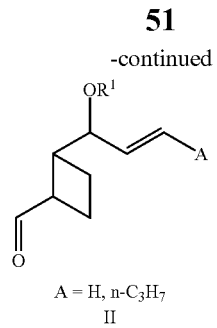

A = H, n-C$_3$H$_7$
II

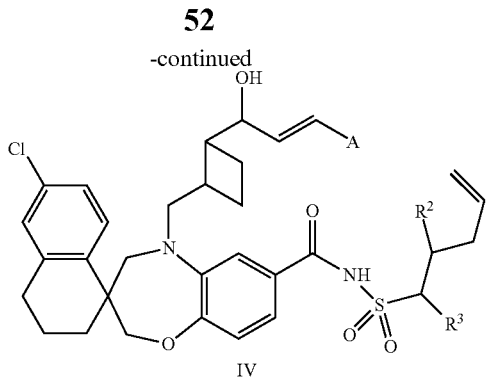

IV

Intermediates IV can be prepared using standard peptide like chemistry. For example, DMAP was added to carboxylic acid Intermediate AA and Intermediate EE in an appropriate solvent at a temperature below RT, preferably about 0° C., followed by the addition of EDC hydrochloride. The mixture was warmed to ambient temperature, to provide carboxamide IV.

General Procedure 3

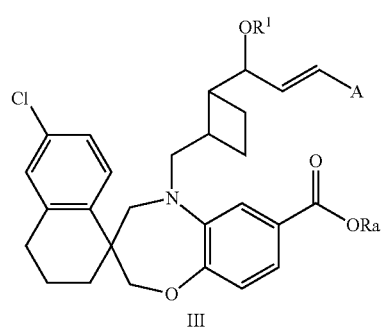

III

Intermediates III can be prepared using standard chemistry techniques. For example, cyclobutane carbaldehyde II was combined with oxazepine I in an appropriate solvent at a temperature below RT, preferably about 0° C. Sodium cyanoborohydride was added, and the mixture was added to NaOH solution, to provide compound III.

General Procedure 2

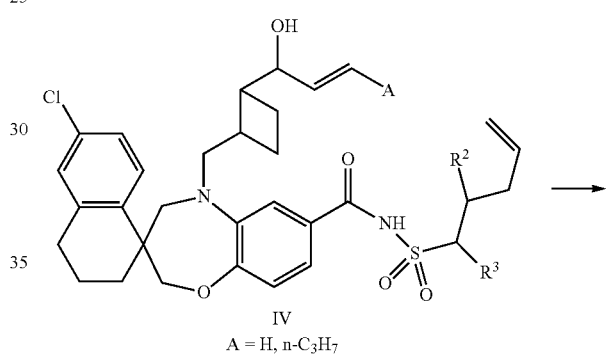

IV
A = H, n-C$_3$H$_7$

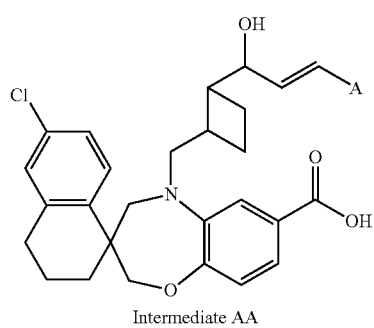

Intermediate AA

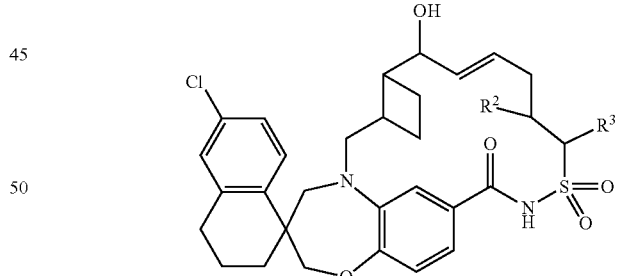

EXAMPLE A

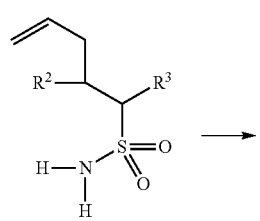

Intermediate EE
A = H, n-C$_3$H$_7$

Example A intermediates can be prepared using standard chemistry techniques. For example, carboxamide IV was combined with DCM followed by the addition of Hoveyda-Grubbs II. The mixture was cooled to ambient temperature to provide Example A.

General Procedure 4

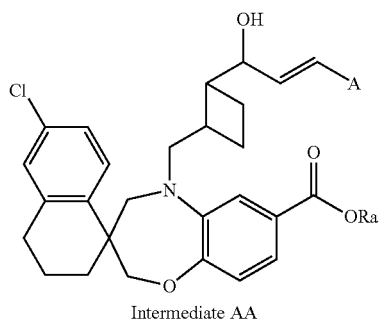

Intermediate AA

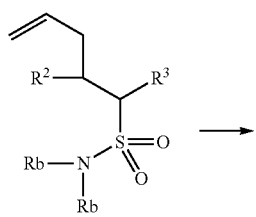

Intermediate EE
A = H, n-C$_3$H$_7$

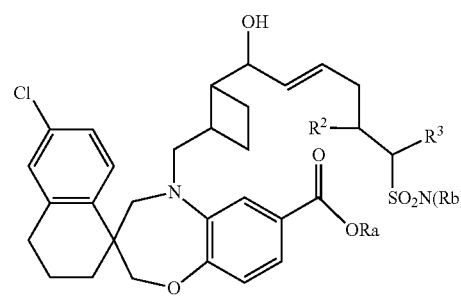

V

Intermediates V can be prepared using standard chemistry techniques. For example, Intermediate AA was combined with Intermediate EE in an appropriate solvent followed by the addition of Hoveyda-Grubbs II to provide compound V.

General Procedure 5

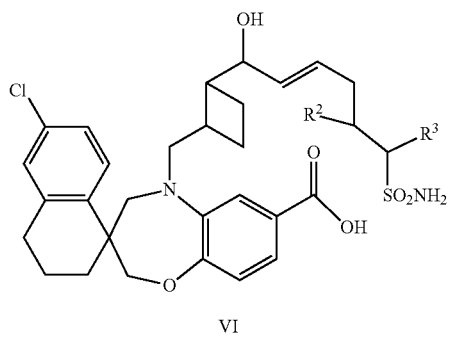

VI

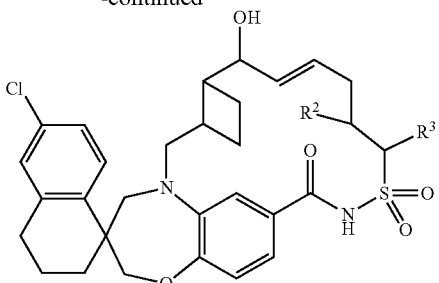

EXAMPLE A

Example A intermediates can be prepared using standard chemistry techniques. For example, N,N-dimethylpyridin-4-amine was combined with compound VI in an appropriate solvent at a temperature below RT, preferably about 0° C., followed by the addition of N-(3-dimethylaminopropyl)-N'-ethylcarbodiimide hydrochloride. The resulting mixture warmed to ambient temperature to provide Example A.

General Procedure 6

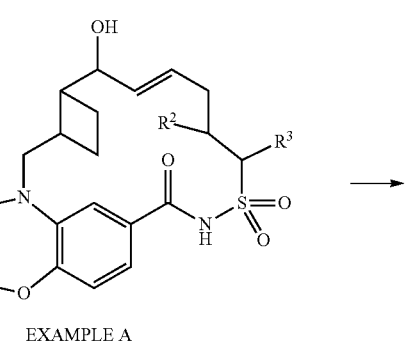

EXAMPLE A

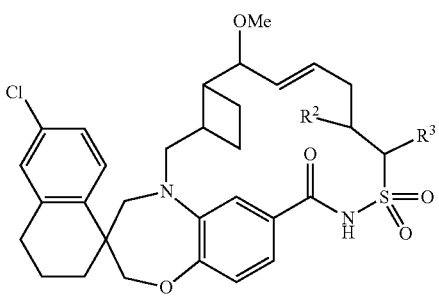

EXAMPLE B

Example B intermediates can be prepared using standard chemistry techniques. For example, sodium hydride was added to a solution of Example A at a temperature below RT, preferably about 0° C. followed by the addition of MeI. The resulting mixture warmed to ambient temperature to provide Example B.

General Procedure 7

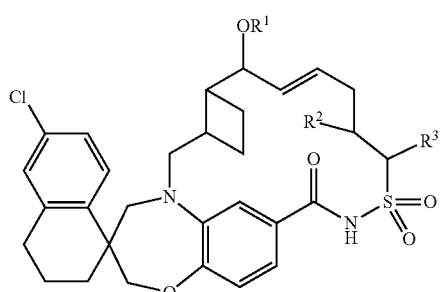

EXAMPLE A or B
R¹ = H, Me

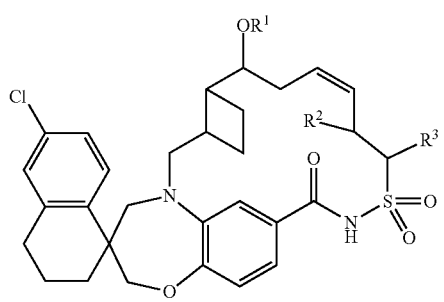

VII

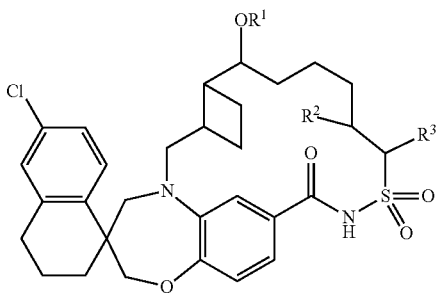

EXAMPLE C

Intermediates such as Example C can be prepared using standard chemistry techniques. For example, Example A and/or B and/or VII and platinum (IV) oxide were combined in an appropriate solvent at ambient temperature to provide Example C.

Compounds of the present invention generally can be prepared combining and further elaborating synthetic intermediates generated from commercially available starting materials. The syntheses of these intermediates are outlined below and further exemplification is found in the specific examples provided.

Intermediate AA11A (S)-6'-CHLORO-5-(((1R,2R)-2-((S)-1-HYDROXY-ALLYL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLIC ACID

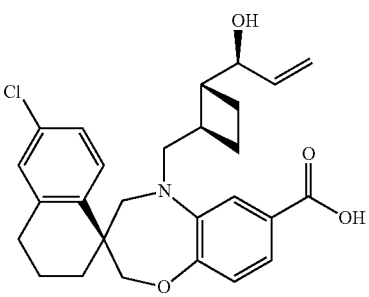 [SMILES: C=C[C@H](O)[C@@H]1CC[C@H]1CN1C[C@@]2(CCCc3cc(Cl)ccc32)COc2ccc(C(=O)O)cc21]

STEP 1: (R)-6-CHLORO-3,4-DIHYDRO-2H-SPIRO[NAPHTHALENE-1,2'-OXIRANE] AND (R)-6-CHLORO-3,4-DIHYDRO-2H-SPIRO[NAPHTHALENE-1,2'-OXIRANE]

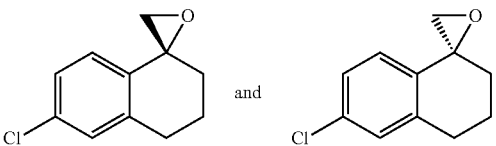 [SMILES: Clc1ccc2c(c1)CCC[C@]21CO1 ; Clc1ccc2c(c1)CCC[C@@]21CO1]

A 2 L 4-necked-RBF was charged with 6-chloro-3,4-dihydro-1(2H)-naphthalenone (123 g, 681 mmol), trimethylsulfonium iodide (143 g, 701 mmol), and DMSO (1100 mL). KOH (76 g, 1362 mmol) (pellets) was added. The suspension was stirred at ambient temperature for 2 days, after which time crude $^1$H NMR showed no remaining starting material. The solution was poured into 800 g of crushed ice, rinsed with MTBE (200 mL), and an additional portion of MTBE (700 mL) was added. The resulting mixture was stirred for 5 min and after partition, the bottom aqueous layer was extracted with MTBE twice (500 mL, 300 mL), and combined with the main MTBE extract. The combined organic stream was washed with brine (2×600 mL) and 330 g of Al$_2$O$_3$ (neutral) was added. The resulting suspension was stirred for 5 min at 22° C., filtered, and washed with MTBE (400 mL). The filtrate was concentrated to give the product as a red viscous oil (125 g, 94%).

STEP 2: (S)-6-CHLORO-1,2,3,4-TETRAHYDRONAPHTHALENE-1-CARBALDEHYDE AND (R)-6-CHLORO-1,2,3,4-TETRAHYDRONAPHTHALENE-1-CARBALDEHYDE

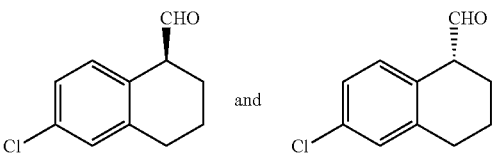 [SMILES: O=C[C@H]1CCCc2cc(Cl)ccc21 ; O=C[C@@H]1CCCc2cc(Cl)ccc21]

A 3 L 3-necked-RBF was charged with racemic 6-chloro-3,4-dihydro-2H-spiro[naphthalene-1,2'-oxirane] (160 g, 822 mmol) and THF (1760 mL). After the batch was cooled to −8° C. with a dry ice/IPA bath, boron trifluoride diethyl etherate (5.07 mL, 41.1 mmol) was added over 3 min. An exotherm raised the batch temp to 10° C. instantly. The batch was stirred at −5 to 0° C. for 5 min, and LC/MS analysis of a sample (quenched into cold NaHCO$_3$ solution) showed complete conversion. The reaction was quenched by the addition of sat. NaHCO$_3$ (300 ML) at −5° C. followed by MTBE (400 mL) and the mixture was transferred to a separatory funnel and rinsed with MTBE (240 mL). After partition, the aqueous layer was discarded along with some white solid (likely boric acid or borax). The organic layer was washed with brine (350 mL) and concentrated under reduced pressure to give a red oil. The crude material was used directly in Step 4.

STEP 3: (6-CHLORO-1,2,3,4-TETRAHYDRONAPHTHALENE-1,1-DIYL)DIMETHANOL

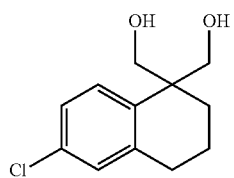 [SMILES: OCC1(CO)CCCc2cc(Cl)ccc21]

Racemic 6-chloro-1,2,3,4-tetrahydro-1-naphthalenecarbaldehyde was charged onto a 3 L 3-necked-RBF and rinsed with diethylene glycol (1000 mL). Formaldehyde (37% solution in H$_2$O; 652 mL, 8757 mmol) was added and the resulting biphasic emulsion was cooled to 5° C. with a dry ice/IPA bath. KOH (45% aqueous solution, 652 mL, 11.9 mol) was added over ~30 min, maintaining the temperature below 20° C. After complete addition, the batch (20° C.) was slowly heated to 45° C. (Caution: exothermic reaction) and aged for 1 h. HPLC showed complete conversion. Some viscous insoluble tar was formed, which was removed prior to aqueous workup. To the batch was added brine (500 mL) and the mixture was extracted with DCM until the product content in the aqueous phase was less than 5%. The combined DCM extract was concentrated to 750 mL as a red oil, washed with H$_2$O (500 mL), and the product began to crystallize out. Upon separation, the clear top aqueous layer was discarded and the bottom layer was stirred in ice/H$_2$O bath for 30 min, filtered, and washed with DCM (~100 mL) and H$_2$O (100 mL). The product was dried under dry air/vacuum to give a first crop (113 g, 498 mmol, 57% yield). The DCM layer from the resulting mother liquor was separated and concentrated to 200-300 g (KF=0.5%), seeded, and stirred in ice/H$_2$O bath for 30 min. The product was filtered, washed with DCM (50 mL), and dried in dry air/vacuum to give a second crop (14.3 g, 63.1 mmol, 7% yield) for a combined total yield of 6-chloro-1,2,3,4-tetrahydronaphthalene-1,1-diyl)dimethanol of 127 g (64%).

STEP 4: (S)-(6-CHLORO-1-(HYDROXYMETHYL)-1,2,3,4-TETRAHYDRONAPHTHALEN-1-YL)METHYL 4-BROMOBENZOATE

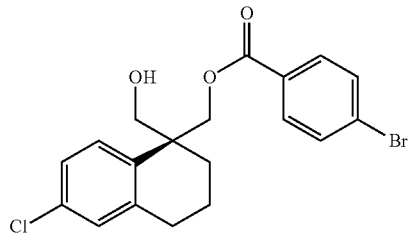 [SMILES: O=C(OC[C@@]1(CO)CCCc2cc(Cl)ccc21)c1ccc(Br)cc1]

To a solution of 2,6-bis((R)-5,5-dibutyl-4-phenyl-4,5-dihydrooxazol-2-yl)pyridine (R,R-Kang Catalyst) (1.57 g, 2.64 mmol) in dry DCM (450 mL), copper(II) chloride (0.355 g, 2.64 mmol) was added and the resulting green colored solution was stirred at rt for 1 h. This solution was added via cannula to a solution of (6-chloro-1,2,3,4-tetrahydronaphthalene-1,1-diyl)dimethanol (30 g, 132.73 mmol) in dry DCM (800 mL). The resulting mixture was cooled to −78° C. and a light green colored precipitation was observed. A solution of 4-bromobenzoyl chloride (34.77 g, 158.79 mmol) in DCM (500 mL) was then slowly added, followed by the dropwise addition of N-ethyl-N-isopropylpropan-2-amine (20 g, 154 mmol). The resulting reaction mixture was stirred at −78° C. for 3 h, then it was quenched with pH 3 phosphate buffer (1 L) and warmed to ambient temperature with vigorous stirring. The mixture was then diluted with DCM (2 L) and the layers were separated. The organic phase was washed with pH 3 buffer (1 L), sat. NaHCO$_3$ (1 L), and brine (2 L) then it was dried over Na$_2$SO$_4$, filtered, and concentrated. The crude material was purified by column chromatography over SiO$_2$ gel (100-200 mesh, 80% DCM in Hex) to afford pure (S)-(6-chloro-1-(hydroxymethyl)-1,2,3,4-tetrahydronaphthalen-1-yl)methyl 4-bromobenzoate (45 g, 84%; e.r=91.4:8.6). ChiralCel® OD-H (250 mm×4.6 mm); Mobile Phase: n-Hexane:IPA: 90:10; Run Time: 20 min; flow rate: 1 mL/min; sample preparation: IPA. Retention time (major peak)—9.32 min; Retention time (minor peak)—11.46 min).

STEP 5: (R)-(6-CHLORO-1-FORMYL-1,2,3,4-TETRAHYDRONAPHTHALEN-1-YL)METHYL 4-BROMOBENZOATE

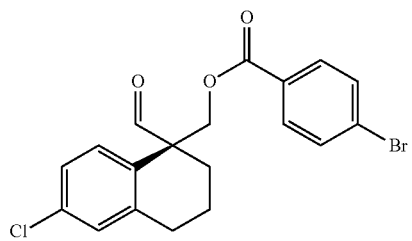 [SMILES: O=C[C@]1(COC(=O)c2ccc(Br)cc2)CCCc2cc(Cl)ccc21]

To a stirred solution of (S)-(6-chloro-1-(hydroxymethyl)-1,2,3,4-tetrahydronaphthalen-1-yl)methyl 4-bromobenzoate (100 g, 244.5 mmol) in DCM (2.5 L), Dess-Martin periodinane (121.4 g, 293.3 mmol) was added at 10° C. The cooling bath was removed after addition and the reaction mixture was stirred for 30 min at ambient temperature. H₂O (9 mL) was then added and the resulting biphasic mixture was stirred at ambient temperature for 30 min. The reaction mixture was cooled to 0° C., and quenched with 2 L of a 1:1 mixture of 10% Na₂S₂O₃/sat. NaHCO₃ solution. The reaction mixture was stirred further at ambient temperature for 10 min, then the layers were separated and the aqueous layer was extracted with EtOAc (2×1.5 L). The combined organic layer was washed with 1 L of 10% Na₂S₂O₃/sat. NaHCO₃ solution and 1 L of brine, then it was dried over Na₂SO₄, filtered, and concentrated. Purification of the residue by column chromatography over SiO₂ gel (100-200 mesh, 5% EtOAc/Hex) provided (R)-(6-chloro-1-formyl-1,2,3,4-tetrahydronaphthalen-1-yl)methyl 4-bromobenzoate (80 g, 81%).

The enantiomeric purity of the title compound could be improved by the following procedure: (R)-(6-chloro-1-formyl-1,2,3,4-tetrahydronaphthalen-1-yl)methyl 4-bromobenzoate (190 g) was added in toluene (950 mL) and heated to 50° C. to complete dissolution. The homogeneous solution was cooled to ambient temperature and seeded with racemic compound. The solution was cooled to –25° C., and aged overnight. The mother liquor was then decanted and concentrated to afford 160 g of enantiomerically enriched (R)-(6-chloro-1-formyl-1,2,3,4-tetrahydronaphthalen-1-yl)methyl 4-bromobenzoate (94% ee as determined by chiral HPLC). Chiral HPLC conditions: Column: ChiralCel® OD-H (250 mm×4.6 mm); Mobile Phase: n-Hexane:IPA: 90:10. Run Time: 20 min. Flow rate: 1 mL/min. Sample preparation: ethanol. Retention time (major peak): 8.488 min (96.97%); Retention time (minor peak): 9.592 min (3.03%).

STEP 6: (R)-(6-CHLORO-1-(DIMETHOXYMETHYL)-1,2,3,4-TETRAHYDRONAPHTHALEN-1-YL)METHANOL

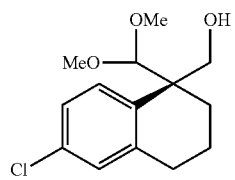

To a solution of (R)-(6-chloro-1-formyl-1,2,3,4-tetrahydronaphthalen-1-yl)methyl 4-bromobenzoate (75 g, 183.8 mmol) in anhydrous MeOH (1 L), p-TsOH (1 g, 9.2 mmol) and trimethyl orthoformate (58.4 mL, 551 mmol) were added and the reaction mixture was refluxed until the starting material was completely consumed (~4 h). The reaction mass was concentrated to 50% volume and diluted with THF (1 L) and 1N NaOH (1 L, 1 mol). The resulting reaction mixture was stirred at 40° C. overnight and then concentrated under reduced pressure. The residue was diluted with EtOAc (1.5 L). The aqueous layer was separated and extracted with EtOAc (2×500 mL) and the combined organic layers were washed with 1N NaOH (1 L) and brine (1 L), dried over Na₂SO₄ and concentrated under reduced pressure. The crude material was purified by column chromatography over 100-200 mesh size SiO₂ gel (10% EtOAc/Hex) to give pure (R)-(6-chloro-1-(dimethoxymethyl)-1,2,3,4-tetrahydronaphthalen-1-yl)methanol as a light brown thick oil (44 g, 89%).

STEP 7: TERT-BUTYL-4-FLUORO-3-NITROBENZOATE

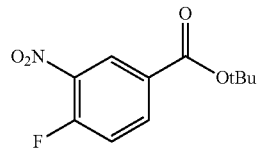 [SMILES: CC(C)(C)OC(=O)c1ccc(F)c([N+](=O)[O-])c1]

To a solution of 4-fluoro-3-nitrobenzoic acid (100 g, 540.2 mmol) in t-butanol (2.5 L), DMAP (13.18 g, 108.04 mmol) and di tert-butyl dicarbonate (248 mL, 1080.4 mmol) were added and the reaction mixture was heated at 40° C. overnight. Upon completion, the reaction mixture was diluted with H₂O and the aqueous phase was extracted with EtOAc (3×1.5 L). The combined organic layer was washed further with H₂O (1×1 L), brine (1×1 L), and dried over Na₂SO₄. The solvent was removed under reduced pressure and the crude material thus obtained was purified by column chromatography (100-200 mesh size SiO₂ gel, eluting with a gradient of 100% Hex to 5% EtOAc in Hex) affording pure tert-butyl-4-fluoro-3-nitrobenzoate (70 g, 54%) as light yellow solid.

STEP 8: (R)-TERT-BUTYL 4-((6-CHLORO-1-(DIMETHOXYMETHYL)-1,2,3,4-TETRAHYDRONAPHTHALEN-1-YL)METHOXY)-3-NITROBENZOATE

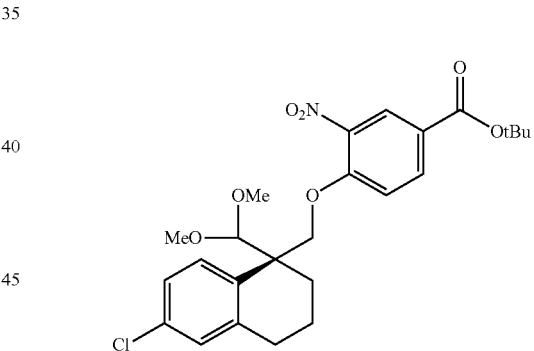

A solution of (R)-(6-chloro-1-(dimethoxymethyl)-1,2,3,4-tetrahydronaphthalen-1-yl)methanol (70 g, 259.2 mmol) in dry THF (3.5 L) was cooled to 0° C., and LiHMDS (1 M in THF; 363 mL, 363 mmol) was added dropwise. After 5 min, a solution of tert-butyl 4-fluoro-3-nitrobenzoate (74.9 g, 311 mmol) in THF (500 mL) was added dropwise via dropping funnel and the resulting mixture was warmed to ambient temperature. Upon completion (~1 h), the mixture was cooled to 0° C., quenched with sat. NH₄Cl solution (1 L) and extracted with EtOAc (3×1 L). The combined organic layers were washed with NH₄Cl (1 L) and brine (1 L), dried over Na₂SO₄ and concentrated under reduced pressure. The crude material thus obtained was purified by column chromatography using 100-200 mesh size SiO₂ gel (5% EtOAc/hexane) to afford (R)-tert-butyl 4-((6-chloro-1-(dimethoxymethyl)-1,2,3,4-tetrahydronaphthalen-1-yl)methoxy)-3-nitrobenzoate as yellow thick oil (110 g, 87% yield).

STEP 9A: (R)-4-((6-CHLORO-1-FORMYL-1,2,3,4-TETRAHYDRONAPHTHALEN-1-YL)METHOXY)-3-NITROBENZOIC ACID

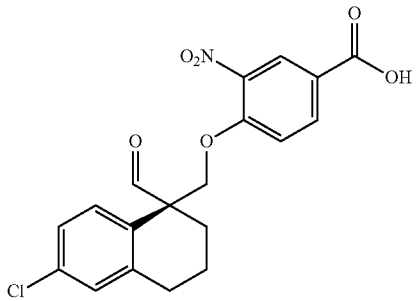 [SMILES: O=C[C@]1(COc2ccc(C(=O)O)cc2[N+](=O)[O-])CCCc2cc(Cl)ccc21]

To a solution of (R)-tert-butyl 4-((6-chloro-1-(dimethoxymethyl)-1,2,3,4-tetrahydronaphthalen-1-yl)methoxy)-3-nitrobenzoate (35 g, 71.25 mmol) in MeCN (1 L), erbium triflate (4.3 g, 7.1 mmol) and $H_2O$ (13 mL) were added. The resulting mixture was heated to 80° C. overnight. The solvent was then removed under reduced pressure and the residue was dissolved in $Et_2O$ (1.5 L) and washed with 1N HCl (500 mL) and brine (500 mL). The organic layer was dried over $Na_2SO_4$, filtered, and concentrated to afford (R)-4-((6-chloro-1-formyl-1,2,3,4-tetrahydronaphthalen-1-yl)methoxy)-3-nitrobenzoic acid (30 g), which was used without further purification.

Alternatively, (R)-4-((6-chloro-1-formyl-1,2,3,4-tetrahydronaphthalen-1-yl)methoxy)-3-nitrobenzoic acid may be prepared from (6-chloro-1,2,3,4-tetrahydronaphthalene-1,1-diyl)dimethanol (Step 4) as follows:

A 250 mL 3-necked-RBF was charged with copper (II) chloride (0.095 g, 0.02 eq), 2,6-bis((R)-5,5-dibutyl-4-phenyl-4,5-dihydrooxazol-2-yl)pyridine (0.42 g, 0.02 eq) and THF (28.5 g, 4V). After inertion with $N_2$, the batch was stirred at 20° C. for 0.5 h. To the homogenous green solution was added (6-chloro-1,2,3,4-tetrahydronaphthalene-1,1-diyl)dimethanol (8.0 g, 1.00 eq) followed by THF (14.2 g, 2V) and 4-methylmorpholine (3.75 g, 1.05 eq). The reaction mixture was cooled to −20° C., and a solution of 1-napthoyl chloride (7.06 g, 1.05 eq) in THF (21.3 g, 3 V) was added to the batch over 0.5 h maintaining the temperature below −15° C. After aging at −20° C. for 20 h, an aliquot of the reaction slurry was sampled and assayed by HPLC. The slurry was directly filtered through a glass-fritted funnel while maintaining the temperature at −20° C. The filter cake was washed with two portions of cold (<−10° C.) THF (2×14.2 g, 2V) rinsed through the reaction vessel. The filter cake (4-methylmorpholine·HCl) was transferred to a labeled container. The mother liquor and washes were concentrated to a minimum volume and distillative solvent swap by charging toluene until the batch volume is 6V and toluene/THF ratio is >98:2 (v/v) as measured by QNMR. To the batch at 20° C. was added heptane (11 g, 2V) and the slurry was heated to 85° C. (dissolution observed). The solution was cooled to 75° C., and charged with seed (0.27 g, 0.02 eq). The slurry was cooled to 20° C. over 3 h and aged for >1 h. The batch was filtered through a glass-fritted filter and the cake was washed with toluene/heptane (3:1 v/v) (11 g, 2V) then toluene/heptane (1:1 v/v) (11 g, 2V). The cake was dried under $N_2$ for 12 h at ambient temperature and the cake was assayed dry by QNMR (<1 wt % toluene and heptane). The product was obtained as an off-white solid (8.75 g, 63% after wt adjustment).

A 60 L jacketed reactor vented with a bleach scrubber was charged with (S)-(6-chloro-1-(hydroxymethyl)-1,2,3,4-tetrahydronaphthalen-1-yl)methy 11-naphthoate (2.693 Kg, 88.6 wt %, 6.3 mol) followed by DCM (17.9 Kg, 5 vol) and $EtNiPr_2$ (2.84 Kg, 3.5 eq). After $N_2$ inertion, the batch was agitated and cooled to 0° C. To the alcohol slurry mixture in the reactor was added a solution of freshly prepared sulfur trioxide pyridine (2.10 Kg, 2.5 eq of sulfur trioxide pyridine in 7.43 Kg, 3 vol. DMSO) over 30 min while maintaining the batch temperature below 15° C. After addition, HPLC assay showed >99% conversion. The batch was quenched by the addition of $H_2O$ (14 L, 5 vol) over ~20 min. maintaining the batch temperature below 15° C., and then toluene (16.8 L, 6 vol) was added. After partition, the organic layer was treated with $H_2O$ (14 L, 5 vol) and toluene (16.8 L, 6 vol). The top organic layer was washed with 2 N HCl twice (14 L each, 5 vol) and brine (14 L, 5 vol). The organic layer was drained to a clean container, assayed by HPLC and then transferred back to the clean 60 L reactor through an inline filter. The batch was concentrated to a minimal volume and solvent switched to MeOH until the batch volume was 28 L (10 vol) and MeOH/toluene ratio was 3:1 (v/v) as measured by QNMR. The batch was then transferred to a 30 L jacketed reactor through an inline filter. After adjustment of the batch temperature to 30° C., the batch was seeded with the aldehyde (51 g, 0.02 eq) as a slurry in MeOH (400 mL). After the slurry was aged for 30 min at 30° C., the batch was solvent switched by distillation with MeOH until the batch volume is 11 L (4 vol) and MeOH/toluene ratio is ≥99:1 (v/v). The batch was then cooled to 5° C., and MeOH/$H_2O$ mixture (3.70 Kg MeOH+1.34 Kg $H_2O$) was added over 1.5 h to bring the total solvent volume to approximately 5.5 vol and final MeOH/$H_2O$ to 90/10 (v/v). The batch was heated to 65° C. over 30 min, and cooled to 20° C. over 2 h and aged for 2 h. The batch was filtered through an Aurora® filter fitted with ≤25 μm filter cloth. The cake was washed with MeOH/$H_2O$ (10:1) (1×2 vol), then MeOH/$H_2O$ (2:1) (1×2 vol). The cake was dried under $N_2$ at ambient temperature for ≥4 h until dry to give the product as an off-white solid (1.99 Kg, 72% after wt % adjustment).

A 3-necked 250 mL RBF was charged with (R)-(6-chloro-1-formyl-1,2,3,4-tetrahydronaphthalen-1-yl)methyl 1-naphthoate (10 g, 94.4 wt %, 95.3% LCAP, >99% ee), methanol (100 mL), trimethyl orthoformate (7 mL), and TsOH $H_2O$ (0.24 g). The RBF was inerted with $N_2$, and agitation was initiated. The batch was heated to 60° C., and aged for 2 h. HPLC assay showed 98% conversion.

The batch was concentrated under vacuum (~150-190 torr, external temp ~40° C.) to minimal volume using a rotoevaporator. The batch was turned over to THF by charging THF three times (50 mL each time) and distilling under vacuum (~165 torr, external temp ~40° C.). After each of the first two THF charges, the batch was concentrated down to a minimal volume, and after the last THF charge and distillation QNMR analysis of a sample showed the target ratio of >20/1 THF/MeOH (v/v). LiOH·$H_2O$ (10.46 g, 10 eq) and $H_2O$ (50 mL) were charged to the 3-necked 250 mL RBF. The reaction mixture was heated to 65° C. and aged for 18 h. HPLC assay showed >99% conversion. The batch was cooled to 20° C., and transferred to a 500-mL separatory funnel. MTBE (106 mL) was charged to the separatory funnel and the funnel was shaken well. After settling for 5 min, the bottom aqueous layer was drained. The top organic layer was washed with 20% $K_2CO_3$ twice (32 mL and 11 mL). The batch was transferred to a 250 mL RBF. Assay by HPLC showed <2% naphthanoic acid by-product. The batch was concentrated to a minimal volume at reduced pressure on the rotoevaporator (300 mbar, external temp ~40° C.). The batch was turned over to THF using a rotoevaporator (~250 mbar, external temp ~40° C.) by adding and distilling THF (~50 mL, ~50 mL). After each THF charge, the batch was distilled down to a minimal volume. THF (50 mL) was charged to the 250 mL RBF. KF of a sample showed 0% $H_2O$ (≤0.1% acceptable). The batch was polish filtered (60 mL medium-frit funnel) into a clean and dry 250 mL 3-necked-RBF using THF (50 mL) for rinsing and volume adjusting. To the batch was added 4-fluoro-3-nitrobenzoic acid (4.61 g, 1.0 eq), the mixture was cooled to −20° C., and 20% potassium tert-butoxide THF solution (40 mL) was added over 1.5 h, maintaining the batch temperature at −20±10° C. (exothermic). After complete addition, the batch was aged at −20° C., and an aliquot assayed by HPLC after 1.5 h showed 98% conversion. To the batch in the flask was added sat. $NH_4Cl$ solution (10 mL), maintaining the temperature at −20±10° C., followed by addition of $H_2O$ (20 mL) and MeTHF (34 mL) at −20±20° C. The mixture was warmed to 20° C., and agitated for 13 h. The batch was transferred to a separatory funnel, allowed to settle for ~5 min, and the bottom aqueous layer was removed keeping the rag with the organic stream. The top organic stream was washed with sat. $NH_4Cl$ solution (10 mL) and $H_2O$ (20 mL) at 20° C. After ~5 min of settling, the aqueous layer was separated. To the total crude organic stream (KF=14%) was added MSA (4 mL) in a 250 mL 3-necked-RBF. The batch was heated to reflux (65° C.) for 25 h and LC assay showed full conversion (≥97%).

The batch was cooled to <20° C., and $K_3PO_4 \cdot H_2O$ (4.5 g) and $H_2O$ (7 mL) were added. The batch was transferred to a separatory funnel and the bottom aqueous layer was drained to give the aldehyde product crude solution. The combined organic crude stream was concentrated to minimum volume using a rotary evaporator. To the batch in a 500 mL RBF was charged AcOH (~50 mL, ~50 mL) and distilled using a rotary evaporator at reduced pressure (30 mbar, external temp ~40° C.). The THF level was measured by QNMR and none was observed. The mixture was transferred to a 250 mL 3-necked RBF and AcOH was added to adjust the total volume to ~40 mL, when crystallization occurred. To the batch was added $H_2O$ (12 mL) over ~1 h. After aging for >1 h, LC assay of supernatant concentration was 9 mg/mL. If concentration is >10 mg/mL then a small portion of $H_2O$ (0.2 vol) can be added; after checking by LC, repeat if necessary. The batch was filtered, washed with 20% $H_2O$/AcOH (23 mL) and dried under $N_2$/vacuum for 3.25 h to give the title compound (8.22 g) as an off-white solid (82% yield corrected for purity).

STEP 9B: (R)-TERT BUTYL 4-((6-CHLORO-1-FORMYL-1,2,3,4-TETRAHYDRONAPHTHA-LEN-1-YL)METHOXY)-3-NITROBENZOATE

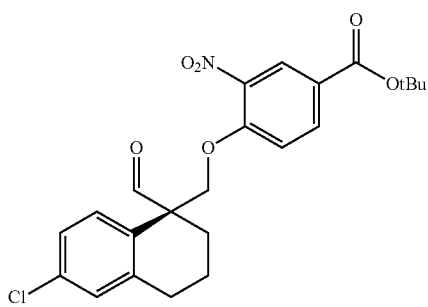 [SMILES: CC(C)(C)OC(=O)c1ccc(OC[C@@]2(C=O)CCCc3cc(Cl)ccc32)c([N+](=O)[O-])c1]

To a solution of (R)-tert-butyl 4-((6-chloro-1-(dimethoxymethyl)-1,2,3,4-tetrahydronaphthalen-1-yl)methoxy)-3-nitrobenzoate (1 g, 2.033 mmol) in anhydrous acetone (41 mL) was added Amberlyst®-15 (1 g, 2.033 mmol; pre-washed with 2×10 mL dry acetone). The mixture was heated to 50° C. for 3.5 h, then filtered and rinsed with DCM. The filtrate was concentrated and dried under high vacuum overnight (it turned a dark red color). LC/MS and NMR analysis suggested ~10% of corresponding carboxylic acid was present as well as 0.5 eq mesityl oxide. The mixture was advanced to Step 11 without further purification.

STEP 10: (S)-6'-CHLORO-3',4,4',5-TETRA-HYDRO-2H,2'H-SPIRO[BENZO[B][1,4]OXAZEPINE-3,1'-NAPHTHALENE]-7-CARBOX-YLIC ACID

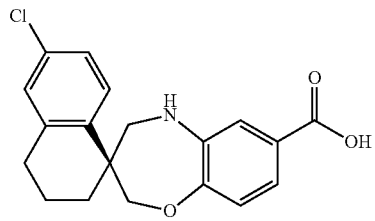 [SMILES: O=C(O)c1ccc2c(c1)NC[C@@]1(CCCc3cc(Cl)ccc31)CO2]

A solution of crude (R)-4-((6-chloro-1-formyl-1,2,3,4-tetrahydronaphthalen-1-yl)methoxy)-3-nitrobenzoic acid (30 g, 77.10 mmol) in AcOH (1 L) was heated to 70° C., and iron powder (28 g, 500 mmol) was added. The resulting mixture was heated for ~4 h at 70° C. AcOH was then removed under reduced pressure and the residue was dissolved in DCE (1 L). Sodium triacetoxy borohydride (46.5 g, 740 mmol) was added portion-wise and the reaction mixture was stirred at ambient temperature for 1 h. The reaction was then quenched with $H_2O$ followed by 10% aqueous citric acid (500 mL). The aqueous phase was extracted with DCM (2×1 L) and the combined organic layer was washed with brine (500 mL), dried over $Na_2SO_4$ and concentrated under reduced pressure. The residue was purified by column chromatography using 100-200 mesh size $SiO_2$ gel (40% EtOAc/Hex) to afford pure (S)-6'-chloro-3',4,4',5-tetrahydro-2H,2'H-spiro[benzo[b][1,4]oxazepine-3,1'-naphthalene]-7-carboxylic acid as white solid (24 g, 99% after two steps). Alternatively, (S)-6'-chloro-3',4,4',5-tetrahydro-2H,2'H-spiro[benzo[b][1,4]oxazepine-3,1'-naphthalene]-7-carboxylic acid with ((1S,4R)-7,7-dimethyl-2-oxobicyclo[2.2.1]heptan-1-yl)methanesulfonic acid (1:1) may be prepared as follows:

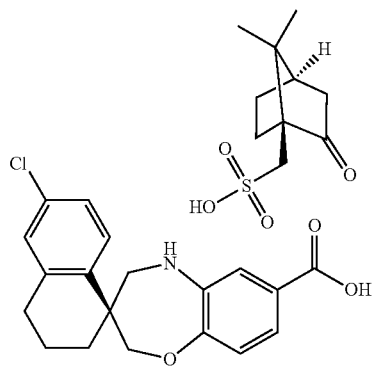

A pressure reactor was charged with (R)-4-((6-chloro-1-formyl-1,2,3,4-tetrahydronaphthalen-1-yl)methoxy)-3-nitrobenzoic acid (20 g, 94 wt %6), 5% Pt/S/C wet (2.2 g), THF (400 mL) and titanium isopropoxide (0.5 mL). The reactor was sealed, purged with inert gas (3 cycles, at least once with stirring), and then purged with $H_2$ (1 cycle). The reactor was pressurized with $H_2$ to 70 psig, stirring (950 rpm) was initiated, and the temperature was increased to 90° C. maintaining the $H_2$ pressure in the reactor (70 psig at 22-30° C. 80 psig at 50-60° C., and 90 psig at 88-91° C.). After 16 h, the reactor was cooled to ambient temperature and purged with inert gas (3 cycles). HPLC analysis of the reaction confirmed >98% conversion.

The reaction mixture was filtered through a Celite® pad (2 inch) using additional THF for rinses, and the filtrate was concentrated under reduced pressure at 40° C. To the residue was added IPA (60 mL) and 2-4% aqueous MeOH (10 mL). The mixture was stirred for 10 min and then it was filtered through a Celite® pad (2 inch). MeOH was evaporated under reduced pressure at 40° C., and to the concentrated IPA solution cooled to ambient temperature was added a solution of +CSA (56.0 g) in IPA (200 mL) dropwise over 2 h. After 10% of the CSA solution has been added, the mixture was seeded with crystals of the title compound (10-15 mg) followed by the addition of the remaining CSA solution. After stirring at ambient temperature overnight, the mixture was filtered, and the filter cake was washed with 100 mL of IPA and dried under vacuum/$N_2$ at ambient temperature. The product is isolated as a white solid: (S)-6'-chloro-3',4,4',5-tetrahydro-2H,2'H-spiro[benzo[b][1,4]oxazepine-3,1'-naphthalene]-7-carboxylic acid with ((1S,4R)-7,7-dimethyl-2-oxobicyclo[2.2.1]heptan-1-yl)methanesulfonic acid (1:1) (85-88% yield, >99.5% ee).

STEP 11A: (S)-METHYL 6'-CHLORO-3',4,4',5-TETRAHYDRO-2H,2'H-SPIRO[BENZO[B][1,4]OXAZEPINE-3,1'-NAPHTHALENE]-7-CARBOXYLATE

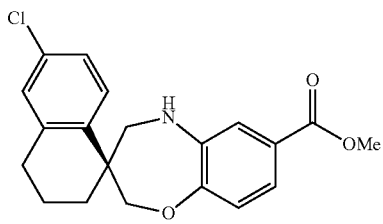 [SMILES: COC(=O)c1ccc2c(c1)NC[C@@]1(CCCc3cc(Cl)ccc31)CO2]

To a solution of (S)-6'-chloro-3',4,4',5-tetrahydro-2H,2'H-spiro[benzo[b][1,4]oxazepine-3,1'-naphthalene]-7-carboxylic acid (130 g, 379 mmol) in methanol (6 L) was added Amberlyst®-15 (130 g, pre-washed with anhydrous methanol) and heated to reflux for 10 h. Amberlyst® was then removed by filtration and rinsed with methanol (3×300 mL). The combined filtrate was concentrated and the residue was purified by column chromatography to give pure (S)-methyl 6'-chloro-3',4,4',5-tetrahydro-2H,2'H-spiro[benzo[b][1,4]oxazepine-3,1'-naphthalene]-7-carboxylate as a white solid (105 g, 77%). Chiral HPLC conditions: Column: ChiralCel® OD-H (250 mm×4.6 mm, 5 µm); Mobile Phase: n-Hexane:EtOH: 95:05. Run Time: 25 mm. Flow rate: 1 mL/min. Retention time (minor peak): 10.162 min (1.98%); Retention time (major peak): 12.292 min (98.02%).

STEP 11B: (S)-TERTBUTYL 6'-CHLORO-3',4,4',5-TETRAHYDRO-2H,2'H-SPIRO[BENZO[B][1.4]OXAZEPINE-3,1'-NAPHTHALENE]-7-CARBOXYLATE

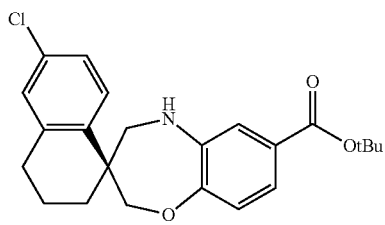 [SMILES: CC(C)(C)OC(=O)c1ccc2c(c1)NC[C@@]1(CCCc3cc(Cl)ccc31)CO2]

To a solution of (R)-tert-butyl 4-((6-chloro-1-formyl-1,2,3,4-tetrahydronaphthalen-1-yl)methoxy)-3-nitrobenzoate (0.9 g, 2.018 mmol) in AcOH (20.22 mL, 353 mmol) at 70° C. was added iron (0.676 g, 12.11 mmol). The mixture was stirred vigorously for 4 h, then concentrated, and the residue was diluted with 20 mL 1,2-DCE. Sodium triacetoxyhydroborate (1.711 g, 8.07 mmol) was added and the mixture was stirred at ambient temperature for 20 min. Upon quenching by addition of 20 mL $H_2O$, a thick slurry was formed. 20 mL 10% citric acid solution was added and the mixture became lighter in color. The layers were separated and the aqueous layer was extracted with 2×20 mL DCM. The combined organics were washed with 10 mL 10% citric acid and 10 mL brine, dried over $MgSO_4$, filtered, and concentrated. The residue was deposited on 3 g $SiO_2$ gel and purified using 5-10% EtOAc in Hex to give (S)-tert-butyl 6'-chloro-3',4,4',5-tetrahydro-2H,2'H-spiro[benzo[b][1,4]oxazepine-3,1'-naphthalene]-7-carboxylate (557 mg, 1.393 mmol, 69.0% yield). Further elution with 30% EtOAc in Hex provided (S)-6'-chloro-3',4,4',5-tetrahydro-2H,2'H-spiro[benzo[b][1,4]oxazepine-3,1'-naphthalene]-7-carboxylic acid (132 mg, 0.384 mmol, 19.02% yield).

STEP 12: (1R,2S)-1,2-CYCLOBUTANEDIYLDIMETHANOL

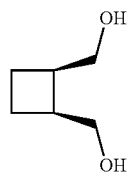

To a rapidly stirred solution of LAH (1.0 M solution in THF, 1000 mL, 1000 mmol) at ambient temperature in a 3000 mL 3-necked RBF under a stream of argon, solid (1R,5S)-3-oxabicyclo[3.2.0]heptane-2,4-dione (40 g, 317 mmol) was gradually added over 2 h, maintaining the internal temperature of the reaction mixture below 50° C. The reaction was stirred overnight at ambient temperature under argon. After 16 h, the reaction mixture was cooled by an ice bath to 10° C., and, under a fast stream of argon, a solution of 36 mL $H_2O$ was added drop wise by addition funnel at a rate that maintained the temperature between 12-15° C., approximately 1 mL/min, with vigorous stirring (500 rpm). The mixture was then vigorously stirred (500 rpm) in the ice-bath for 1 h, then removed from the bath and stirred to rt for 1 h before cooling again with an ice bath to 5-10° C. To the mixture was added 36 mL of a 15% NaOH aqueous solution over a period of 45 min, maintaining the temperature between 10-20° C. To the mixture was added 108 mL H$_2$O drop wise by addition funnel, maintaining the temperature between 10-20° C., over ~1 h. Upon completed addition of the H$_2$O, the flask was removed from the ice bath, equilibrated to rt and left to stir vigorously under argon overnight. After stirring for 16 h, the mixture was filtered and the filtrate concentrated under reduced pressure to afford a colorless, slightly opaque oil. The oil was taken up in Et$_2$O and stirred over anhydrous MgSO$_4$ and filtered through a pad of Celite®. The filtrate concentrated under reduced pressure to afford 32.8 g of a colorless oil, which was used in the next step without further purification (89% yield).

STEP 13:
CIS-CYCLOBUTANE-1,2-DIYLBIS(METHYLENE) DIACETATE

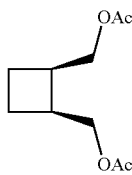 [SMILES: CC(=O)OC[C@H]1CC[C@H]1COC(C)=O]

Ac$_2$O (2.59 mL; 3.0 eq) was added to the CIS-1,2-cyclobutanediyldimethanol (1.06 g, 9.15 mmol) and the resulting solution was heated to 50° C. After stirring overnight, the mixture was assayed by GC and showed complete conversion. The mixture was then diluted with 15 mL of heptane and concentrated under vacuum to give a clear oil. The oil was dissolved in 15 mL heptane and concentrated back down to an oil (azeotropic removal of Ac$_2$O) to give the title compound as an oil (1.827 g, 88% yield, 88.3% purity by QNMR using benzyl benzoate as an internal standard).

STEP 14:
((1R,2S)-2-(HYDROXYMETHYL)CYCLOBUTYL) METHYL ACETATE

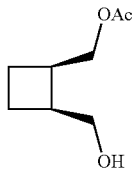 [SMILES: CC(=O)OC[C@@H]1CC[C@@H]1CO]

A 12 L 3-neck-RBF equipped with mechanical stirrer was charged with a 1M sodium citrate solution (prepared by mixing sodium citrate tribasic dihydrate; 682 g, 2320 mmol) and H$_2$O to reach total volume ~2.3 L) and 3.48 L H$_2$O (~25° C.). The mixture was cooled using an ice/H$_2$O bath to −20.2° C. pH-8.46 (measured with pH probe). Amano Lipase from *Pseudomonas fluorescens* (41.8 g, 1547 mmol) was then added in one charge (pH ~ 8.12) and the mixture was vigorously stirred at ambient temperature for ~5 min. (1R,2S)-cyclobutane-1,2-diylbis(methylene) diacetate (348 g, 1547 mmol) was added in one charge and the resulting mixture was stirred vigorously at ambient temperature monitoring internal temperature and pH. After stirring the mixture overnight (~20.9° C. and pH-5.45) an aliquot was collected, extracted with IPAc, diluted with MeCN and analyzed by GC and the reaction was deemed complete (1.21% SM leftover, 0.17% of enantiomer, 1.8% of diol). Celite® (70 g) added to the reaction mixture and the slurry was filtered through a Celite® pad on a medium porosity glass filter (fast filtration, 15-20 min), rinsing with 2.5 L IPA. The biphasic mixture was transferred into a 12 L-extractor and stirred for 1 min. The aqueous layer was separated and extracted with IPAc (1×4 L), and the combined organic extract was concentrated in vacuo obtaining 337.28 g (99.6% ee; ~50-60 mol % of residual IPA by $^1$HNMR: QNMR: 37.63 mg+benzyl benzoate (Aldrich catalog #B6630, lot #MKBG9990V, 61.27 mg; Result: ~65 wt %; corrected yield 89%). The crude product was used as such for the next step.

STEP 15:
((1R,2R)-2-FORMYLCYCLOBUTYL)METHYL ACETATE

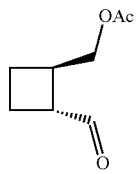 [SMILES: CC(=O)OC[C@@H]1CC[C@H]1C=O]

A 2-L Atlas reactor was charged with ((1R,2S)-2-(hydroxymethyl)cyclobutyl)methyl acetate (126.39 g, 79.6 wt % by QNMR; 636 mmol) and 1 L of DCM and the jacket temperature was set to 20° C. Iodobenzene diacetate (225 g, 700 mmol) was added as a solid (endothermic addition: the temperature decreased to 15° C.). TEMPO (3.97 g, 25.4 mmol) was added as a solid in one portion resulting in a cloudy orange solution, which became clear over the course of 20 min. After stirring at 20° C. overnight, an aliquot was collected, diluted with MeOH, and analyzed by GC. An Additional kicker charge of iodobenzene diacetate and TEMPO can be used to push the reaction to completion if necessary. The reaction mixture was then cooled to 1.8° C. (internal temperature, ice/dry ice/H$_2$O bath) and DIPEA (194 mL, 1113 mol) was added drop-wise via addition funnel over 65 min keeping internal temperature<5° C. The cooling bath was removed and the mixture was allowed to warm to ambient temperature with stirring. After 48 h an aliquot was collected, diluted with methanol, and analyzed by GC showing a 12:1 ratio of trans:cis isomers. The reaction mixture was then cooled to <5° C. (ice/H$_2$O bath) and H$_2$O (230 mL) was added over ~10 min (internal temperature reached 14° C.). The organic layer was separated, washed with H$_2$O (125 mL) and IM aqueous NaH$_2$PO$_4$ (90 mL) and concentrated in vacuo to afford 273.4 g of ((1R,2R)-2-formylcyclobutyl)methyl acetate (QNMR: 68.85 mg+benzyl benzoate (Aldrich catalog #B6630, Lot #MKBG9990V, 72.36 mg). The crude product was used as such for next step.

STEP 16: ((1R,2R)-2-((R)-(1H-BENZO[D][1,2,3]TRIAZOL-1-YL)(HYDROXY)METHYL)CYCLOBUTYL)METHYL ACETATE

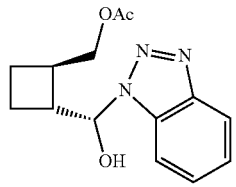 [SMILES: CC(=O)OC[C@@H]1CCC1[C@@H](O)n1nnc2ccccc21]

To a solution of crude ((1R,2R)-2-formylcyclobutyl) methyl acetate (5 g, 10.27 mmol) in 8 mL MTBE was added benzotriazole (1.296 g, 10.00 mmol) as a solid (slightly exothermic). The clear solution became increasingly cloudy and a precipitate formed. The mixture was allowed to equilibrate overnight at ambient temperature then heptane was added (6 mL). After aging for 6 h the mixture was filtered at ambient temperature and washed with 10 mL of 1:1 MTBE/heptane. The white solid was air dried on the frit under vacuum obtaining 2.48 g of ((1R,2R)-2-((R)-(1H-benzo[d][1,2,3]triazol-1-yl)(hydroxy)methyl)cyclobutyl) methyl acetate.

STEP 17: (S)-METHYL 5-(((1S,2R)-2-ACETOXYCYCLOBUTYL)METHYL)-6'-CHLORO-3',4,4',5-TETRAHYDRO-2H,2'H-SPIRO[BENZO[B][1,4]OXAZEPINE-3,1'-NAPHTHALENE]-7-CARBOXYLATE

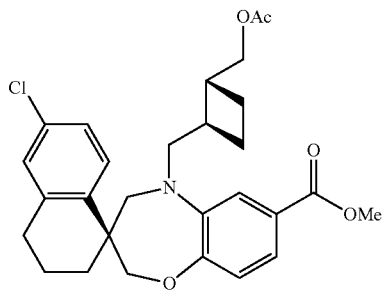 [SMILES: COC(=O)c1ccc2c(c1)N(C[C@@H]1CC[C@H]1COC(C)=O)C[C@@]1(CCCc3cc(Cl)ccc31)CO2]

((1R,2R)-2-Formylcyclobutyl)methyl acetate (from Step 16; 4.36 g, 27.9 mmol) was added to a solution of (S)-methyl 6'-chloro-3',4,4',5-tetrahydro-2H,2'H-spiro[benzo[b][1,4]oxazepine-3,1'-naphthalene]-7-carboxylate (5.0 g, 13.97 mmol) (Step 12) in DCM (78 mL) and AcOH (38.8 mL). The solution was stirred at ambient temperature for 10 min, then cooled to 0° C., and sodium cyanoborohydride (1.463 mL, 27.9 mmol) was added slowly over 1 h. The mixture was stirred at 0° C. for 10 min, then poured slowly into cold NaOH solution, and extracted with EtOAc (120 mL). The organic phase was washed with brine, dried over anhydrous $Na_2SO_4$, and concentrated. The residue was loaded to a 220 g ISCO gold column and eluted with 0% to 10% EtOAc/Hex to provide the title compound 6.0 g of the title compound as a white solid. m/z (ESI +ve ion) 498.1 $(M+H)^+$.

STEP 18A: (S)-METHYL 6'-CHLORO-5-(((1R,2R)-2-(HYDROXYMETHYL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLATE

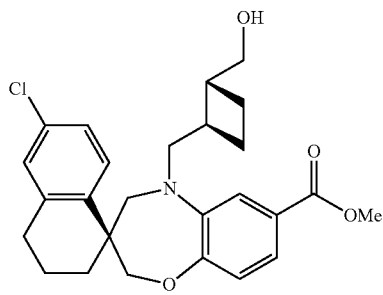 [SMILES: COC(=O)c1ccc2c(c1)N(C[C@@H]1CC[C@H]1CO)C[C@@]1(CCCc3cc(Cl)ccc31)CO2]

KOH (0.278 mL, 10.14 mmol) was added to a solution of (S)-methyl 5-(((1R,2S)-2-(acetoxymethyl)cyclobutyl)methyl)-6'-chloro-3',4,4',5-tetrahydro-2H,2'H-spiro[benzo[b][1,4]oxazepine-3,1'-naphthalene]-7-carboxylate (from Step 18; 1.530 g, 3.07 mmol) in MeOH (99 mL). The mixture was stirred at ambient temperature for 4 h, then neutralized with 1N HCl to pH=7, and concentrated under reduced pressure. The aqueous residue was extracted with EtOAc (400 mL) and the organic extract was washed with brine, dried over anhydrous $Na_2SO_4$, and filtered through a short plug of $SiO_2$ gel to afford the title compound as a white solid. (1.354 g was obtained. m/z (ESI, +ve ion) 456.2 $(M+H)^+$)

Alternatively, (S)-methyl 6'-chloro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylate may be prepared as follows:

To a slurry of (S)-6'-chloro-3',4,4',5-tetrahydro-2H,2'H-spiro[benzo[b][1,4]oxazepine-3,1'-naphthalene]-7-carboxylic acid with ((1S,4R)-7,7-dimethyl-2-oxobicyclo[2.2.1]heptan-1-yl)methanesulfonic acid (1:1) (Step 11) (32.22 g, 52.5 mmol) and ((1R,2R)-2-((R)-(1H-benzo[d][1,2,3]triazol-1-yl)(hydroxy)methyl)cyclobutyl)methyl acetate (Step 17) (15.89 g, 57.7 mmol) in DCM (226 mL, 7 mL/g) was added sodium triacetoxylborohydride (13.90 g, 65.6 mmol) in 4 portions over 30 min. Additional ((1R,2R)-2-((R)-(1H-benzo[d][1,2,3]triazol-1-yl)(hydroxy)methyl)cyclobutyl) methyl acetate (2.89 g, 10.50 mmol) and sodium triacetoxyborohydride (2.78 g, 13.12 mmol) were added to drive the reaction to completion (determined by HPLC assay). 80 mL of $H_2O$ was then added and the resulting mixture was agitated for 5 min. The layers were separated, the organic phase was washed with 60 mL $H_2O$ and 20 mL of brine, and then concentrated to an oil under reduced pressure. The residue was dissolved in 50 mL of MeOH and 40 mL of 5N NaOH were then added at ambient temperature (exothermic). Upon reaction completion (determined by HPLC assay), the reaction mixture was partitioned between 133 mL of MTBE and 35 mL of 1.5 M citric acid. The organic phase was transferred to a RBF and the solvent was exchanged to MeCN via atmospheric distillation. This solution was seeded at 62° C. (a slurry developed), was allowed to reach ambient temperature, and then aged overnight. The slurry was filtered at 20.5° C. through a coarse frit glass sinter funnel and the filter cake was washed using 60 mL of MeCN, then dried in a vacuum oven at 40° C. to constant weight. Final mass: 21.87 g (96.4 wt % by HPLC).

A 100 mL 3-necked-RBF was charged with (S)-6'-chloro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylic acid (4.53 g, 1.0 eq), MeOH (45 mL, 10 vol), and then a prepared solution of SOCl$_2$ (11.28 mL, 1.0M in MeCN, 1.1 eq). Under an atmosphere of N$_2$, the batch was heated to 55° C., and stirred for 18 h (or until >99% conversion as determined by HPLC). The reaction mixture was then allowed to cool to 20° C. over 2 h. To the resulting white slurry was added Hunig's base (3.94 mL, 2.2 eq) and after aging for 0.5 h, H$_2$O (9.0 mL, 2 V) was added as antisolvent over 1 h. The white slurry was aged for >2 h and the batch was filtered through a glass-fritted filter and the cake was washed with MeOH/H$_2$O (5:1 v/v) (9.0 mL, 2V) then MeOH/H$_2$O (2:1 v/v) (9.0 mL, 2V). The cake was dried under N$_2$ with vacuum for 12 h at ambient temperature. The product was obtained as a white solid (4.36 g, 92% yield).

STEP 18B: (S)-TERTBUTYL 6'-CHLORO-5-(((1R,2R)-2-(HYDROXYMETHYL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLATE

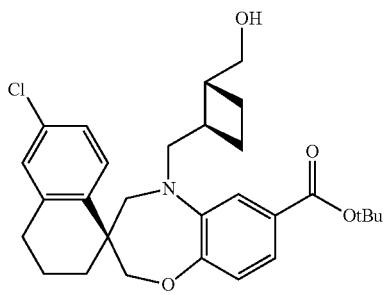 [SMILES: CC(C)(C)OC(=O)c1ccc2c(c1)N(C[C@@H]1CC[C@H]1CO)C[C@@]1(CCCc3cc(Cl)ccc31)CO2]

The title compound was synthesized from (S)-tertbutyl 6'-chloro-3',4,4',5-tetrahydro-2H,2'H-spiro[benzo[b][1,4]oxazepine-3,1'-naphthalene]-7-carboxylate (Intermediate AA11A, Step 12B) following the procedures described for Intermediate AA11A, Steps 18-19A).

STEP 19A: (S)-METHYL 6'-CHLORO-5-(((1R,2R)-2-FORMYLCYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLATE

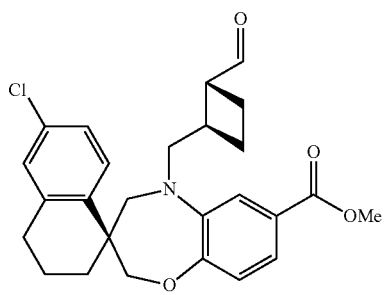 [SMILES: COC(=O)c1ccc2c(c1)N(C[C@@H]1CC[C@H]1C=O)C[C@@]1(CCCc3cc(Cl)ccc31)CO2]

To a cooled (−70° C.) solution of DMSO (7.12 mL, 2.5 eq) and DCM (183 mL, 10 vol) in a 1 L 3-necked-RBF inerted with N$_2$ was added oxalyl chloride (26.1 mL, LOM in DCM, 1.3 eq) at a rate to maintain temperature below −70° C. The batch was aged below −70° C. for 30 min and then a prepared solution of (S)-methyl 6'-chloro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylate (from Step 19A; 18.3 g, 1.0 eq) in DCM (183 mL, 10 vol) was added at a rate to maintain reaction temperature<−70° C. The batch was aged for 1.5 h and then Et$_3$N (22.4 mL, 4.0 eq) was added at a rate to maintain batch temperature <−70° C. After aging for 1 h, the batch was allowed to warm to −20° C., and H$_2$O (366 mL, 20 vol) was added. The batch was agitated at 20° C., and the phases separated. The organic layer was washed with 2×1N HCl (183 mL, 10 vol) and brine (183 mL, 10 vol). The organic layer was polish filtered and concentrated in vacuo to afford (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (19.91 g, 94% yield corrected for wt %) as a tan foam.

STEP 19B: (S)-TERTBUTYL 6'-CHLORO-5-(((1R,2R)-2-FORMYLCYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLATE

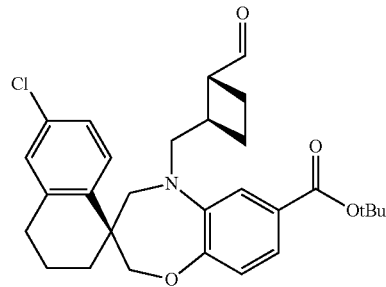 [SMILES: CC(C)(C)OC(=O)c1ccc2c(c1)N(C[C@@H]1CC[C@H]1C=O)C[C@@]1(CCCc3cc(Cl)ccc31)CO2]

The title compound was synthesized from (S)-tertbutyl 6'-chloro-5-(((1R,2R)-2-(hydroxymethyl)cyclobutyl)methyl)-3',4,4',5-tetrahydro-2H,2'H-spiro[benzo[b][1,4]oxazepine-3,1'-naphthalene]-7-carboxylate (Intermediate AA 11A, Step 19B) following the procedure described for Intermediate AA11A, step 20A.

STEP 20: (S)-METHYL 6'-CHLORO-5-(((1R,2R)-2-((S)-1-HYDROXYALLYL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLATE

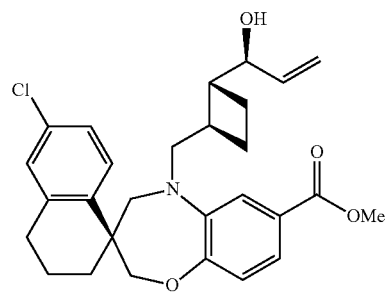 [SMILES: C=C[C@H](O)[C@@H]1CC[C@H]1CN1C[C@@]2(CCCc3cc(Cl)ccc32)COc2ccc(C(=O)OC)cc21]

An oven dried 3-necked-RBF equipped with a pressure-equalizing addition funnel, thermocouple, and magnetic stirbar was cooled to ambient temperature under a purge of argon gas. The flask was charged with (1R,2S)-2-morpholino-1-phenylpropan-1-ol (40.2 g, 182 mmol; prepared according to the literature procedure by Brubaker, J. D.; Myers, A. G. Org. Lett. 2007, 9, 3523-3525) against a positive pressure of argon. The addition funnel was charged with toluene (450 mL), which was dropped into the reactor. The solution was cooled in an ethyleneglycol-$CO_2$ bath (~−12° C.) and treated with butyllithium solution (2.5 M in Hex, 72.6 mL, 182 mmol), causing a white solid to precipitate that gradually went into solution as it was stirred over 30 min. Divinylzinc solution (605 mL, 182 mmol; prepared according to Brubaker, J. D.; Myers, A. G. Org. Lett. 2007, 9, 3523-3525. The concentration of divinylzinc solution was determined by titrating against iodine (Krasovskiy, A.; Knochel, P. Synthesis 2006, 890-891; concentration was generally ~0.25M) was added, and the solution was aged with stirring in the cold bath for 1 h; the internal temperature was −15° C. (S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (from Step 20A; 48.5 g, 107 mmol) (azeotroped thrice with toluene) was added as a solution in toluene (200 mL, 150 mL+2×25 mL cannula/vial rinse) via cannula (16 G), over ~20 min. The internal temperature rose to −10° C. The mixture was stirred for 90 min while maintaining the internal reaction temperature below −5° C. The addition funnel was charged with 30% w/w aqueous citric acid (450 mL), then the reaction was quenched by adding the solution to the reaction mixture. The reactor was removed from the bath and permitted to stir at ambient temperature. The solution was transferred to a separatory funnel and the flask was rinsed with toluene and 30% aqueous citric acid (50 mL each). The layers were mixed and then separated. The organic layer was washed with $H_2O$ (250 mL), then brine (250 mL), and finally dried with $MgSO_4$. The solution was filtered and concentrated to yield a yellow oil, ~90 g after vacuum overnight, 20:1 dr. This was split into 3 batches and purified by column chromatography 10 to 20% EtOAc/Hex 1.5 kg $SiO_2$, to provide (S)-methyl-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylate (43.3 g, 84%). The aqueous layer and washings were placed in an ice/$H_2O$ bath and basified to pH>13 by addition of 8N aqueous NaOH. This solution was then extracted with toluene (3×250 mL). The combined organic extracts were washed with $H_2O$ (250 mL) and brine (250 mL), then dried with $MgSO_4$. The solution was filtered and concentrated to recover the ligand in >95% yield.

STEP 21: (S)-6'-CHLORO-5-(((1R,2R)-2-((S)-1-HYDROXYALLYL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLIC ACID

To a solution of (S)-methyl 6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylate (from Step 21; 4.59 g, 9.52 mmol) in a mixture of THF (18 mL), MeOH (6.00 mL) and $H_2O$ (6.00 mL) was added LiOH·$H_2O$ (0.799 g, 19.05 mmol) and the reaction was stirred at 50° C. for 4 h. The reaction mixture was concentrated to ~15 mL, cooled to 0° C., and acidified with 2N HCl to pH=3. The resulting viscous oil was diluted with 20 mL of $H_2O$ and 50 mL of EtOAc and a clear two-layer mixture was obtained. More EtOAc (ca. 200 mL) was added and the organic layer was separated, washed with brine, dried with $MgSO_4$, filtered and concentrated under reduced pressure. The crude material was loaded onto a column (220 g), and purified with EtOAc in Hex using the following gradient: 0-2.5 min 0% of EtOAc, 2.5 m-6 m 0-20% EtOAc, 6 m-35 m 20-60% EtOAc, 35 m-40 m 70% EtOAc to give (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (4.22 g, 9.02 mmol, 95% yield) as a white solid.

Intermediate AA12A (S)-6'-CHLORO-5-(((1R,2R)-2-((S,E)-1-HYDROXYHEX-2-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLIC ACID

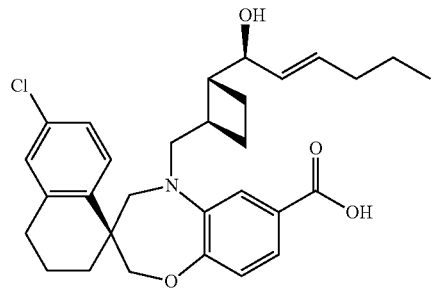 [SMILES: CCC/C=C/[C@H](O)[C@@H]1CC[C@H]1CN1C[C@@]2(CCCc3cc(Cl)ccc32)COc2ccc(C(=O)O)cc21]

STEP 1A: (S)-METHYL 6'-CHLORO-5-(((1R,2R)-2-((S,E)-1-HYDROXYHEX-2-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLATE

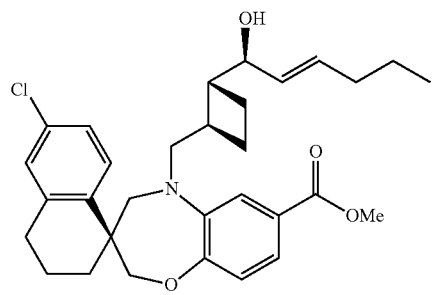 [SMILES: CCC/C=C/[C@H](O)[C@@H]1CC[C@H]1CN1C[C@@]2(CCCc3cc(Cl)ccc32)COc2ccc(C(=O)OC)cc21]

Under argon atmosphere, a dry 3-necked-RBF charged with dry Hex (27 mL) was cooled to 0° C. To this solution was added borane-methyl sulfide complex (3.29 mL, 34.6 mmol) and cyclohexene (7.01 mL, 69.3 mmol) and the mixture was stirred at 0° C. for 2 h. To the resulting white suspension was added 1-pentyne (3.41 mL, 34.6 mmol) and the mixture was stirred at ambient temperature for 0.5 h. The mixture was then cooled to −78° C., and diethylzinc, 1.0 M solution in Hex (32.3 mL, 32.3 mmol) was added. After addition the mixture was warmed to 0° C., stirred for 3 min then recooled to −78° C. This solution was named solution A. A separate flask was charged with a mixture of ((S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, Step 20A, 5.24 g, 11.54 mmol) and (2s)-3-exo-(morpholino) isoborneol (0.486 g, 2.032 mmol) in Hex (50.9 mL) and toluene (16.97 mL). The mixture was stirred at ambient temperature until all solid was dissolved, then cooled to 0° C. Under argon atmosphere 54 mL of solution A was added slowly via syringe during 1.6 h. After stirring for 5 min at 0° C., the mixture was quenched with sat. NH$_4$Cl solution (70 mL), diluted with H$_2$O (30 mL) and extracted with EtOAc (3×270 mL), washed with brine, dried over anhydrous Na$_2$SO$_4$ and concentrated. The residue was loaded to a 330 g ISCO gold column and eluted with 0% to 5% EtOAc/Hex, to provide the title compound 3.8 g as a white solid. m/z (ESI, +ve ion) 524.1 (M+H)$^+$.

STEP 1B (S)-TERTBUTYL 6'-CHLORO-5-(((1R,2R)-2-((S,E)-1-HYDROXYHEX-2-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLATE AND (S)-TERTBUTYL 6'-CHLORO-5-(((1R,2R)-2-((R,E)-1-HYDROXYHEX-2-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLATE

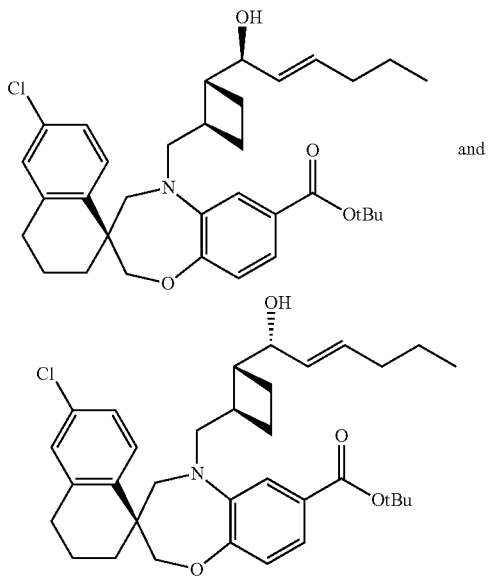

and

The title compound was synthesized from (S)-tert-butyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (3.19 g, Intermediate AA11A, Step 20B) following the procedure described for Intermediate AA12A, Step 1A. The crude material was absorbed onto a plug of SiO$_2$ and purified on a 330 g ISCO gold column eluting with 0 to 15% EtOAc in heptanes over 45 min to provide (S)-tertbutyl 6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate (2.36 g). Further elution provided (S)-tert-butyl 6'-chloro-5-(((1R,2R)-2-((R,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate (0.45 g).

STEP 2: (S)-6'-CHLORO-5-(((1R,2R)-2-((S,E)-1-HYDROXYHEX-2-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLIC ACID

A mixture of (S)-methyl 6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate (from Intermediate AA12A, Step A; 4.6 g, 8.78 mmol) and LiOH·H$_2$O (3.68 g, 88 mmol) in MeOH (98 mL) and THF (98 mL) (with a few drops of H$_2$O) was stirred at 50° C. overnight. The solvent was removed and the residue was acidified with 1N HCl to pH 2-3. The mixture was extracted with EtOAc (80 mL×3) and the combined organic layer was washed with brine (10 mL), dried over anhydrous MgSO$_4$ and concentrated under reduced pressure to give (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (4.25 g, 8.34 mmol, 95% yield).

Alternatively, the title compound may be synthesized as follows:

To a solid mixture of (S)-tert-butyl 6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate (Intermediate AA12A, Step 1B, first eluting isomer, 4.50 g 7.95 mmol) and LiOH·H$_2$O (1.66 g, 39.7 mmol) was added solvent dioxane/MeOH (1:1) (159 mL). The mixture was heated to 65° C., and stirred overnight. The mixture was then diluted with H$_2$O and acidified with 1.0 N HCl to pH-4. The organic solvents were evaporated under reduced pressure and to the residue was added H$_2$O. The aqueous mixture was then extracted with EtOAc three times, and the combined organic extract was concentrated. The residue was purified on a 120 g SiO$_2$ gel column eluting with a gradient of 0-70% EtOAc in Hex to provide (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (3.80 g, 7.45 mmol, 94% yield).

Intermediate AA13A (S)-6'-CHLORO-5-(((1R,2R)-2-((S)-1-HYDROXYBUT-3-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLIC ACID

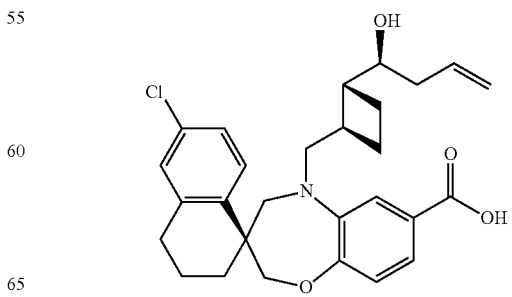

STEP 1A: (S)-METHYL 6'-CHLORO-5-(((1R,2R)-2-((S)-1-HYDROXYBUT-3-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLATE

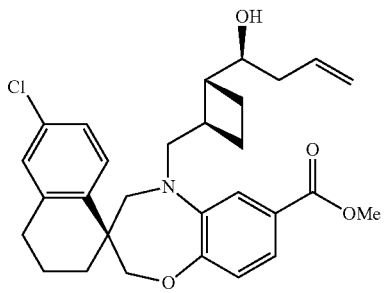 [SMILES: C=CC[C@H](O)[C@@H]1CC[C@H]1CN1C[C@@]2(CCCc3cc(Cl)ccc32)COc2ccc(C(=O)OC)cc21]

An oven-dried 200-mL flask charged with a suspension of (1R,2R)—N-methyl-1-phenyl-1-(((1S,5S,10R)-10-(trimethylsilyl)-9-borabicyclo[3.3.2]decan-9-yl)oxy)propan-2-amine (5.40 g, 14.54 mmol) in Et$_2$O (73 mL) under argon was cooled to −78° C., and treated with allylmagnesium bromide (13.22 mL, 13.22 mmol) solution, dropwise. The mixture was allowed to warm to ambient temperature and stirred for 1 h. The solution (~0.17 M; solution A) was then recooled to −78° C.

A separate 200 mL flask charged with ((S)-methyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, Step 20A, 2.0 g, 4.41 mmol) in Et$_2$O (22.03 mL) under argon was cooled to −78° C. To this solution was added 40 mL of the above-referenced solution A and the resulting mixture was stirred at −78° C. for 40 min. 4-methylmorpholine 4-oxide (3.10 g, 26.4 mmol) was then added and the mixture was allowed to warm to ambient temperature for 10 min. Methanol (10 mL) was added and the volatile organics were evaporated under reduced pressure at ambient temperature. Additional methanol (100 mL) was added and after stirring at ambient temperature for 1 h the mixture was concentrated. The residue was diluted with EtOAc (450 mL), washed with 1N HCl (15 mL), Na$_2$CO$_3$ solution (10 mL), and brine (6 mL), dried over anhydrous Na$_2$SO$_4$ and concentrated. The residue was loaded to a 220 g ISCO gold column and eluted with 0% to 5% EtOAc/Hex, to provide 1.88 g of the title compound as a white solid. m/z (ESI, +ve ion) 496.0 (M+H)$^+$.

STEP 1B: (S)-TERTBUTYL 6'-CHLORO-5-(((1R,2R)-2-((S)-1-HYDROXYBUT-3-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLATE

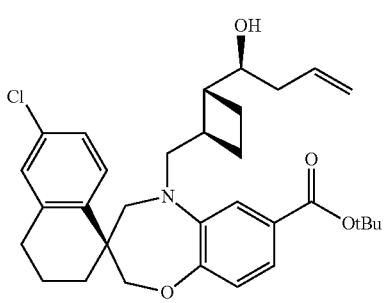 [SMILES: C=CC[C@H](O)[C@@H]1CC[C@H]1CN1C[C@@]2(CCCc3cc(Cl)ccc32)COc2ccc(C(=O)OC(C)(C)C)cc21]

The title compound was synthesized from (S)-tert-butyl 6'-chloro-5-(((1R,2R)-2-formylcyclobutyl)methyl)-3',4,4',5-tetrahydro-2H,2'H-spiro[benzo[b][1,4]oxazepine-3,1'-naphthalene]-7-carboxylate (Intermediate AA11A, Step 20B; 3.0 g) following the procedure described for Intermediate AA13A, Step 1A. The crude material was purified on a 220 g SiO$_2$ gel column eluting with 5% EtOAc in Hex over 60 min to provide (S)-tert-butyl 6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylate (2.19 g).

STEP 2: (S)-6'-CHLORO-5-(((1R,2R)-2-((S)-1-HYDROXYBUT-3-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLIC ACID

A mixture of (S)-methyl 6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylate (from Intermediate AA13A, Step 1A; 1.88 g, 3.79 mmol) and LiOH solution (1M) (34.1 mL, 34.1 mmol) in MeOH (34 mL) and THF (50 mL) was stirred at 65° C. for 50 min. After cooling to ambient temperature, the mixture was acidified with 1N HCl to pH 2 to 3, extracted with EtOAc (350 mL), dried over anhydrous Na$_2$SO$_4$ and concentrated to provide 1.82 g of the title compound as a white solid. m/z (ESI, +ve ion) 482.0 (M+H)$^+$.

Alternatively, the title compound may be synthesized as follows:

To a solution of (S)-tert-butyl 6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylate (Intermediate AA13A, Step 1B; 250 mg, 0.465 mmol) in DCM (3.717 mL) at ambient temperature, TFA (0.929 mL) was added and the reaction mixture was stirred for 4 h. The crude reaction mixture was then concentrated, the residue was taken up in EtOAc, washed once with sat. NaHCO$_3$, dried over MgSO$_4$, filtered and concentrated to give a white foam. The crude material was used as such, without further purification.

Intermediate EE11

N,N-BIS(4-METHOXYBENZYL)AMINE

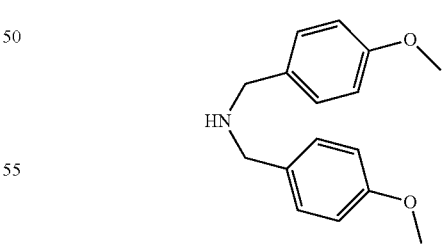

A solution of 4-methoxybenzaldehyde (Spectrochem; 100 g, 734.5 mmol) and 4-methoxybenzyl amine (G.L.R.; 100 g, 734.5 mmol) in toluene (0.8 L) was refluxed at 130° C. using a Dean-Stark apparatus for 6 h. The reaction was monitored by TLC and upon completion, excess solvent was removed under reduced pressure and the residue was dissolved in methanol (0.8 L). The resulting solution was cooled to 0° C., and sodium borohydride (36.12 g, 954.8 mmol) was added in portions. After complete addition, the reaction mixture was stirred for 3 h at ambient temperature. Methanol was removed, and the residue was diluted with H₂O (1.0 L) and EtOAc (2.0 L). The layers were separated and the aqueous layer was extracted with EtOAc (2×1.0 L). The combined organic layer was washed with H₂O, brine, and dried over Na₂SO₄. Solvent was removed under reduced pressure and the crude material obtained was purified by column chromatography over SiO₂ gel (100-200 mesh size) eluting with a gradient of 100% Hex to 25% EtOAc in Hex affording the title compound (160 g, 84.6%) as a colorless but opaque liquid.

Intermediate EE12

N,N-BIS(4-METHOXYBENZYL) METHANESULFONAMIDE

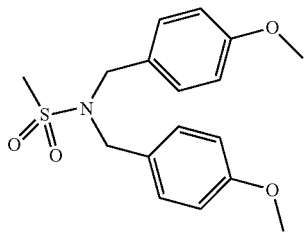 [SMILES: COc1ccc(CN(Cc2ccc(OC)cc2)S(C)(=O)=O)cc1]

A mixture of methanesulfonamide (Sigma-Aldrich, 5 g, 52.6 mmol), p-methoxybenzyl chloride (14.98 mL, 110 mmol), K₂CO₃ anhydrous (36.3 g, 263 mmol) and potassium iodide (0.873 g, 5.26 mmol) in anhydrous 2-butanone (175 mL) was refluxed (75° C.) overnight. The reaction was monitored by TLC and LC/MS and upon completion, the mixture was cooled to ambient temperature, filtered, washed with Et₂O and concentrated. The crude material (17.54 g, 52.3 mmol, 99% yield) was used with no further purification. MS (ESI, positive ion) m/z: 358.1 (M+Na).

Intermediate EE13

N,N-BIS(4-METHOXYBENZYL) ETHANESULFONAMIDE

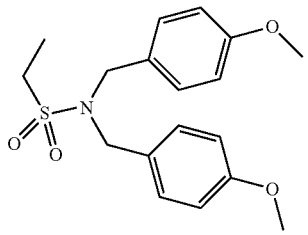 [SMILES: CCS(=O)(=O)N(Cc1ccc(OC)cc1)Cc1ccc(OC)cc1]

To a solution of N,N-bis(4-methoxybenzyl)amine (Intermediate EE11; 200 g, 775.19 mmol) in DCM (2.5 L) was added Et₃N (336.17 mL, 2325.5 mmol), and the reaction mixture was cooled to 0° C. Ethanesulfonyl chloride (95 mL, 1007.75 mmol) was added in drop-wise manner followed by DMAP (19.0 g, 155.03 mmol). The resulting reaction mixture was stirred at ambient temperature for 30 min. The reaction was monitored by TLC and upon completion, the mixture was diluted with H₂O and the layers were separated and the aqueous phase was extracted with DCM (3×1.5 L). The combined organic layer was washed with H₂O, brine, and dried over Na₂SO₄. The solvent was removed under reduced pressure to afford the crude material which was purified by column chromatography over SiO₂ gel (100-200 mesh), eluting with a gradient of 0-12% EtOAc in Hex affording the title compound (145 g, 53.4%) as a white fluffy solid.

Intermediate EE14

N,N-BIS(4-METHOXYBENZYL) PROPANESULFONAMIDE

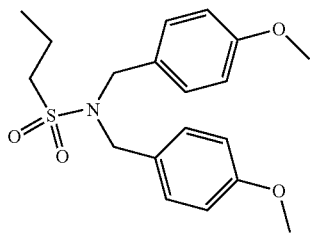 [SMILES: CCCS(=O)(=O)N(Cc1ccc(OC)cc1)Cc1ccc(OC)cc1]

To a solution of N,N-bis(4-methoxybenzyl)amine (Intermediate EE11; 405 g, 1569.7 mmol) in DCM (4.0 L) was added Et₃N (681.0 mL, 4709.3 mmol), and the reaction mixture was cooled to 0° C. Propanesufonyl chloride (231 mL, 2040.6 mmol) was added in a drop-wise manner followed by DMAP (38.3 g, 313.9 mmol). The resulting mixture was stirred at ambient temperature for 30 min. The reaction was monitored by TLC and upon completion, the mixture was diluted with 2.0 L of H₂O, the layers were separated and the aqueous phase was extracted with DCM (3×2.0 L). The combined organic layer was washed with H₂O, brine, and dried over Na₂SO₄. The solvent was removed under reduced pressure to afford the crude material which was purified by column chromatography over SiO₂ gel (100-200 mesh), eluting with a gradient of 0-12% EtOAc in Hex affording the title compound (300 g, 52.44%) as white fluffy solid.

Intermediate EE15

BUT-3-ENE-1-SULFONAMIDE

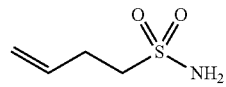

STEP 1: SODIUM BUT-3-ENE-1-SULFONATE

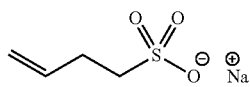

A mixture of 4-bromo-1-butene (LLBChem, 3.01 mL, 29.6 mmol) and sodium sulfite (4.11 g, 32.6 mmol) in H₂O (20 mL) was stirred at 110° C. overnight. The reaction was monitored by TLC and upon completion, H₂O was removed under reduced pressure and the residue was triturated with acetone. The solid obtained was filtered to afford the title compound as a white solid (4.53 g) which was used as such in next step.

STEP 2: BUT-3-ENE-1-SULFONAMIDE

A mixture of sodium but-3-ene-1-sulfonate (4.50 g, 28.5 mmol) and phosphorus oxychloride (70 mL) was stirred at 135° C. for 7 h. Phosphorus oxychloride was then removed under reduced pressure to obtain a dark residue containing a white solid. This residue was diluted with MeCN (20 mL), and then filtered to remove the precipitate. The filtrate was cooled to 0° C., and treated with ammonia solution (30% aqueous) (30 mL) dropwise. After complete addition, the reaction was stirred at 0° C. for 30 min. The mixture was diluted with EtOAc (300 mL), washed with brine, and dried over anhydrous Na$_2$SO$_4$. The solvent was removed under reduced pressure and the residue was purified by column chromatography over SiO$_2$ gel (100-200 mesh; eluting with 1:1 EtOAc/Hex), affording the title compound as a white solid (1.55 g, yield: 40%). MS (ESI, positive ion) m/z: 117.1 (M+1).

Intermediate EE16

N,N-BIS(4-METHOXYBENZYL)BUT-3-ENE-1-SULFONAMIDE

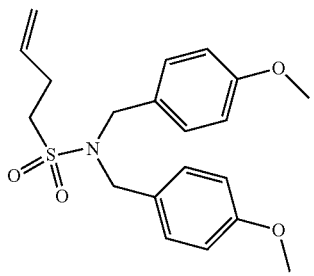 [SMILES: C=CCCS(=O)(=O)N(Cc1ccc(OC)cc1)Cc1ccc(OC)cc1]

A mixture of but-3-ene-1-sulfonamide (Intermediate EE15; 1.5 g, 11.10 mmol), p-methoxybenzyl chloride (3.76 mL, 27.7 mmol), K$_2$CO$_3$ anhydrous (7.67 g, 55.5 mmol) and sodium iodide (0.166 g, 1.110 mmol) in anhydrous 2-butanone (55.5 mL) was refluxed (75° C.) overnight. The reaction was monitored by TLC and LC/MS and upon completion, the mixture was cooled to ambient temperature, filtered, and concentrated. The crude material was absorbed onto a plug of SiO$_2$ gel and purified by chromatography through SiO$_2$ gel (100-200 mesh), eluting with 0 to 30% EtOAc in Hex, to provide the title compound (4.10 g, 10.92 mmol, 98% yield) as a colorless oil. MS (ESI, positive ion) m/z: 376.2 (M+1).

Intermediate EE17

(R)-PENT-4-ENE-2-SULFONAMIDE

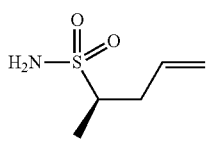

STEP 1: (S)—N,N-BIS(4-METHOXYBENZYL)PENT-4-ENE-2-SULFONAMIDE AND (R)—N,N-BIS(4-METHOXYBENZYL)PENT-4-ENE-2-SULFONAMIDE

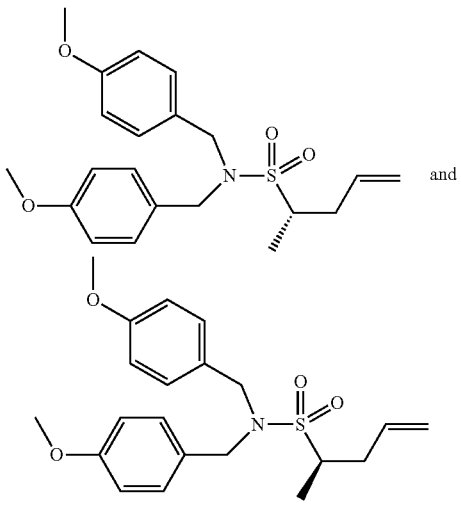

N,N-bis(4-methoxybenzyl)but-3-ene-1-sulfonamide (Intermediate EE16; 50.0 g, 133.2 mmol) was azeotroped with toluene and dried under vacuum for 1 h. THF (890 mL) was added and the mixture was cooled to −78° C. Butyl lithium (2.5 M in Hex, 63.9 mL, 159.9 mmol) was then added and the reaction mixture was stirred at −78° C. for 1 h. This anion solution was added slowly to a solution of MeI (16.8 mL, 266.5 mmol) in THF (300 mL) cooled to −78° C. The resulting reaction mixture was stirred for another 15 min at −78° C. On completion of the reaction (monitored by TLC) the mixture was quenched with sat. NH$_4$Cl solution and extracted with EtOAc. The organic layer was dried over Na$_2$SO$_4$ and concentrated under reduced pressure to obtain crude material which was purified by column chromatography over SiO$_2$ gel eluting with 5-10% EtOAc in Hex to provide the title compound as a racemic mixture (22.0 g) of semisolid nature. Separation of the enantiomers by SFC (Column: Chiralpak® AD-H, 50×250 mm, 5 µm; Mobile Phase A: CO$_2$; Mobile Phase B: Ethanol; Isocratic: 40% B with CO$_2$ recycler on; Flow Rate: 200 g/min; Loading: 2.0 mL of sample prepared as above (~100 mg); Detection: UV; 230 nm; Cycle Time: 5 min; Total Elution Time: 10 min; Instrument: Thar 350 (Lakers)) provided (S)—N,N-bis(4-methoxybenzyl)pent-4-ene-2-sulfonamide as the first eluting isomer (retention time: 2.22 min) and (R)—N,N-bis(4-methoxybenzyl)pent-4-ene-2-sulfonamide as the second eluting isomer (retention time: 2.57 min).

STEP 2: (R)-PENT-4-ENE-2-SULFONAMIDE

To a solution of (R)—N,N-bis(4-methoxybenzyl)pent-4-ene-2-sulfonamide (Intermediate EE17, Step 1, second eluting isomer; 221 mg, 0.567 mmol) in DCM (2.8 mL), was added trifluoroacetic acid (1.7 mL, 22.70 mmol) dropwise (the clear solution very rapidly turned dark). After stirring for 7 h (TLC 30% EtOAc/Hex showed complete loss of starting material) the mixture was diluted with EtOAc, washed with sat. NaHCO$_3$, back extracted with EtOAc, dried over MgSO$_4$, and concentrated. The crude material was purified via chromatography (12 g ISCO gold column: 0-40% EtOAc Hex) to provide (R)-pent-4-ene-2-sulfonamide (70 mg, 0.469 mmol, 83% yield)

Intermediate EE172

(S)-PENT-4-ENE-2-SULFONAMIDE

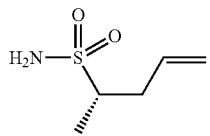

This intermediate was synthesized from (S)—N,N-bis(4-methoxybenzyl)pent-4-ene-2-sulfonamide (Intermediate EE17, Step 1, first eluting isomer) using the procedure described for Intermediate EE17, Step 2.

Intermediate EE18

(R)-HEX-5-ENE-3-SULFONAMIDE

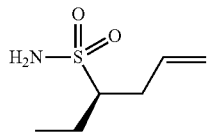

STEP 1: (S)—N,N-BIS(4-METHOXYBENZYL) HEX-5-ENE-3-SULFONAMIDE AND (R)—N,N-BIS(4-METHOXYBENZYL)HEX-5-ENE-3-SULFONAMIDE

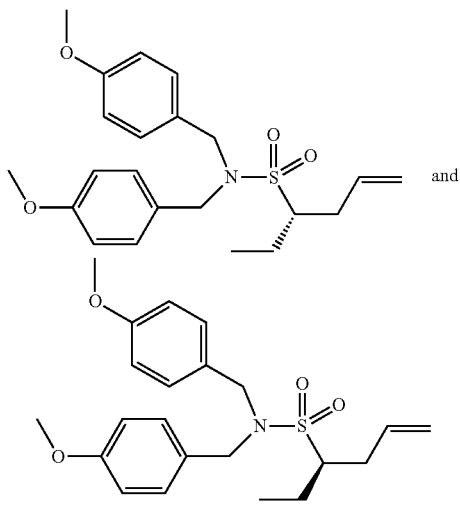

N,N-bis(4-methoxybenzyl)but-3-ene-1-sulfonamide (Intermediate EE16; 40.0 g, 106.6 mmol) was azeotroped in toluene under vacuum for 2 h. THF (700 mL) was added under argon atmosphere and the reaction mixture was cooled to −78° C. Butyl lithium (2.5 M in Hex; 71.6 mL, 127.9 mmol) was added and the reaction mixture was stirred at −78° C. for 1 h. This anion solution was added slowly to a solution of ethyl iodide (36.44 mL, 340.1 mmol) in THF (40 mL) cooled to −78° C. The resulting reaction mixture was then quenched with sat. NH$_4$Cl solution, allowed to reach ambient temperature and extracted with EtOAc. The organic layer was dried over Na$_2$SO$_4$ and concentrated under reduced pressure to obtain crude material which was purified by column chromatography over SiO$_2$ gel eluting with 5-10% EtOAc in Hex to provide the title compound as a racemic mixture (24 g) of semisolid nature. MS (ESI, positive ion) m/z; 404.03 (M+1). Separation of the enantiomers by SFC (Sample preparation: 14.4 g/200 mL (72 mg/mL) sample solution in MeOH:DCM (3:1); Column: Chiralpak® AD-H, 30×250 mm, 5 μm; Mobile Phase A: CO$_2$; Mobile Phase B: MeOH (20 mM NH$_3$); Isocratic: 50% B, Flow Rate: 100 mL/min; Outlet Pressure: 100 bar; Loading: 1.0 mL of sample solution prepared as above (72 mg); Detection: UV @ 227 nm; Cycle Time: 8 min; Total Elution Time: 17 min; Instrument: Thar 350 SFC) provided (S)—N,N-bis(4-methoxybenzyl)hex-5-ene-3-sulfonamide as the first eluting isomer and (R)—N,N-bis(4-methoxybenzyl)hex-5-ene-3-sulfonamide as the second eluting isomer.

STEP 2: (R)-HEX-5-ENE-3-SULFONAMIDE

This intermediate was synthesized from (R)—N,N-bis(4-methoxybenzyl)hex-5-ene-3-sulfonamide (Intermediate EE18, Step 1, second eluting isomer) using the procedure described for Intermediate EE17, Step 2.

Intermediate EE182

(S)-HEX-5-ENE-3-SULFONAMIDE

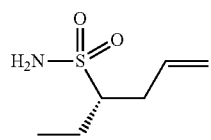

This intermediate was synthesized from (S)—N,N-bis(4-methoxy benzyl)hex-5-ene-3-sulfonamide (Intermediate EE18, Step 1, first eluting isomer) using the procedure described for Intermediate EE17, Step 2.

Intermediate EE19

N,N-BIS(4-METHOXYBENZYL) PENT-4-ENE-1-SULFONAMIDE

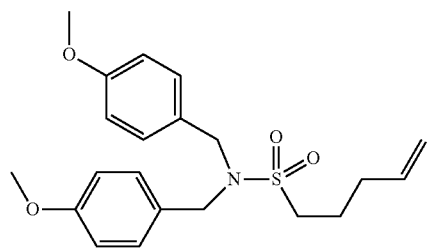 [SMILES: C=CCCCS(=O)(=O)N(Cc1ccc(OC)cc1)Cc1ccc(OC)cc1]

STEP 1: SODIUM PENT-4-ENE-1-SULFONATE

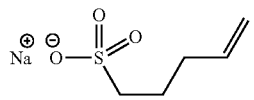

To a 3 L 3-necked-RBF equipped with a mechanical stirrer, a N₂ gas inlet, a condenser, and a temperature probe was charged 5-bromo-1-pentene (Sigma Aldrich, 200 g, 1342 mmol), sodium sulfite (Strem Chemicals; 186 g, 1476 mmol), and H₂O (400 mL). The mixture was heated to reflux (set at 100° C. and refluxed at 93-94° C.) 4 h; aliquot NMR showed >95% conversion. The mixture was concentrated and azeotroped with acetone to remove H₂O. The crude solid was washed with acetone and filtered to afford sodium pent-4-ene-1-sulfonate (350 g, 2033 mmol).

STEP 2: PENT-4-ENE-1-SULFONAMIDE

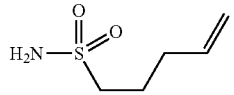

To a 3 L 3-necked-RBF equipped with a mechanical stirrer, a N₂ gas inlet, a condenser, and a temperature probe was charged sodium pent-4-ene-1-sulfonate (100 g, 581 mmol) (~150 g of crude material from Step 1) and phosphorus oxychloride (Sigma Aldrich; 532 mL, 5808 mmol). The mixture was heated to 90° C. for 18 h after which the reaction was filtered and the solid was washed with MeCN. The organic solution was concentrated and azeotroped with MeCN to remove POCl₃ to afford 85 g pent-4-ene-1-sulfonyl chloride intermediate. This material (solution in 300 mL MeCN) was charged onto a 1 L 3-necked-RBF equipped with a mechanical stirrer, a N₂ gas inlet, a condenser, and a temperature probe. The reaction was cooled to 0-5° C., and NH₄OH (Sigma Aldrich; 28% NH₃; 404 mL, 2904 mmol) was added slowly over 30 min. The reaction was stirred at 0-5° C. for 1 h, after which EtOAc (300 mL) was added and the mixture was extracted with EtOAc and concentrated to afford pent-4-ene-1-sulfonamide (50 g, 335 mmol, 57.7% yield) as a brown oil.

STEP 3: N,N-BIS(4-METHOXYBENZYL)PENT-4-ENE-1-SULFONAMIDE

The title compound was synthesized from pent-4-ene-1-sulfonamide (4.5 g, 30.2 mmol) following the procedure described for Intermediate EE16. Purification of the crude material provided N,N-bis(4-methoxybenzyl)pent-4-ene-1-sulfonamide (11.4 g, 29.3 mmol, 97% yield) as a colorless oil.

Intermediate EE20

(R)-HEX-5-ENE-2-SULFONAMIDE

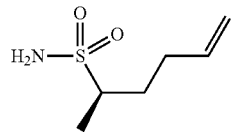

STEP 1: (S)—N,N-BIS(4-METHOXYBENZYL)HEX-5-ENE-2-SULFONAMIDE AND (R)—N,N-BIS(4-METHOXYBENZYL)HEX-5-ENE-2-SULFONAMIDE

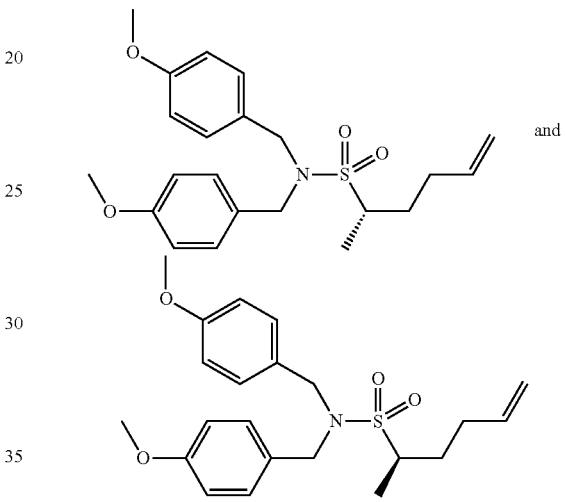

A solution of N,N-bis(4-methoxybenzyl)ethanesulfonamide (Intermediate EE13; 140.0 g, 400.64 mmol) in THF (1.4 L, THF was purged with argon for 15 min before using) was cooled to −78° C., and butyl lithium solution (2.6 M in Hex, 200.0 mL, 520.83 mmol) was added drop-wise. The resulting solution was stirred at −78° C. for 10 min, and 4-bromo-1-butene (73.2 mL, 721.15 mmol) was added over 2 min. After 5 min, the reaction was allowed to reach ambient temperature and stir for 1 h. The reaction was monitored by TLC and upon completion, the mixture was quenched with sat. NH₄Cl solution (400 mL) and the resulting aqueous layer was extracted with EtOAc (2×1.0 L). The combined organic layer was washed with brine and dried over Na₂SO₄. The solvent was removed under reduced pressure to afford the crude material which was purified by column chromatography (SiO₂ gel 100-200 mesh) eluting with a gradient of 0-4% acetone in Hex affording the title compound (racemic mixture, 80.0 g, 49.5%) as a colorless thick oil. MS (ESI, positive ion) m/z: 404.25 (M+1). Separation of the enantiomers by SFC (Sample preparation: 75 g/1.5 L (50 mg/mL) sample solution in MeOH; Column: Chiralpak® IF, 21×250 mm, 5 μm; Mobile Phase A: CO₂; Mobile Phase B: MeOH (0.2% DEA); Isocratic: 40% B; Flow Rate: 80 mL/min; Outlet Pressure: 100 bar; Loading: 3.0 mL of sample solution prepared as above (150 mg); Detection: UV @d; 225 nm; Cycle Time: 3.9 min; Total Elution Time: 6 min; Instrument: Thar 80 SFC) provided (S)—N,N-bis(4-methoxybenzyl)hex-5-ene-2-sulfonamide as the first eluting isomer and (R)—N,N-bis(4-methoxybenzyl)hex-5-ene-2-sulfonamide as the second eluting isomer.

STEP 2: (R)-HEX-5-ENE-2-SULFONAMIDE

The title compound was synthesized from (R)—N,N-bis(4-methoxybenzyl)hex-5-ene-2-sulfonamide (Intermediate EE20, Step 1, second eluting isomer) using the procedure described for Intermediate EE17, Step 2.

Intermediate EE202

(S)-HEX-5-ENE-2-SULFONAMIDE

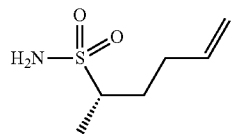

The title compound was synthesized from (S)—N,N-bis(4-methoxybenzyl)hex-5-ene-2-sulfonamide (Intermediate EE20, Step 1, first eluting isomer) using the procedure described for Intermediate EE17, Step 2.

Intermediate EE21

(R)-HEPT-6-ENE-3-SULFONAMIDE

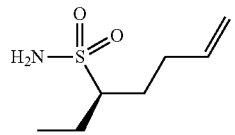

STEP 1: (S)—N,N-BIS(4-METHOXYBENZYL)HEPT-6-ENE-3-SULFONAMIDE AND (R)—N,N-BIS(4-METHOXYBENZYL)HEPT-6-ENE-3-SULFONAMIDE

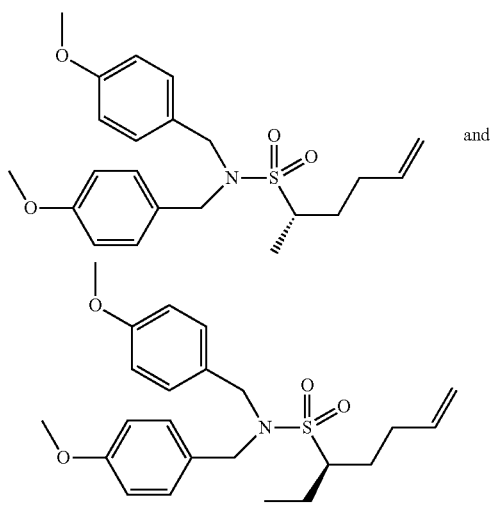

The title compound was synthesized from N,N-bis(4-methoxybenzyl)propanesulfonamide (Intermediate EE14) using the procedure described for Intermediate AA20, Step 1. Separation of the enantiomers by SFC (Sample preparation: 40.55 g/170 mL (238.5 mg/mL) sample solution in MeOH; Column: Chiralpak® AD-H, 50×150 mm, 5 μm; Mobile Phase A: $CO_2$; Mobile Phase B: MeOH (20 mM $NH_3$); Isocratic: 50% B; Flow Rate: 190 mL/min; Outlet Pressure: 100 bar; Loading: 1.5 mL of sample solution prepared as above (357.8 mg); Detection: UV @ 227 nm; Cycle Time: 17.5 min; Total Elution Time: 21 min; Instrument: Thar 350 SFC) provided (S)—N,N-bis(4-methoxybenzyl)hept-6-ene-3-sulfonamide as the first eluting isomer and (R)—N,N-bis(4-methoxybenzyl)hept-6-ene-3-sulfonamide as the second eluting isomer.

STEP 2: (R)-HEPT-6-ENE-3-SULFONAMIDE

The title compound was synthesized from (R)—N,N-bis(4-methoxybenzyl)hept-6-ene-3-sulfonamide (Intermediate EE21, Step 1, second eluting isomer) using the procedure described for Intermediate EE17, Step 2.

Intermediate EE212

(S)-HEPT-6-ENE-3-SULFONAMIDE

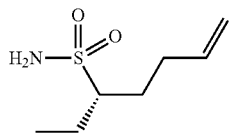

The title compound was synthesized from (S)—N,N-bis(4-methoxybenzyl)hept-6-ene-3-sulfonamide (Intermediate EE21, Step 1, first eluting isomer) using the procedure described for Intermediate EE17, Step 2.

Intermediate EE22

(2R,3S)-3-METHYLHEX-5-ENE-2-SULFONAMIDE

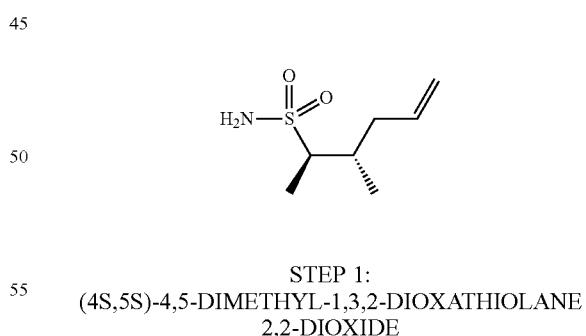

STEP 1: (4S,5S)-4,5-DIMETHYL-1,3,2-DIOXATHIOLANE 2,2-DIOXIDE

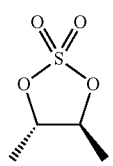

To a 500-mL, 3-necked-RBF (equipped with a H$_2$O-cooled reflux condenser and an HCl trap) was added (2s,3s)-(+)-2,3-butanediol (Aldrich; 15.00 mL, 166 mmol) and CCl$_4$ (120 mL). SOCl$_2$, reagentplus (14.57 mL, 200 mmol) was then added drop wise via a syringe over a period of 20 min and the resulting mixture was heated to 98° C. for 45 min, then allowed to cool to rt. The reaction mixture was then cooled in an ice/H$_2$O bath, MeCN (120 mL) and H$_2$O (150 mL) were added followed by ruthenium(III) chloride (0.035 g, 0.166 mmol). Sodium periodate (53.4 g, 250 mmol) was then added slowly portion wise over 30 min. The resulting biphasic brown mixture was stirred vigorously while allowed to reach rt for a period of 1.5 h (internal temperature never increased above rt). TLC (50% EtOAc in heptanes) showed complete conversion. The crude mixture was then poured into ice H$_2$O and extracted twice with 300 mL of Et$_2$O. The combined organic layers were washed once with 200 mL of sat. sodium bicarbonate, washed once with 200 mL of brine, dried over Na$_2$SO$_4$, and concentrated by rotary evaporation to give (4S,5S)-4,5-dimethyl-1,3,2-dioxathiolane 2,2-dioxide (21.2 g, 139 mmol) as a red oil.

STEP 2: (2S,3S)-3-METHYLHEX-5-EN-2-OL

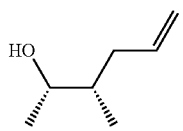

To a 500 mL flask was added (4S,5S)-4,5-dimethyl-1,3,2-dioxathiolane 2,2-dioxide (from Intermediate EE22, Step 1; 21.2 g, 139 mmol) and THF (220 mL) at which time the solution was cooled to −78° C., and was subjected to 3 cycles of evacuation/back-filling with argon. To the solution was added dilithium tetrachlorocuprate(ii), 0.1M solution in THF (69.7 mL, 6.97 mmol). The resulting mixture was stirred at −78° C. for 30 min and then allylmagnesium bromide, 1.0 M solution in Et$_2$O (397 mL, 397 mmol) was added slowly via cannula over 80 mm. The resulting mixture was stirred at 0° C. for 4 h. The mixture was quenched with 200 mL H$_2$O and allowed to reach rt at which time the volatiles were removed by rotary evaporation. To the aqueous residue was then added 50% H$_2$SO$_4$ (150 mL), the mixture was stirred for 5 min, Et$_2$O was then added (400 mL) and the mixture was stirred vigorously at rt overnight. The layers were separated; the aqueous layer was extracted with 300 mL Et$_2$O and the combined organic layers were washed with 300 mL of sat. NaHCO$_3$, dried over Na$_2$SO$_4$, filtered and concentrated by rotary evaporation to give (2S,3S)-3-methylhex-5-en-2-ol (6.7 g, 58.7 mmol) as a clear oil.

STEP 3: 2-(((2R,3S)-3-METHYLHEX-5-EN-2-YL)THIO)PYRIMIDINE

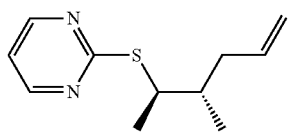

To a 2000 mL dry RBF containing a stirring solution of tributylphosphine (57.7 mL, 231 mmol) in 1000 mL degassed THF (sparged with argon for 30 min plus 5 cycles of pump/add argon) at 0° C. was added diethyl azodicarboxylate (40 wt. % solution in toluene; 103 mL, 262 mmol) drop wise under an atmosphere of argon. A solution of (2S,3S)-3-methylhex-5-en-2-ol (from Intermediate EE22, Step 2; 17.6 g, 154 mmol; dried over Na$_2$SO$_4$) was added drop wise as a solution in 50 mL of THF to the solution of phosphine/diethyl azodicarboxylate complex, via syringe-filter (0.45 um). The resulting ROH/diethyl azodicarboxylate/tri-n-butylphosphine mixture was aged at zero degrees for 15 min (solution turned light orange), at which time pyrimidine-2-thiol (49.3 g, 439 mmol) was added gradually to the top of the reaction vessel (as a solid) under positive argon pressure. The reaction was stirred at 0° C. for 1 h then at rt 15 h (reaction not complete at 12 h by LC/MS). The crude reaction was then filtered to remove excess pyrimidine-2-thiol, diluted with 1000 mL of EtOAc, extracted twice with 500 mL of 1 N K$_K$CO$_3$, and once with 500 mL of brine. The aqueous layer was back extracted with 300 mL of EtOAc and the combined organic layers were dried over Na$_2$SO$_4$. The organic solution was then filtered, the solvent removed by rotary evaporation and the crude filtered to remove the (E)-diethyl diazene-1,2-dicarboxylate generated in the reaction. The filtrate (125 g) was passed through a SiO$_2$ plug (500 g SiO$_2$, eluting with 2 L of DCM) to give 75 g of crude product after solvent removal. The crude product was purified again on a Combiflash® (125 g gold SiO$_2$ column), eluting with 10% EtOAc in heptanes to give 2-(((2R,3S)-3-methylhex-5-en-2-yl)thio)pyrimidine (20.37 g, 98 mmol) as a light yellow oil.

STEP 4: 2-(((2R,3S)-3-METHYLHEX-5-EN-2-YL)SULFONYL)PYRIMIDINE

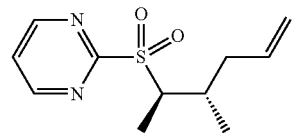 [SMILES: C=CC[C@H](C)[C@@H](C)S(=O)(=O)c1ncccn1]

To a 500 mL 3-necked-RBF with a reflux condenser was added phenylphosphonic acid (3.95 g, 24.96 mmol), sodium tungstate oxide dihydrate (8.23 g, 24.96 mmol), tetrabutylammonium sulfate (50 wt. % solution in H$_2$O, 28.7 mL, 24.96 mmol), a catalytic amount of hydrogen peroxide (30% in H$_2$O, 12.75 mL, 125 mmol), toluene (200 mL) and 2-(((2R,3S)-3-methylhex-5-en-2-yl)thio)pyrimidine (from Intermediate EE22, Step 3: 52 g, 250 mmol). The reaction was stirred at 45° C. for 5 mm at which time hydrogen peroxide 30% in H$_2$O (58.6 mL, 574 mmol) was added portion wise (10 mL at a time). Five min after the first portion of hydrogen peroxide was added, an exotherm was observed (65° C.), the reaction was taken out of oil bath, the addition was stopped and the flask placed in a H$_2$O bath until temperature stabilizes. The flask was taken out of the H$_2$O bath and the portion wise addition of hydrogen peroxide was continued at a rate in which the internal temperature stayed between 45° C. and 55° C. (~40 mm). An ice bath was utilized if the temperature went above 60° C. and an oil bath was used if the temperature fell below 45° C. The reaction was then stirred at 45° C. for 1 h. The reaction was diluted with 1400 mL of EtOAc and extracted two times with 500 mL of H$_2$O and once with 500 mL of brine. The organic layer was dried over Na$_2$SO$_4$, filtered, concentrated, and the crude purified on a Combiflash® (330 g gold SiO$_2$ column per 30 grams of crude), eluting with 0%-50% EtOAc in heptanes to give 2-(((2R,3S)-3-methylhex-5-en-2-yl)sulfonyl)pyrimidine (55.7 g, 232 mmol) as a light yellow oil.

STEP 5: SODIUM (2R,3S)-3-METHYLHEX-5-ENE-2-SULFINATE

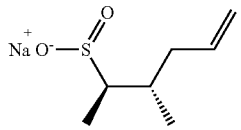

To a solution of 2-(((2R,3S)-3-methylhex-5-en-2-yl)sulfonyl)pyrimidine (from Intermediate EE22, Step 4; 52 g, 216 mmol) in MeOH (400 mL) at rt was added sodium methoxide solution (51.0 mL, 223 mmol) over 70 min. The sodium methoxide was added portion wise, the internal temperature was monitored, and the addition was slowed or the reaction was cooled in a H$_2$O bath, never letting the internal temperature exceeded 30° C. The mixture was concentrated by rotary evaporation and the waxy solid was triturated with MTBE (add 200 mL MTBE, stir for 1 h using a spatula to break up clumps), filtered (use a stream of N$_2$ over filter cake), and washed with 100 mL of cold MTBE to obtain sodium (2R,3S)-3-methylhex-5-ene-2-sulfinate (46 g, 250 mmol) as a an off white solid.

STEP 6: (2R,3S)-3-METHYLHEX-5-ENE-2-SULFONAMIDE

To a 1000 mL 3-necked-RBF was added sodium (2R,3S)-3-methylhex-5-ene-2-sulfinate (from Intermediate EE22, Step 5; 46 g, 225 mmol), 500 mL of H$_2$O and KOAc (44.1 g, 449 mmol) at rt. The flask was place in a 45° C. oil bath and hydroxylamine-O-sulfonic acid (21.09 g, 187 mmol) was added portion wise over 90 min. The internal temperature of the reaction was monitored and the reaction was removed from the oil bath (if needed) to control exotherm (Tmax=55° C.). The reaction was monitored by LC/MS every 10 min and was complete after the addition of 0.83 eq. of hydroxylamine-O-sulfonic acid. The mixture was then cooled to rt and was extracted with 1000 mL of EtOAc. The organic phase was extracted three times with 500 mL of 1 N HCl, two times with 300 mL of sat. sodium bicarbonate, once with 200 mL of brine, dried over Na$_2$SO$_4$, filtered, and concentrated by rotary evaporation to provide (2R,3S)-3-methylhex-5-ene-2-sulfonamide (32 g, 181 mmol) as a white solid.

EXAMPLE 1

(1S,3'R,6'R,7'S,8'E)-6-CHLORO-7'-HYDROXY-11',11'-DIMETHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

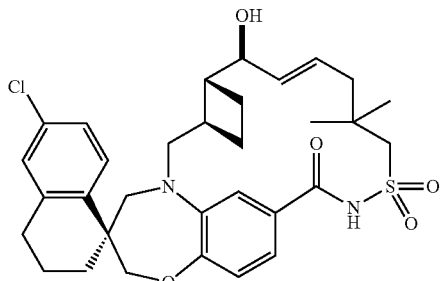

STEP 1: 2,2-DIMETHYLPENT-4-EN-1-OL

To a 100 mL flask was added methyl 2,2-dimethylpent-4-enoate (Sigma-Aldrich; 8.40 g, 59.1 mmol), lithium tetrahydroborate (4.06 mL, 124 mmol) and then slowly (1 mL every 5 min) MeOH (5.26 mL, 130 mmol). The reaction was stirred at 22° C. for 2 h. The reaction was then quenched with 300 mL of H$_2$O and extracted 2 times with 300 mL of Et$_2$O. The organic layer was dried over Na$_2$SO$_4$, filtered, and the solvent was removed by rotary evaporation (slowly over 4 h with the H$_2$O bath at 0° C., and slowly reducing the pressure, no trace product in the trap) to give 2,2-dimethylpent-4-en-1-ol (6.75 g, 59.1 mmol, 100% yield) as a clear oil.

STEP 2: 2,2-DIMETHYLPENT-4-EN-1-YL METHANESULFONATE

To a solution of 2,2-dimethylpent-4-en-1-ol (from Step 1, 6.5 g, 56.9 mmol) in DCM (40 mL) cooled to −78° C. was added MsCl (6.75 mL, 85 mmol). After addition the mixture was placed in an ice bath and stirred for 16 h (bath was at rt after 16 h). The reaction was filtered and diluted with 400 mL of DCM. The organic layer was extracted once with 200 mL of H$_2$O and again with 200 mL of 1N HCl. The organic layer was dried over Na$_2$SO$_4$, filtered, and concentrated to give an orange oil. The crude product was purified on a Combiflash® (80 g gold SiO$_2$ column), eluting with 10% to 50% EtOAc in heptanes, to give 2,2-dimethylpent-4-en-1-yl methanesulfonate (6.66 g, 34.6 mmol, 60.8% yield) as a clear oil.

STEP 3: 2-((2,2-DIMETHYLPENT-4-EN-1-YL)THIO)PYRIMIDINE

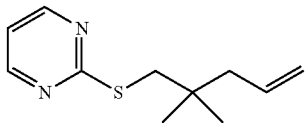

A solution of pyrimidine-2-thiol (962 mg, 8.58 mmol) and sodium methoxide (30 wt % solution in methanol, 1.825 mL, 9.83 mmol) in MeOH (8 mL) was treated with a solution of 2,2-dimethylpent-4-en-1-yl methanesulfonate (1500 mg, 7.80 mmol) in 2 mL of MeOH. To the solution was added 20 mL of DMF and then the solution was degassed by bubbling argon through the reaction mixture for 10 min. The reaction was heated to 130° C. while venting off MeOH through two 18 gauge needles for 11 h. The reaction was diluted with 300 mL of EtOAc and extracted twice with 200 mL of brine. The organic layer was dried over $Na_2SO_4$, filtered, concentrated, and the crude was purified on a Combiflash® (24 g gold $SiO_2$ column), eluting with 10% to 50% EtOAc in heptanes, to give 2-((2,2-dimethylpent-4-en-1-yl)thio)pyrimidine (1250 mg, 6.00 mmol, 77% yield) as a clear oil.

STEP 4: 2-((2,2-DIMETHYLPENT-4-EN-1-YL)SULFONYL)PYRIMIDINE

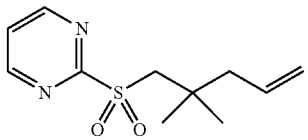 [SMILES: C=CCC(C)(C)CS(=O)(=O)c1ncccn1]

To a 25 mL flask were added phenylphosphonic acid (0.056 mL, 0.504 mmol), sodium tungstate oxide dihydrate (0.051 mL, 0.504 mmol), tetrabutylammonium sulfate (50 wt. % solution in $H_2O$, 0.580 mL, 0.504 mmol) and hydrogen peroxide (30% in $H_2O$, 1.287 mL, 12.60 mmol). The reaction was stirred at 22° C. for 5 min at which time 2-((2,2-dimethylpent-4-en-1-yl)thio)pyrimidine (from Step 3, 1050 mg, 5.04 mmol) was added as a solution in 5 mL of toluene. The reaction was stirred 22° C. for 30 mm than at 50° C. for 1 h. The reaction was diluted with 300 mL of EtOAc and extracted once with 100 mL of $H_2O$ and then once with 100 mL of brine. The organic layer was dried over $Na_2SO_4$, filtered, concentrated and the crude was purified on a Combiflash® (12 g gold $SiO_2$ column), eluting with 10% to 50% EtOAc in heptanes, to give 2-((2,2-dimethylpent-4-en-1-yl)sulfonyl)pyrimidine (910 mg, 3.79 mmol, 75% yield) as a clear oil.

STEP 5: SODIUM 2,2-DIMETHYLPENT-4-ENE-1-SULFINATE

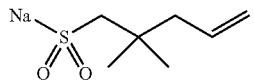

To a 100 mL flask was added 2-((2,2-dimethylpent-4-en-1-yl)sulfonyl)pyrimidine (from Step 4, 910 mg, 3.79 mmol) and MeOH (20 mL) at which time sodium methoxide solution (30 wt % solution in methanol, 0.710 mL, 3.79 mmol) was added at 22° C., and the mixture was stirred for 45 min. The reaction mixture was then concentrated by rotary evaporation and the residue was triturated with $Et_2O$. The solid was collected and dried to give sodium 2,2-dimethylpent-4-ene-1-sulfinate (465 mg, 2.52 mmol, 66.7% yield) as a bright orange solid.

STEP 6: 2,2-DIMETHYLPENT-4-ENE-1-SULFONAMIDE

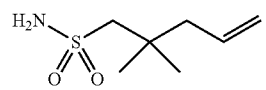

To a solution of sodium 2,2-dimethylpent-4-ene-1-sulfinate (from Step 5, 465 mg, 2.52 mmol) and sodium acetate (414 mg, 5.05 mmol) in $H_2O$ (20 mL) at rt was added hydroxylamine-o-sulfonic acid (571 mg, 5.05 mmol). The mixture was heated to 50° C., and stirred for 1 h then stirred at rt for 4 h. The mixture was extracted with EtOAc, the organic phase was dried over $Na_2SO_4$, filtered and concentrated. The crude was purified on a Combiflash® (12 g gold $SiO_2$ column), eluting with 10% to 50% EtOAc in heptanes, to provide 2,2-dimethylpent-4-ene-1-sulfonamide (246 mg, 1.388 mmol, 55.0% yield) as a white solid.

STEP 7: (S)-6'-CHLORO-5-(((1R,2R)-2-((S,E)-1-HYDROXY-5,5-DIMETHYL-6-SULFAMOYL-HEX-2-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLIC ACID

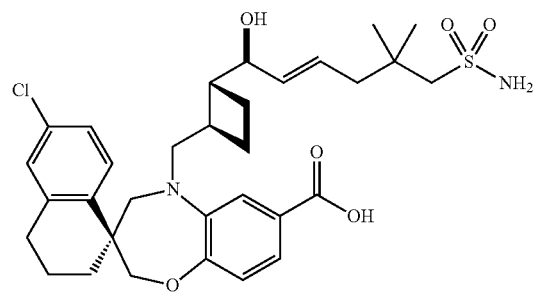

To a 100 mL flask was added (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A; 100 mg, 0.196 mmol), 2,2-dimethylpent-4-ene-1-sulfonamide (from Step 6, 104 mg, 0.588 mmol) and DCE (2 mL). The solution was sparged with argon for 15 min at which time (1,3-dimesitylimidazolidin-2-ylidene)(2-isopropoxybenzylidene)ruthenium(VI) chloride (12.29 mg, 0.020 mmol) was added as a 0.2 mL solution in DCE at rt. The mixture was stirred at rt for 16 h. The reaction mixture was then bubbled with air for 5 min and filtered. The solvent was removed from the filtrate and the crude product was directly purified on a Combiflash® (12 g gold SiO₂ column), eluting with 50%-90% EtOAc in heptanes+0.2% AcOH, to give (S)-6'-chloro-5-(((1R,2R)-2-((S,E)-1-hydroxy-5,5-dimethyl-6-sulfamoylhex-2-en-1-yl)cyclobutyl)methyl)-3',4',5-tetrahydro-2H,2'H-spiro[benzo[b][1,4]oxazepine-3,1'-naphthalene]-7-carboxylic acid (98 mg, 0.159 mmol, 81% yield) as a white solid.

STEP 8: (1S,3'R,6'R,7'S,8'E)-6-CHLORO-7'-HYDROXY-11',11'-DIMETHYL-3,4-DIHYDRO-2H, 15'H-SPIRO[NAPHTHALENE-1,22'-[20]OXA[13]THIA[1,14]DIAZATETRACYCLO[14.7.2.0³,⁶.0¹⁹,²⁴]PENTACOSA[8,16,18,24]TETRAEN]-15'-ONE 13',13'-DIOXIDE

To a 250 mL flask containing (S)-6'-chloro-5-(((1R,2R)-2-((S,E)-1-hydroxy-5,5-dimethyl-6-sulfamoylhex-2-en-1-yl)cyclobutyl)methyl)-3',4',5-tetrahydro-2H,2'H-spiro[benzo[b][1,4]oxazepine-3,1'-naphthalene]-7-carboxylic acid (from Step 7, 98 mg, 0.159 mmol) which was previously dried by azeotroping twice with 5 mL of toluene, was added N,N-dimethylpyridin-4-amine (33.0 mg, 0.270 mmol) and 100 mL of DCM. The reaction mixture was cooled to 0° C. at which N-(3-dimethylaminopropyl)-N'-ethylcarbodiimide hydrochloride (60.9 mg, 0.318 mmol) was added. The reaction was stirred at rt for 12 h. The mixture was then quenched with 100 mL of 1N HCl and extracted with 300 mL of DCM. The organic layer were dried over anhydrous Na₂SO₄, filtered, and concentrated by rotary evaporation. The crude was first purified on a Combiflash® (12 g gold SiO₂ column), eluting with 30%-70% EtOAc in heptanes+0.2% AcOH, followed by preparative reverse-phase HPLC (Gemini™ Prep C₁₈ 5 μm column; Phenomenex, Torrance, CA; gradient elution of 10% to 90% MeCN in H₂O, where both solvents contain 0.1% TFA, 45 min method), to give (1S,3'R,6'R,7'S,8'E)-6-chloro-7'-hydroxy-11',11'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (2.5 mg, 4.17 μmol, 2.63% yield) as a white solid. ¹H NMR (400 MHz, CDCl₃) δ 8.35 (br. s., 1H), 7.70 (d, J=8.4 Hz, 1H), 7.18 (dd, J=2.2, 8.5 Hz, 1H), 7.09 (d, J=2.2 Hz, 1H), 6.93 (s, 2H), 6.85-6.79 (m, 1H), 5.98-5.82 (m, 1H), 5.69 (dd, J=8.1, 15.4 Hz, 1H), 4.27-4.17 (m, 1H), 4.14-4.01 (m, 2H), 4.15-3.94 (m, 1H), 3.79-3.60 (m, 2H), 3.25 (d, J=13.3 Hz, 2H), 3.14-2.95 (m, 1H), 2.86-2.62 (m, 2H), 2.49-2.21 (m, 3H), 2.14-1.89 (m, 4H), 1.86-1.80 (m, 3H), 1.69-1.61 (m, 1H), 1.48-1.36 (m, 1H), 1.26 (s, 6H). m/z (ESI, +ve ion) 599.0 (M+H)⁺.

EXAMPLE 2

(1S,3'R,6'R,7'S,8'E,11'S,12'R)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[8,16,18,24]TETRAEN]-15'-ONE 13',13'-DIOXIDE

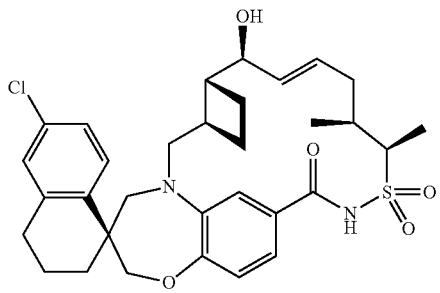

STEP 1

(S)-6'-CHLORO-5-(((1R,2R)-2-((S)-1-HYDROXYALLYL)CYCLOBUTYL)METHYL)-N-(((2R,3S)-3-METHYLHEX-5-EN-2-YL)SULFONYL)-3',4',5-TETRAHYDRO-2H,2'H-SPIRO[BENZO[B][1,4]OXAZEPINE-3,1'-NAPHTHALENE]-7-CARBOXAMIDE

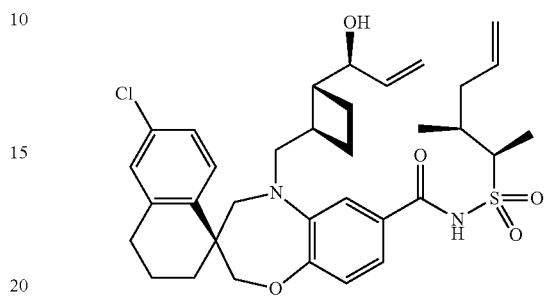

DMAP (3.42 g, 28.0 mmol) was added to a solution of (S)-6'-chloro-5-(((1R,2R)-2-((S)-1-hydroxyallyl)cyclobutyl)methyl)-3',4',5-tetrahydro-2H,2'H-spiro[benzo[b][1,4]oxazepine-3,1'-naphthalene]-7-carboxylic acid (Intermediate AA11A; 7.7 g, 16.45 mmol) and (2R,3S)-3-methylhex-5-ene-2-sulfonamide (Intermediate EE22; 5.83 g, 32.9 mmol) in DCM (411 mL) cooled to 0° C. EDC hydrochloride (6.31 g, 32.9 mmol) was then added slowly portionwise. The mixture was stirred while allowing to reach ambient temperature overnight. The mixture was washed with 1N HCl and brine and the aqueous layer was back-extracted with EtOAc. The combined organics were dried over MgSO₄, filtered and concentrated. The yellow oily residue was loaded onto a 220 ISCO gold column and purified eluting with 0% to 20% EtOAc (containing 0.3% AcOH)/heptanes, to provide (S)-6'-chloro-5-(((1R,2R)-2-((S)-1-hydroxyallyl)cyclobutyl)methyl)-N-(((2R,3S)-3-methylhex-5-en-2-yl)sulfonyl)-3',4',5-tetrahydro-2H,2'H-spiro[benzo[b][1,4]oxazepine-3,1'-naphthalene]-7-carboxamide (7.89 g, 12.58 mmol, 76% yield).

STEP 2: (1S,3'R,6'R,7'S,8'E,11'S,12'R)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[8,16,18,24]TETRAEN]-15'-ONE 13',13'-DIOXIDE

To a 20 L reactor blanketed in argon was charged 14 L of 1,2-DCE. (S)-6'-chloro-5-(((1R,2R)-2-((S)-1-hydroxyallyl)cyclobutyl)methyl)-N-(((2R,3S)-3-methylhex-5-en-2-yl)sulfonyl)-3',4',5-tetrahydro-2H,2'H-spiro[benzo[b][1,4]oxazepine-3,1'-naphthalene]-7-carboxamide (18.75 g, 29.9 mmol) was added as a solution in 400 mL 1,2-DCE followed by a 400 mL rinse. The reactor was sealed and purged with argon. Hoveyda-Grubbs II (1.873 g, 2.99 mmol) was added as a solution in 150 mL of 1,2-DCE followed by a 50 mL rinse. The reactor was heated to 60° C. over 1 h with an argon sweep of the headspace and held at temperature for 9 h. The reaction was quenched by the addition of 2-(2-(vinyloxy)ethoxy)ethanol (1.501 g, 11.36 mmol), cooled to ambient temperature, and concentrated to ~200 mL volume by rotary evaporation. The reaction was transferred to a 1 L RBF and diluted to 500 mL volume with 1,2-DCE. The reaction was treated with 52 g of Silicycle Si-Thiol (Sili-Cycle Inc., Quebec City, Quebec CANADA Cat #R51030B) with stirring for 9 h at 40° C., filtered and rinsed with 2×65 mL DCM. The solution was passed through a Whatman GF/F filter cup (GE Healthcare Bio-Sciences Pittsburgh, PA, USA) to afford a transparent yellow solution. The reaction was concentrated to afford a crude product mass of 27.4 g. The residue was slurried in 250 mL IPAc and evaporated to dryness three times. The reaction was suspended in 270 mL IPAc, heated to dissolution, allowed to cool to ambient temperature, and stirred for 18. The solids were filtered and washed with 65 mL IPAc. The solid was air-dried for 30 min then placed under high vacuum for 3 h to afford 12.56 g of (1S,3'R,6'R,7'S,8'E,11'S,12'R)-6-chloro-7'-hydroxy-11',12'-dimethyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide which is 91.7% by weight. $^1$H NMR (500 MHz, CD$_2$Cl$_2$) δ 8.06 (s, 1H), 7.71 (d, J=8.56 Hz, 1H), 7.17 (dd, J=8.44, 2.32 Hz, 1H), 7.09 (d, J=2.20 Hz, 1H), 6.91 (s, 3H), 5.81 (ddd, J=14.92, 7.82, 4.16 Hz, 1H), 5.71 (dd, J=15.41, 8.31 Hz, 1H), 4.16-4.26 (m, 2H), 3.83 (d, J=14.43 Hz, 1H), 3.69 (d, J=14.43 Hz, 1H), 3.25 (d, J=14.43 Hz, 1H), 3.04 (dd, J=15.28, 9.66 Hz, 1H), 2.68-2.84 (m, 2H), 2.41 (app qd, J=9.80, 3.70 Hz, 1H), 2.25-2.34 (m, 1H), 1.93-2.00 (m, 5H), 1.74-2.11 (m, 9H), 1.62-1.73 (m, 1H), 1.43 (d, J=7.09 Hz, 3H) 1.35-1.42 (m, 1H) 1.03 (d, J=6.60 Hz, 3H). MS (ESI, +ve ion) m/z 599.2 (M+H)$^+$.

EXAMPLE 3

(1S,3'R,6'R,7'S,8'Z,11'S,12'R)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

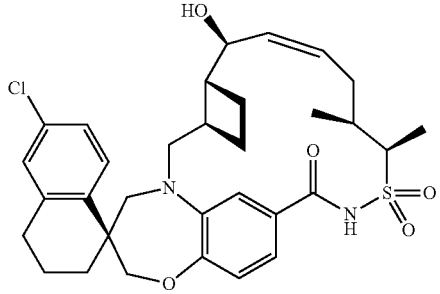

A 1000 mL RBF was charged with (S)-6'-chloro-5-(((1R,2R)-2-((S)-1-hydroxyallyl)cyclobutyl)methyl)-N-(((2R,3S)-3-methylhex-5-en-2-yl)sulfonyl)-3',4,4',5-tetrahydro-2H,2'H-spiro[benzo[b][1,4]oxazepine-3,1'-naphthalene]-7-carboxamide (Example 2, Step 1, 710 mg, 1.132 mmol) and DCM (569.00 mL). The solution was sparged with argon for 15 min, then Hoveyda-Grubbs II (70.9 mg, 0.113 mmol) was added. The mixture was stirred at 45° C. for 15 h. The reaction mixture was sparged with air for 20 min while cooling to ambient temperature, then concentrated under reduced pressure. The crude oil was absorbed onto a plug of SiO$_2$ gel and purified through a 220 g ISCO gold column, eluting with 10-20 (15 min)-50% EtOAc (containing 0.3% AcOH) in heptanes over 36 min to provide (1S,3'R,6'R,7'S,8'Z,11'S,12'R)-6-chloro-7'-hydroxy-11',12'-dimethyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 3) as the first eluting minor isomer followed by (1S,3'R,6'R,7'S,8'E,11'S,12'R)-6-chloro-7'-hydroxy-11',12'-dimethyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 2) as the second eluting major isomer. The semi-pure material thus obtained was loaded onto a SiO$_2$ gel column and purified eluting with 5% acetone in DCM to provide the title compound. $^1$H NMR (500 MHz, CD$_2$Cl$_2$) δ 8.83 (br. s., 1H), 7.71 (d, J=8.3 Hz, 1H), 7.17 (dd, J=2.3, 8.4 Hz, 1H), 7.11 (dd, J=1.6, 8.2 Hz, 1H), 7.0) (d, J=2.2 Hz, 1H), 7.02 (s, 1H), 6.93 (d, J=8.1 Hz, 1H), 5.82-5.75 (m, 1H), 5.67 (dd, J=6.5, 11.4 Hz, 1H), 4.43 (s, 1H), 4.12-4.05 (m, 2H), 3.85-3.76 (m, 2H), 3.67 (d, J=14.4 Hz, 1H), 3.25 (d, J=14.4 Hz, 1H), 3.28-3.19 (m, 1H), 2.83-2.65 (m, 3H), 2.38-2.23 (m, 2H), 2.19-2.11 (m, 2H), 2.10-1.99 (m, 3H), 1.97-1.87 (m, 2H), 1.87-1.80 (m, 1H), 1.79-1.70 (m, 2H), 1.47 (d, J=7.3 Hz, 3H), 1.47-1.40 (m, 1H), 1.06 (d, J=6.6 Hz, 3H). MS (ESI, +ve ion) m/z 599.1 (M+H)$^+$.

EXAMPLE 4

(1S,3'R,6'R,7'S,8'E,11'S,12'R)-6-CHLORO-7'-METHOXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-ONE-13',13'-DIOXIDE

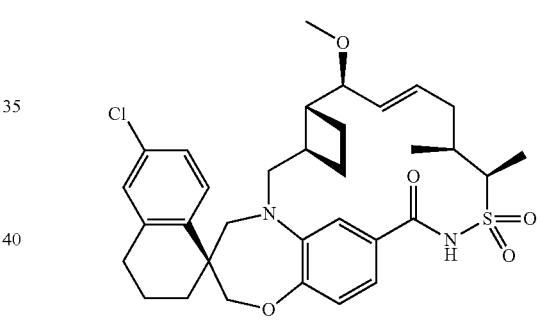

To a slurry of (1S,3'R,6'R,7'S,8'E,11'S,12'R)-6-chloro-7'-hydroxy-11',12'-dimethyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 2; 32.6 g, 49.1 mmol) (containing 9.8% toluene, starting material was not completely soluble in Me-THF) and MeI (15.2 mL, 245 mmol) in Me-THF (820 mL) was added KHMDS (1.0 M in THF, 167 mL, 167 mmol) dropwise for 30 min while maintaining reaction temperature between −44° C., and −38° C. under N$_2$. After the mixture was stirred at −44° C. for min, the reaction was allowed to warm to rt and stirred for 1.5 h (LC/MS confirmed the reaction was complete). The reaction mixture was cooled to 5° C., quenched (170 mL of sat. aqueous NH$_4$Cl and 170 mL of H$_2$O) while maintaining temperature between 5° C., and 14° C., and acidified (340 mL of 10% aqueous citric acid). The organic layer was separated and the aqueous layer was back-extracted with EtOAc (500 mL). The combined organic layers were washed with brine (3×500 mL), dried (MgSO$_4$), and concentrated under reduced pressure to provide a crude target compound (30.1 g, 49.1 mmol, quantitatively) (purity>98% with no over 1% major impurity from HPLC) as a bright yellow solid. After the same scale reaction was repeated four times, all the crude products (4×49.1 mmol=196 mmol) were dissolved in EtOAc, combined, and concentrated under reduced pressure. Then the combined crude product was recrystallized as follows: ethanol (800 mL) was added to the crude product and the resulting slurry solution was shaken while heating the solution for 20 min. $H_2O$ (250 mL) was added dropwise for 30 min at rt and the slurry was cooled down to 0° C. After the slurry was kept in an ice bath for 4 h, the solid product was filtered through filter paper. The filter cake was rinsed with ice-cold 30% $H_2O$ in EtOH (300 mL) and air-dried for 2 days. The product was further dried under high vacuum at 40° C. for 4 days to provide the pure target compound (115 g, 188 mmol, 96% yield) as a white solid. $^1H$ NMR (6(0) MHz, DMSO-$d_6$) δ 11.91 (s, 1H), 7.65 (d, J=8.6 Hz, 1H), 7.27 (dd, J=8.5, 2.3 Hz, 1H), 7.17 (d, J=2.4 Hz, 1H), 7.04 (dd, J=8.2, 2.0 Hz, 1H), 6.90 (d, J=8.2 Hz, 1H), 6.76 (d, J=1.8 Hz, 1H), 5.71 (ddd, J=15.1, 9.7, 3.5 Hz, 1H), 5.50 (ddd, J=15.2, 9.2, 1.1 Hz, 1H), 4.08 (qd, J=7.2, 7.2, 7.2, 1.5 Hz, 1H), 4.04 (d, J=12.3 Hz, 1H), 3.99 (d, J=12.3 Hz, 1H), 3.73 (d, J=14.9 Hz, 1H), 3.56 (d, J=14.1 Hz, 1H), 3.53 (dd, J=9.1, 3.3 Hz, 1H), 3.19 (d, J=14.1 Hz, 1H), 3.09 (s, 3H), 3.03 (dd, J=15.4, 10.4 Hz, 1H), 2.79 (dt, J=17.0, 3.5, 3.5 Hz, 1H), 2.69 (ddd, J=17.0, 10.7, 6.3 Hz, 1H), 2.44-2.36 (m, 1H), 2.24-2.12 (m, 2H), 2.09 (ddd, J=15.5, 9.6, 2.3 Hz, 1H), 1.97 (dt, J=13.6, 3.6, 3.6 Hz, 1H), 1.91-1.80 (m, 4H), 1.80-1.66 (m, 3H), 1.38 (td, J=12.3, 12.3, 3.5 Hz, 1H), 1.33 (d, J=7.2 Hz, 3H), 0.95 (d, J=6.8 Hz, 3H); [α]$_D$ (24° C., c=0.0103 g/mL, DCM)=−86.07°; m.p. 222.6-226.0° C.; FT-IR (KBr): 3230 (b), 2931 (b), 1688 (s), 1598 (s), 1570 (s), 1505 (s), 1435 (s), 1384 (s), 1335 (s), 1307 (s), 1259 (s), 1155 (s), 1113 (s), 877 (s), 736 (s) cm$^{-1}$; Anal. Calcd. for $CH_3H_{41}ClN_2O_5S$: C, 64.64; H, 6.74; N, 4.57; Cl, 5.78; S, 5.23. Found: C, 64.71; H, 6.81; N, 4.65; Cl, 5.81; S, 5.11; HRMS (ESI) m/z 613.2493 [M+H]$^+$ ($C_{33}H_{41}ClN_2O_5S$ requires 613.2503).

The mother liquor was concentrated under reduced pressure and further purification of the residue by flash column chromatography (200 g $SiO_2$, 10% and 10% to 45% and 45% EtOA/Hex w/0.3% AcOH, gradient elution) provided additional pure product (3.1 g, 5.1 mmol, 2.6%) as an off-white solid.

EXAMPLE 5

(1S,3'R,6'R,7'S,8'Z,11'S,12'R)-6-CHLORO-7'-METHOXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

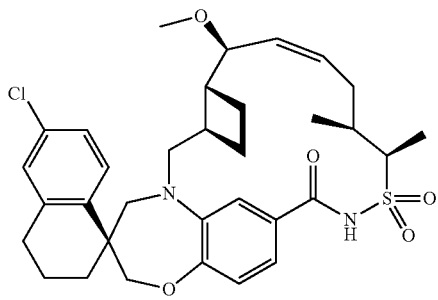

To a solution of (1S,3'R,6'R,7'S,8'Z,11'S,12'R)-6-chloro-7'-hydroxy-11',12'-dimethyl-3,4-dihydro-2h,15'h-spiro [naphthalene-1,22'-[20]oxa[13]thia[1,14]diazatetracyclo [14.7.2.0$^{3,6}$.0$^{19,24}$]pentacosa[8,16,18,24]tetraen]-15'-one 13',13'-dioxide (Example 3; 34 mg; 0.057 mmol) in THF cooled to 0° C. was added sodium hydride (60% dispersion in mineral oil; 22.70 mg, 0.567 mmol). The reaction mixture was stirred at 0° C. for 20 min, and then MeI (0.018 mL, 0.284 mmol) was added. The reaction mixture was stirred at ambient temperature for 1 h, then quenched with aqueous $NH_4Cl$, and diluted with EtOAc. The organic layer was dried over $MgSO_4$ and concentrated. Purification of the crude material via column chromatography eluting with 10-40% EtOAc (containing 0.3% AcOH)/heptanes provided (1S,3'R, 6'R,7'S,8'Z,11'S,12'R)-6-chloro-7'-methoxy-11',12'-dimethyl-3,4-dihydro-2h,15'h-spiro[naphthalene-1,22'-[20]oxa [13]thia[1,14]diazatetracyclo[14.7.2.0$^{3,6}$.0$^{19,24}$]pentacosa [8,16,18,24]tetraen]-15'-one 13',13'-dioxide (34 mg, 0.054 mmol, 95% yield). $^1H$ NMR (400 MHz, $CD_2Cl_2$) δ 8.29 (s, 1H), 7.71 (d, J=8.4 Hz, 1H), 7.17 (dd, J=2.2, 8.5 Hz, 1H), 7.09 (d, J=2.3 Hz, 1H), 7.01 (dd, J=1.6, 7.8 Hz, 1H), 6.92 (d, J=8.2 Hz, 1H), 6.88 (s, 1H), 5.90-5.80 (m, 1H), 5.54 (t, J=10.2 Hz, 1H), 4.14-4.04 (m, 3H), 3.87-3.79 (m, 2H), 3.73 (d, J=14.7 Hz, 1H), 3.32 (d, J=14.5 Hz, 1H), 3.23 (s, 3H), 3.28-3.19 (m, 1H), 2.82-2.73 (m, 2H), 2.62 (t, J=10.6 Hz, 1H), 2.55-2.44 (m, 1H), 2.29-2.21 (m, 1H), 2.10-1.97 (m, 4H), 1.97-1.80 (m, 4H), 1.75 (dd, J=8.9, 18.7 Hz, 1H), 1.48 (d, J=7.4 Hz, 3H), 1.43 (br. s., 1H), 1.08 (d, J=6.5 Hz, 3H). MS (ESI, +ve ion) m/z 613.3 (M+H)$^+$.

EXAMPLE 6

(1S,3'R,6'R,7'S,11'S,12'R)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[16,18,24]TRIEN]-15'-ONE 13',13'-DIOXIDE

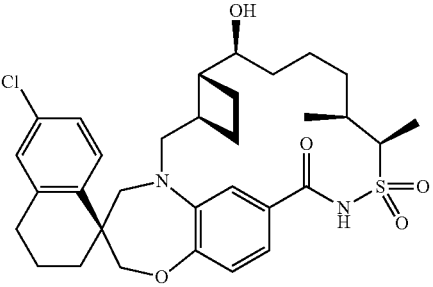

A mixture of (1S,3'R,6'R,7'S,8'E,11'S,12'R)-6-chloro-7'-hydroxy-11',12'-dimethyl-3,4-dihydro-2h,15'h-spiro[naphthalene-1,22'-[20]oxa[13]thia[1,14]diazatetracyclo [14.7.2.0$^{3,6}$.0$^{19,24}$]pentacosa[8,16,18,24]tetraen]-15'-one 13',13'-dioxide (Example 2, 7.5 mg, 0.013 mmol) and platinum (IV) oxide (2.84 mg, 0.013 mmol) in EtOAc (1.536 mL) was stirred under an atmosphere of $H_2$ (balloon) at ambient temperature for 45 min. The reaction mixture was then filtered through a syringe filter. The crude material was purified by chromatography through a Redi-Sep® pre-packed $SiO_2$ gel column (4 g), eluting with 15% to 50% EtOAc (containing 0.3% AcOH)/heptanes, to provide the title product. $^1H$ NMR (400 MHz, $CD_2Cl_2$) δ 8.24 (br. s., 1H), 7.71 (d, J=8.4 Hz, 1H), 7.17 (dd, J=2.3, 8.4 Hz, 1H), 7.09 (d, J=2.2 Hz, 1H), 7.06 (d, J=1.8 Hz, 1H), 6.99 (dd, J=2.0, 8.0 Hz, 1H), 6.93 (d, J=8.2 Hz, 1H), 4.10 (s, 2H), 4.05 (ddd, J=1.2, 7.2, 14.3 Hz, 1H), 3.82 (d, J=15.3 Hz, 1H), 3.74-3.69 (br, S., 1H), 3.68 (d, J=14.3 Hz, 1H), 3.23 (d, J=14.3 Hz, 1H), 3.06 (dd, J=7.3, 15.4 Hz, 1H), 2.84-2.68 (m, 2H), 2.38 (d, J=3.5 Hz, 2H), 2.08-1.96 (m, 3H), 1.96-1.88 (m, 1H), 1.88-1.75 (m, 2H), 1.74-1.56 (m, 4H), 1.47 (d, J=12.1 Hz, 2H), 1.40 (d, J=7.2 Hz, 3H), 1.32-1.26 (m, 2H), 1.23-1.15 (m, 2H), 1.00 (d, J=6.8 Hz, 3H). MS (ESI, +ve ion) m/z 601.2 (M+H)+.

EXAMPLE 7

(1S,3'R,6'R,7'S,11'S,12'R)-6-CHLORO-7'-METHOXY-11', 12'-DIMETHYL-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[16,18,24]TRIEN]-15'-ONE 13',13'-DIOXIDE

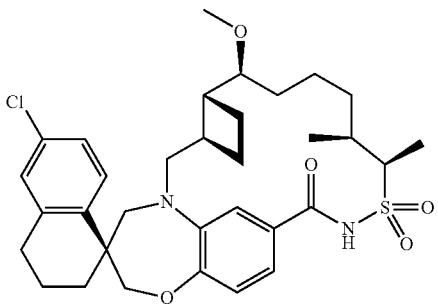

The title compound was synthesized from a mixture of (1S,3'R,6'R,7'S,8'E,11'S,12'R)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one-13',13'-dioxide (Example 4) following the procedure described in Example 6. ¹H NMR (500 MHz, CD₂Cl₂) δ 8.14 (s, 1H), 7.72 (d, J=8.6 Hz, 1H), 7.17 (dd, J=2.2, 8.6 Hz, 1H), 7.09 (d, J=2.2 Hz, 1H), 7.00 (d, J=1.7 Hz, 1H), 6.95 (dd, J=2.0, 8.1 Hz, 1H), 6.92 (d, J=8.1 Hz, 1H), 4.10 (s, 2H), 4.07 (ddd, J=1.2, 7.1, 14.2 Hz, 1H), 3.81 (dd, J=2.0, 15.2 Hz, 1H), 3.68 (d, J=14.2 Hz, 1H), 3.25 (s, 3H), 3.22 (dd, J=9.0, 14.4 Hz, 1H), 3.03 (dd, J=8.6, 15.4 Hz, 1H), 2.83-2.69 (m, 2H), 2.60-2.51 (m, 1H), 2.41-2.32 (m, 1H), 2.07-2.01 (m, 1H), 1.99-1.88 (m, 2H), 1.88-1.77 (m, 1H), 1.76-1.68 (m, 1H), 1.68-1.58 (m, 2H), 1.53-1.46 (m, 2H), 1.45-1.42 (m, 1H), 1.40 (d, J=7.1 Hz, 3H), 1.29 (br. s., 1H), 1.25-1.21 (m, 2H), 1.20-1.10 (m, 2H), 0.99 (d, J=6.8 Hz, 3H). MS (ESI, +ve ion) m/z 615.1 (M+H)+.

EXAMPLE 8

(1S,3'R,6'R,7'S,8'E)-6-CHLORO-7'-HYDROXY-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[8,16,18,24]TETRAEN]-15'-ONE 13',13'-DIOXIDE

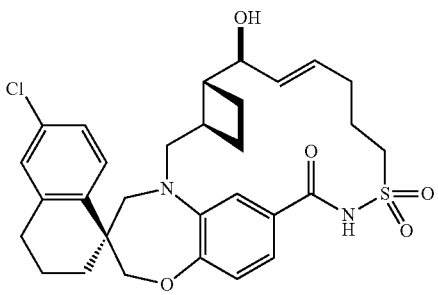

Step 1: (S)-6'-CHLORO-5-(((1R,2R)-2-((S,E)-1-HYDROXY-6-SULFAMOYLHEX-2-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLIC ACID

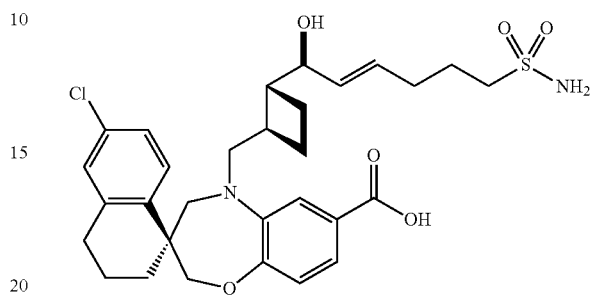

To a 100 mL flask was added (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A; 500 mg, 0.980 mmol), pent-4-ene-1-sulfonamide (Intermediate EE19; 878 mg, 5.88 mmol), and DCE (14 mL). The solution was sparged with argon for 15 min at which time Hoveyda-Grubbs II (61.4 mg, 0.098 mmol) was added as a 0.2 mL solution in DCE at rt. The mixture was stirred at rt and sparged with argon (the vial was vented) for 2 h. The reaction mixture was then bubbled with air for 5 min and filtered to separate the insoluble sulfonamide homodimer. The crude product was purified on a Combiflash® (24 g gold SiO₂ column), eluting with 50%-90% EtOAc in heptanes+ 0.2% AcOH) to give (S)-6'-chloro-5-(((1R,2R)-2-((S,E)-1-hydroxy-6-sulfamoylhex-2-en-1-yl)cyclobutyl)methyl)-3',4,4',5-tetrahydro-2h,2'h-spiro[benzo[b][1,4]oxazepine-3,1'-naphthalene]-7-carboxylic acid (439 mg, 0.745 mmol, 76% yield) as a white solid.

Step 2: (1S,3'R,6'R,7'S,8'E)-6-CHLORO-7'-HYDROXY-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[8,16,18,24]TETRAEN]-15'-ONE 13',13'-DIOXIDE To a 1 L flask containing (S)-6'-chloro-5-(((1R,2R)-2-((S,E)-1-hydroxy-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic acid (from Step 1, 439 mg, 0.745 mmol), which was previously dried by azeotroping twice with 10 mL of toluene, was added N,N-dimethylpyridin-4-amine (155 mg, 1.267 mmol) and 400 mL of DCM. The reaction mixture was cooled to 0° C. at which time N-(3-dimethylaminopropyl)-N'-ethylcarbodiimide hydrochloride (286 mg, 1.490 mmol) was slowly added. The reaction was then stirred at rt for 18 h. The mixture was quenched with 200 mL of 1N HCl and extracted with 600 mL of EtOAc. The organic layer was dried over anhydrous Na₂SO₄, filtered, and concentrated by rotary evaporation. The crude product was purified on a Combiflash® (24 g gold SiO₂ column), eluting with 30%-70% EtOAc in heptanes, to give the title compound as a white solid. ¹H NMR (500 MHz, CD₃OD) δ 7.75 (d, J=8.3 Hz, 1H), 7.20 (dd, J=2.9, 7.6 Hz, 11H), 7.12 (d, J=3.7 Hz, 1H), 7.00 (dd, J=1.7, 8.8 Hz, 1H), 6.94 (d, J=8.3 Hz, 1H), 6.88 (d, J=2.2 Hz, 1H), 5.95-5.86 (m, 1H), 5.70 (dd, J=8.8, 15.9 Hz, 1H), 4.25-4.19 (m, 1H), 4.22 (dd, J=4.4, 8.6 Hz, 1H), 4.14-4.06 (m, 3H), 4.14-4.05 (m, 3H), 3.84 (d, J=15.2 Hz, 1H), 3.68 (d, J=15.2 Hz, 1H), 3.09 (dd, J=8.3, 15.9 Hz, 1H), 2.87-2.74 (m, 2H), 2.45-2.30 (m, 3H), 2.14-1.88 (m, 5H), 1.86-1.69 (m, 4H). m/z (ESI, +ve ion) 571.2 (M+H)$^+$.

EXAMPLE 9

(1S,3'R,6'R,7'S,8'E)-6-CHLORO-7'-METHOXY-3,4-DI-HYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

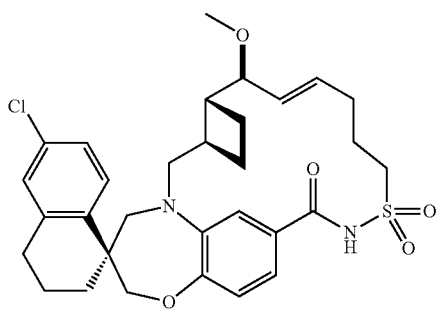

To a 100 mL flask was added (1S,3'R,6'R,7'S,8'E)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 8, 138 mg, 0.242 mmol), THF (10 mL), and sodium hydride (29.0 mg, 1.208 mmol). The reaction was stirred at rt for 15 min at which time MeI (0.092 mL, 1.480 mmol) was added. The reaction was stirred at rt for 2 h at which time additional sodium hydride (58.0 mg, 2.42 mmol) and MeI (0.092 mL, 1.480 mmol) were added and the reaction was stirred at rt for an additional 16 h. The reaction was quenched with 100 mL of satd NH$_4$C and extracted with 400 mL of EtOAc. The organic layer was dried over Na$_2$SO$_4$, filtered, and the solvent was removed by rotary evaporation. The crude product was purified on a Combiflash® (12 g gold SiO$_2$ column), eluting with 10% to 50% EtOAc in heptanes, to give (1S,3'R,6'R,7'S,8'E)-6-chloro-7'-methoxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (120 mg, 0.205 mmol, 85% yield) as an off white solid. $^1$H NMR (400 MHz, CDCl$_3$) δ 8.02 (s, 1H), 7.70 (d, J=8.6 Hz, 1H), 7.19 (dd, J=2.2, 8.5 Hz, 1H), 7.10 (d, J=2.2 Hz, 1H), 6.97-6.87 (m, 2H), 6.84 (d, J=1.6 Hz, 1H), 5.88 (ddd, J=5.2, 8.1, 15.1 Hz, 1H), 5.53 (dd, J=8.7, 15.4 Hz, 1H), 4.30 (ddd, J=4.8, 9.8, 15.0 Hz, 1H), 4.15-3.98 (m, 2H), 3.84-3.69 (m, 2H), 3.67 (dd, J=3.8, 8.7 Hz, 1H), 3.36-3.21 (m, 2H), 3.25 (s, 3H), 3.01 (dd, J=10.3, 15.2 Hz, 1H), 2.87-2.64 (m, 2H), 2.52-2.29 (m, 3H), 2.25-1.91 (m, 5H), 1.88-1.75 (m, 3H), 1.71-1.60 (m, 2H), 1.41 (t, J=12.4 Hz, 1H). m/z (ESI, +ve ion) 585.0 (M+H)$^+$.

EXAMPLE 10

(1S,3'R,6'R,7'S)-6-CHLORO-7'-HYDROXY-3,4-DI-HYDRO-2H,15'HSPIRO[NAPHTHALENE-1,22'[20]OXA[13]THIA[1,14]DIAZATETRACYCLO[14.7.2.0$^{3,6}$.0$^{19,24}$]PENTACOSA[16,18,24]TRIEN]-15'-ONE 13',13'-DIOXIDE

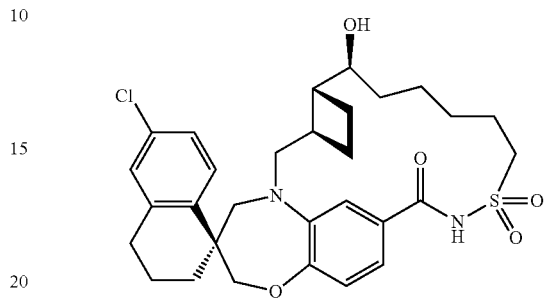

Step 1: (1'S)—N-(BUT-3-EN-1-YLSULFONYL)-6'-CHLORO-5-(((1R,2R)-2-(1-HYDROXYBUT-3-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXAMIDE

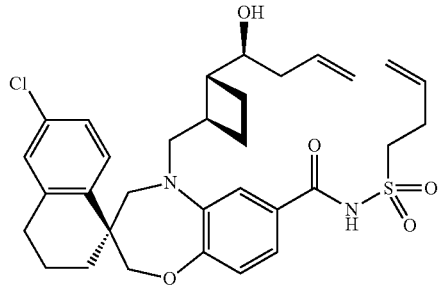

DMAP (0.830 g, 6.80 mmol) was added to a solution of (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA13A; 1.82 g, 3.78 mmol) and but-3-ene-1-sulfonamide (EE15; 1.873 g, 13.86 mmol) in DCM (140 mL) which was cooled to 0° C. EDC (1.303 g, 6.80 mmol) was added portion by portion and it was stirred at ambient temperature for 16 h. The reaction mixture was diluted with EtOAc (400 mL), washed with 1N HCl solution (2×5 mL), brine (3 mL), dried over anhydrous Na$_2$SO$_4$, and concentrated. The residue was loaded to a 80 g ISCO gold column and eluted with 0% to 15% EtOAc (containing 0.3% AcOH)/Hex (containing 0.3% AcOH) to provide the title compound (2.09 g) as a white solid. m/z (ESI, +ve ion) 599.0 (M+H)$^+$.

Step 2: (1S,3'R,6'R,7'S,9'E)-6-CHLORO-7'-HYDROXY-3,4-DIHYDRO-2H,15'H-SPIRO[NAPHTHALENE-1,22'-[20]OXA[13]THIA[1,14]DIAZATETRACYCLO [14.7.2.0$^{3,6}$.0$^{19,24}$]PENTACOSA[9,16,18,24]TETRAEN]-15'-ONE 13',13'-DIOXIDE

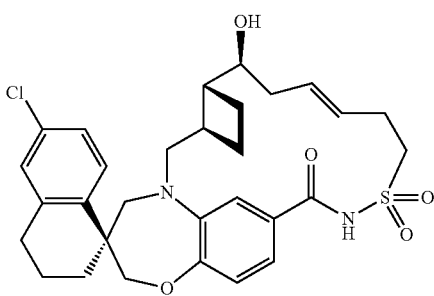

A 1 L RBF was charged with ('S)—N-(but-3-en-1-ylsulfonyl)-6'-chloro-5-(((1R,2R)-2-(1-hydroxybut-3-en-1-yl)cyclobutyl)methyl)-3',4,4',5-tetrahydro-2H,2'H-spiro [benzo[b][1,4]oxazepine-3,1'-naphthalene]-7-carboxamide (from Step 1, 1.02 g, 1.70 mmol) in toluene (587 mL). The mixture was stirred at ambient temperature for 10 min to dissolve the solid starting material and then subjected to three cycles of evacuation/back-filling with $N_2$. To the homogeneous solution was added a solution of Hoveyda-Grubbs II (0.213 g, 0.340 mmol) in toluene (20 mL). After the mixture was stirred at 106° C. under $N_2$ for 75 min, air was blown for 10 min to deactivate the catalyst, and then concentrated. The residue was loaded to a 330 g ISCO gold column and eluted with 0% to 25% EtOAc (containing 0.3% AcOH)/Hex (containing 0.3% AcOH). The second peak was the title compound (0.27 g) as a white solid. $^1$H NMR (400 MHz, CD$_2$Cl$_2$) δ 9.96 (br. s., 1H), 7.78-7.65 (m, 1H), 7.37 (dd, J=1.96, 8.22 Hz, 1H), 7.16 (dd, J=2.35, 8.61 Hz, 1H), 7.10 (d, J=2.15 Hz, 1H), 7.04 (br. s., 1H), 6.98 (m, 1H), 5.66-5.47 (m, 2H), 4.23-4.09 (m, 2H), 3.98 (ddd, J=5.18, 10.56, 15.55 Hz, 1H), 3.86 (dd, J=3.81, 9.49 Hz, 1H), 3.64-3.49 (m, 2H), 3.38 (td, J=4.74, 15.36 Hz, 2H), 2.92 (br. s., 1H), 2.81 (br. s., 1H), 2.79-2.73 (m, 2H), 2.73-2.63 (m, 1H), 2.52 (d, J=12.72 Hz, 1H), 2.40-2.25 (m, 2H), 2.18 (d, J=8.22 Hz, 1H), 2.01-1.52 (m, 8H). m/z (ESI, +ve ion) 571.0 (M+H)$^+$.

Step 3: (S,3'R,6'R,7'S)-6-CHLORO-7'-HYDROXY-3,4-DIHYDRO-2H,15'HSPIRO[NAPHTHALENE-1,22'[20]OXA[13]THIA[1,14]DIAZATETRACYCLO[14.7.2.0$^{3,6}$.0$^{19,24}$]PENTACOSA[16,18,24]TRIEN]-15'-ONE 13',13'-DIOXIDE A mixture of (1S,3'R,6'R,7'S,9'E)-6-chloro-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide (from Step 2, 0.112 g, 0.196 mmol) and platinum (IV) oxide (0.045 g, 0.196 mmol) in EtOAc (33 mL) was stirred under $H_2$ at ambient temperature for 3 h. The mixture was filtered through syringe filter to remove solid catalyst and the solution was concentrated to provide title compound (112 mg) as a white solid. $^1$H NMR (400 MHz, CD$_2$Cl$_2$) δ 8.93 (m, 1H), 7.71 (m, 1H), 7.15 (m, 3H), 7.09 (d, J=2.35 Hz, 1H), 6.95 (m, 1H), 4.10 (m, 2H), 3.78-3.62 (m, 4H), 3.46-3.34 (m, 1H), 3.26 (d, J=14.28 Hz, 1H), 3.16 (dd, J=9.00, 15.26 Hz, 1H), 2.82-2.71 (m, 2H), 2.45-2.33 (m, 1H), 2.26-2.16 (m, 1H), 2.08-1.16 (m, 17H). m/z (ESI, +ve ion) 573.2 (M+H)$^+$.

EXAMPLE 11

(1S,3'R,6'R,7'S,8'E,12'R)-6-CHLORO-7'-HYDROXY-12'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE AND EXAMPLE 12. (1S,3'R,6'R,7'S,8'E,12'S)-6-CHLORO-7'-HYDROXY-12'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

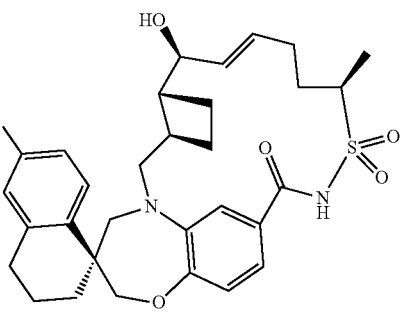

Example 11

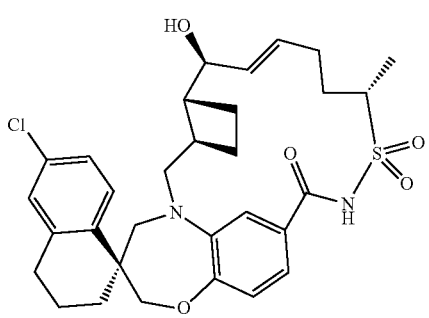

Example 12

The title compound was prepared in an analogous manner to that described in Example 2 using a mixture of (R)-hex-5-ene-sulfonamide (Intermediate EE20) and of (S)-hex-5-ene-sulfonamide (Intermediate EE202), and the desired product, (1S,3'R,6'R,7'S,8'E,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (the 1st epimer out of preparative reverse-phase HPLC, Example 11) and (1S,3'R,6'R,7'S,8'E,12'S)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (the 2nd epimer out of preparative reverse-phase HPLC, Example 12) were isolated. Cocrystal structure of Example 11 confirms that the methyl group at the 12-position has an R stereochemistry. (1S,3'R,6'R,7'S,8'E,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide: $^1$H NMR (400 MHz, CD$_3$OD) δ 7.74 (d, J=8.0 Hz, 1H), 7.19 (dd, J=3.5, 11.5 Hz, 1H), 7.12 (d, J=1.8 Hz, 1H), 7.01 (d, J=9.2 Hz, 1H), 7.01 (d, J=7.6 Hz, 1H), 6.94 (d, J=8.0 Hz, 1H), 6.88 (s, 1H), 5.89-5.81 (m, 1H), 5.73 (dd, 0.1=7.4, 14.5

Hz, 1H), 4.22 (dd, J=3.5, 7.6 Hz, 1H), 4.18-4.12 (m, 1H), 4.09 (d, J=2.0 Hz, 2H), 3.85 (d, J=15.1 Hz, 1H), 3.85 (d, J=15.3 Hz, 1H), 3.68 (d, J=14.1 Hz, 1H), 3.08 (dd, J=10.2, 15.1 Hz, 1H), 2.87-2.73 (m, 2H), 2.48-2.18 (m, 4H), 2.11 (d, J=13.7 Hz, 1H), 2.05-1.65 (m, 8H), 1.52 (d, J=6.8 Hz, 3H), 1.47-1.41 (m, 1H). m/z (ESI, +ve ion) 585.2 (M+H)$^+$; (1S,3'R,6'R,7'S,8'E,12'S)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide: $^1$H NMR (400 MHz, CD$_3$OD) δ 7.73 (d, J=9.2 Hz, 1H), 7.19 (dd, J=2.5, 8.6 Hz, 1H), 7.13 (d, J=2.3 Hz, 1H), 7.12-7.10 (m, 1H), 7.05 (dd, J=1.8, 8.0 Hz, 1H), 6.94 (d, J=8.6 Hz, 1H), 5.93-5.83 (m, 1H), 5.65 (dd, J=5.5, 15.5 Hz, 1H), 4.12 (d, J=6.8 Hz, 2H), 4.06 (dd, J=4.1, 10.2 Hz, 1H), 3.91 (dd, J=6.3, 12.5 Hz, 1H), 3.67-3.55 (m, 2H), 3.53-3.46 (m, 1H), 3.29-3.08 (m, 1H), 2.88-2.70 (m, 2H), 2.64-2.52 (m, 1H), 2.49-2.31 (m, 2H), 1.98-1.91 (m, 3H), 1.99-1.89 (m, 4H), 1.86-1.73 (m, 4H), 1.49 (d, J=7.4 Hz, 3H). m/z (ESI, +ve ion) 585.2 (M+H)$^+$.

EXAMPLE 13

(1S,3'R,6'R,7'S,8'E,12'R)-6-CHLORO-7'-METHOXY-12'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

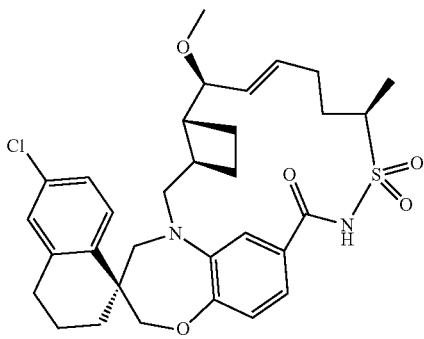 [SMILES: CO[C@H]1/C=C/CC[C@@H](C)S(=O)(=O)NC(=O)c2ccc3c(c2)N(C[C@@H]2CC[C@H]21)C[C@@]1(CCCc2cc(Cl)ccc21)CO3]

The title compound was prepared in an analogous manner to that described in Example 4 using (1S,3'R,6'R,7'S,8'E,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 11), and the desired product, (1S,3'R,6'R,7'S,8'E,12'R)-6-chloro-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[18,16,18,24]tetraen]-15'-one 13',13'-dioxide was isolated as a white solid. $^1$H NMR (400 MHz, CD$_3$OD) δ 7.75 (d, J=8.4 Hz, 1H), 7.19 (dd, J=1.8, 8.8 Hz, 1H), 7.12 (d, J=2.0 Hz, 1H), 7.00 (dd, J=2.2, 7.8 Hz, 1H), 6.95 (d, J=8.4 Hz, 1H), 6.86 (d, J=1.6 Hz, 1H), 5.92-5.84 (m, 1H), 5.58 (dd, J=9.0, 15.1 Hz, 1H), 4.85-4.85 (m, 1H), 4.20 (ddd, J=3.0, 6.7, 9.8 Hz, 1H), 4.08 (d, J=2.2 Hz, 2H), 3.86 (d, J=15.3 Hz, 1H), 3.73 (dd, J=2.9, 8.6 Hz, 1H), 3.67 (d, J=14.1 Hz, 1H), 3.26-3.23 (m, 3H), 3.08 (dd, J=10.3, 15.2 Hz, 1H), 2.88-2.72 (m, 2H), 2.54-2.25 (m, 4H), 2.12 (d, J=13.1 Hz, 1H), 1.99-1.71 (m, 7H), 1.53 (d, J=6.8 Hz, 3H), 1.50-1.40 (m, 1H). m/z (ESI, +ve ion) 599.2 (M+H)$^+$.

EXAMPLE 14

(1S,3'R,6'R,7'S,12'R)-6-CHLORO-7'-HYDROXY-12'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[16,18,24]TRIEN]-15'-ONE 13',13'-DIOXIDE

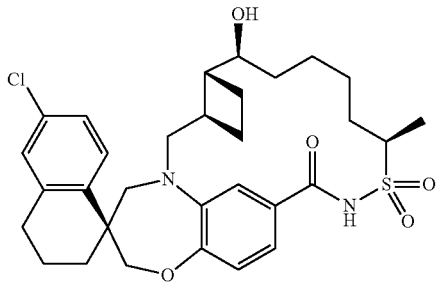 [SMILES: C[C@@H]1CCCC[C@H](O)[C@@H]2CC[C@H]2CN2C[C@@]3(CCCc4cc(Cl)ccc43)COc3ccc(cc32)C(=O)NS1(=O)=O]

STEP 1: (S)-6'-CHLORO-5-(((1R,2R)-2-((S)-1-HYDROXYBUT-3-EN-1-YL)CYCLOBUTYL)METHYL)-N—((R)-PENT-4-EN-2-YLSULFONYL)-3',4,4',5-TETRAHYDRO-2H,2'H-SPIRO[BENZO[B][1,4]OXAZEPINE-3,1'-NAPHTHALENE]-7-CARBOXAMIDE

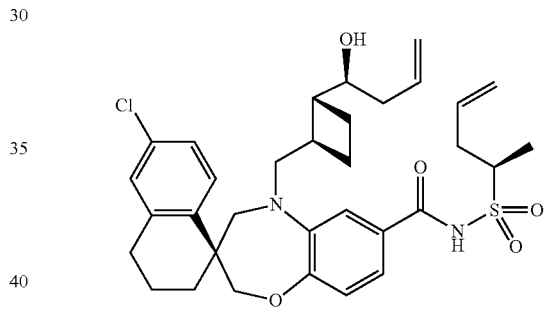

The title compound was synthesized from (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA13A; 166 mg, 0.344 mmol) and (R)-pent-4-ene-2-sulfonamide (intermediate EE17; 87 mg, 0.585 mmol) following the procedure described for Example 2, Step 1. Purification of the crude material provided (S)-6'-chloro-5-(((1R,2R)-2-((S)-1-hydroxybut-3-en-1-yl)cyclobutyl)methyl)-N—((R)-pent-4-en-2-ylsulfonyl)-3',4,4',5-tetrahydro-2H,2'H-spiro[benzo[b][1,4]oxazepine-3,1'-naphthalene]-7-carboxamide (134 mg, 0.219 mmol, 63.5% yield).

STEP 2

(1S,3'R,6'R,7'S,9'E,12'R)-6-CHLORO-7'-HYDROXY-12'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[9,16,18,24]TETRAEN]-15'-ONE 13',13'-DIOXIDE AND (1S,3'R,6'R,7'S,9'Z,12'R)-6-CHLORO-7'-HYDROXY-12'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[9,16,18,24]TETRAEN]-15'-ONE 13',13'-DIOXIDE

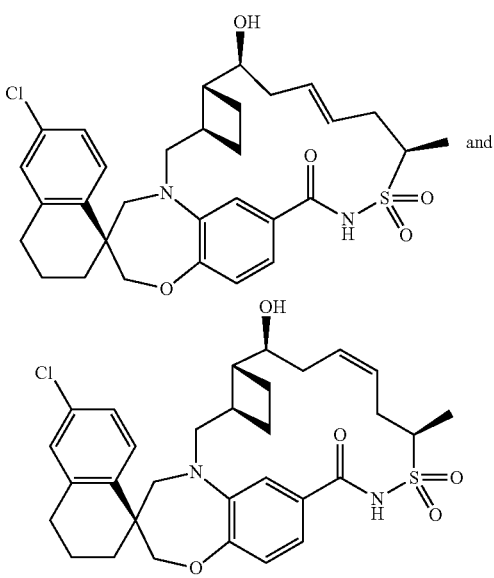

A 500 mL RBF was charged with (S)-6'-chloro-5-(((1R,2R)-2-((S)-1-hydroxybut-3-en-1-yl)cyclobutyl)methyl)-N—((R)-pent-4-en-2-ylsulfonyl)-3',4,4',5-tetrahydro-2H,2'H-spiro[benzo[b][1,4]oxazepine-3,1'-naphthalene]-7-carboxamide (134 mg, 0.219 mmol) in toluene (146.00 mL). The mixture was stirred at ambient temperature for 10 min to dissolve the solid starting material and then subjected to three cycles of evacuation/back-filling with N₂. To the homogeneous solution was added a solution of Hoveyda-Grubbs II (27.4 mg, 0.044 mmol) in toluene (8 mL) at ambient temperature. The mixture was stirred at 106° C. under N₂ for 80 min. Air was blown through the solution for 10 min to deactivate the catalyst, and then the mixture was concentrated. The crude dark oil was absorbed onto a plug of SiO₂ gel and purified by chromatography through a 24 g ISCO column, eluting with 10% to 20% to 40% EtOAc (containing 0.3% AcOH) in Hex over 90 min. to provide a mixture of the title compounds.

STEP 3: (1S,3'R,6'R,7'S,12'R)-6-CHLORO-7'-HYDROXY-12'-METHYL-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[16,18,24]TRIEN]-15'-ONE 13',13'-DIOXIDE

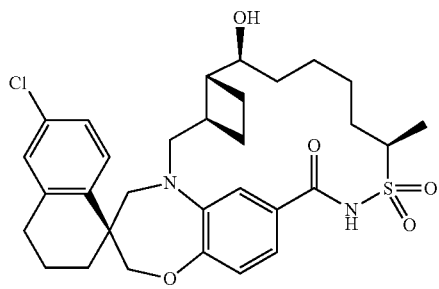 [SMILES: C[C@@H]1CCCC[C@H](O)[C@@H]2CC[C@H]2CN2C[C@@]3(CCCc4cc(Cl)ccc43)COc3ccc(cc32)C(=O)NS1(=O)=O]

The title compound (94 mg, 0.160 mmol, 79% yield) was synthesized from a mixture of (1S,3'R,6'R,7'S,9'E,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide and (1S,3'R,6'R,7'S,9'Z,12'R)-6-chloro-7'-hydroxy-12'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide (from Step 2, 119 mg, 0.203 mmol) following the procedure described for Example 6. ¹H NMR (400 MHz, CD₂Cl₂) δ 9.03 (br. s., 1H), 7.71 (d, J=8.4 Hz, 1H), 7.16 (dd, J=2.3, 8.4 Hz, 1H), 7.13 (dd, J=2.2, 8.2 Hz, 1H), 7.10 (br. s., 1H), 7.09 (d, J=2.3 Hz, 1H), 6.93 (d, J=8.2 Hz, 1H), 4.09 (s, 2H), 3.86 (td, J=5.3, 6.8 Hz, 1H), 3.74 (d, J=14.1 Hz, 1H), 3.70 (br. s., 1H), 3.65 (d, J=14.9 Hz, 1H), 3.25 (d, J=14.1 Hz, 1H), 3.13 (dd, J=8.2, 15.5 Hz, 1H), 2.85-2.68 (m, 2H), 2.44 (quin, J=8.8 Hz, 1H), 2.25 (ddd, J=5.5, 9.6, 17.8 Hz, 1H), 2.04-1.94 (m, 2H), 1.89 (dt, J=5.0, 9.5 Hz, 2H), 1.85-1.77 (m, 2H), 1.76-1.68 (m, 2H), 1.68-1.60 (m, 4H), 1.60-1.50 (m, 3H), 1.48 (d, J=7.0 Hz, 3H), 1.46-1.35 (m, 2H). MS (ESI, +ve ion) m/z 587.1 (M+H)⁺.

EXAMPLE 15

(1S,3'R,6'R,7'S,12'S)-6-CHLORO-7'-HYDROXY-12'-METHYL-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[16,18,24]TRIEN]-15'-ONE 13',13'-DIOXIDE

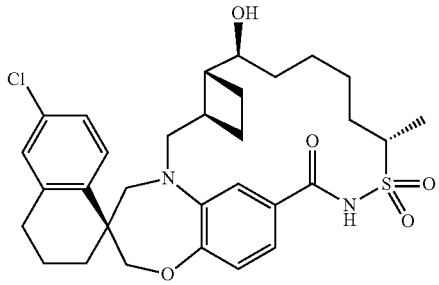 [SMILES: C[C@H]1CCCC[C@H](O)[C@@H]2CC[C@H]2CN2C[C@@]3(CCCc4cc(Cl)ccc43)COc3ccc(cc32)C(=O)NS1(=O)=O]

STEP 1: (S)-6'-CHLORO-5-(((1R,2R)-2-((S)-1-HYDROXYBUT-3-EN-1-YL)CYCLOBUTYL)METHYL)-N—((S)-PENT-4-EN-2-YLSULFONYL)-3',4,4',5-TETRAHYDRO-2H,2'H-SPIRO[BENZO[B][1,4]OXAZEPINE-3,1'-NAPHTHALENE-7-CARBOXAMIDE

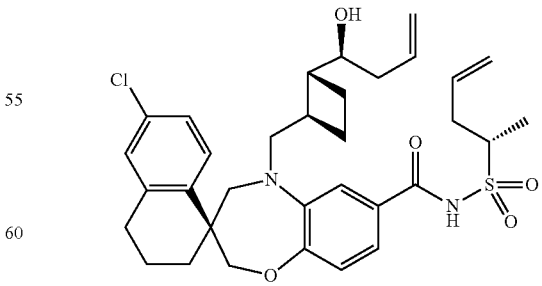

The title compound was synthesized from (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA13A; 15 mg, 0.031 mmol) and (S)-pent-4-ene-2-sulfonamide (Intermediate EE172; 5.6 mg, 0.037 mmol) following the procedure described for Example 2, Step 1. Purification of the crude material provided (S)-6'-chloro-5-(((1R,2R)-2-((S)-1-hydroxybut-3-en-1-yl)cyclobutyl)methyl)-N—((S)-pent-4-en-2-ylsulfonyl)-3',4,4',5-tetrahydro-2H,2'H-spiro[benzo[b][1,4]oxazepine-3,1'-naphthalene]-7-carboxamide (19 mg, 0.031 mmol).

STEP 2

(1S,3'R,6'R,7'S,9'Z,12'S)-6-CHLORO-7'-HYDROXY-12'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[9,16,18,24]TETRAEN]-15'-ONE 13',13'-DIOXIDE AND (1S,3'R,6'R,7'S,9'E,12'S)-6-CHLORO-7'-HYDROXY-12'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[9,16,18,24]TETRAEN]-15'-ONE 13',13'-DIOXIDE

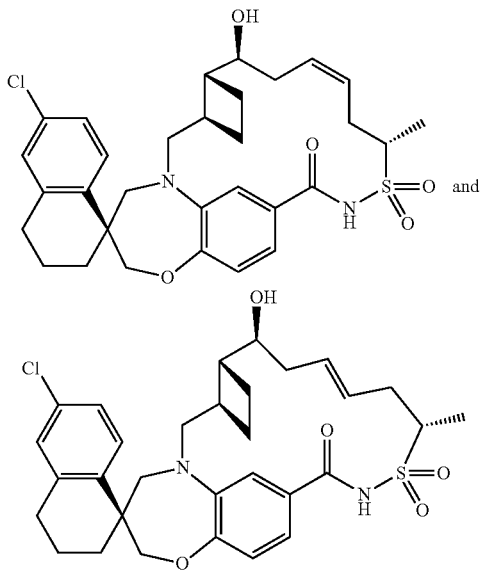

and

The title compound was synthesized from (S)-6'-chloro-5-(((1R,2R)-2-((S)-1-hydroxybut-3-en-1-yl)cyclobutyl)methyl)-N—((S)-pent-4-en-2-ylsulfonyl)-3',4,4',5-tetrahydro-2H,2'H-spiro[benzo[b][1,4]oxazepine-3,1'-naphthalene]-7-carboxamide (from Step 1, 42.5 mg, 0.067 mmol) following the procedure described for Example 14, Step 2. Purification by chromatography through a 24 g ISCO column, eluting with 10% to 20% to 40% EtOAc (containing 0.3% AcOH) in Hex over 90 min. followed by a second purification through a 12 g ISCO column, eluting with 0% to 30% EtOAc (containing 0.3% AcOH) in Hex provided (1S,3'R,6'R,7'S,9'Z,12'S)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide as the first eluting isomer (13.4 mg, 0.023 mmol 34.3% yield) and (1S,3'R,6'R,7'S,9'E,12'S)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide was obtained as the second eluting isomer (13.2 mg, 0.023 mmol 34.3% yield).

STEP 3: (1S,3'R,6'R,7'S,12'S)-6-CHLORO-7'-HYDROXY-12'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[16,18,24]TRIEN]-15'-ONE 13',13'-DIOXIDE

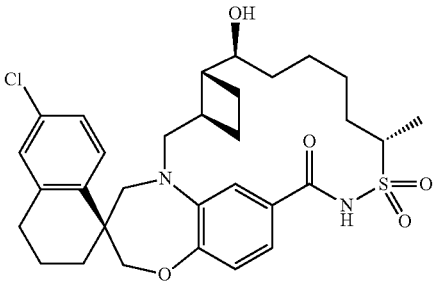 [SMILES: C[C@H]1CCCC[C@H](O)[C@@H]2CC[C@H]2CN2C[C@@]3(CCCc4cc(Cl)ccc43)COc3ccc(cc32)C(=O)NS1(=O)=O]

The title compound (7.5 mg, 0.013 mmol, 71% yield) was synthesized from a mixture of (1S,3'R,6'R,7'S,9'E,12'S)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'S,9'Z,12'S)-6-chloro-7'-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide (from Step 2, 10.8 mg, 0.018 mmol) following the procedure described for Example 6. $^1$H NMR (400 MHz, CD$_2$Cl$_2$) δ 9.72 (br. s., 1H), 7.71 (d, J=8.6 Hz, 1H), 7.30 (dd, J=2.0, 8.4 Hz, 1H), 7.28 (s, 1H), 7.16 (dd, J=2.4, 8.5 Hz, 1H), 7.09 (d, J=2.3 Hz, 1H), 6.94 (d, J=8.4 Hz, 1H), 4.10-4.05 (m, 2H), 3.85-3.76 (m, 1H), 3.70 (d, J=15.1 Hz, 1H), 3.60 (br. s., 1H), 3.60 (d, J=13.9 Hz, 1H), 3.26 (d, J=14.3 Hz, 1H), 3.23-3.14 (m, 1H), 2.83-2.69 (m, 2H), 2.33 (quin, J=8.6 Hz, 1H), 2.12 (quin, J=8.2 Hz, 1H), 2.04-1.94 (m, 2H), 1.94-1.85 (m, 1H), 1.84-1.71 (m, 5H), 1.71-1.64 (m, 2H), 1.64-1.52 (m, 3H), 1.49 (d, J=7.2 Hz, 3H), 1.52-1.43 (m, 2H), 1.38-1.28 (m, 2H). MS (ESI, +ve ion) m/z 587.2 (M+H)$^+$.

EXAMPLE 16

(1S,3'R,6'R,7'S,12'R)-6-CHLORO-7'-METHOXY-12'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[16,18,24]TRIEN]-15'-ONE 13',13'-DIOXIDE

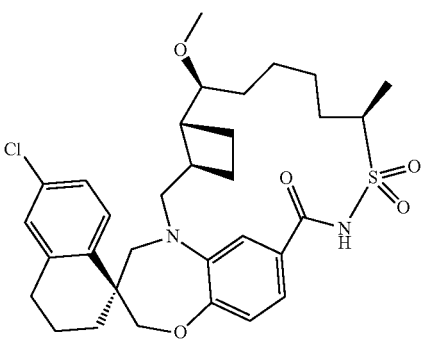 [SMILES: CO[C@H]1CCCC[C@@H](C)S(=O)(=O)NC(=O)c2ccc3c(c2)N(C[C@@H]2CC[C@H]21)C[C@@]1(CCCc2cc(Cl)ccc21)CO3]

A mixture of (1S,3'R,6'R,7'S,8'E,12'R)-6-chloro-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15-one 13',13'-dioxide (Example 13; 5 mg, 8.34 μmol) and platinum (iv) oxide (0.379 mg, 1.67 μmol, Omega) in EtOAc (2.8 mL) were stirred under H$_2$ (balloon) at rt for 3 hr, then filtered through Celite® to remove solid catalyst, concentrated, and purified by preparative reverse-phase HPLC (Gemini™ Prep C$_{18}$ 5 μm column; gradient elution of 40% to 95% MeCN in H$_2$O, where both solvents contain 0.1% TFA, 30 min method) to give (1S,3'R,6'R,7'S,12'R)-6-chloro-7'-methoxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide (4.4 mg, 7.32 μmol). $^1$H NMR (400 MHz, CD$_3$OD) δ 7.73 (d, J=8.4 Hz, 1H), 7.16 (d, J=8.7 Hz, 1H), 7.11-7.03 (m, 2H), 6.93 (d, J=9.1 Hz, 2H), 4.14-4.03 (m, 3H), 3.83 (d, J=14.7 Hz, 1H), 3.69 (d, J=14.3 Hz, 1H), 3.33-3.29 (m, 3H overlap with solvent), 3.23 (d, J=14.5 Hz, 1H), 3.06 (dd, J=9.1, 15.4 Hz, 1H), 2.85-2.71 (m, 2H), 2.62 (d, J=8.2 Hz, 1H), 2.36 (t, J=8.5 Hz, 1H), 2.10-1.84 (m, 5H), 1.84-1.56 (m, 6H), 1.55-1.40 (m, 6H), 1.38-1.24 (m, 3H). m/z (ESI, +ve ion) 601.2 (M+H)$^+$.

EXAMPLE 17

(1S,3'R,6'R,7'S,8'E,12'R)-6-CHLORO-12'-ETHYL-7'-HYDROXY-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

EXAMPLE 18

(1S,3'R,6'R,7'S,8'Z,12'R)-6-CHLORO-12'-ETHYL-7'-HYDROXY-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE AND

EXAMPLE 19

(1S,3'R,6'R,7'S,8'E,12'S)-6-CHLORO-12'-ETHYL-7'-HYDROXY-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

Example 17

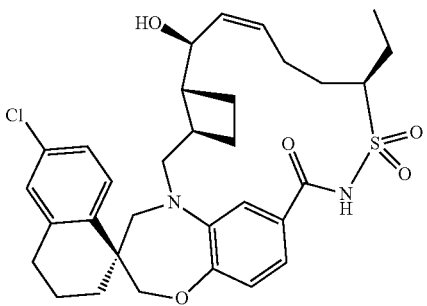

Example 18

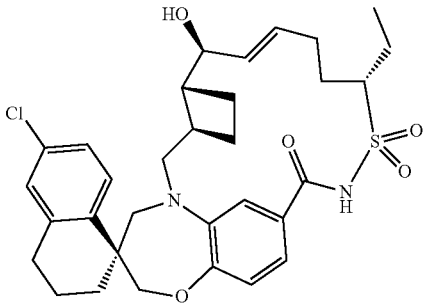

Example 19

The title compound was prepared in an analogous manner to that described in Example 2 using (S)-6'-chloro-5-(((1R,2R)-2-((S)-1-hydroxyallyl)cyclobutyl)methyl)-3',4,4',5-tetrahydro-2H,2'H-spiro[benzo[b][1,4]oxazepine-3,1'-naphthalene]-7-carboxylic acid (Intermediate AA1 IA) and a racemic mixture of (R)-hept-6-ene-3-sulfonamide (Intermediate EE21) and (S)-hept-6-ene-3-sulfonamide (Intermediate EE212), and the desired products, (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 17) as the first eluting major isomer out of preparative reverse-phase HPLC, (1S,3'R,6'R,7'S,8'Z,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 18) as the second eluting minor isomer out of preparative reverse-phase HPLC, and (1S,3'R,6'R,7'S,8'E,12'S)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 19) as the third eluting major isomer out of preparative reverse-phase HPLC were isolated. (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 17): $^1$H NMR (400 MHz, CD$_3$OD) δ 7.75 (d, J=8.4 Hz, 1H), 7.19 (dd, J=2.0, 8.8 Hz, 1H), 7.12 (d, J=2.2 Hz, 1H), 7.00 (dd. J=1.8, 8.0 Hz, 1H), 6.93 (d, J=8.2 Hz, 1H), 6.87 (d, J=1.6 Hz, 1H), 5.90-5.82 (m, 1H), 5.73 (dd, J=7.8, 15.1 Hz, 1H), 4.21 (dd, J=3.7, 7.8 Hz, 1H), 4.09 (dd, J=12.1, 14.7 Hz, 2H), 4.02 (dd, J=6.5, 13.5 Hz, 1H), 3.85 (d, J=15.1 Hz, 1H), 3.68 (d, J=14.1 Hz, 1H), 3.29 (d, J=14.3 Hz, 1H), 3.08 (dd, J=10.0, 15.3 Hz, 1H), 2.88-2.73 (m, 2H), 2.46-2.22 (m, 4H), 2.16-2.05 (m, 2H), 2.02-1.79 (m, 8H), 1.73 (dd, J=9.0, 17.6 Hz, 1H), 1.46 (t, J=12.6 Hz, 1H), 1.20 (t, J=7.5 Hz, 3H). m/z (ESI, +ve ion) 599.2 (M+H)$^+$; (1S,3'R,6'R,7'S,8'Z,12'R)-6-chloro-12'-ethyl-7'-hydroxy-3, 4-dihydro-2H,15'H-spiro[naphthalene-1,22'-[20]oxa[13] thia[1,14]diazatetracyclo[14.7.2.0³,⁶.0¹⁹,²⁴]pentacosa[8,16,18,24]tetraen]-15'-one 13',13'-dioxide (Example 18). ¹H NMR (500 MHz, CD₃OD) δ 7.75 (d, J=8.6 Hz, 1H), 7.19 (dd, J=2.3, 8.4 Hz, 1H), 7.12 (d, J=2.2 Hz, 1H), 7.03 (dd, J=2.0, 8.1 Hz, 1H), 6.97-6.92 (m, 2H), 5.62-5.55 (m, 2H), 4.49 (dd, J=3.5, 7.9 Hz, 1H), 4.09 (dd, J=12.5, 21.8 Hz, 2H), 3.88 (d, J=15.7 Hz, 1H), 3.71 (d, J=14.4 Hz, 1H), 3.62 (br. s., 11H), 2.87-2.74 (m, 2H), 2.49-2.38 (m, 3H), 2.26-2.10 (m, 3H), 2.06-1.89 (m, 8H), 1.84-1.73 (m, 3H), 1.55-1.40 (m, 1H), 1.16 (t, J=7.5 Hz, 3H). m/z (ESI, +ve ion) 599.2 (M+H)⁺; and (1S,3'R,6'R,7'S,8'E,12'S)-6-chloro-12'-ethyl-7'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 19); ¹H NMR (400 MHz, CD₃OD) δ 7.74 (d, J=8.6 Hz, 1H), 7.19 (dd, J=2.3, 8.4 Hz, 1H), 7.13 (d, J=2.2 Hz, 11H), 7.08-7.02 (m, 2H), 6.95 (d, J=9.0 Hz, 1H), 5.92 (ddd, J=5.9, 14.7, 21.5 Hz, 1H), 5.66 (dd, J=6.1, 15.3 Hz, 1H), 4.15-4.05 (m, 3H), 3.74-3.62 (m, 3H), 3.47 (d, J=14.3 Hz, 1H), 3.51-3.43 (m, 1H), 2.88-2.74 (m, 2H), 2.58-2.33 (m, 3H), 2.24-2.03 (m, 4H), 1.97-1.73 (m, 8H), 1.63-1.45 (m, 1H), 1.17 (t, J=7.5 Hz, 3H). m/z (ESI, +ve ion) 599.2 (M+H)⁺.

EXAMPLE 20

(1S,3'R,6'R,7'S,8'E,12'R)-6-CHLORO-12'-ETHYL-7'-METHOXY-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[8,16,18,24]TETRAEN]-15'-ONE 13',13'-DIOXIDE

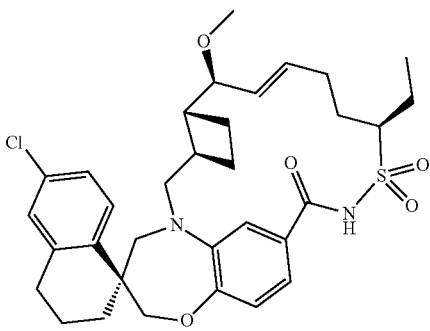 [SMILES: CC[C@@H]1CC/C=C/[C@H](OC)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 4 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 17), and the desired product, (1S,3'R,6'R,7'S,8'E,12'R)-6-chloro-12'-ethyl-7'-methoxy-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15-one 13',13'-dioxide was isolated as a white solid. ¹H NMR (400 MHz, CD₃OD) δ 7.75 (d, J=8.6 Hz, 1H), 7.18 (dd, J=2.2, 8.6 Hz, 1H), 7.12 (d, J=2.0 Hz, 1H), 7.00 (dd, J=1.8, 8.2 Hz, 1H), 6.94 (d, J=8.0 Hz, 1H), 6.86 (d, J=1.6 Hz, 1H), 5.94-5.85 (m, 1H), 5.58 (dd, J=8.9, 15.2 Hz, 1H), 4.13-4.02 (m, 3H), 3.85 (d, J=14.9 Hz, 1H), 3.74 (dd, J=3.9, 9.0 Hz, 1H), 3.68 (d, J=14.3 Hz, 1H), 3.26 (s, 3H), 3.22-3.04 (m, 1H), 2.88-2.73 (m, 2H), 2.54-2.39 (m, 2H), 2.33 (t, J=7.4 Hz, 2H), 2.12 (qd, J=7.3, 14.4 Hz, 2H), 2.02-1.69 (m, 10H), 1.45 (t, J=12.0 Hz, 1H), 1.21 (t, J=7.5 Hz, 3H). m/z (ESI, +ve ion) 613.2 (M+H)⁺.

EXAMPLE 21

(1S,3'R,6'R,7'S,12'R)-6-CHLORO-12'-ETHYL-7'-METHOXY-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[16,18,24]TRIEN]-15'-ONE 13',13'-DIOXIDE

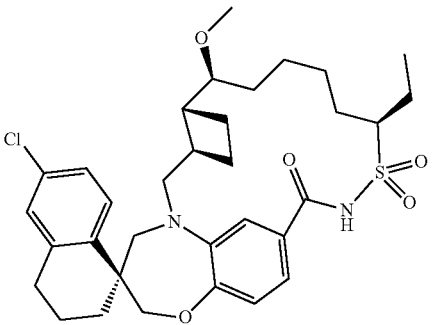 [SMILES: CC[C@@H]1CCCC[C@H](OC)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 6 using (1S,3'R,6'R,7'S,8'E,12'R)-6-chloro-12'-ethyl-7'-methoxy-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 20), and the desired products, (1S,3'R,6'R,7'S,12'R)-6-chloro-12'-ethyl-7'-methoxy-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide was isolated. ¹H NMR (500 MHz, CD₃OD) δ 7.76 (d, J=8.6 Hz, 1H), 7.19 (dd, J=2.3, 8.4 Hz, 1H), 7.13 (d, J=2.2 Hz, 1H), 7.06 (dd, J=2.0, 8.3 Hz, 1H), 7.00 (d, J=1.7 Hz, 1H), 6.95 (d, J=8.3 Hz, 1H), 4.11 (ddd, J=2.9, 12.0, 14.2 Hz, 2H), 3.88-3.81 (m, 2H), 3.69 (d, J=14.2 Hz, 1H), 3.30 (s, 3H), 3.12 (dd, J=8.1, 14.9 Hz, 1H), 2.86-2.74 (m, 2H), 2.69-2.62 (m, 1H), 2.35 (t, J=7.7 Hz, 1H), 2.15-2.05 (m, 2H), 2.01-1.85 (m, 5H), 1.82-1.63 (m, 4H), 1.47 (br. s., 5H), 1.42-1.24 (m, 4H), 1.18 (t, J=7.6 Hz, 3H). m/z (ESI, +ve ion) 615.2 (M+H)⁺.

EXAMPLE 22

(1S,3'R,6'R,7'S,12'R)-12'-ETHYL-7'-HYDROXY-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[16,18,24]TRIEN]-15'-ONE 13',13'-DIOXIDE

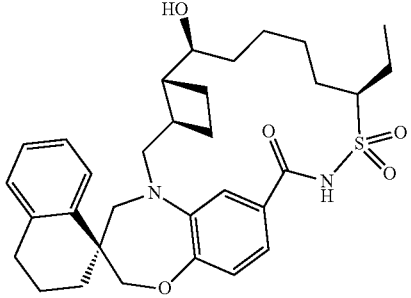 [SMILES: CC[C@@H]1CCCC[C@H](O)[C@@H]2CC[C@H]2CN2C[C@@]3(CCCc4ccccc43)COc3ccc(cc32)C(=O)NS1(=O)=O]

A mixture of (1S,3'R,6'R,7'S,8'Z,12'R)-6-chloro-12'-ethyl-T-hydroxy-3,4-dihydro-2H,15'H-spiro[naphthalene-1, 22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 18; 5.2 mg, 8.68 µmol) and palladium 10 wt. % (dry basis) on activated carbon, wet (4.6 mg, 4.34 µmol) in 1:1 ratio of EtOAc:EtOH (3.0 mL) was stirred under H₂ at rt overnight, then filtered through Celite® to remove solid catalyst. The organic layer was concentrated and purified by preparative reverse-phase HPLC (Gemini™ Prep C₁₈ 5 µm column; gradient elution of 40% to 95% MeCN in H₂O, where both solvents contain 0.1% TFA, 30 min method) to give (1S,3'R,6'R,7'S,12'R)-12'-ethyl-7'-hydroxy-3,4-dihydro-2H,15'H-spiro[naphthalene-1,22'-[20]oxa[13]thia[1,14]diazatetracyclo[14.7.2.0³,⁶.0¹⁹,²⁴]trien]-15'-one 13',13'-dioxide (1.9 mg, 3.35 µmol). ¹H NMR (400 MHz, CD₃OD) δ 7.77 (d, J=7.0 Hz, 1H), 7.21-7.02 (m, 4H), 6.97 (d, J=8.2 Hz, 1H), 6.93 (d, J=2.2 Hz, 1H), 4.13 (dd, J=12.1, 22.7 Hz, 2H), 3.92-3.80 (m, 2H), 3.76-3.70 (m, 2H), 3.13 (dd, J=8.8, 19.2 Hz, 1H), 2.87-2.75 (m, 2H), 2.44-2.29 (m, 2H), 2.15-2.04 (m, 2H), 1.99-1.37 (m, 17H), 1.18 (t, J=7.6 Hz, 3H). m/z (ESI, +ve ion) 567.2 (M+H)⁺.

EXAMPLE 23

(1S,3'R,6'R,7'S,12'S)-6-CHLORO-12'-ETHYL-7'-HYDROXY-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[16,18,24]TRIEN]-15'-ONE 13',13'-DIOXIDE

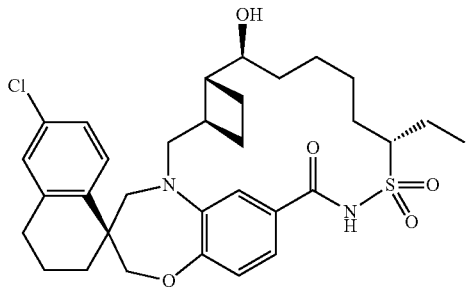 [SMILES: CC[C@H]1CCCC[C@H](O)[C@@H]2CC[C@H]2CN2C[C@@]3(CCCc4cc(Cl)ccc43)COc3ccc(cc32)C(=O)NS1(=O)=O]

STEP 1

(S)-6'-CHLORO-N—((R)-HEX-5-EN-3-YLSULFONYL)-5-(((1R,2R)-2-((S)-1-HYDROXYBUT-3-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXAMIDE AND (S)-6'-CHLORO-N—((S)-HEX-5-EN-3-YLSULFONYL)-5-(((1R,2R)-2-((S)-1-HYDROXYBUT-3-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXAMIDE

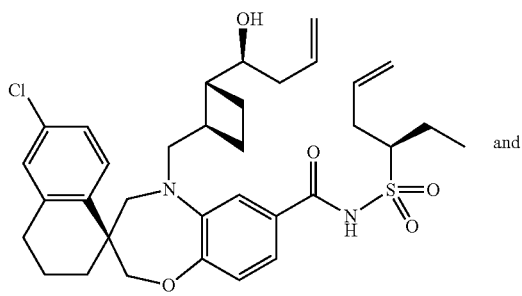

and

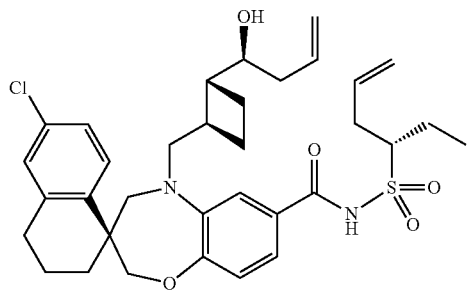

The title compounds were synthesized from (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA13A; 224 mg, 0.465 mmol) and a racemic mixture of (R)-hex-5-ene-3-sulfonamide (Intermediate EE18) and (S)-hex-5-ene-3-sulfonamide (Intermediate EE182; 167 mg, 1.023 mmol) following the procedure described for Example 2, Step 1. Purification of the crude material provided a mixture of (S)-6'-chloro-N—((R)-hex-5-en-3-ylsulfonyl)-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide and (S)-6'-chloro-N—((S)-hex-5-en-3-ylsulfonyl)-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide (235 mg, 0.375 mmol, 81% yield).

STEP 2

(1S,3'R,6'R,7'S,9'Z,12'S)-6-CHLORO-12'-ETHYL-7'-HYDROXY-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[9,16,18,24]TETRAEN]-15'-ONE 13',13'-DIOXIDE AND (1S,3'R,6'R,7'S,9'E,12'S)-6-CHLORO-12'-ETHYL-7'-HYDROXY-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[9,16,18,24]TETRAEN]-15'-ONE 13',13'-DIOXIDE

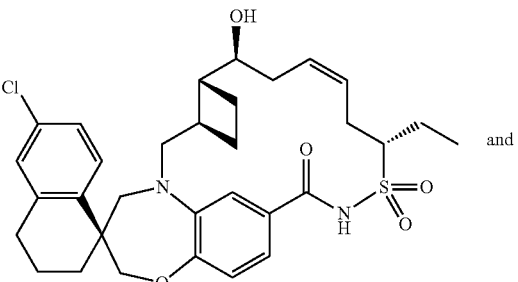

and

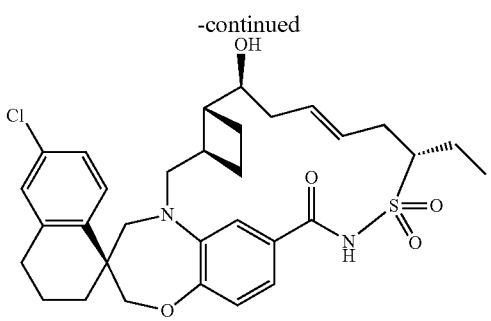

The title compound was synthesized from a mixture of (S)-6'-chloro-N—((R)-hex-5-en-3-ylsulfonyl)-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide and (S)-6'-chloro-N—((R)-hex-5-en-3-ylsulfonyl)-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxamide (from Step 1, 235 mg, 0.375 mmol) following the procedure described for Example 14, Step 2. The crude material was subjected to a first purification by chromatography through a 24 g ISCO column, eluting with 10% to 20% to 40% EtOAc (containing 0.3% AcOH) in Hex over 60 min to provide a mixture of the title compounds.

STEP 3: (1S,3'R,6'R,7'S,12'S)-6-CHLORO-12'-ETHYL-7'-HYDROXY-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[16,18,24]TRIEN]-15'-ONE 13',13'-DIOXIDE

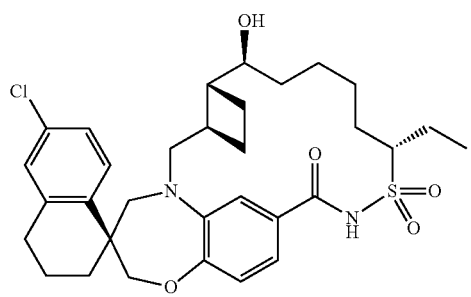 [SMILES: CC[C@H]1CCCC[C@H](O)[C@@H]2CC[C@H]2CN2C[C@@]3(CCCc4cc(Cl)ccc43)COc3ccc(cc32)C(=O)NS1(=O)=O]

The title compound (6.3 mg, 0.010 mmol, 52.3% yield) was synthesized from a mixture of (1S,3'R,6'R,7'S,9'Z,12'S)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'S,9'E,12'S)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide (from Step 2, 12 mg, 0.020 mmol) following the procedure described for Example 6. $^1$H NMR (400 MHz, CD$_2$Cl$_2$) δ 10.11 (br. s., 1H), 7.70 (d, J=8.6 Hz, 1H), 7.36 (dd, J=2.1, 8.3 Hz, 1H), 7.28 (d, J=1.8 Hz, 1H), 7.15 (dd, J=2.3, 8.4 Hz, 1H), 7.08 (d, J=2.3 Hz, 1H), 6.93 (d, J=8.2 Hz, 1H), 4.06 (d, J=11.5 Hz, 1H), 3.99 (d, J=12, 1 Hz, 1H), 3.76 (d, J=15.5 Hz, 1H), 3.65-3.61 (m, 1H), 3.59 (d, J=14.1 Hz, 1H), 3.57-3.50 (m, 1H), 3.16 (d, J=14.3 Hz, 1H), 3.09 (dd, J=8.5, 15.2 Hz, 1H), 2.83-2.67 (m, 2H), 2.25 (quin, J=9.0 Hz, 1H), 2.20-2.08 (m, 3H), 2.03-1.88 (m, 3H), 1.89-1.74 (m, 7H), 1.72-1.57 (m, 3H), 1.55-1.39 (m, 2H), 1.36-1.19 (m, 2H), 1.10 (t, J=7.4 Hz, 3H). MS (ESI, +ve ion) m/z 601.2 (M+H)$^+$.

EXAMPLE 24

(1S,3'R,6'R,7'S,8'E,11'S,12'R)-6-CHLORO-12'-ETHYL-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$] PENTACOSA[8,16,18,24]TETRAEN]-15'-ONE 13',13'-DIOXIDE

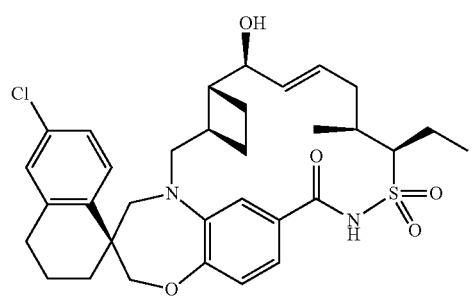 [SMILES: CC[C@@H]1[C@@H](C)C/C=C/[C@H](O)[C@@H]2CC[C@H]2CN2C[C@@]3(CCCc4cc(Cl)ccc43)COc3ccc(cc32)C(=O)NS1(=O)=O]

STEP 1: (3R,4S)—N,N-BIS(4-METHOXYBENZYL)-4-METHYLHEPT-6-ENE-3-SULFONAMIDE AND (3S,4S)—N,N-BIS(4-METHOXYBENZYL)-4-METHYLHEPT-6-ENE-3-SULFONAMIDE

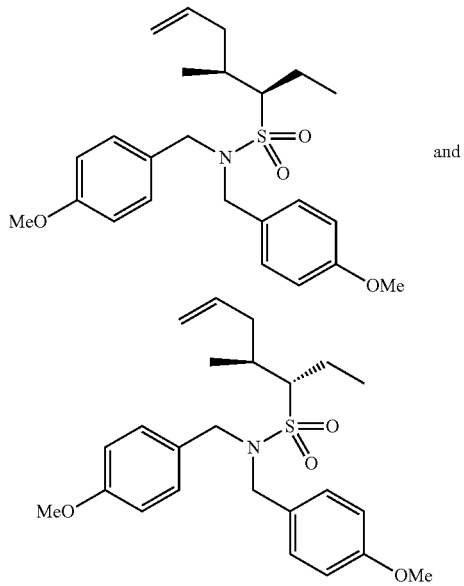

The title compounds were synthesized from N,N-bis(4-methoxybenzyl)propane-1-sulfonamide (Intermediate EE14; 1512 mg, 4.16 mmol) and (R)-pent-4-en-2-yl 4-methylbenzenesulfonate (prepared according to the procedure by Sigman, M. S. et al.; *J. Am. Chem. Soc.*, 2012, 134(28), 11408-11411; 1999 mg, 8.32 mmol) following the procedure described for Example 26, step 1. (3R,4S)—N,N-bis(4-methoxy benzyl)-4-methylhept-6-ene-3-sulfonamide and (3S,4S)—N,N-bis(4-methoxybenzyl)-4-methylhept-6-ene-3-sulfonamide were obtained as an inseparable mixture (335 mg, 0.776 mmol, 18.7% yield).

STEP 2: (3R,4S)-4-METHYLHEPT-6-ENE-3-SULFONAMIDE AND (3S,4S)-4-METHYLHEPT-6-ENE-3-SULFONAMIDE

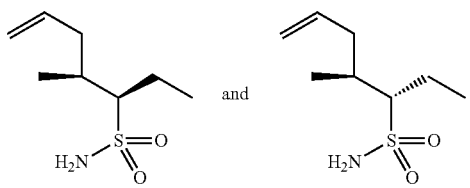

The title compounds were synthesized from (3R,4S)—N,N-bis(4-methoxybenzyl)-4-methylhept-6-ene-3-sulfonamide and (3S,4S)—N,N-bis(4-methoxy benzyl)-4-methylhept-6-ene-3-sulfonamide (335 mg, 0.776 mmol, Step 1) following the procedure described for Example 26, Step 2. (3R,4S)-4-methylhept-6-ene-3-sulfonamide and (3S,4S)-4-methylhept-6-ene-3-sulfonamide were obtained as an inseparable mixture (67.6 mg, 0.35 mmol, 45.5% yield).

STEP 3

(S)-6'-CHLORO-5-(((1R,2R)-2-((1S,5S,6R,E)-1-HYDROXY-5-METHYL-6-SULFAMOYLOCT-2-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLIC ACID AND (S)-6'-CHLORO-5-(((1R,2R)-2-((1S,5S,6S,E)-1-HYDROXY-5-METHYL-6-SULFAMOYLOCT-2-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLIC ACID

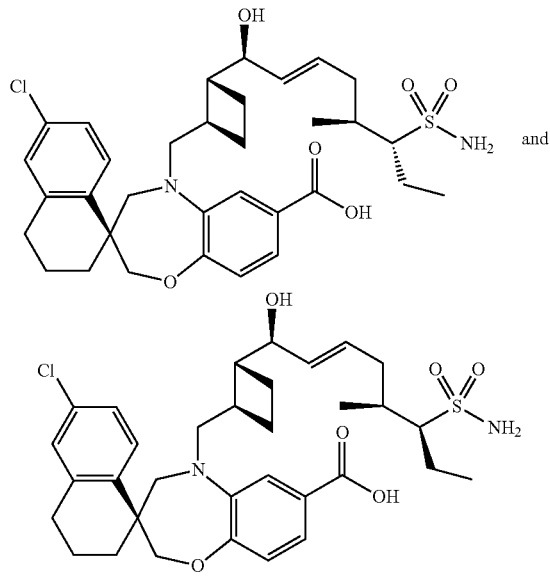

The title compounds were synthesized from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A; 40 mg, 0.078 mmol) and a mixture of (3R,4S)-4-methylhept-6-ene-3-sulfonamide and (3S,4S)-4-methylhept-6-ene-3-sulfonamide (67.6 mg, 0.35 mmol) following the procedure described for Example 26, Step 3. The mixture of (S)-6'-chloro-5-(((1R,2R)-2-((1S,5S,6R,E)-1-hydroxy-5-methyl-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5S,6S,E)-1-hydroxy-5-methyl-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic acid (46 mg, 0.073 mmol, 92% yield) was carried on to the next step.

STEP 4. (1S,3'R,6'R,7'S,8'E,11'S,12'R)-6-CHLORO-12'-ETHYL-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

The title compound was synthesized from (S)-6'-chloro-5-(((1R,2R)-2-((1S,5S,6R,E)-1-hydroxy-5-methyl-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5S,6S,E)-1-hydroxy-5-methyl-6-sulfamoyloct-2-en-1-yl)cyclobutyl)methyl)-3',4,4',5-tetrahydro-2H,2'H-spiro[benzo[b][1,4]oxazepine-3,1'-naphthalene]-7-carboxylic acid (63 mg, 0.100 mmol) following the procedure described for Example 26, Step 4. The crude material was purified by chromatography through a 12 g ISCO gold column, eluting with 10-40-50% EtOAc (containing 0.3% AcOH) in Hex over 24 min, to provide (1S,3'R,6'R,7'S,8'E,11'S,12'R)-6-chloro-12'-ethyl-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide as the second eluting major isomer. This material was repurified by chromatography through a 12 g ISCO gold column, eluting with 0-10% acetone in DCM to provide the title compound (20 mg, 0.033 mmol, 32.7% yield). $^1$H NMR (400 MHz, CD$_2$Cl$_2$) δ 8.33 (br. s., 1H), 7.71 (d, J=8.4 Hz, 1H), 7.17 (dd, J=2.3, 8.4 Hz, 1H), 7.09 (d, J=2.3 Hz, 1H), 6.96-6.88 (m, 3H), 5.86 (ddd, J=3.9, 9.0, 15.1 Hz, 1H), 5.71 (dd, J=8.2, 15.1 Hz, 1H), 4.22 (dd, J=3.9, 8.2 Hz, 1H), 4.09-4.08 (m, 2H), 3.98 (ddd, J=1.2, 3.7, 8.8 Hz, 1H), 3.82 (d, J=14.7 Hz, 1H), 3.69 (d, J=14.3 Hz, 1H), 3.25 (d, J=14.3 Hz, 1H), 3.04 (dd, J=9.5, 15.4 Hz, 1H), 2.85-2.69 (m, 2H), 2.41 (ddd, J=3.7, 9.8, 18.4 Hz, 1H), 2.35-2.24 (m, 1H), 2.21-2.11 (m, 1H), 2.10-2.03 (m, 2H), 1.99-1.90 (m, 3H), 1.90-1.74 (m, 5H), 1.67 (quin, J=9.5 Hz, 2H), 1.45-1.34 (m, 1H), 1.27 (t, J=7.4 Hz, 3H), 1.02 (d, J=6.8 Hz, 3H). MS (ESI, +ve ion) m/z 613.0 (M+H)$^+$.

123
EXAMPLE 25

(1S,3'R,6'R,7'S,8'E,11'S,12'R)-6-CHLORO-12'-ETHYL-7'-METHOXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$] PENTACOSA[8,16,18,24]TETRAEN]-15'-ONE 13',13'-DIOXIDE

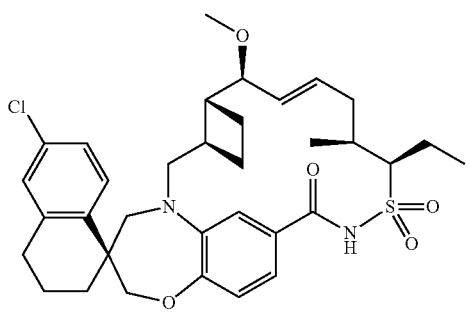 [SMILES: CC[C@@H]1[C@@H](C)C/C=C/[C@H](OC)[C@@H]2CC[C@H]2CN2C[C@@]3(CCCc4cc(Cl)ccc43)COc3ccc(cc32)C(=O)NS1(=O)=O]

The title compound was synthesized from (1S,3'R,6'R,7'S,8'E,11'S,12'R)-6-chloro-12'-ethyl-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 24; 10 mg, 0.016 mmol) following the procedure described for Example 4. Purification of the crude material via column chromatography eluting with 10-40% EtOAc (containing 0.3% AcOH) in heptanes provided (1S,3'R,6'R,7'S,8'E,11'S,12'R)-6-chloro-12'-ethyl-7'-methoxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (7.3 mg, 0.012 mmol, 71.4% yield). $^1$H NMR (500 MHz, CD$_2$Cl$_2$) δ 8.13 (s, 1H), 7.71 (d, J=8.6 Hz, 1H), 7.17 (dd, J=2.2, 8.6 Hz, 1H), 7.09 (d, J=2.0 Hz, 1H), 6.91 (s, 2H), 6.87 (s, 1H), 5.84 (ddd, J=3.4, 9.6, 15.1 Hz, 1H), 5.51 (dd, J=9.0, 15.2 Hz, 1H), 4.11-4.06 (m, 2H), 4.04-4.00 (m, 1H), 3.82 (d, J=15.4 Hz, 1H), 3.69 (d, J=14.2 Hz, 1H), 3.64 (dd, J=3.3, 9.2 Hz, 1H), 3.25 (d, J=14.2 Hz, 1H), 3.18 (s, 3H), 3.03 (dd, J=10.1, 15.3 Hz, 1H), 2.84-2.69 (m, 2H), 2.44 (ddd, J=3.2, 9.8, 18.6 Hz, 1H), 2.33 (quin, J=8.8 Hz, 1H), 2.28-2.21 (m, 1H), 2.15-2.09 (m, 1H), 2.09-2.02 (m, 2H), 2.01-1.90 (m, 3H), 1.90-1.73 (m, 4H), 1.72-1.61 (m, 1H), 1.39 (t, J=12.6 Hz, 1H), 1.28 (t, J=7.31 Hz, 3H), 1.02 (d, J=6.8 Hz, 3H). MS (ESI, +ve ion) m/z 627.1 (M+H)$^+$.

EXAMPLE 26

(1S,3'R,6'R,7'S,8'E,11'R,12'R)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'S)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

124

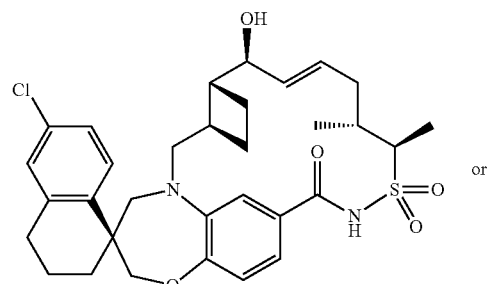

STEP 1: (2R,3R)—N,N-BIS(4-METHOXYBENZYL)-3-METHYLHEX-5-ENE-2-SULFONAMIDE AND (2S,3R)—N,N-BIS(4-METHOXYBENZYL)-3-METHYLHEX-5-ENE-2-SULFONAMIDE

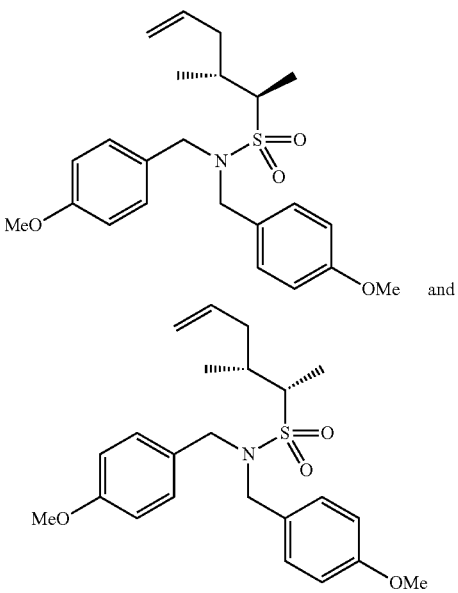

N,N-bis(4-methoxybenzyl)ethanesulfonamide (Intermediate EE13; 1030 mg, 2.95 mmol) was azeotroped in toluene under vacuum for 2 h. Under argon, THF was added and the solution was cooled to −78° C. N-butyllithium solution (2.5 M in Hex, 1.533 mL, 3.83 mmol) was then added and the mixture was stirred at −78° C. for 60 min. (S)-pent-4-en-2-yl 4-methylbenzenesulfonate (prepared according to the procedure by Sigman, M. S. et al., *J. Am. Chem. Soc.,* 2012, 134(28), 11408-11411; 1417 mg, 5.90 mmol) was added as a solution in 3 mL. THF was then added. After 5 min the mixture was allowed to warm to ambient temperature and stirred overnight under argon. The mixture was quenched with satd NH₄Cl and extracted with EtOAc, dried over MgSO₄, and concentrated. The crude material was injected into a SiO₂ gel cartridge and purified by chromatography through a 40 g ISCO column, eluting with 5% to 10% to 20% to 40% EtOAc in Hex, to provide a 2.3:1 mixture of the title compounds (420 mg, 1.00 mmol, 34.1% yield).

STEP 2: (2R,3R)-3-METHYLHEX-5-ENE-2-SULFONAMIDE AND (2S,3R)-3-METHYLHEX-5-ENE-2-SULFONAMIDE

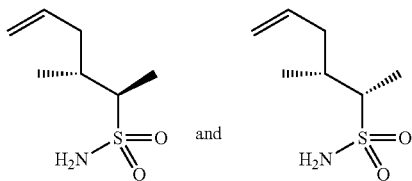

To a solution of (2R,3R)—N,N-bis(4-methoxybenzyl)-3-methylhex-5-ene-2-sulfonamide and (2S,3R)—N,N-bis(4-methoxybenzyl)-3-methylhex-5-ene-2-sulfonamide (2.3:1 mixture of diastereomers; 420 mg, 1.00 mmol) and anisole (1.093 mL, 10.06 mmol) in DCM (5.029 mL) at ambient temperature was slowly added trifluoroacetic acid (2.99 mL, 40.2 mmol). After stirring overnight, the mixture was concentrated. The residue was diluted with EtOAc, washed with satd NaHCO₃, back extracted with EtOAc, dried over MgSO₄, and concentrated. The crude material was purified via chromatography on a 24 g ISCO gold column eluting with a gradient of 0-50% EtOAc in Hex) to provide a 2.3:1 mixture of the title compounds (153 mg, 0.863 mmol, 86% yield).

STEP 3

(S)-6'-CHLORO-5-(((1R,2R)-2-((1S,5R,6R,E)-1-HYDROXY-5-METHYL-6-SULFAMOYLHEPT-2-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLIC ACID AND (S)-6'-CHLORO-5-(((1R,2R)-2-((1S,5R,6S,E)-1-HYDROXY-5-METHYL-6-SULFAMOYLHEPT-2-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLIC ACID

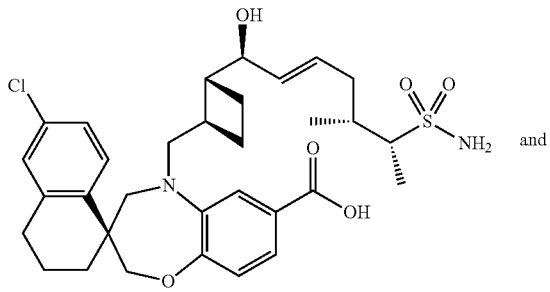

and

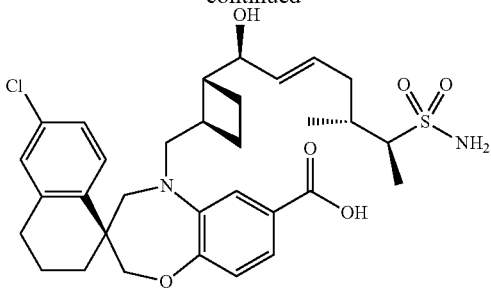

A vial was charged with (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A; 75 mg, 0.147 mmol) and a 2.3:1 mixture of (2R,3R)-3-methylhex-5-ene-2-sulfonamide and (2S, 3R)-3-methylhex-5-ene-2-sulfonamide (153 mg, 0.863 mmol) in 1,2-DCE (2.101 mL). The solution was sparged with argon, then Hoveyda-Grubbs II (9.21 mg, 0.015 mmol) was added as a solution in 1 mL 1,2-DCE at ambient temperature. The resulting mixture was stirred (sparging with argon and venting the vial) at ambient temperature. After 2 h the reaction mixture was sparged with air for 5 min and filtered to separate the insoluble sulfonamide homodimer. The filtrate was directly injected into a 12 g ISCO gold column, and purified eluting with 0-20-50-100% EtOAc in Hex over 16 min to give a mixture of the title compounds (74 mg, 0.120 mmol, 82% yield).

STEP 4

(1S,3'R,6'R,7'S,8'E,11'R,12'R)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[8,16,18,24]TETRAEN]-15'-ONE 13',13'-DIOXIDE OR (1S,3'R,6'R,7'S,8'E,11'R,12'S)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[8,16,18,24]TETRAEN]-15'-ONE 13',13'-DIOXIDE

N,N-dimethylpyridin-4-amine (24.90 mg, 0.204 mmol) was added to a solution of(S)-6'-chloro-5-(((1R,2R)-2-((1S,5R,6R,E)-1-hydroxy-5-methyl-6-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5R,6S,E)-1-hydroxy-5-methyl-6-sulfamoylhept-2-en-1-yl)cyclobutyl)methyl)-3',4,4',5-tetrahydro-2H,2'H-spiro[benzo[b][1·4]oxazepine-3,1'-naphthalene]-7-carboxylic acid (74 mg, 0.120 mmol) (previously azeotroped with 2.0 mL PhMe for 3 h) in DCM (59.900 mL) at 0° C. N-(3-dimethylaminopropyl)-'N'-ethylcarbodiimide hydrochloride (46.0 mg, 0.240 mmol) was then slowly added portion-wise and the resulting mixture was stirred while allowing to warm to ambient temperature for 15 h. The mixture was washed with 1N HCl and brine, the aqueous was back extracted with EtOAc, and the combined organics were dried over anhydrous magnesium sulfate, then concentrated. The crude material was purified by chromatography through a 12 g ISCO gold column, eluting with 10-40-50% EtOAc (containing 0.3% AcOH) in Hex over 24 min, to provide (1S,3'R,6'R,7'S,8'E,11'R,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,11'R,12'S)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide as the first eluting major isomer (19.5 mg, 0.033 mmol, 27.1% yield, 90% purity). ¹H NMR (400 MHz, CD₂Cl₂) δ 8.31 (br. s., 1H), 7.65 (d, J=8.4 Hz, 1H), 7.62 (br. s., 1H), 7.14 (dd, J=2.4, 8.5 Hz, 1H), 7.10 (d, J=2.3 Hz, 1H), 6.93 (dd, J=2.0, 8.2 Hz, 1H), 6.90 (d, J=8.0 Hz, 1H), 5.66 (dd, J=3.7, 15.8 Hz, 1H), 5.58-5.45 (m, 1H), 4.22 (s, 2H), 4.15-4.08 (m, 2H), 3.87 (br. s., 1H), 3.74 (d, J=13.9 Hz, 1H), 3.33 (d, J=14.1 Hz, 1H), 3.11 (d, J=13.9 Hz, 1H), 2.79-2.69 (m, 2H), 2.57-2.39 (m, 2H), 2.06-1.92 (m, 2H), 1.91-1.81 (m, 4H), 1.80-1.73 (m, 4H), 1.71-1.55 (m, 2H), 1.41 (d, J=7.4 Hz, 3H), 1.04 (d, J=6.7 Hz, 3H). MS (ESI, +ve ion) m/z 599.1 (M+H)⁺.

EXAMPLE 27

(1S,3'R,6'R,7'S,8'E,11'R,12'S)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[8,16,18,24]TETRAEN]-15'-ONE 13',13'-DIOXIDE OR (1S,3'R,6'R,7'S,8'E,11'R,12'R)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[8,16,18,24]TETRAEN]-15'-ONE 13',13'-DIOXIDE

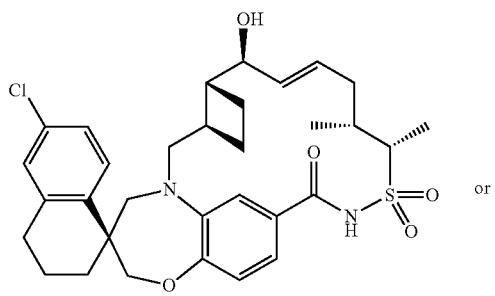

or

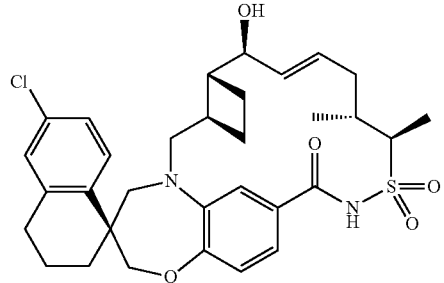

The title compound was synthesized as described for Example 26, Step 4. (1S,3'R,6'R,7'S,8'E,11'R,12'S)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,1'R,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide was isolated as the second eluting minor isomer (11.5 mg, 0.019 mmol, 16.0% yield, 95% purity). ¹H NMR (400 MHz, CD₂Cl₂) δ 9.08-8.57 (m, 1H), 7.72 (d, J=8.4 Hz, 1H), 7.17 (dd, J=2.3, 8.6 Hz, 11H), 7.09 (d, J=2.3 Hz, 11H), 7.06 (d, J=8.6 Hz, 1H), 6.93 (d, J=8.0 Hz, 1H), 6.83 (s, 1H), 6.03 (ddd, J=5.3, 8.2, 15.7 Hz, 1H), 5.76 (dd, J=7.8, 15.7 Hz, 1H), 4.20 (dd, J=3.2, 7.9 Hz, 1H), 4.14-4.03 (m, 3H), 3.78-3.63 (m, 2H), 3.29 (d, J=14.3 Hz, 11H), 3.12 (dd, J=9.9, 15.4 Hz, 1H), 2.85-2.68 (m, 2H), 2.62 (br. s., 1H), 2.55-2.42 (m, 1H), 2.36 (dq, J=3.2, 9.2 Hz, 1H), 2.26-2.16 (m, 1H), 2.14-2.07 (m, 1H), 2.04-1.93 (m, 3H), 1.90 (dd, J=4.1, 9.2 Hz, 1H), 1.87-1.74 (m, 3H), 1.73-1.63 (m, 1H), 1.46 (d, J=7.2 Hz, 3H), 1.46-1.39 (m, 1H), 1.07 (d, J=7.0 Hz, 3H). MS (ESI, +ve ion) m/z 599.0 (M+H)⁺.

EXAMPLE 28

(1S,3'R,6'R,7'S,8'E,11'S,12'S)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴] PENTACOSA[8,16,18,24]TETRAEN]-15'-ONE 13',13'-DIOXIDE

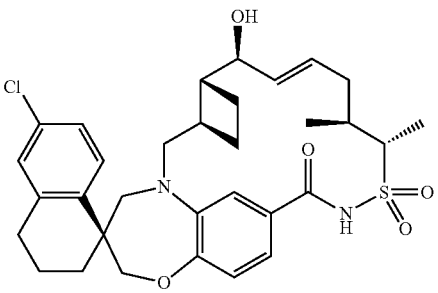 [SMILES: C[C@H]1C/C=C/[C@H](O)[C@@H]2CC[C@H]2CN2C[C@@]3(CCCc4cc(Cl)ccc43)COc3ccc(cc32)C(=O)NS(=O)(=O)[C@H]1C]

STEP 1: (2R,3S)—N,N-BIS(4-METHOXYBENZYL)-3-METHYLHEX-5-ENE-2-SULFONAMIDE AND (2S,3S)—N,N-BIS(4-METHOXYBENZYL)-3-METHYLHEX-5-ENE-2-SULFONAMIDE

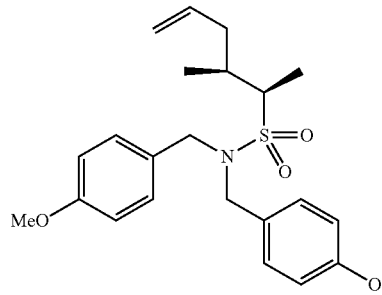

and

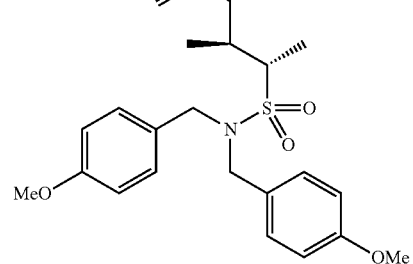

The title compounds were synthesized from N,N-bis(4-methoxybenzyl)ethanesulfonamide (Intermediate EE13;

1148 mg, 3.29 mmol) and (R)-pent-4-en-2-yl 4-methylbenzenesulfonate (prepared according to the procedure by Sigman, M. S. et al.; *J. Am. Chem. Soc.*, 2012, 134(28), 11408-11411; 1579 mg, 6.57 mmol) following the procedure described for Example 26, Step 1. (2R,3S)—N,N-bis(4-methoxybenzyl)-3-methylhex-5-ene-2-sulfonamide and (2S,3S)—N,N-bis(4-methoxybenzyl)-3-methylhex-5-ene-2-sulfonamide were obtained as a 2.4:1 mixture (539 mg, 1.29 mmol, 39.3% yield).

STEP 2: (2R,3S)-3-METHYLHEX-5-ENE-2-SULFONAMIDE AND (2S,3S)-3-METHYLHEX-5-ENE-2-SULFONAMIDE

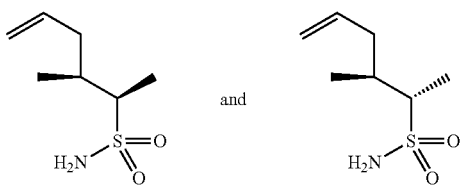

The title compounds were synthesized from (2R,3S)—N,N-bis(4-methoxybenzyl)-3-methylhex-5-ene-2-sulfonamide and (2S,3S)—N,N-bis(4-methoxybenzyl)-3-methylhex-5-ene-2-sulfonamide (539 mg; 1.29 mmol) following the procedure described for Example 26, Step 2. (2R,3S)-3-methylhex-5-ene-2-sulfonamide and (2S,3S)-3-methylhex-5-ene-2-sulfonamide were obtained as a 2.3:1 mixture (203 mg, 1.15 mmol, 89% yield).

STEP 3

(S)-6'-CHLORO-5-(((1R,2R)-2-((1S,5S,6R,E)-1-HYDROXY-5-METHYL-6-SULFAMOYLHEPT-2-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLIC ACID AND (S)-6'-CHLORO-5-(((1R,2R)-2-((1S,5S,6S,E)-1-HYDROXY-5-METHYL-6-SULFAMOYLHEPT-2-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLIC ACID

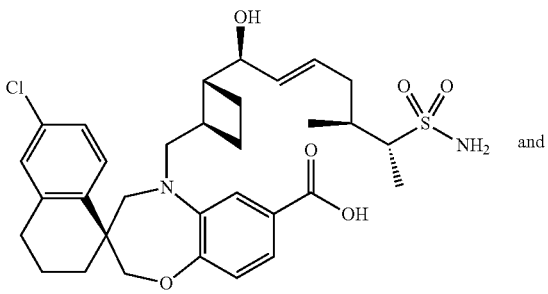

and

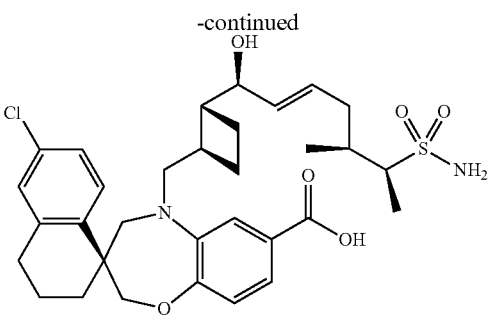

The title compounds were synthesized from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A; 75 mg, 0.147 mmol) and a 2.3:1 mixture of (2R,3S)-3-methylhex-5-ene-2-sulfonamide and (2S,3S)-3-methylhex-5-ene-2-sulfonamide (153 mg, 0.863 mmol) following the procedure described for Example 26, Step 3. The mixture of (S)-6'-chloro-5-(((1R,2R)-2-((1S,5S,6R,E)-1-hydroxy-5-methyl-6-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5S,6S,E)-1-hydroxy-5-methyl-6-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylic acid (73 mg, 0.118 mmol, 80% yield) was carried on to the next step.

STEP 4. (1S,3'R,6'R,7'S,8'E,11'S,12'S)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

The title compound was synthesized from (S)-6'-chloro-5-(((1R,2R)-2-((1S,5S,6R,E)-1-hydroxy-5-methyl-6-sulfamoylhept-2-en-1-23 yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5S,6S,E)-1-hydroxy-5-methyl-6-sulfamoylhept-2-en-1-yl)cyclobutyl)methyl)-3',4,4',5-tetrahydro-2H,2'H-spiro[benzo[b][1,4]oxazepine-3,1'-naphthalene]-7-carboxylic acid (73 mg, 0.118 mmol) following the procedure described for Example 26, Step 4. The crude material was purified by chromatography through a 12 g ISCO gold column, eluting with 10-40-50% EtOAc (containing 0.3% AcOH) in Hex over 24 min, to provide (1S,3'R,6'R,7'S,8'E,11'S,12'S)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide as the first eluting minor isomer. This material was repurified via preparative reverse-phase HPLC eluting with 50-70% MeCN (containing 0.1% TFA) in H$_2$O (containing 0.1% TFA) to provide the title compound (5.8 mg, 0.0097 mmol, 8.2% yield, 90% purity). $^1$H NMR (400 MHz, CD$_2$Cl$_2$) δ 8.21 (s, 1H), 7.71 (d, J=8.4 Hz, 1H), 7.18 (dd, J=2.3, 8.4 Hz, 1H), 7.14 (dd, J=2.1, 8.1 Hz, 1H), 7.09 (d, J=2.3 Hz, 1H), 6.95 (d, J=8.2 Hz, 1H), 6.69 (br. s., 1H), 6.10-5.99 (m, 1H), 5.67 (dd, J=6.4, 15.4 Hz, 1H), 4.20-4.14 (m, 1H), 4.11 (d, J=12.1 Hz, 1H), 4.06 (d, J=11.9 Hz, 1H), 3.84-3.74 (m, 1H), 3.76 (d, J=15.5 Hz, 1H), 3.65 (d, J=14.7 Hz, 1H), 3.44 (d, J=14.7 Hz, 1H), 3.33-3.20 (m, 1H), 2.86-2.70 (m, 2H), 2.60-2.48 (m, 2H), 2.31-2.20 (m, 2H), 2.08-1.98 (m, 2H), 1.97-1.80 (m, 4H), 1.79-1.68 (m, 1H), 1.67-1.49 (m, 2H), 1.46 (d, J=7.2 Hz, 3H), 1.42 (br. s., 1H), 1.08 (d, J=7.0 Hz, 3H). MS (ESI, +ve ion) m/z 599.1 (M+H)$^+$.

EXAMPLE 29

(1S,3'R,6'R,7'S,8'E,11'S)-6-CHLORO-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R)-6-CHLORO-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

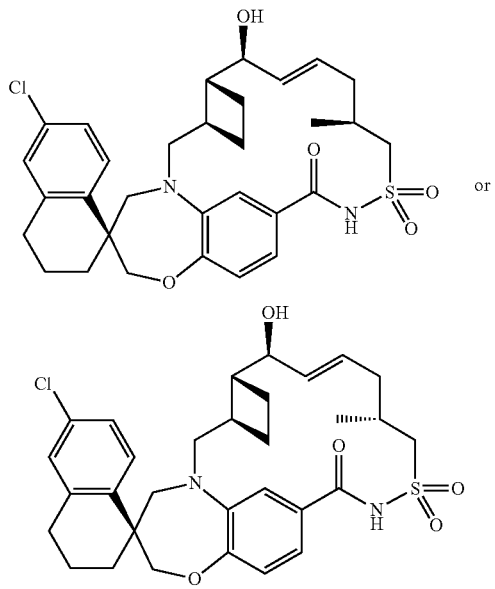

or

STEP 1: (S)—N,N-BIS(4-METHOXYBENZYL)-2-METHYLPENT-4-ENE-1-SULFONAMIDE AND (R)—N,N-BIS(4-METHOXYBENZYL)-2-METHYLPENT-4-ENE-1-SULFONAMIDE

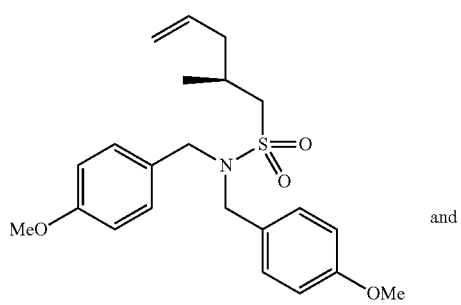

and

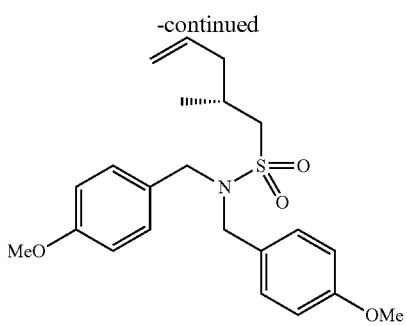

N,N-bis(4-methoxybenzyl)methanesulfonamide (Intermediate EE12; 1.05 g, 3.13 mmol) was azeotroped in PhMe under vacuum for 12 h. Under argon, THF (21 mL) was added and the solution was cooled to −78° C. Butyllithium solution (2.5 M in Hex; 1.63 mL, 4.07 mmol) was then added and the mixture was stirred at −78° C. for 30 min. Pent-4-en-2-yl 4-methylbenzenesulfonate (prepared according to the procedure by Sigman, M. S. et al.; *J. Am. Chem. Soc.*, 2012, 134(28), 11408-11411; 1.3 g, 5.41 mmol) was added as a solution in 1.5 mL THF. After complete addition the mixture was allowed to warm to ambient temperature and stir overnight. LC/MS analysis showed 50% conversion to the desired product; prolonged stirring for a further 24 h did not improve the conversion. The mixture was then quenched with satd NH$_4$Cl, and extracted with EtOAc, dried over MgSO$_4$ and concentrated. The crude material was purified by chromatography through a 24 g ISCO column, eluting with 10% to 20% to 60% EtOAc in Hex, to provide a racemic mixture of (S)—N,N-bis(4-methoxybenzyl)-2-methylpent-4-ene-1-sulfonamide and (R)—N,N-bis(4-methoxybenzyl)-2-methylpent-4-ene-1-sulfonamide (408 mg, 1.01 mmol, 32% yield).

STEP 2: (S)-2-METHYLPENT-4-ENE-1-SULFONAMIDE AND (R)-2-METHYLPENT-4-ENE-1-SULFONAMIDE

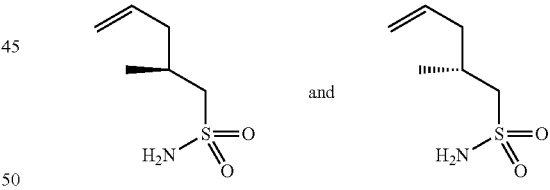

and

The title compounds were synthesized from (S)—N,N-bis(4-methoxybenzyl)-2-methylpent-4-ene-1-sulfonamide and (R)—N,N-bis(4-methoxybenzyl)-2-methylpent-4-ene-1-sulfonamide (506 mg, 1.25 mmol) following the procedure described for Example 26, Step 2. (S)-2-methylpent-4-ene-1-sulfonamide and (R)-2-methylpent-4-ene-1-sulfonamide were obtained as a racemic mixture (152 mg, 0.93 mmol, 74% yield).

STEP 3

(1'S)-TERT BUTYL 6'-CHLORO-5-(((1R,2R)-2-((1S,5S,E)-1-HYDROXY-5-METHYL-6-SULFAMOYLHEX-2-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLATE AND (1'S)-

TERT BUTYL 6'-CHLORO-5-(((1R,2R)-2-((1S,5R,E)-1-HYDROXY-5-METHYL-6-SULFAMOYLHEX-2-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLATE

2'H-SPIRO[BENZO[B][1,4]OXAZEPINE-3,1'-NAPHTHALENE]-7-CARBOXYLIC ACID

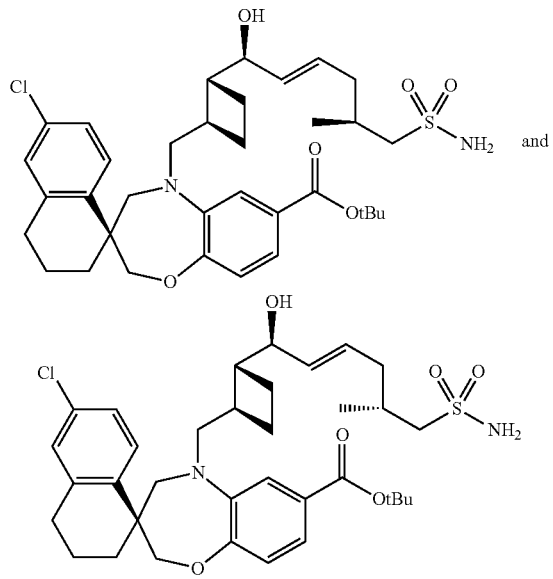

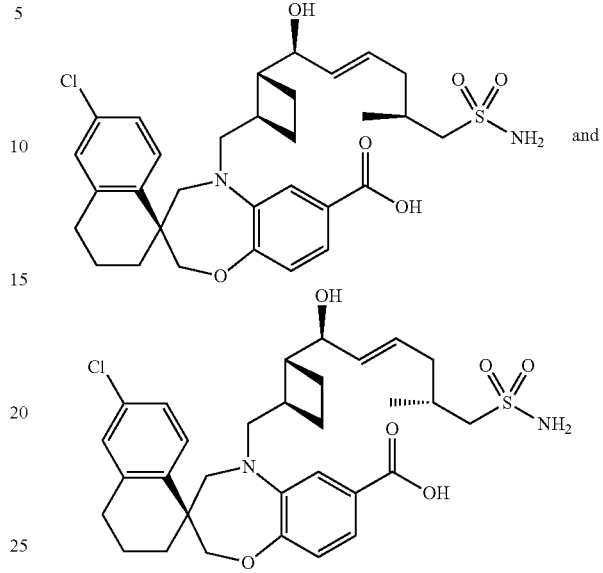

A vial was charged with ((S)-tert-butyl 6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylate (Intermediate AA12A, Step 1B, first eluting isomer; 120 mg, 0.212 mmol) and a racemic mixture of (S)-2-methylpent-4-ene-1-sulfonamide and (R)-2-methylpent-4-ene-1-sulfonamide (156 mg, 0.954 mmol) in 1,2-DCE (3.028 mL). The solution was sparged with argon and Hoveyda-Grubbs II (13.28 mg, 0.021 mmol) was added as a solution in 1.5 mL 1,2-DCE at ambient temperature. The mixture was stirred (sparging with argon and venting the vial) at ambient temperature for 1.5 h (70% conversion by LC/MS analysis). The reaction mixture was then sparged with air for 5 min, concentrated, and directly injected into a 24 g ISCO gold column, and purified eluting with 0-20-50-100% EtOAc/Hex over 16 min to give a mixture of (1'S)-tert butyl 6'-chloro-5-((1R,2R)-2-((1S,5S,E)-1-hydroxy-5-methyl-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylate and (1'S)-tert butyl 6'-chloro-5-(((1R,2R)-2-((1S,5R,E)-1-hydroxy-5-methyl-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylate (63 mg, 0.096 mmol, 45.1% yield).

STEP 4

(S)-6'-CHLORO-5-(((1R,2R)-2-((1S,5S,E)-1-HYDROXY-5-METHYL-6-SULFAMOYLHEX-2-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLIC ACID AND (S)-6'-CHLORO-5-(((1R,2R)-2-((1S,5R,E)-1-HYDROXY-5-METHYL-6-SULFAMOYLHEX-2-EN-1-YL)CYCLOBUTYL)METHYL)-3',4,4',5-TETRAHYDRO-2H,

To a solid mixture of (1'S)-tert butyl 6'-chloro-5-(((1R,2R)-2-((1S,5S,E)-1-hydroxy-5-methyl-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylate and (1'S)-tert butyl 6'-chloro-5-(((1R,2R)-2-((1S,5R,E)-1-hydroxy-5-methyl-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylate (63 mg, 0.096 mmol) and LiOH monohydrate (0.013 mL, 0.478 mmol) was added a 1:1 mixture of dioxane/MeOH (1.911 mL). The reaction was heated to 70° C. Virtually no reaction was observed after 1.5 h; $H_2O$ (~0.4 mL) was added and the mixture was stirred for 40 h. The mixture was then quenched with 1 N HCl (1.0 mL), diluted with brine, extracted with EtOAc, dried over $MgSO_4$, and concentrated. The crude material obtained was taken on to the next step without further purification.

STEP 5

(1S,3'R,6'R,7'S,8'E,11'S)-6-CHLORO-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R)-6-CHLORO-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

The title compound was synthesized from (S)-6'-chloro-5-(((1R,2R)-2-((1S,5S,E)-1-hydroxy-5-methyl-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5R,E)-1-hydroxy-5-methyl-6-sulfamoylhex-2-en-1-yl)cyclobutyl)methyl)-3',4,4',5-tetrahydro-2H,2'H-spiro[benzo[b][1,4]oxazepine-3,1'-naphthalene]-7-carboxylic acid (57 mg, 0.095 mmol) following the procedure described for Example 26, Step 4. The crude material was purified by chromatography through a 12 g ISCO gold column, eluting with 10-40-50% EtOAc (containing 0.3% AcOH) in Hex over 24 min, to provide (1S,3'R,6'R,7'S,8'E,11'S)-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R)-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide as the first eluting minor isomer (11 mg, 0.019 mmol, 19.9% yield, 90% purity). $^1$H NMR (400 MHz, CD$_2$Cl$_2$) δ 8.41 (s, 1H), 7.66 (d, J=8.4 Hz, 1H), 7.50 (br. s., 1H), 7.15 (dd, J=2.3, 8.4 Hz, 1H), 7.10 (d, J=2.3 Hz, 1H), 6.95 (dd, J=2.0, 8.2 Hz, 1H), 6.90 (d, J=8.0 Hz, 1H), 5.69 (dd, J=4.3, 15.8 Hz, 1H), 5.63-5.54 (m, 1H), 4.20 (s, 2H), 4.04 (d, J=15.3 Hz, 1H), 3.94 (dd, J=2.2, 5.2 Hz, 1H), 3.89-3.81 (m, 1H), 3.74-3.63 (m, 1H), 3.39 (d, J=15.3 Hz, 1H), 3.26-3.17 (m, 1H), 3.09-2.96 (m, 1H), 2.81-2.71 (m, 2H), 2.57-2.41 (m, 2H), 2.16 (dd, J=6.5, 11.7 Hz, 1H), 1.92-1.76 (m, 6H), 1.75-1.63 (m, 3H), 1.62-1.41 (m, 2H), 1.19 (d, J=6.1 Hz, 3H). MS (ESI, +ve ion) m/z 585.1 (M+H)$^+$.

[20]oxa[13]thia[1,14]diazatetracyclo[14.7.2.0$^{3,6}$.0$^{19,24}$]pentacosa[8,16,18,24]tetraen]-15'-one 13',13'-dioxide was isolated as the second eluting major isomer (11.6 mg, 0.020 mmol, 21.0% yield). $^1$H NMR (400 MHz, CD$_2$Cl$_2$) δ 8.44 (br. s., 1H), 7.71 (d, J=8.4 Hz, 1H), 7.17 (dd, J=2.3, 8.6 Hz, 1H), 7.09 (d, J=2.3 Hz, 1H), 6.95-6.90 (m, 2H), 6.89 (s, 1H), 5.82 (ddd, J=5.1, 7.6, 15.1 Hz, 1H), 5.70 (dd, J=8.2, 15.3 Hz, 1H), 4.24 (dd, J=3.9, 12.3 Hz, 1H), 4.20 (dd, J=4.7, 8.8 Hz, 1H), 4.10-4.05 (m, 2H), 3.82 (d, J=14.9 Hz, 1H), 3.69 (d, J=14.3 Hz, 1H), 3.25 (d, J=14.3 Hz, 1H), 3.05 (dd, J=9.6, 15.1 Hz, 11H), 2.98 (dd, J=8.0, 15.3 Hz, 1H), 2.84-2.67 (m, 2H), 2.41 (ddd, J=4.3, 9.8, 18.0 Hz, 1H), 2.36-2.28 (m, 1H), 2.24 (ddd, J=2.2, 7.9, 15.2 Hz, 1H), 2.08-1.99 (m, 2H), 1.98-1.87 (m, 3H), 1.87-1.74 (m, 4H), 1.68 (dd, J=9.4, 18.8 Hz, 1H), 1.46-1.35 (m, 1H), 1.15 (d, J=6.5 Hz, 3H). MS (ESI, +ve ion) m/z 585.1 (M+H)$^+$.

EXAMPLE 31

(1S,3'R,6'R,7'S,8'E,11'S)-6-CHLORO-7'-METHOXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R)-6-CHLORO-7'-METHOXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

EXAMPLE 30

(1S,3'R,6'R,7'S,8'E, 11'R)-6-CHLORO-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'S)-6-CHLORO-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

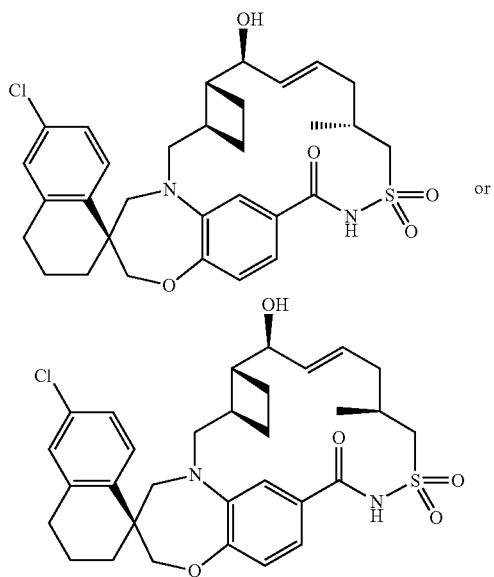

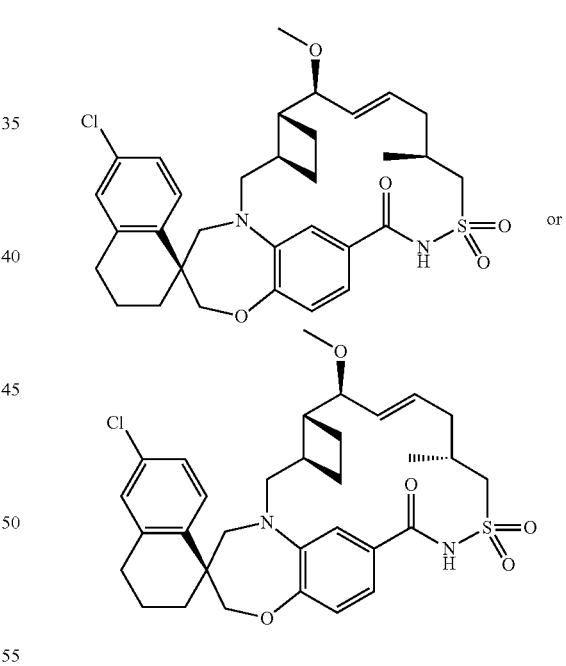

The title compound was synthesized as described for Example 29, Step 5. (1S,3'R,6'R,7'S,8'E, 11'R)-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S)-6-chloro-7'-hydroxy-11'-methyl-3,4-dihydro-2H,15'H-spiro[naphthalene-1,22'-

The title compound was synthesized from (1S,3'R,6'R,7'S,8'E,11'S)-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R)-6-chloro-7'-hydroxy-11'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 29, 8.0 mg, 0.014 mmol) following the procedure described for Example 4. Purification of the crude material provided (1S,3'R,6'R,7'S,8'E,11'S)-6-chloro-7'-methoxy-11'-methyl-3,4-dihydro-2H, 15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,11'R)-6-chloro-7'-methoxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (8.1 mg, 0.014 mmol, 99% yield, 94% purity). ¹H NMR (400 MHz, CD₂Cl₂) δ 8.22 (s, 1H), 7.69 (d, J=8.4 Hz, 1H), 7.16 (dd, J=2.3, 8.6 Hz, 1H), 7.09 (d, J=2.3 Hz, 1H), 6.97-6.88 (m, 3H), 5.84 (td, 1=6.3, 15.6 Hz, 1H), 5.48 (dd, J=7.3, 15.4 Hz, 1H), 4.15-4.03 (m, 2H), 3.64 (dd, J=6.5, 15.3 Hz, 1H), 3.61-3.56 (m, 2H), 3.55-3.46 (m, 2H), 3.38 (d, J=14.1 Hz, 1H), 3.29 (s, 3H), 3.23 (d, J=14.1 Hz, 1H), 2.84-2.68 (m, 2H), 2.48-2.31 (m, 2H), 2.27-2.15 (m, 3H), 2.02-1.93 (m, 1H), 1.93-1.82 (m, 3H), 1.77-1.63 (m, 3H), 1.56-1.44 (m, 1H), 1.16 (d, J=6.5 Hz, 3H). MS (ESI, +ve ion) m/z 599.0 (M+H)⁺.

EXAMPLE 32

(1S,3'R,6'R,7'S,8'E,11'R)-6-CHLORO-7'-METHOXY-11'-METHYL-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[8,16,18,24]TETRAEN]-15'-ONE 13',13'-DIOXIDE OR (1S,3'R,6'R,7'S,8'E,11'S)-6-CHLORO-7'-METHOXY-11'-METHYL-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[8,16,18,24]TETRAEN]-15'-ONE 13',13'-DIOXIDE chloro-7'-methoxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴] pentacosa[8,16,18,24]tetraen]-15-one 13',13'-dioxide or (1S,3'R,6'R,7'S,8'E,11'S)-6-chloro-7'-methoxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴] pentacosa[8,16,18,24]tetraen]-15'-one 13',13'-dioxide (8.1 mg, 0.014 mmol, 99% yield). ¹H NMR (400 MHz, CD₂Cl₂) δ 8.18 (s, 1H), 7.71 (d, J=8.6 Hz, 1H), 7.17 (dd, J=2.3, 8.6 Hz, 1H), 7.09 (d, J=2.3 Hz, 1H), 6.93-6.87 (m, 2H), 6.82 (s, 1H), 5.82 (ddd, J=5.7, 7.6, 14.9 Hz, 1H), 5.52 (dd, J=9.2, 15.3 Hz, 1H), 4.32 (dd, J=4.9, 15.3 Hz, 1H), 4.07 (s, 2H), 3.81 (d, J=14.9 Hz, 1H), 3.70 (d, J=14.3 Hz, 1H), 3.64 (dd, J=3.5, 9.2 Hz, 1H), 3.23 (d, J=14.3 Hz, 1H), 3.19 (s, 3H), 3.02 (dd, J=6.1, 15.3 Hz, 1H), 2.99 (dd, J=3.2, 15.2 Hz, 1H), 2.85-2.67 (m, 2H), 2.44 (ddd, J=3.3, 9.6, 18.6 Hz, 1H), 2.36-2.23 (m, 2H), 2.15-2.02 (m, 1H), 2.00-1.89 (m, 2H), 1.88-1.82 (m, 1H), 1.82-1.74 (m, 2H), 1.71-1.62 (m, 1H), 1.59-1.48 (m, 2H), 1.44-1.34 (m, 1H), 1.14 (d, J=6.8 Hz, 3H). MS (ESI, +ve ion) m/z 599.0 (M+H)⁺.

EXAMPLE 33

(1S,3'R,6'R,7'S,8'E,11'R)-6-CHLORO-11'-ETHYL-7'-HYDROXY-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[8,16,18,24]TETRAEN]-15'-ONE 13',13'-DIOXIDE

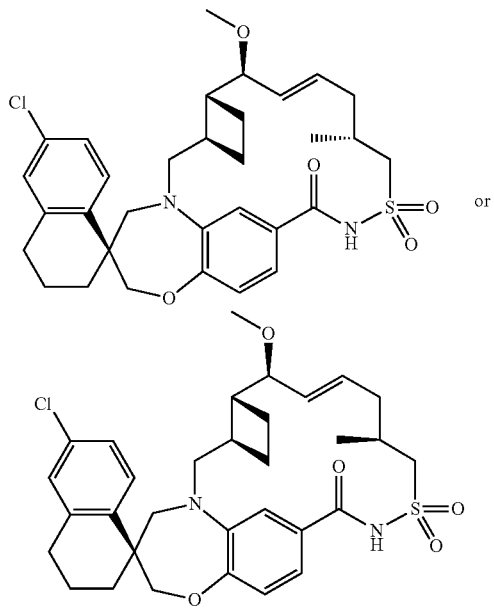 or

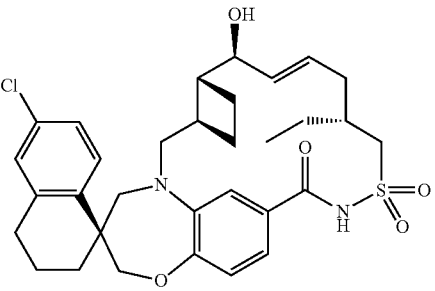 [SMILES: CC[C@@H]1C/C=C/[C@H](O)[C@@H]2CC[C@H]2CN2C[C@@]3(CCCc4cc(Cl)ccc43)COc3ccc(cc32)C(=O)NS(=O)(=O)C1]

The title compound was synthesized from (1S,3'R,6'R,7'S,8'E,11'R)-6-chloro-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide or (1S,3'R,6'R,7'S,8'E,11'S)-6-chloro-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[8,16,18,24]tetraen]-15'-one 13',13'-dioxide (Example 30; 8.0 mg, 0.014 mmol) following the procedure described for Example 4. Purification of the crude material provided (1S,3'R,6'R,7'S,8'E, 11'R)-6-

STEP 1: (S)-2-ETHYL-N,N-BIS(4-METHOXYBENZYL)PENT-4-ENE-1-SULFONAMIDE AND (R)-2-ETHYL-N,N-BIS(4-METHOXYBENZYL)PENT-4-ENE-1-SULFONAMIDE

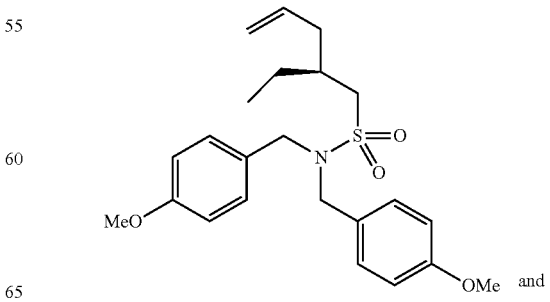 and

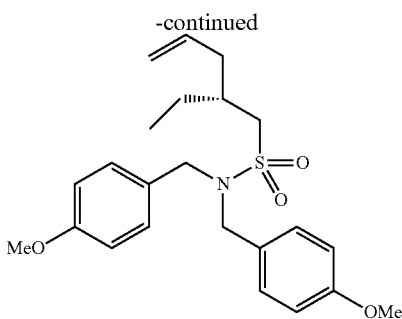

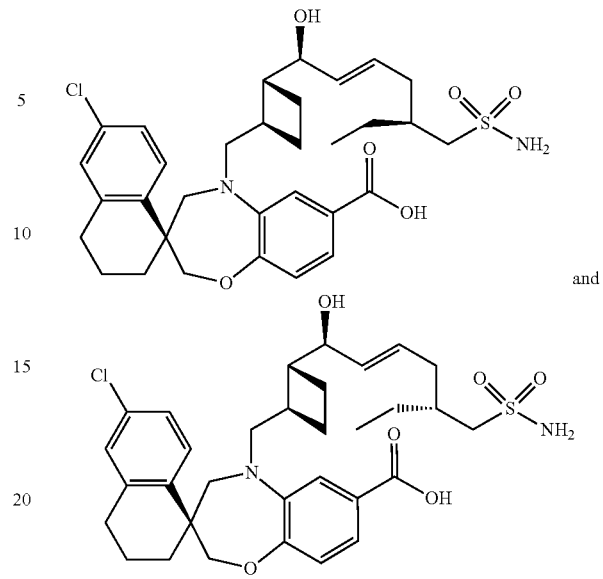

The title compound was synthesized from N,N-bis(4-methoxybenzyl)methanesulfonamide (Intermediate EE12; 1.10 g, 3.28 mmol) and hex-5-en-3-yl 4-methylbenzenesulfonate (prepared according to the procedure by Sigman, M. S. et al.; *J. Am. Chem. Soc.*, 2012, 134(28), 11408-11411; 1.50 g, 5.90 mmol) according to the procedure described for Intermediate 26, Step 1. (S)-2-ethyl-N,N-bis(4-methoxybenzyl)pent-4-ene-1-sulfonamide and (R)-2-ethyl-N,N-bis(4-methoxybenzyl)pent-4-ene-1-sulfonamide were obtained as a racemic mixture (435 mg, 1.04 mmol, 31.8% yield).

STEP 2: (S)-2-ETHYLPENT-4-ENE-1-SULFONAMIDE AND (R)-2-ETHYLPENT-4-ENE-1-SULFONAMIDE

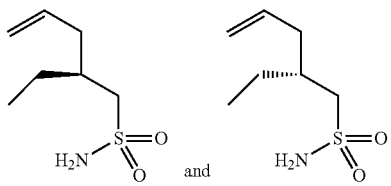

The title compound was synthesized from a racemic mixture of (S)-2-ethyl-N,N-bis(4-methoxybenzyl)pent-4-ene-1-sulfonamide and (R)-2-ethyl-N,N-bis(4-methoxybenzyl)pent-4-ene-1-sulfonamide (435 mg, 1.04 mmol) according to the procedure described for Example 26, Step 2. (S)-2-ethylpent-4-ene-1-sulfonamide and (R)-2-ethylpent-4-ene-1-sulfonamide were obtained as a racemic mixture (149 mg, 0.84 mmol, 81% yield).

STEP 3:
(S)-6'-CHLORO-5-(((1R,2R)-2-((1S,5S,E)-1-HYDROXY-5-(SULFAMOYLMETHYL)HEPT-2-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLIC ACID AND (S)-6'-CHLORO-5-(((1R,2R)-2-((S,5R,E)-1-HYDROXY-5-(SULFAMOYLMETHYL)HEPT-2-EN-1-YL)CYCLOBUTYL)METHYL)-3',4,4',5-TETRAHYDRO-2H,2'H-SPIRO[BENZO[B][1,4]OXAZEPINE-3,1'-NAPHTHALENE]-7-CARBOXYLIC ACID

The title compounds were synthesized from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A; 80 mg, 0.157 mmol) and a mixture of (S)-2-ethylpent-4-ene-1-sulfonamide and (R)-2-ethylpent-4-ene-1-sulfonamide (149 mg, 0.84 mmol) following the procedure described for Example 26, Step 3. Purification of the crude material eluting with a gradient of 0-20-50-100% EtOAc in heptanes followed by a gradient of 20-50% EtOAc (containing 0.3% AcOH) in heptanes provided an inseparable mixture of (S)-6'-chloro-5-(((1R,2R)-2-((1S,5S,E)-1-hydroxy-5-(sulfamoylmethyl)hept-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5R,E)-1-hydroxy-5-(sulfamoylmethyl)hept-2-en-1-yl)cyclobutyl)methyl)-3',4,4',5-tetrahydro-2H,2'H-spiro[benzo[b][1,4]oxazepine-3,1'-naphthalene]-7-carboxylic acid (75 mg, 0.122 mmol, 77% yield).

STEP 4. 1S,3'R,6'R,7'S,8'E,11'R)-6-CHLORO-11'-ETHYL-7'-HYDROXY-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

The title compound was synthesized from (S)-6'-chloro-5-(((1R,2R)-2-((1S,5S,E)-1-hydroxy-5-(sulfamoylmethyl)hept-2-en-1-yl)cyclobutyl)methyl)-3',4,4',5-tetrahydro-2H,2'H-spiro[benzo[b][1,4]oxazepine-3,1'-naphthalene]-7-carboxylic acid and (S)-6'-chloro-5-(((1R,2R)-2-((1S,5R,E)-1-hydroxy-5-(sulfamoylmethyl)hept-2-en-1-yl)cyclobutyl)methyl)-3',4,4',5-tetrahydro-2H,2'-spiro[benzo[b][1,4]oxazepine-3,1'-naphthalene]-7-carboxylic acid (75 mg, 0.122 mmol) following the procedure described for Example 26, Step 4. The crude material was purified by chromatography through a 12 g ISCO gold column, eluting with 10-30-50% EtOAc (containing 0.3% AcOH) in Hex over 24 min, to provide (1S,3'R,6'R,7'S,8'E,11'R)-6-chloro-11'-ethyl-7'-hydroxy-3,4-dihydro-2H,15'H-spiro[naphthalene-1,22'-[20]oxa[13]thia[1,14]diazatetracyclo [14.7.2.0$^{3,6}$.0$^{19,24}$] pentacosa[8,16,18,24]tetraen]-15'-one 13',13'-dioxide as the first eluting isomer (20.4 mg, 0.034 mmol, 28.0% yield). $^1$H NMR (400 MHz, CD$_2$Cl$_2$) δ 8.45 (br. s., 1H), 7.67 (d, J=8.6

Hz, 1H), 7.44 (br. s., 1H), 7.15 (dd, J=2.3, 8.4 Hz, 1H), 7.10 (d, J=2.3 Hz, 1H), 6.96 (dd, J=1.8, 8.0 Hz, 1H), 6.91 (d, J=8.0 Hz, 1H), 5.71 (dd, J=4.7, 15.7 Hz, 1H), 5.66-5.55 (m, 1H), 4.24-4.13 (m, 2H), 3.96 (br. s., 1H), 3.92 (d, J=15.7 Hz, 1H), 3.79 (br. s., 1H), 3.64 (d, J=13.3 Hz, 1H), 3.42 (d, J=14.5 Hz, 1H), 3.30-3.11 (m, 2H), 2.79-2.71 (m, 2H), 2.56-2.41 (m, 2H), 2.29 (dd, J=5.5, 13.9 Hz, 1H), 1.91-1.75 (m, 7H), 1.75-1.63 (m, 4H), 1.45 (dt, J=7.6, 14.3 Hz, 2H), 0.92 (t, J=7.3 Hz, 3H). MS (ESI, +ve ion) m/z 599.0 (M+H)+.

EXAMPLE 34

(1S,3'R,6'R,7'S,8'E,11'S)-6-CHLORO-11'-ETHYL-7'-HYDROXY-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[8,16,18,24]TETRAEN]-15'-ONE 13',13'-DIOXIDE

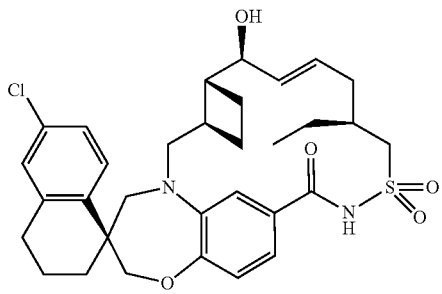 [SMILES: CC[C@H]1C/C=C/[C@H](O)[C@@H]2CC[C@H]2CN2C[C@@]3(CCCc4cc(Cl)ccc43)COc3ccc(cc32)C(=O)NS(=O)(=O)C1]

The title compound was synthesized as described for Example 33, Step 4. (1S,3'R,6'R,7'S,8'E,11'S)-6-chloro-11'-ethyl-7'-hydroxy-3,4-dihydro-2H,15'H-spiro[naphthalene-1,22'-[20]oxa[13]thia[1,14]diazatetracyclo [14.7.2.0³,⁶.0¹⁹,²⁴]pentacosa[8,16,18,24]tetraen]-15'-one 13',13'-dioxide as the second eluting isomer. This material was repurified eluting with 60% EtOAc in heptanes to provide the pure title compound (15.7 mg, 0.026 mmol, 21.6% yield). ¹H NMR (500 MHz, CD₂Cl₂) δ 8.59 (br. s., 1H), 7.69 (d, J=8.6 Hz, 1H), 7.15 (dd, J=2.3, 8.4 Hz, 1H), 7.08 (d, J=2.2 Hz, 1H), 6.93 (dd, J=2.0, 8.1 Hz, 1H), 6.90 (d, J=8.1 Hz, 1H), 6.85 (d, J=1.5 Hz, 1H), 5.81 (td, J=6.6, 15.2 Hz, 1H), 5.68 (dd. J=8.3, 15.2 Hz, 1H), 4.19 (dd, J=3.9, 8.1 Hz, 1H), 4.12 (dd, J=5.9, 15.4 Hz, 1H), 4.06 (s, 2H), 3.78 (d, J=14.9 Hz, 1H), 3.68 (d, J=14.4 Hz, 1H), 3.23 (d, J=14.2 Hz, 1H), 3.13 (dd, J=6.7, 15.5 Hz, 1H), 3.02 (dd, J=9.7, 15.3 Hz, 1H), 2.82-2.68 (m, 2H), 2.39 (ddd, J=4.2, 9.8, 18.1 Hz, 1H), 2.36-2.25 (m, 2H), 2.06-1.96 (m, 3H), 1.96-1.88 (m, 2H), 1.87-1.70 (m, 4H), 1.69-1.56 (m, 3H), 1.42-1.35 (m, 1H), 0.90 (t, J=7.5 Hz, 3H). MS (ESI, +ve ion) m/z 599.2 (M+H)+.

EXAMPLE 35

(1S,3'R,6'R,7'S,11'R,12'R)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[16,18,24]TRIEN]-15'-ONE 13',13'-DIOXIDE OR (1S,3'R,6'R,7'S,11'R,12'S)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[16,18,24]TRIEN]-15'-ONE 13',13'-DIOXIDE

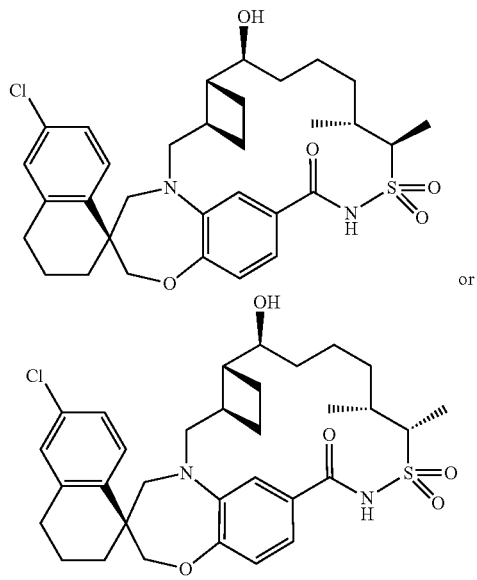

A mixture of (1S,3'R,6'R,7'S,8'E,11'R,12'R)-6-chloro-7'-hydroxy-11',12'-dimethyl-3,4-dihydro-2H,15'H-spiro[naphthalene-1,22'-[20]oxa[13]thia[1,14]diazatetracyclo [14.7.2.0³,⁶.0¹⁹,²⁴]pentacosa[8,16,18,24]tetraen]-15'-one 13',13'-dioxide or (1S,3'R,6'R,7'S,8'E,11'R,12'S)-6-chloro-7'-hydroxy-11',12'-dimethyl-3,4-dihydro-2H,15'H-spiro [naphthalene-1,22'-[20]oxa[13]thia[1,14]diazatetracyclo [14.7.2.0³,⁶.0¹⁹,²⁴]pentacosa[8,16,18,24 tetraen]-15'-one 13',13'-dioxide (Example 26; 17 mg, 0.028 mmol) and platinum (IV) oxide (6.44 mg, 0.028 mmol) in EtOAc (3.5 mL) were stirred under H₂ (balloon) at ambient temperature for 50 min. The reaction mixture was then filtered through a syringe filter. The crude material was purified by chromatography through a Redi-Sepn pre-packed SiO₂ gel column (4 g), eluting with 20% to 50% EtOAc (containing 0.3% AcOH) in heptanes, to provide (1S,3'R,6'R,7'S,11'R,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[16,18,24]trien]-15'-one 13',13'-dioxide or (1S,3'R,6'R,7'S,11'R,12'S)-6-chloro-7'-hydroxy-11',12'-dimethyl-3,4-dihydro-2H,15'H-spiro [naphthalene-1,22'-[20]oxa[13]thia[1,14]diazatetracyclo [14.7.2.0³,⁶.0¹⁹,²⁴]pentacosa[16,18,24]trien]-15'-one 13', 13'-dioxide (12.1 mg, 0.020 mmol, 70.9% yield). ¹H NMR (500 MHz, CD₂Cl₂) δ 8.55 (br. s., 1H), 7.67 (d, J=8.6 Hz, 1H), 7.48 (br. s., 1H), 7.14 (dd, J=2.4, 8.6 Hz, 1H), 7.09 (d, J=2.2 Hz, 1H), 7.03 (dd, J=1.7, 8.1 Hz, 1H), 6.92 (d, J=8.3 Hz, 1H), 4.22-4.13 (m, 2H), 4.05-3.96 (m, 1H), 3.66 (br. s., 1H), 3.61 (d, J=13.7 Hz, 1H), 3.51-3.45 (m, 1H), 3.43 (d, J=14.4 Hz, 1H), 3.28 (d, J=12.2 Hz, 1H), 2.81-2.69 (m, 2H), 2.62-2.53 (m, 1H), 2.48-2.41 (m, 1H), 2.16-2.08 (m, 2H), 1.91 (q, J=9.0 Hz, 1H), 1.87-1.78 (m, 3H), 1.78-1.72 (m, 1H), 1.68 (q, J=8.6 Hz, 2H), 1.59 (dd, J=6.1, 10.3 Hz, 2H), 1.50-1.43 (m, 1H), 1.41 (d, J=7.1 Hz, 3H), 1.37-1.25 (m, 4H), 1.00 (d, J=6.8 Hz, 3H). MS (ESI, +ve ion) m/z 601.0 (M+H)+.

EXAMPLE 36

(1S,3'R,6'R,7'S,11'R,12'S)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[16,18,24]

TRIEN]-15'-ONE 13',13'-DIOXIDE OR (1S,3'R,6'R,7'S,11'R,12'R)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[16,18,24]TRIEN]-15'-ONE 13',13'-DIOXIDE

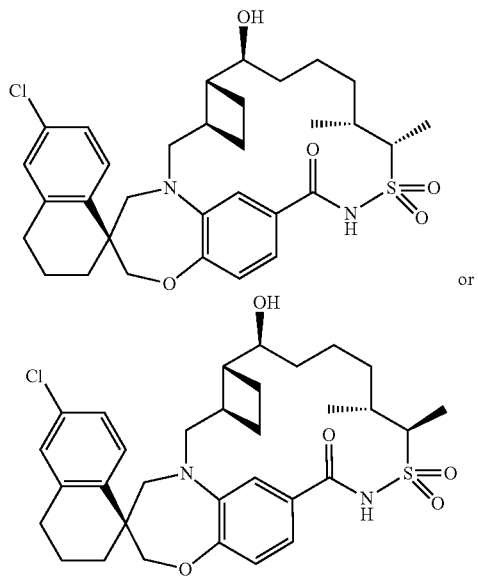

The title compound was synthesized from (1S,3'R,6'R,7'S,8'E,11'R,12'S)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 27; 9.4 mg, 0.016 mmol) following the procedure described for Example 35. Purification of the crude material provided (1S,3'R,6'R,7'S,11'R,12'S)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide or (1S,3'R,6'R,7'S,11'R,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide (5.2 mg, 0.0087 mmol, 55.1% yield). $^1$H NMR (500 MHz, CD$_2$Cl$_2$) δ 9.70 (br. s., 1H), 7.70 (d, J=8.6 Hz, 1H), 7.17 (dd, J=2.2, 8.3 Hz, 1H), 7.16 (d, J=8.3 Hz, 1H), 7.10 (d, J=2.2 Hz, 1H), 6.97 (d, J=8.1 Hz, 1H), 4.18 (d, J=11.7 Hz, 1H), 4.12 (d, J=12.0 Hz, 1H), 3.69-3.57 (m, 3H), 3.49 (d, J=14.7 Hz, 1H), 3.38 (d, J=14.2 Hz, 1H), 3.33 (br. s., 1H), 2.90 (d, J=4.6 Hz, 2H), 2.82-2.70 (m, 2H), 2.46-2.36 (m, 1H), 2.31-2.20 (m, 1H), 2.11-2.01 (m, 1H), 1.99-1.91 (m, 3H), 1.90-1.78 (m, 3H), 1.77-1.70 (m, 2H), 1.70-1.62 (m, 4H), 1.61-1.55 (m, 1H), 1.45 (m, 1H), 1.42 (d, J=7.3 Hz, 3H), 0.97 (d, J=6.8 Hz, 3H). MS (ESI, +ve ion) m/z 601.1 (M+H)$^+$.

EXAMPLE 37. (1S,3'R,6'R,7'S,11'S,12'S)-6-CHLORO-7'-HYDROXY-11',12'-DIMETHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[16,18,24]TRIEN]-15'-ONE 13',13'-DIOXIDE

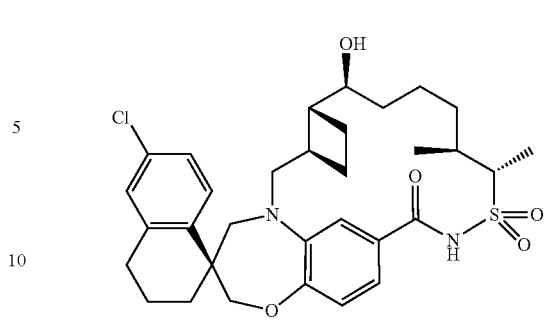

The title compound was synthesized from (1S,3'R,6'R,7'S,8'E,11'S,12'S)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 28; 3.9 mg, 0.0065 mmol) following the procedure described for Example 35. Purification of the crude material provided (1S,3'R,6'R,7'S,11'S,12'S)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[16,18,24]trien]-15'-one 13',13'-dioxide (2.8 mg, 0.0047 mmol, 71.6% yield, 90% purity). $^1$H NMR (500 MHz, CD$_2$Cl$_2$) δ 10.44 (s, 1H), 7.73 (d, J=8.3 Hz, 1H), 7.43 (dd, J=2.2, 8.3 Hz, 1H), 7.32 (d, J=2.2 Hz, 1H), 7.17 (dd, J=2.4, 8.6 Hz, 1H), 7.09 (d, J=2.4 Hz, 1H), 6.96 (d, J=8.3 Hz, 1H), 4.10-4.05 (m, 2H), 3.87 (d, J=15.4 Hz, 1H), 3.66 (d, J=13.9 Hz, 1H), 3.61 (q, J=8.8 Hz, 1H), 3.55 (ddd, J=1.2, 7.1, 14.4 Hz, 1H), 3.16 (d, J=14.2 Hz, 1H), 3.09 (dd, J=8.7, 15.3 Hz, 1H), 2.84-2.69 (m, 2H), 2.46-2.37 (m, 1H), 2.34 (d, J=8.6 Hz, 1H), 2.24 (quin, J=8.8 Hz, 1H), 2.17-2.08 (m, 2H), 2.06 (d, J=8.8 Hz, 1H), 2.04-1.96 (m, 1H), 1.96-1.87 (m, 1H), 1.86-1.71 (m, 5H), 1.71-1.61 (m, 2H), 1.51-1.46 (m, 1H), 1.45-1.41 (m, 1H), 1.40 (d, J=7.3 Hz, 3H), 1.35-1.28 (m, 1H), 1.03 (d, J=6.8 Hz, 3H). MS (ESI, +ve ion) m/z 601.1 (M+H)$^+$.

EXAMPLE 38

(1S,3'R,6'R,7'S,11'S)-6-CHLORO-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[16,18,24]TRIEN]-15'-ONE 13',13'-DIOXIDE OR (1S,3'R,6'R,7'S,11'R)-6-CHLORO-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[16,18,24]TRIEN]-15'-ONE 13',13'-DIOXIDE

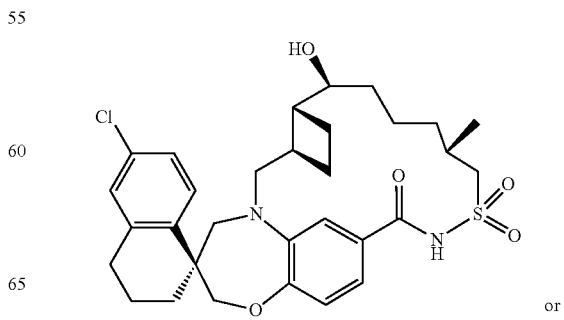

-continued

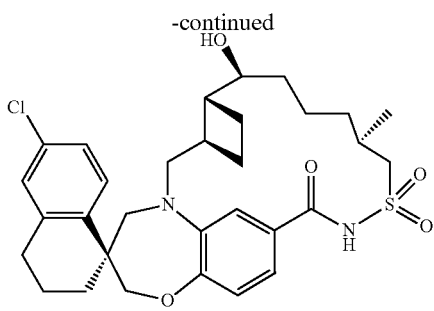

STEP 1: (S)-BENZYL(2-METHYLBUT-3-EN-1-YL)SULFANE AND (R)-BENZYL(2-METHYL-BUT-3-EN-1-YL)SULFANE

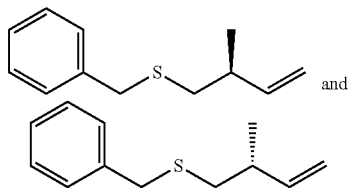

A mixture of 2-methylbut-3-en-1-ol (1.198 mL, 11.61 mmol), phenylmethanethiol (2.044 mL, 17.42 mmol) and 2-(tributylphosphoranylidene) MeCN (4.67 mL, 17.42 mmol) were heated at 100° C. for 2 h. The reaction mixture was cooled to rt, diluted with EtOAc, washed with satd NH$_4$Cl aqueous solution and brine, dried over Na$_2$SO$_4$, and concentrated. The crude product was absorbed into 30 g of SiO$_2$ gel and dried and then purified by chromatography on SiO$_2$ gel eluting with Hex to provide the title product as a colorless oil (1.62 g, 72.4%). $^1$H NMR (400 MHz, CDCl$_3$) δ 7.44-7.27 (m, 5H), 5.84 (ddd, J=17.17, 10.32, 6.75 Hz, 1H), 5.16-5.03 (m, 2H), 3.79 (s, 2H), 2.58-2.39 (m, 3H), 1.19-1.14 (m, 3H).

STEP 2: (S)-2-METHYLBUT-3-ENE-1-SULFONAMIDE AND (R)-2-METHYLBUT-3-ENE-1-SULFONAMIDE

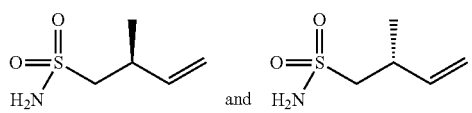

To a mixture of (S)-benzyl(2-methylbut-3-en-1-yl)sulfane, (R)-benzyl(2-methylbut-3-en-1-yl)sulfane (0.650 g, 3.38 mmol) and iodosobenzene (2.454 g, 11.15 mmol) in 133 mL of ether was slowly added concentrated HCl (18.31 mL, 220 mmol) with vigorous stirring. The resulting mixture was stirred for 30 min. The reaction mixture was settled and layers separated. The organic layer was concentrated under reduced pressure. The residue was dried under high vacuum for 1 h. The solution of residue in 8 mL of DCM was added into a mixture of ammonia, 7.0 M solution in methanol (2.414 mL, 16.90 mmol), N,N-DIPEA (2.94 mL, 16.90 mmol) and 4-(dimethylamino)pyridine (8.26 mg, 0.068 mmol) in 10 mL of DCM. The reaction mixture was concentrated after stirring at rt for 16 h. The crude product was purified by chromatography on SiO$_2$ gel eluting with 0% to 60% EtOAc in hexane to provide the title compound (0.076 g, 15.1%). $^1$H NMR (400 MHz, CDCl$_3$) δ 5.82 (ddd, J=17.36, 10.03, 7.63 Hz, 1H), 5.21-5.05 (m, 4H), 3.25-3.07 (m, 2H), 2.92-2.78 (m, 1H), 1.20 (d, J=6.85 Hz, 3H).

STEP 3

(S)-6'-CHLORO-5-(((1R,2R)-2-((S)-1-HYDROXYBUT-3-EN-1-YL)CYCLOBUTYL)METHYL)-N—(((S)-2-METHYLBUT-3-EN-1-YL)SULFONYL)-3',4,4',5-TETRAHYDRO-2H,2'H-SPIRO[BENZO[B][1,4]OXAZEPINE-3,1'-NAPHTHALENE]-7-CARBOXAMIDE AND (S)-6'-CHLORO-5-(((1R,2R)-2-((S)-1-HYDROXYBUT-3-EN-1-YL)CYCLOBUTYL)METHYL)-N—(((R)-2-METHYLBUT-3-EN-1-YL)SULFONYL)-3',4,4',5-TETRAHYDRO-2H,2'H-SPIRO[BENZO[B][1,4]OXAZEPINE-3,1'-NAPHTHALENE]-7-CARBOXAMIDE

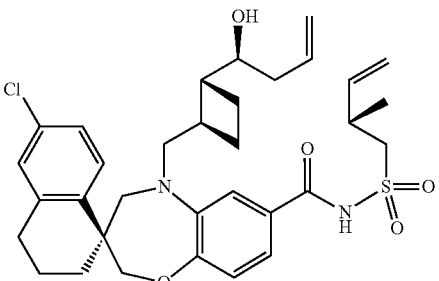

and

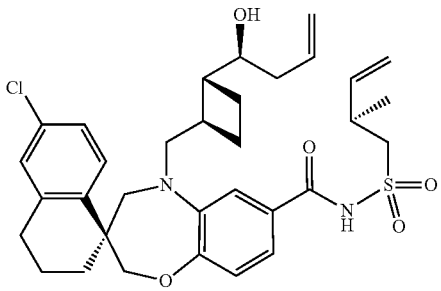

A mixture of (S)-6'-chloro-5-(((1R,2R)-2-((S)-1-hydroxybut-3-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA13A; 0.010 g, 0.021 mmol), (S)-2-methylbut-3-ene-1-sulfonamide and (R)-2-methylbut-3-ene-1-sulfonamide (0.019 g, 0.124 mmol), 1-(3-dimethylaminopropyl)-3-ethylcarbodiimide hydrochloride (0.012 g, 0.062 mmol) and 4-(dimethylamino)pyridine (7.60 mg, 0.062 mmol) in DCM (0.5 mL) was stirred at rt for 16 h. The mixture was directly loaded onto a column (5 g SiO$_2$ gel) for purification by chromatography, eluting with 0% to 50% EtOAc (containing 0.2% AcOH) in hexane to provide the title compound (0.011 g, 86%). m/z (ESI, +ve ion) 613.2 (M+H)$^+$.

STEP 4

(1S,3'R,6'R,7'S,9'E,11'R)-6-CHLORO-7'-HYDROXY-11'-METHYL-3,4-DIHYDRO-2H,15H-SPIRO[NAPHTHALENE-1,22'-[20]OXA[13]THIA[1,14]DIAZATETRACYCLO[14.7.2.0$^{3,6}$.0$^{19,24}$]PENTACOSA[9,16,18,24]TETRAEN]-15'-ONE 13',13'-DIOXIDE (116762-34-3) AND (1S,3'R,6'R,7'S,9'E,11'S)-6-CHLORO-7'-HY-

DROXY-11'-METHYL-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[9,16,18,24]TETRAEN]-15'-ONE 13',13'-DIOXIDE AND (1S,3'R,6'R,7'S,9'Z,11'R)-6-CHLORO-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[9,16,18,24]TETRAEN]-15'-ONE 13',13'-DIOXIDE AND (1S,3'R,6'R,7'S,9'Z,11'S)-6-CHLORO-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[9,16,18,24]TETRAEN]-15'-ONE 13',13'-DIOXIDE

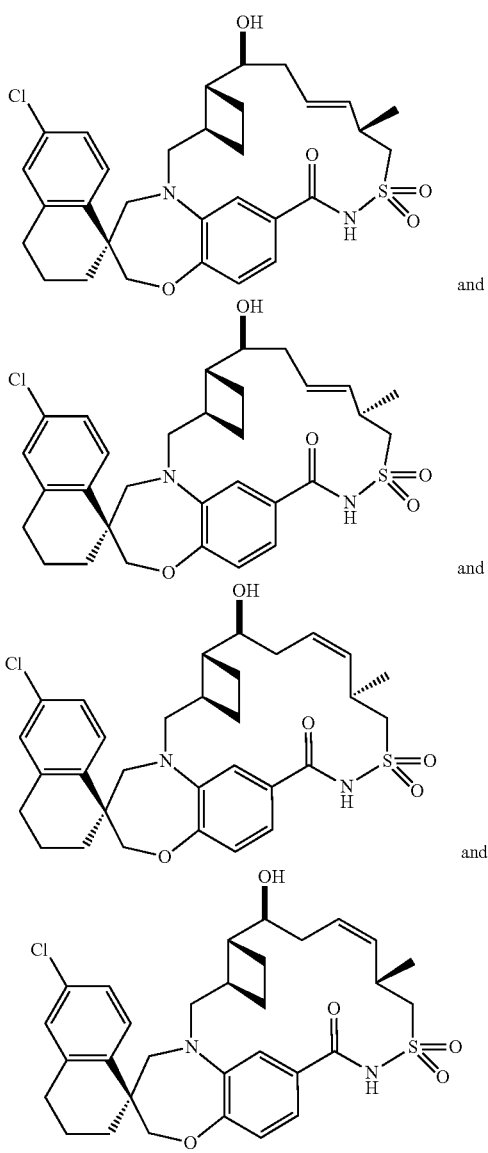

and and and

A solution of (S)-6'-chloro-5-((((1R,2R)-2-((S)-1-hydroxybut-3-en-1-yl)cyclobutyl)methyl)-N—(((S)-2-methylbut-3-en-1-yl)sulfonyl)-3',4,4',5-tetrahydro-2H,2'H-spiro[benzo[b][1,4]oxazepine-3,1'-naphthalene]-7-carboxamide and (S)-6'-chloro-5-((((1R,2R)-2-((S)-1-hydroxybut-3-en-1-yl)cyclobutyl)methyl)-N—(((R)-2-methylbut-3-en-1-yl) sulfonyl)-3',4,4',5-tetrahydro-2H,2'H-spiro[benzo[b][1,4]oxazepine-3,1'-naphthalene]-7-carboxamide (21 mg, 0.034 mmol) in toluene (80 mL) was subjected to three cycles of evacuation/back-filling with $N_2$. To the homogeneous solution was added a solution of Hoveyda-Grubbs II (4.29 mg, 6.85 μmol) in 1 mL of toluene at rt. The reaction mixture was stirred at 106° C. under $N_2$ for 2 h. Air was blown into mixture. The reaction was cooled to rt and concentrated. The residue was purified by preparative reverse-phase HPLC (Gemini™ Prep C18 5 μm column; gradient elution of 40% to 90% MeCN in $H_2O$, where both solvents contained 0.1% TFA, 30 min method) to provide a mixture of the title compounds.

STEP 5

(1S,3'R,6'R,7'S,11'S)-6-CHLORO-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[16,18,24]TRIEN]-15'-ONE 13',13'-DIOXIDE OR (1S,3'R,6'R,7'S,11'R)-6-CHLORO-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[16,18,24]TRIEN]-15'-ONE 13',13'-DIOXIDE

A mixture of (1S,3'R,6'R,7'S,9'E,11'R)-6-chloro-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide (116762-34-3) and (1S,3'R,6'R,7'S,9'E,11'S)-6-chloro-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide and (1S,3'R,6'R,7'S,9'Z,11'R)-6-chloro-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetra en]-15'-one 13',13'-dioxide and (1S,3'R,6'R,7'S,9'Z,1'S)-6-chloro-7'-hydroxy-11'-methyl-3,4-dihydro-2H,15'H-spiro[naphthalene-1,22'-[20]oxa[13]thia[1,14]diazatetracyclo[14.7.2.0³,⁶.0¹⁹,²⁴]pentacosa[9,16,18,24]tetraen]-15'-one 13',13'-dioxide (from Step 4, 1.6 mg, 2.73 μmol) and platinum (iv) oxide (0.621 mg, 2.73 μmol) in EtOAc (2.0 mL) was stirred under $H_2$ (balloon) at rt for 2 h. The solid catalyst was filtered off using a syringe filter, and filtrate was concentrated to give the crude product. The crude product was purified by preparative reverse-phase HPLC (Gemini™ Prep C18 5 μm column: gradient elution of 40% to 90% MeCN in $H_2O$, where both solvents contained 0.1% TFA, 30 min method) to provide the title compound as the second eluting isomer as a white solid. $^1$H NMR (500 MHz, $CDCl_3$) δ 9.02 (br. s., 11H), 7.73-7.69 (m, 1H), 7.22-7.16 (m, 3H), 7.09 (d, J=2.20 Hz, 1H), 6.96 (d, J=8.07 Hz, 1H), 4.16-4.09 (m, 2H), 3.88-3.63 (m, 6H), 3.28-3.22 (m, 1H), 3.17 (dd, J=15.16, 5.87 Hz, 1H), 3.13-3.07 (m, 1H), 2.80-2.74 (m, 2H), 2.36-2.29 (m, 2H), 2.21-2.18 (m, 1H), 2.03-1.98 (m, 2H), 1.94-1.77 (m, 2H), 1.75-1.27 (m, 9H), 1.13 (d, J=6.85 Hz, 3H). m/z (ESI, +ve ion) 587.2 (M+H)⁺.

EXAMPLE 39

(1S,3'R,6'R,7'S,11'R)-6-CHLORO-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[16,18,24]TRIEN]-15'-ONE 13',13'-DIOXIDE OR (1S,3'R,6'R,7'S,11'S)-6-

CHLORO-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[16,18,24]TRIEN]-15'-ONE 13',13'-DIOXIDE

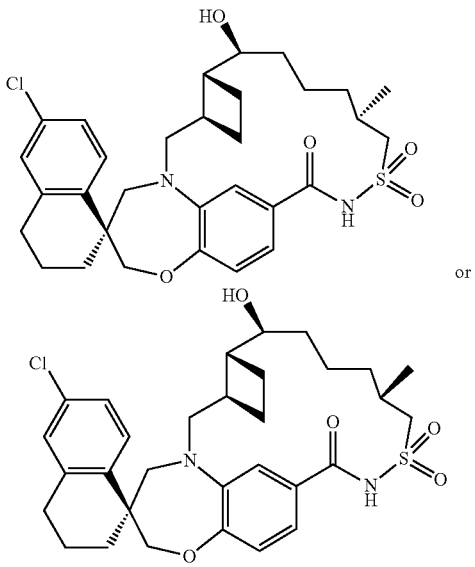

or

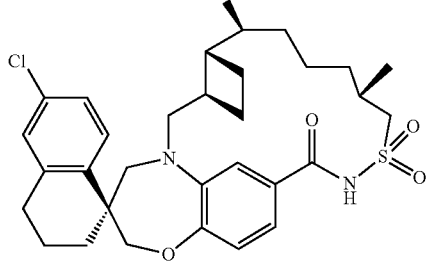

The title compound was isolated as the second eluting isomer out of preparative reverse-phase HPLC in Example 38. $^1$H NMR (400 MHz, CDCl$_3$) δ 9.38 (br. s., 1H), 7.69 (d, J=8.61 Hz, 1H), 7.29 (m, 1H), 7.25-7.15 (m, 2H), 7.10 (d, J=2.35 Hz, 1H), 6.98 (d, J=8.22 Hz, 1H), 4.16 (s, 2H), 3.89-3.83 (m, 1H), 3.67 (d, J=7.83 Hz, 1H), 3.61-3.44 (m, 4H), 3.41 (d, J=12.52 Hz, 2H), 2.81-2.68 (m, 3H), 2.23-2.06 (m, 3H), 2.02-1.72 (m, 5H), 1.64-1.51 (m, 5H), 1.49-1.38 (m, 21H), 1.25-1.13 (m, 1H), 1.06 (d, J=6.85 Hz, 3H). m/z (ESI, +ve ion) 587.1 (M+H)$^+$.

EXAMPLE 40

(1S,3'R,6'R,7'S,8'E)-6-CHLORO-7'-HYDROXY-12',12'-DIMETHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE AND

EXAMPLE 41

(1S,3'R,6'R,7'S,8'Z)-6-CHLORO-7'-HYDROXY-12',12'-DIMETHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

Example 40

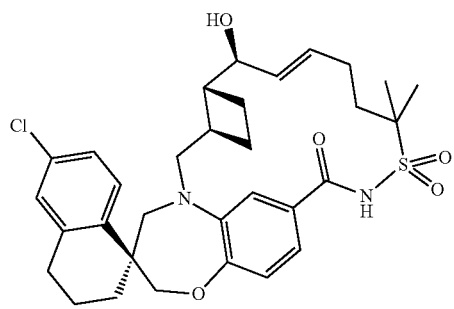

Example 41

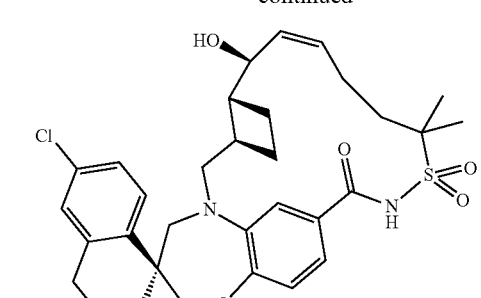

STEP 1:
2-METHYLHEX-5-ENE-2-SULFONAMIDE NH$_2$

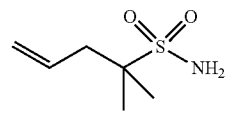

The title compound was prepared in an analogous manner to that described in Intermediate EE20 using 5 eq. butyllithium solution, 2.5 M in hexanes (Aldrich) and 5 eq. of MeI (Aldrich), and the desired product 1-(trifluoromethoxy)hept-6-ene-3-sulfonamide was isolated as a light brown oil.

STEP 2

(1S,3'R,6'R,7'S,8'E)-6-CHLORO-7'-HYDROXY-12',12'-DIMETHYL-3,4-DIHYDRO-2H,15H-SPIRO[NAPHTHALENE-1,22'-[20]OXA[13]THIA[1,14]DIAZATETRACYCLO[[14.7.2.0$^{3,6}$.0$^{19,24}$]PENTACOSA[8,16,18,24]TETRAEN]-15'-ONE 13',13'-DIOXIDE AND (1S,3'R,6'R,7'S,8'Z)-6-CHLORO-7'-HYDROXY-12',12'-DIMETHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

The title compound was prepared in an analogous manner to that described in Example 2, Steps 1 and 2, using Intermediate AA1 IA and 2-methylhex-5-ene-2-sulfonamide from Step 1, and the desired products, (1S,3'R,6'R,7'S,8'E)-6-chloro-7'-hydroxy-12',12'-dimethyl-3,4-dihydro-2H,15'H-spiro[naphthalene-1,22'-[20]oxa 13]thia[1,14]diazatetracyclo[14.7.2.0$^{3,6}$.0$^{19,24}$] pentacosa[8,16,18,24]tetraen]-15-one 13',13'-dioxide (Example 40) as the first eluting major isomer out of preparative reverse-phase HPLC and (1S,3'R,6'R,7'S,8'Z)-6-chloro-7'-hydroxy-12',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 41) as the second eluting major isomer out of preparative reverse-phase HPLC was isolated. (1S,3'R,6'R,7'S,8'E)-6-chloro-7'-hydroxy-12',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 40): $^1$H NMR (500 MHz, CD$_3$OD) δ 7.75 (d, J=8.6 Hz, 1H), 7.20 (d, J=2.2, 8.6 Hz, 1H), 7.13 (d, J=2.2 Hz, 1H), 7.07 (br. s., 1H), 6.94 (d, J=7.8 Hz, 2H), 5.82 (br. s., 1H), 5.65 (dd, J=7.5, 15.5 Hz, 1H), 4.17 (br. s., 1H), 4.10 (dd, J=12.0, 46.0 Hz, 2H), 3.78 (d, J=14.4 Hz, 1H), 3.67 (d, J=13.4 Hz, 1H), 3.11-3.00 (m, 1H), 2.87-2.75 (m, 2H), 2.54 (br. s., 1H), 2.41-2.07 (m, 5H), 2.01-1.88 (m, 3H), 1.80 (dd, J=8.1, 14.2 Hz, 3H), 1.70 (dd, J=9.0, 18.3 Hz, 1H), 1.54-1.42 (m, 2H), 1.45 (d, J=8.1 Hz, 6H). m/z (ESI, +ve ion) 599.2 (M+H)+; (1S,3'R,6'R,7'S,8'Z)-6-chloro-7'-hydroxy-12',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 41): $^1$H NMR (400 MHz, CD$_3$OD) δ 7.76 (d, J=8.6 Hz, 1H), 7.29 (d, J=7.8 Hz, 1H), 7.20 (dd, J=2.2, 8.4 Hz, 1H), 7.17 (br. s., 1H), 7.13 (d, J=2.2 Hz, 1H), 6.96 (d, J=7.5 Hz, 1H), 5.68-5.60 (m, 1H), 5.53 (dd, J=8.4, 11.2 Hz, 1H), 4.59 (dd, J=1.8, 8.6 Hz, 1H), 4.11 (s, 2H), 4.07 (d, J=13.7 Hz, 1H), 3.74 (d, J=15.3 Hz, 1H), 3.45 (d, J=14.5 Hz, 1H), 2.90-2.75 (m, 2H), 2.72-2.53 (m, 1H), 2.50-2.40 (m, 1H), 2.40-2.23 (m, 2H), 2.14 (d, J=13.1 Hz, 1H), 2.08-1.96 (m, 4H), 1.96-1.78 (m, 5H), 1.53 (d, J=12.7 Hz, 6H) 1.52-1.46 (m, 1H). m/z (ESI, +ve ion) 599.2 (M+H)+.

EXAMPLE 42

(1S,3'R,6'R,7'S)-6-CHLORO-7'-HYDROXY-12',12'-ETHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[16,18,24]TRIEN]-15'-ONE 13',13'-DIOXIDE

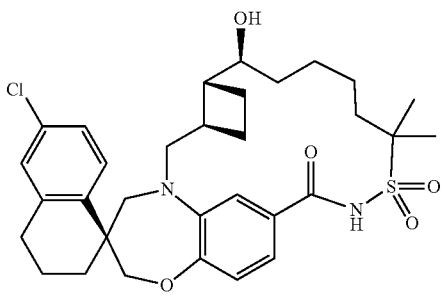 [SMILES: CC1(C)CCCC[C@H](O)[C@@H]2CC[C@H]2CN2C[C@@]3(CCCc4cc(Cl)ccc43)COc3ccc(cc32)C(=O)NS1(=O)=O]

STEP 1. N,N-BIS(4-METHOXYBENZYL)2-METHYLPENT-4-ENE-2-SULFONAMIDE

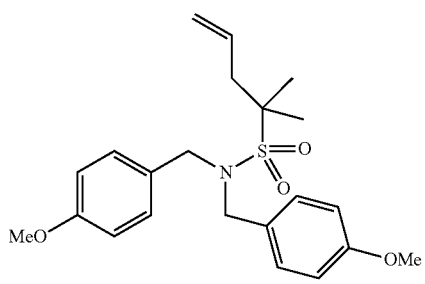 [SMILES: C=CCC(C)(C)S(=O)(=O)N(Cc1ccc(OC)cc1)Cc1ccc(OC)cc1]

N,N-bis(4-methoxybenzyl)but-3-ene-1-sulfonamide (Intermediate EE16; 500 mg, 1.332 mmol) was azeotroped in PhMe under vacuum for 1 h. Under argon, THF was added and the solution was cooled to −78° C. Butyllithium solution (Sigma Aldrich, 2.5 M in hexanes; 1.065 mL, 2.66 mmol) was then added and the mixture was stirred at −78° C. for 60 min. MeI (Sigma Aldrich; 0.166 mL, 2.66 mmol) was added and the mixture was stirred at −78° C. for an additional 30 min, (LC/MS analysis showed complete conversion to a 1:1 mixture of mono and di-methylated products). The mixture was quenched with satd NH$_4$Cl, allowed to reach ambient temperature, extracted with EtOAc, dried over MgSO$_4$, and concentrated. The crude material was purified through a 24 g ISCO gold column eluting with a gradient of 5-10% EtOAc in hexanes to provide N,N-bis(4-methoxybenzyl)-2-methylpent-4-ene-2-sulfonamide (173 mg, 0.429 mmol, 32.2% yield).

STEP 2.
2-METHYLPENT-4-ENE-2-SULFONAMIDE

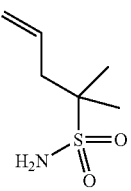

To a solution of N,N-bis(4-methoxybenzyl)-2-methylpent-4-ene-2-sulfonamide (173 mg, 0.429 mmol) in DCM, thioanisole (0.503 mL, 4.29 mmol) was added followed by the dropwise addition of trifluoroacetic acid (1.2 mL, 16.15 mmol). After stirring for 6 h (TLC in 30% EtOAc/hexanes showed complete loss of starting material) the mixture was diluted with EtOAc, washed with satd NaHCO$_3$, back extracted with EtOAc, dried over MgSO$_4$ and concentrated. The crude material was purified via chromatography through a 12 g ISCO gold column eluting with a gradient of 10-50% EtOAc hexanes to provide 2-methylpent-4-ene-2-sulfonamide (45 mg, 0.276 mmol, 64.3% yield).

STEP 3

(S)-6'-CHLORO-5-(((1R,2R)-2-((S)-1-HYDROXYBUT-3-EN-1-YL)CYCLOBUTYL)METHYL)-N-((2-METHYLPENT-4-EN-2-YL)SULFONYL)-3',4',5-TETRAHYDRO-2H,2'H-SPIRO[BENZO[B][1,4]OXAZEPINE-3,1'-NAPHTHALENE]-7-CARBOXAMIDE

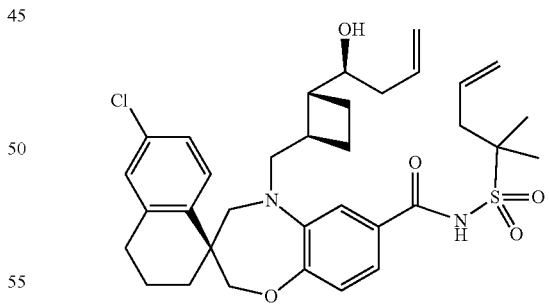

The title compound was synthesized from (S)-6'-chloro-5-(((1R,2R)-2-((S)-1-hydroxybut-3-en-1-yl)cyclobutyl)methyl)-3',4',5-tetrahydro-2H,2'H-spiro[benzo[b][1,4]oxazepine-3,1'-naphthalene]-7-carboxylic acid (Intermediate AA13A; 41 mg, 0.085 mmol) and 2-methylpent-4-ene-2-sulfonamide (45 mg, 0.276 mmol) following the procedure described for Example 2, Step 1. Purification of the crude material provided (S)-6'-chloro-5-(((1R,2R)-2-((S)-1-hydroxybut-3-en-1-yl)cyclobutyl)methyl)-N-((2-methylpent-4-en-2-yl)sulfonyl)-3',4',5-tetrahydro-2H,2'H- spiro[benzo[b][1,4]oxazepine-3,1'-naphthalene]-7-carboxamide (45.8 mg, 0.073 mmol, 86% yield).

STEP 4

(1S,3'R,6'R,7'S,9'Z)-6-CHLORO-7'-HYDROXY-12',12'-DIMETHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[9,16,18,24]TETRAEN]-15'-ONE 13',13'-DIOXIDE AND. (1S,3'R,6'R,7'S,9'E)-6-CHLORO-7'-HYDROXY-12',12'-DIMETHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[9,16,18,24]TETRAEN]-15'-ONE 13',13'-DIOXIDE

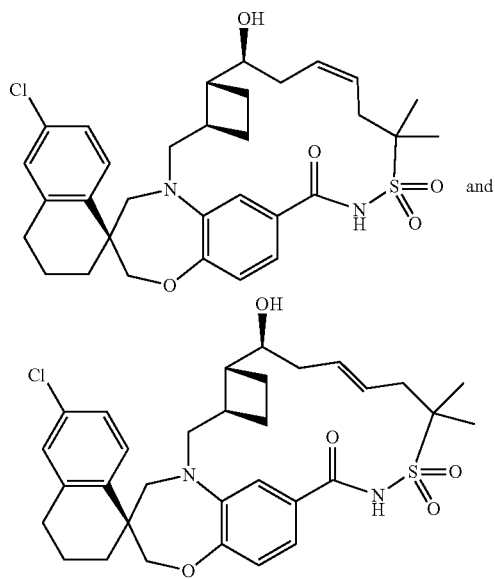

The title compound was synthesized from (S)-6'-chloro-5-(((1R,2R)-2-((S)-1-hydroxybut-3-en-1-yl)cyclobutyl)methyl)-N-((2-methylpent-4-en-2-yl)sulfonyl)-3',4,4',5-tetrahydro-2H,2'H-spiro[benzo[b][1,4]oxazepine-3,1'-naphthalene]-7-carboxamide (45.8 mg, 0.073 mmol) following the procedure described for Example 14, Step 2. The crude material was purified by chromatography through a 12 g ISCO column, eluting with 10% to 20% EtOAc (containing 0.3% AcOH) in hexanes over 90 min to provide a mixture of the title compounds.

STEP 5: (1S,3'R,6'R,7'S)-6-CHLORO-7'-HYDROXY-12',12'-ETHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[16,18,24]TRIEN]-15'-ONE 13',13'-DIOXIDE

The title compound (6.4 mg, 0.011 mmol, 71% yield) was synthesized from a mixture of (1S,3'R,6'R,7'S,9'Z)-6-chloro-7'-hydroxy-12',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide and (1S,3'R,6'R,7'S,9'E)-6-chloro-7'-hydroxy-12',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[9,16,18,24]tetraen]-15'-one 13',13'-dioxide (from Step 4, 9 mg, 0.015 mmol) following the procedure described for Example 14, Step 3. $^1$H NMR (400 MHz, CD$_2$Cl$_2$) δ 10.50 (br. s., 1H), 7.70 (d, J=8.6 Hz, 1H), 7.47 (dd, J=1.2, 8.4 Hz, 1H), 7.35 (s, 1H), 7.14 (dd, J=2.0, 8.2 Hz, 1H), 7.08 (d, J=2.2 Hz, 1H), 6.91 (d, J=8.4 Hz, 1H), 4.02 (d, J=12.1 Hz, 1H), 3.96 (d, J=11.9 Hz, 1H), 3.73 (d, J=15.5 Hz, 1H), 3.64-3.54 (m, 1H), 3.13 (d, J=14.3 Hz, 1H), 3.05 (dd, J=9.1, 15.6 Hz, 1H), 2.94 (d, J=8.6 Hz, 1H), 2.82-2.71 (m, 2H), 2.33 (quin, J=8.6 Hz, 1H), 2.20-2.06 (m, 2H), 2.05-1.96 (m, 2H), 1.95-1.87 (m, 3H), 1.86-1.74 (m, 4H), 1.73-1.59 (m, 4H), 1.49 (s, 3H), 1.47 (s, 3H), 1.44-1.34 (m, 3H). MS (ESI, +ve ion) m/z 601.2 (M+H)$^+$.

EXAMPLE 43

(1S,3'R,6'R,7'S,8'E,11'S,12'R)-6-CHLORO-11',12'-DIMETHYL-7'-(1-METHYLETHOXY)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE-13',13'-DIOXIDE

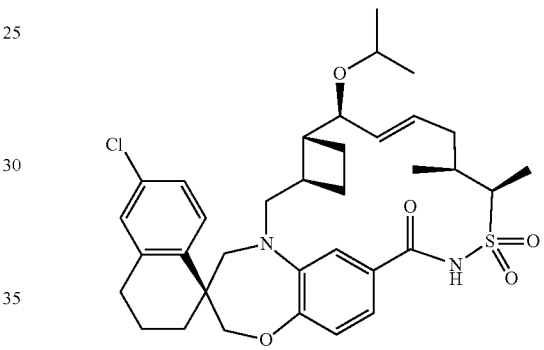

To a solution of (1S,3'R,6'R,7'S,8'E,11'S,12'R)-6-chloro-7'-hydroxy-11',12'-dimethyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 2; 20.4 mg, 0.034 mmol) in THF (0.681 mL) cooled to 0° C. was added sodium hydride (60% dispersion in mineral oil; 13.62 mg, 0.340 mmol). The reaction mixture was stirred at 0° C. for 15 min and then 2-iodopropane (3.40 µl, 0.034 mmol) was added. The reaction mixture was stirred at ambient temperature for 4 days, adding more reagents to drive the reaction. The mixture was then quenched with aq NH$_4$Cl and diluted with EtOAc. The organic layer was dried over MgSO$_4$ and concentrated. The crude material was purified by chromatography through a Redi-Sep® pre-packed SiO$_2$ gel column (4 g), eluting with 10-40% EtOAc (containing 0.3% AcOH)/heptanes to provide the title compound (0.6 mg). $^1$H NMR (500 MHz, CD$_2$Cl$_2$) δ 8.03 (br. s., 1H), 7.71 (d, J=8.3 Hz, 1H), 7.17 (dd, J=2.3, 8.4 Hz, 1H), 7.09 (d, J=2.4 Hz, 1H), 6.91-6.89 (m, 2H), 6.88 (s, 1H), 5.72 (ddd, J=3.4, 9.3, 15.2 Hz, 1H), 5.53 (dd, J=8.8, 15.4 Hz, 1H), 4.29-4.22 (m, 1H), 4.08 (s, 2H), 3.85-3.80 (m, 2H), 3.69 (d, J=14.2 Hz, 1H), 3.59 (td, J=6.1, 12.2 Hz, 1H), 3.28-3.22 (m, 2H), 3.02 (dd, J=9.7, 15.3 Hz, 1H), 2.83-2.70 (m, 214), 2.39-2.24 (m, 2H), 2.20-2.02 (m, 3H), 2.01-1.89 (m, 3H), 1.83 (dd, J=5.6, 12.7 Hz, 1H), 1.81-1.75 (m, 1H), 1.70-1.59 (m, 1H), 1.44 (d, J=7.3 Hz, 3H), 1.43-1.35 (m, 1H), 1.09 (d, J=5.9 Hz, 3H), 1.04 (d, J=6.1 Hz, 3H), 1.02 (d, J=6.8 Hz, 3H). MS (ESI, +ve ion) m/z 641.0 (M+H)$^+$.

EXAMPLE 44

(1S,3'R,6'R,7'S,8'E,11'S,12'S)-6-CHLORO-12'-CYCLO-PROPYL-7-HYDROXY-11'-METHYL-3,4-DIHYDRO-2H,15'H-SPIRO[NAPHTHALENE-1,22'-[20]OXA[13]THIA[1,14] DIAZATETRACYCLO[14.7.2.0$^{3,6}$.0$^{19,24}$] PENTACOSA[8,16,18,24]TETRAEN]-15'-ONE 13',13'-DIOXIDE OR (1S,3'R,6'R,7'S,8'E,11'S,12'R)-6-CHLORO-12'-CYCLOPROPYL-7-HYDROXY-11'-METHYL-3,4-DIHYDRO-2H,15'H-SPIRO[NAPHTHALENE-1,22'-[20]OXA[13]THIA [1,14]DIAZATETRACYCLO[14.7.2.0$^{3,6}$.0$^{19,24}$] PENTACOSA[8,16,18,24]TETRAEN]-15'-ONE 13',13'-DIOXIDE OR (1S,3'R,6'R,7'S,8'E,11'R,12'S)-6-CHLORO-12'-CYCLOPROPYL-7-HYDROXY-11'-METHYL-3,4-DIHYDRO-2H,15'H-SPIRO [NAPHTHALENE-1,22'-[20]OXA[13]THIA[1,14] DIAZATETRACYCLO[14.7.2.0$^{3,6}$.0$^{19,24}$] PENTACOSA[8,16,18,24]TETRAEN]-15'-ONE 13',13'-DIOXIDE OR (1S,3'R,6'R,7'S,8'E,11'R,12'R)-6-CHLORO-12'-CYCLO-PROPYL-7-HYDROXY-11'-METHYL-3,4-DIHYDRO-2H,15'H-SPIRO[NAPHTHALENE-1,22'-[20]OXA[13]THIA[1,14] DIAZATETRACYCLO[14.7.2.0$^{3,6}$.0$^{19,24}$] PENTACOSA[8,16,18,24]TETRAEN]-15'-ONE 13',13'-DIOXIDE

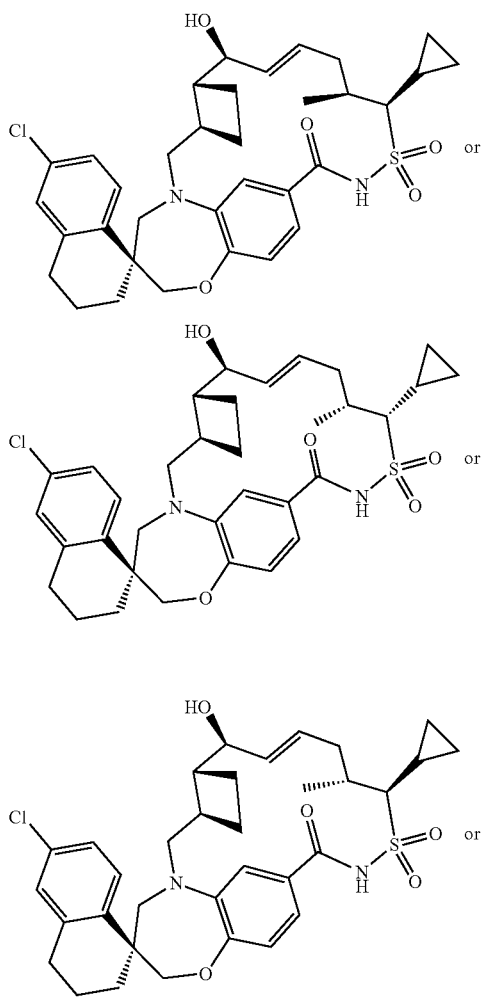

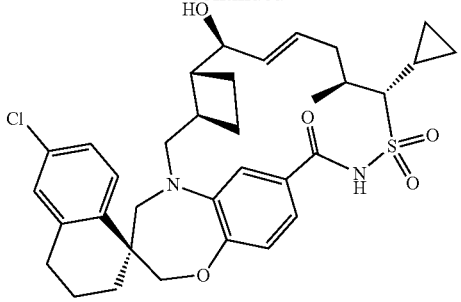

STEP 1; (2S)-METHYLPENT-4-ENAL AND (2R)-METHYLPENT-4-ENAL

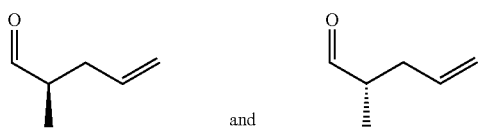

To a solution of oxalyl chloride (6.65 mL, 74.9 mmol) in DCM (30 mL) at −60° C. was added a solution of DMSO anhydrous (10.62 mL, 150 mmol) in DCM (20 mL) under N$_2$ and stirred for 2 min. A solution of 2-methylpent-4-en-1-ol (5.00 g, 49.9 mmol) in DCM (20 mL) was added, and the resulting mixture was stirred for 15 min at −60° C. Et$_3$N (34.7 mL, 250 mmol) was then added and the reaction mixture was stirred at ambient temperature for 20 min. The mixture was quenched with DCM and H$_2$O. The organic layer was washed with brine, dried (MgSO$_4$), and filtered. The filtrate was concentrated to afford the title compound (4.90 g, 100%) without further purification.

STEP 2: (1S,2R)-1-CYCLOPROPYL-2-METHYL-4-PENTEN-1-OL AND (1R,2R)-1-CYCLOPROPYL-2-METHYL-4-PENTEN-1-OL AND (1S,2S)-1-CYCLOPROPYL-2-METHYL-4-PENTEN-1-OL AND (1R,2S)-1-CYCLOPROPYL-2-METHYL-4-PENTEN-1-OL

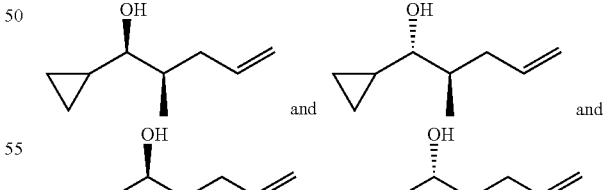

To a solution of (2S)-methylpent-4-enal and (2R)-methylpent-4-enal (9.80 g, 100 mmol) in THF (30 mL) was added cyclopropylmagnesium bromide, 1.0 M in 2-MeTHF (300 mL, 150 mmol) at −78° C. The reaction mixture was stirred at ambient temperature for 3 h. The mixture was quenched with sat. aqueous NH$_4$Cl, and extracted with ether. The organic layer was washed with brine, dried (Na$_2$SO$_4$), and concentrated. The resulting residue was chromatographed (SiO$_2$ gel, 0 to 40%, EtOAc/hexane) to afford the title compound (4.20 g, 30.0%).

STEP 3

(1R,2R)-1-CYCLOPROPYL-2-METHYL-4-PENTENE-1-SULFONAMIDE AND (1R,2R)-1-CYCLOPROPYL-2-METHYL-4-PENTENE-1-SULFONAMIDE AND (1R,2R)-1-CYCLOPROPYL-2-METHYL-4-PENTENE-1-SULFONAMIDE AND (1R,2R)-1-CYCLOPROPYL-2-METHYL-4-PENTENE-1-SULFONAMIDE

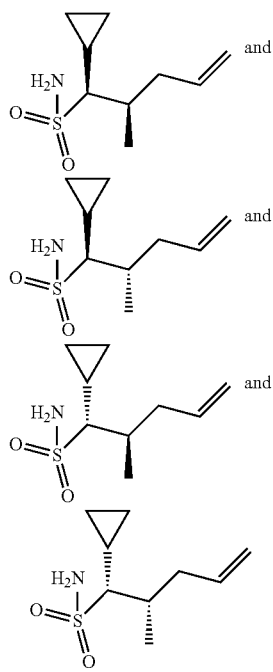

The title compound was prepared from a mixture of (1S,2R)-1-cyclopropyl-2-methyl-4-penten-1-ol, (1R,2R)-1-cyclopropyl-2-methyl-4-penten-1-ol, (1S,2S)-1-cyclopropyl-2-methyl-4-penten-1-ol, and (1R,2S)-1-cyclopropyl-2-methyl-4-penten-1-ol (from Step 2) as a starting alcohol, following a similar procedure described in E22, Steps 3 through 6.

STEP 4

(1S,3'R,6'R,7'S,8'E,11'S,12'S)-6-CHLORO-12'-CYCLOPROPYL-7'-HYDROXY-11'-METHYL-3,4-DIHYDRO-2H,15'H-SPIRO [NAPHTHALENE-1,22'-[20]OXA[13]THIA [1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'S,12'R)-6-CHLORO-12'-CYCLOPROPYL-7'-HYDROXY-11'-METHYL-3,4-DIHYDRO-2H,15'H-SPIRO[NAPHTHALENE-1,22'-[20]OXA[13]THIA [1,14]DIAZATETRACYCLO[14.7.2.0$^{3,6}$.0$^{19,24}$]PENTACOSA[8,16,18,24] TETRAEN]-15'-ONE 13',13'-DIOXIDE OR (1S,3'R,6'R,7'S,8'E,11'R,12'S)-6-CHLORO-12'-CYCLOPROPYL-7'-HYDROXY-11'-METHYL-3,4-DIHYDRO-2H,15'H-SPIRO [NAPHTHALENE-1,22'-[20]OXA[13]THIA[1,14] DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'R)-6-CHLORO-12'-CYCLOPROPYL-7'-HYDROXY-11'-METHYL-3,4-DIHYDRO-2H,15'H-SPIRO[NAPHTHALENE-1,22'-[20]OXA[13]THIA [1,14] DIAZATETRACYCLO[14.7.2.0$^{3,6}$.0$^{19,24}$] PENTACOSA[8,16,18,24]TETRAEN]-15'-ONE 13',13'-DIOXIDE

The title compound was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A) and a mixture of (1R,2R)-1-cyclopropyl-2-methyl-4-pentene-1-sulfonamide, (1R,2R)-1-cyclopropyl-2-methyl-4-pentene-1-sulfonamide, (1R,2R)-1-cyclopropyl-2-methyl-4-pentene-1-sulfonamide, and (1R,2R)-1-cyclopropyl-2-methyl-4-pentene-1-sulfonamide (from Step 3), following a similar procedure described in Example 2, Steps 1 and 2. This crude oil was purified by preparative reverse-phase HPLC (Gemini™ Prep C$_{18}$ 5 μm column; gradient elution of 50% to 90% MeCN in H$_2$O, where both solvents contain 0.1% TFA, 30 min method) to afford the title compound as the first eluting isomer (12 mg, 6.7%). $^1$H NMR (400 MHz, CD$_2$Cl$_2$) δ 8.15 (s, 1H), 7.71 (d, J=8.6 Hz, 1H), 7.17 (dd, J=2.3, 8.6 Hz, 1H), 7.09 (d, J=2.2 Hz, 1H), 6.93-6.88 (m, 3H), 5.91-5.63 (m, 2H), 4.22 (dd, J=3.9, 7.6 Hz, 1H), 3.81 (d, J=15.1 Hz, 1H), 3.68 (d, J=14.3 Hz, 1H), 3.40 (d, J=11.0 Hz, 1H), 3.25 (d, J=14.3 Hz, 1H), 3.04 (dd, J=9.8, 15.3 Hz, 1H), 2.82-2.67 (m, 2H), 2.49-2.23 (m, 3H), 2.14-1.84 (m, 11H), 1.73-1.62 (m, 1H), 1.45-1.34 (m, 1H), 1.20 (d, J=6.8 Hz, 3H), 1.17-1.07 (m, 1H), 0.93-0.76 (m, 3H), 0.50-0.37 (m, 1H). m/z (ESI, +ve ion) 625.2 (M+H)$^+$.

EXAMPLE 45

(1S,3'R,6'R,7'S,8'E,11'S,12'S)-6-CHLORO-12'-CYCLOPROPYL-7'-HYDROXY-11'-METHYL-3,4-DIHYDRO-2H,15'H-SPIRO [NAPHTHALENE-1,22'-[20]OXA[13]THIA[1,14] DIAZATETRACYCLO[14.7.2.0$^{3,6}$.0$^{19,24}$]PENTACOSA[8,16,18,24] TETRAEN]-15'-ONE 13',13'-DIOXIDE OR (1S,3'R,6'R,7'S,8'E,11'S,12'R)-6-CHLORO-12'-CYCLOPROPYL-7'-HYDROXY-11'-METHYL-3,4-DIHYDRO-2H,15'H-SPIRO[NAPHTHALENE-1,22'-[20]OXA[13]THIA[1,14] DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'S)-6-CHLORO-12'-CYCLOPROPYL-7'-HYDROXY-11'-METHYL-3,4-DIHYDRO-2H,15'H-SPIRO [NAPHTHALENE-1,22'-[20]OXA[13]THIA[1,14] DIAZATETRACYCLO[14.7.2.0$^{3,6}$.0$^{19,24}$] PENTACOSA[8,16,18,24]TETRAEN]-15'-ONE 13',13'-DIOXIDE OR (1S,3'R,6'R,7'S,8'E,11'R,12'R)-6-CHLORO-12'-CYCLOPROPYL-7'-HYDROXY-11'-METHYL-3,4-DIHYDRO-2H,15'H-SPIRO[NAPHTHALENE-1,22'-[20]OXA[13]THIA[1,14] DIAZATETRACYCLO[14.7.2.0$^{3,6}$.0$^{19,24}$]PENTACOSA[8,16,18,24]TETRAEN]-15'-ONE 13',13'-DIOXIDE

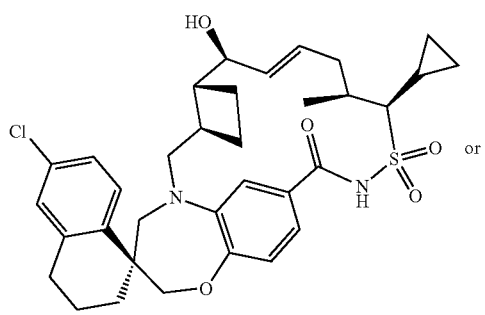

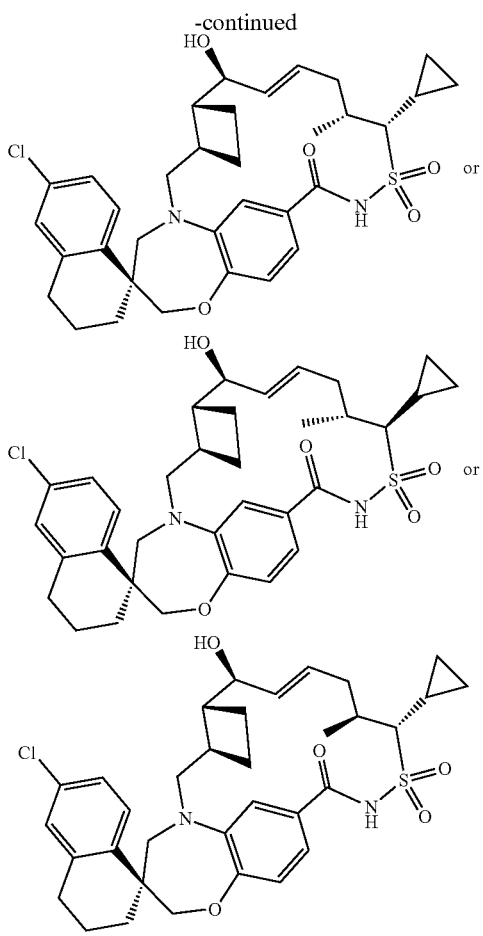

The title compound (5 mg, 2.8%) was obtained as the second eluting isomer from preparative reverse-phase HPLC separation in Example 49. $^1$H NMR (400 MHz, CD$_2$Cl$_2$) δ 9.04 (br. s., 1H), 7.83-7.61 (m, 1H), 7.17 (d, J=8.4 Hz, 1H), 7.09 (m, 1H), 6.97-6.88 (m, 1H), 6.84 (m, 1H), 6.15 (br. s., 1H), 5.92-5.69 (m, 1H), 4.26-4.04 (m, 2H), 3.68 (d, J=14.1 Hz, 1H), 3.36-2.94 (m, 3H), 2.77 (m, 2H), 2.38 (d, J=7.6 Hz, 2H), 2.24-1.87 (m, 6H), 1.69 (dd, J=9.8, 19.4 Hz, 2H), 1.53-1.41 (m, 11H), 1.30-1.06 (m, 101H), 0.83 (d, J=3.1 Hz, 2H), 0.44 (br. s., 1H) m/z (ESI, +ve ion) 625.2 (M+H)$^+$.

EXAMPLE 46

(1S,3'R,6'R,7'S,8'E,11'S,12'S)-6-CHLORO-12'-CYCLOPROPYL-7'-HYDROXY-11'-METHYL-3,4-DIHYDRO-2H,15'H-SPIRO [NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'S,12'R)-6-CHLORO-12'-CYCLOPROPYL-7'-HYDROXY-11'-METHYL-3,4-DIHYDRO-2H,15'H-SPIRO[NAPHTHALENE-1,22'-[20]OXA[13]THIA[1,14] DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'S)-6-CHLORO-12'-CYCLOPROPYL-7-HYDROXY-11'-METHYL-3,4-DIHYDRO-2H,15'H-SPIRO[NAPHTHALENE-1,22'-[20]OXA[13]THIA[1,14] DIAZATETRACYCLO[14.7.2.0$^{3,6}$.0$^{19,24}$]PENTACOSA[8, 16,18,24]TETRAEN]-15'-ONE 13',13'-DIOXIDE OR (1S, 3'R,6'R,7'S,8'E,11'R,12'R)-6-CHLORO-12'-CYCLOPROPYL-7'-HYDROXY-11'-METHYL-3,4-DIHYDRO-2H, 15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

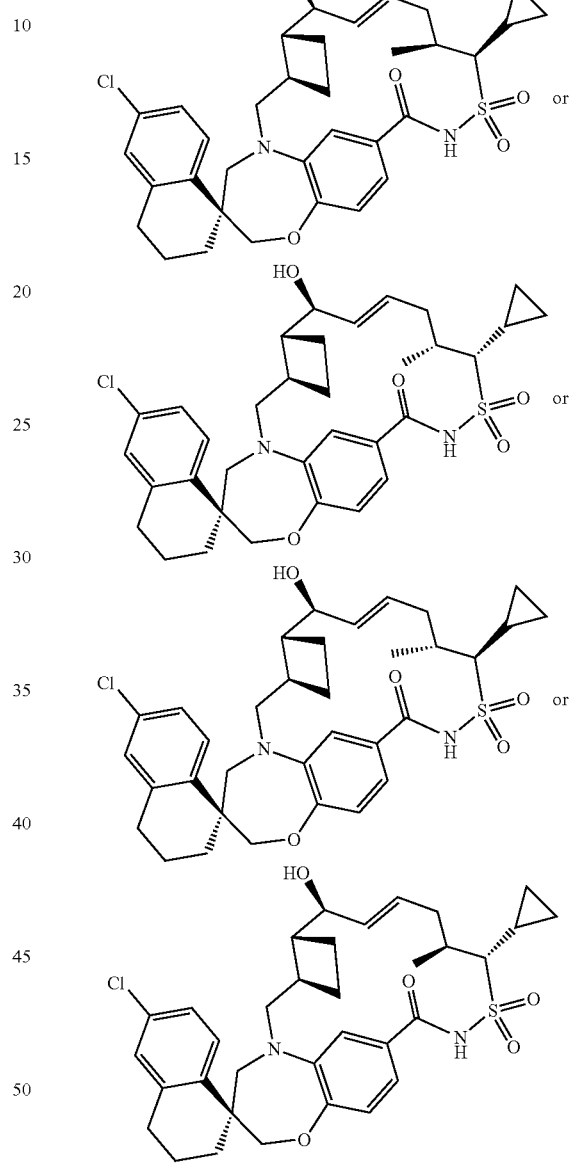

The title compound (9 mg, 5.0%) was obtained as the third eluting isomer from preparative reverse-phase HPLC separation in Example 49. $^1$H NMR (400 MHz, CD$_2$Cl$_2$) δ 8.21 (br. s., 11H), 7.66 (d, J=8.6 Hz, 1H), 7.44 (br. s., 1H), 7.14 (dd, J=2.3, 8.6 Hz, 1H), 7.09 (d, J=2.3 Hz, 1H), 6.94-6.86 (m, 2H), 5.62 (br. s., 2H), 4.20 (s, 2H), 3.92 (d, J=7.4 Hz, 1H), 3.85 (d, J=13.9 Hz, 1H), 3.66 (d, J=14.1 Hz, 1H), 3.39 (d, J=14.3 Hz, 1H), 3.33 (d, J=11.0 Hz, 1H), 3.17 (d, J=13.7 Hz, 1H), 2.74 (t, J=5.3 Hz, 2H), 2.57 (d, J=7.6 Hz, 1H), 2.40 (td, J=8.7, 17.1 Hz, 1H), 2.29-2.16 (m, 1H), 2.03-1.62 (m, 10H), 1.60-1.45 (m, 1H), 1.22 (d, J=6.7 Hz, 3H), 1.17-1.04 (m, 1H), 0.91-0.78 (m, 3H), 0.52-0.41 (m, 1H). m/z (ESI, +ve ion) 625.2 (M+H)$^+$.

EXAMPLE 47

(1S,3'R,6'R,7'S,8'E,11'S,12'S)-6-CHLORO-12'-CYCLOPROPYL-7'-HYDROXY-11'-METHYL-3,4-DIHYDRO-2H,15'H-SPIRO [NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'S,12'R)-6-CHLORO-12'-CYCLOPROPYL-7'-HYDROXY-11'-METHYL-3,4-DIHYDRO-2H,15'H-SPIRO[NAPHTHALENE-1,22'-[20]OXA[13]THIA [1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'S)-6-CHLORO-12'-CYCLOPROPYL-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'R)-6-CHLORO-12'-CYCLOPROPYL-7'-HYDROXY-11'-METHYL-3,4-DIHYDRO-2H,15'H-SPIRO[NAPHTHALENE-1,22'-[20]OXA[13]THIA [1,14] DIAZATETRACYCLO[14.7.2.0$^{3,6}$.0$^{19,24}$]PENTACOSA[8,16,18,24]TETRAEN]-15'-ONE 13',13'-DIOXIDE

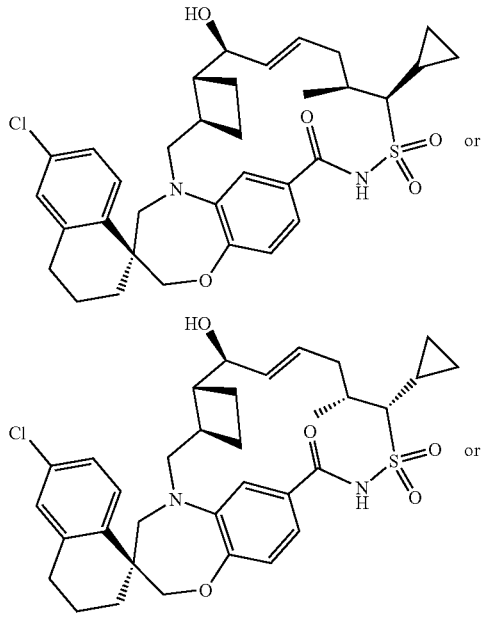

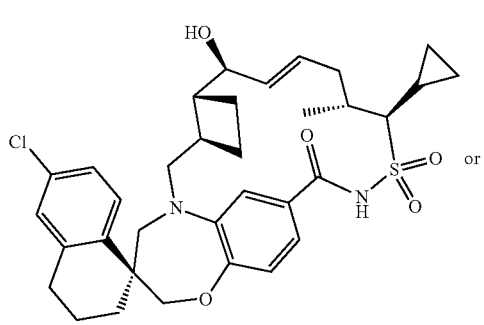

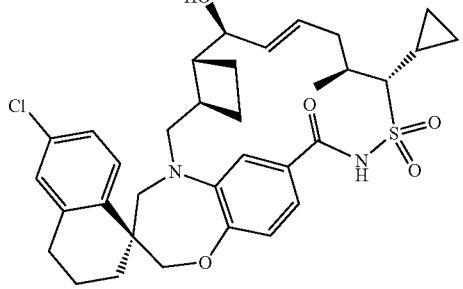

The title compound (3 mg, 1.9%) was obtained as the slowest eluting isomer from preparative reverse-phase HPLC separation in Example 49. $^1$H NMR (400 MHz, CD$_2$Cl$_2$) δ 8.14 (br. s., 1H), 7.71 (d, J=8.6 Hz, 1H), 7.22-7.06 (m, 3H), 6.98-6.91 (m, 1H), 6.62 (br. s., 1H), 6.05 (d, J=7.2 Hz, 1H), 5.69 (dd, J=5.8, 15.2 Hz, 1H), 4.19 (br. s., 1H), 4.15-3.99 (m, 2H), 3.79 (d, J=14.5 Hz, 1H), 3.65 (d, J=14.5 Hz, 1H), 3.43 (d, J=14.5 Hz, 1H), 3.33-3.22 (n, 1H), 2.99 (d, J=11.0 Hz, 1H), 2.86-2.66 (m, 3H), 2.51 (br. s., 2H), 2.32-2.18 (m, 2H), 2.09-1.87 (m, 5H), 1.75 (d, J=10.4 Hz, 2H), 1.52-1.38 (m, 2H), 1.19 (d, J=7.0 Hz, 3H), 1.11 (br. s., 1H), 0.93-0.73 (m, 3H), 0.54-0.40 (m, 1H). m/z (ESI, +ve ion) 625.2 (M+H)$^+$.

EXAMPLE 48

(1S,3'R,6'R,7'S,8'E,11'S,12'S)-6-CHLORO-12'-CYCLOPROPYL-7'-METHOXY-11'-METHYL-3,4-DIHYDRO-2H,15'H-SPIRO [NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E, 11'S,12'R)-6-CHLORO-12'-CYCLOPROPYL-7'-METHOXY-11'-METHYL-3,4-DIHYDRO-2H,15'H-SPIRO[NAPHTHALENE-1,22'-[20]OXA[13]THIA [1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'S)-6-CHLORO-12'-CYCLOPROPYL-7'-METHOXY-11'-METHYL-3,4-DIHYDRO-2H,15'H-SPIRO[NAPHTHALENE-1,22'-[20]OXA[13]THIA [1,14] DIAZATETRACYCLO[14.7.2.0$^{3,6}$.0$^{19,24}$] PENTACOSA [8,16,18,24]TETRAEN]-15'-ONE 13',13'-DIOXIDE OR (1S,3'R,6'R,7'S,8'E,11'R,12'R)-6-CHLORO-12'-CYCLOPROPYL-7'-METHOXY-11'-METHYL-3,4-DIHYDRO-2H,15'H-SPIRO[NAPHTHALENE-1,22'-[20]OXA[13]THIA[1,14] DIAZATETRACYCLO[14.7.2.0$^{3,6}$.0$^{19,24}$]PENTACOSA[8,16,18,24]TETRAEN]-15'-ONE 13',13'-DIOXIDE

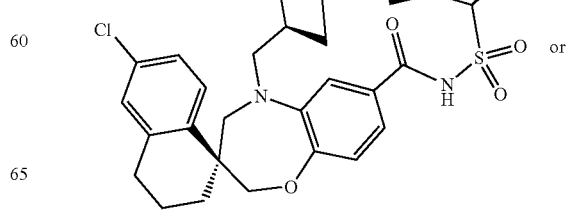

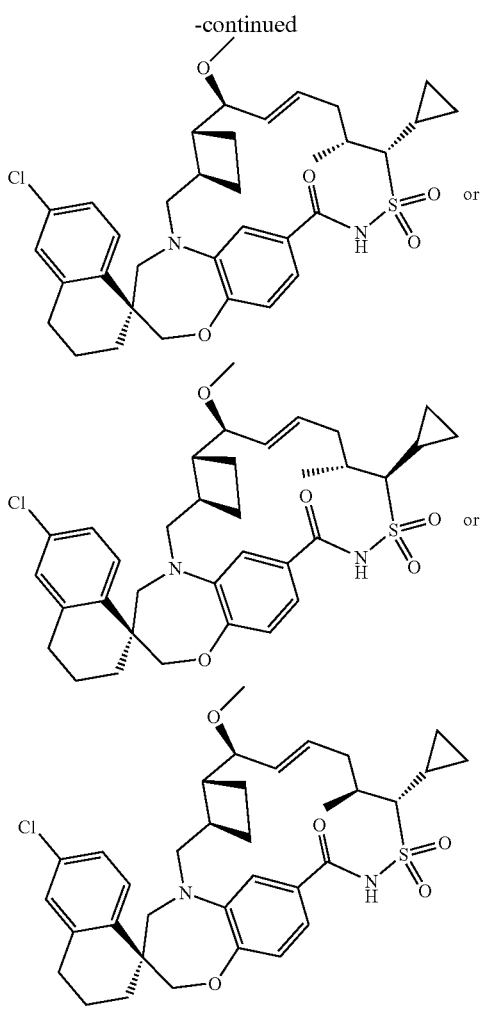

The title compound (9.5 mg, 62%) was prepared from (1S,3'R,6'R,7'S,8'E,11'S,12'S)-6-chloro-12'-cyclopropyl-7'-hydroxy-11'-methyl-3,4-dihydro-2H,15'H-spiro [naphthalene-1,22'-[20]oxa[13]thia[1,14] diazatetracyclo[14.7.2.0³,⁶.0¹⁹,²⁴] pentacosa[8,16,18,24]tetraen]-15'-one 13',13'-dioxide or
(1S,3'R,6'R,7'S,8'E,11'S,12'R)-6-chloro-12'-cyclopropyl-7'-hydroxy-11'-methyl-3,4-dihydro-2H,15'H-spiro[naphthalene-1,22'-[20]oxa[13]thia[1,14] diazatetracyclo [14.7.2.0³,⁶.0¹⁹,²⁴]pentacosa[8,16,18,24] tetraen]-15'-one 13', 13'-dioxide or
(1S,3'R,6'R,7'S,8'E,11'R,12'S)-6-chloro-12'-cyclopropyl-7'-hydroxy-11'-methyl-3,4-dihydro-2H,15'H-spiro[naphthalene-1,22'-[20]oxa[13]thia[1,14] diazatetracyclo[14.7.2.0³,⁶.0¹⁹,²⁴] pentacosa[8,16,18,24]tetraen]-15'-one 13', 13'-dioxide or
(1S,3'R,6'R,7'S,8'E,11'R,12'R)-6-chloro-12'-cyclopropyl-7'-hydroxy-11'-methyl-3,4-dihydro-2H,15'H-spiro[naphthalene-1,22'-[20]oxa[13]thia[1,14] diazatetracyclo[14.7.2.0³,⁶.0¹⁹,²⁴] pentacosa[8,16,18,24]tetraen]-15'-one 13', 13'-dioxide (Example 49) using a similar procedure described in Example 46. $^1$H NMR (400 MHz, CD$_2$Cl$_2$) δ 8.15-7.94 (m, 1H), 7.71 (d, J=8.41 Hz, 1H), 7.17 (dd, J=2.35, 8.41 Hz, 1H), 7.09 (d, J=2.15 Hz, 1H), 6.91 (d, J=0.98 Hz, 2H), 6.86 (s, 1H), 5.81-5.70 (m, J=3.13, 9.39 Hz, 1H), 5.51 (ddd, J=1.17, 8.41, 14.67 Hz, 1H), 4.08 (s, 2H), 3.80 (d, J=15.06 Hz, 1H), 3.69 (d, J=14.28 Hz, 1H), 3.62 (dd, J=3.33, 9.00 Hz, 1H), 3.45 (d, J=10.17 Hz, 1H), 3.25 (d, J=14.28 Hz, 1H), 3.17 (s, 3H), 3.03 (dd, J=10.17, 15.26 Hz, 1H), 2.80-2.72 (m, 2H), 2.59-2.39 (m, 2H), 2.38-2.25 (m, 1H), 2.17-1.73 (m, 8H), 1.72-1.59 (m, 1H), 1.21 (d, J=6.85 Hz, 3H), 1.17-1.08 (m, 1H), 0.92-0.78 (m, 4H), 0.47-0.37 (m, 1H). m/z (ESI, +ve ion) 639.2 (M+H)$^+$.

EXAMPLE 49

(1S,3'R,6'R,7'S,8'E,11'R,12'R)-6-CHLORO-7'-HYDROXY-11'-METHYL-12'-(1-METHYLETHYL)-3,4-DIHYDRO-2H,15'H-SPIRO[NAPHTHALENE-1,22'-[20]OXA[13]THIA[1,14] DIAZATETRACYCLO[14.7.2.0³,⁶.0¹⁹,²⁴] PENTACOSA[8,16,18,24]TETRAEN]-15'-ONE 13',13'-DIOXIDE OR (1S,3'R,6'R,7'S,8'E,11'S,12'S)-6-CHLORO-7'-HYDROXY-11'-METHYL-12'-(1-METHYLETHYL)-3,4-DIHYDRO-2H,15'H-SPIRO[NAPHTHALENE-1,22'-[20]OXA[13]THIA[1,14]DIAZATETRACYCLO [14.7.2.0³,⁶.0¹⁹,²⁴]PENTACOSA[8,16,18,24]TETRAEN]-15'-ONE 13',13'-DIOXIDE OR (1S,3'R,6'R,7'S,8'E,11'S,12'R)-6-CHLORO-7'-HYDROXY-11'-METHYL-12'-(1-METHYLETHYL)-3,4-DIHYDRO-2H,15'H-SPIRO [NAPHTHALENE-1,22'-[20]OXA[13]THIA[1,14] DIAZATETRACYCLO[14.7.2.0³,⁶.0¹⁹,²⁴]PENTACOSA[8,16,18,24]TETRAEN]-15'-ONE 13',13'-DIOXIDE OR (1S,3'R,6'R,7'S,8'E,11'R,12'S)-6-CHLORO-7'-HYDROXY-11'-METHYL-12'-(1-METHYLETHYL)-3,4-DIHYDRO-2H,15'H-SPIRO[NAPHTHALENE-1,22'-[20]-[20]OXA[13]THIA[1,14]DIAZATETRACYCLO[14.7.2.0³,⁶.0¹⁹,²⁴] PENTACOSA[8,16,18,24]TETRAEN]-15'-ONE 13',13'-DIOXIDE

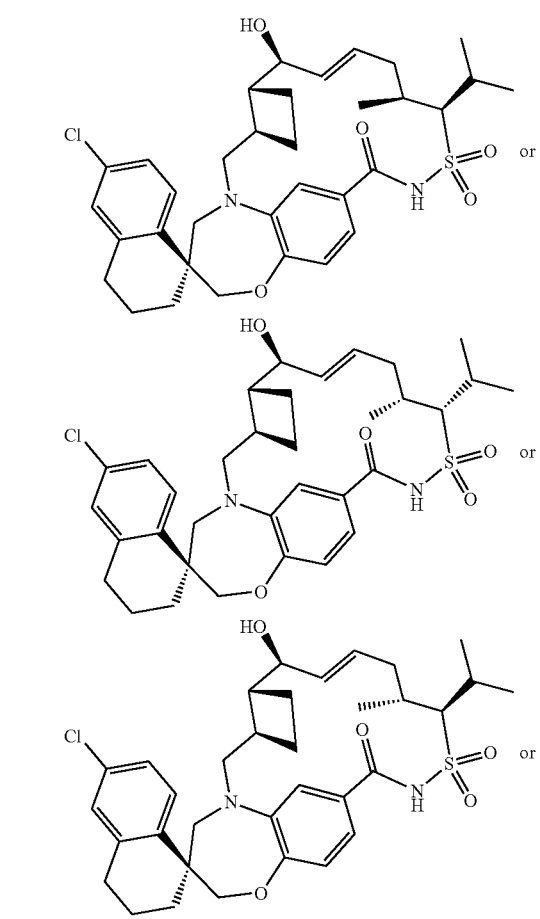

-continued

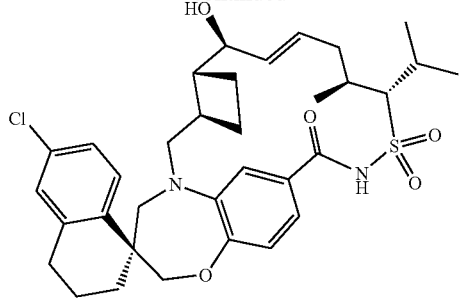

STEP 1: (3R,4R)-2,4-DIMETHYLHEPT-6-EN-3-OL AND (3R,4S)-2,4-DIMETHYLHEPT-6-EN-3-OL AND (3S,4R)-2,4-DIMETHYLHEPT-6-EN-3-OL AND (3S,4S)-2,4-DIMETHYLHEPT-6-EN-3-OL

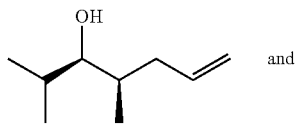
and

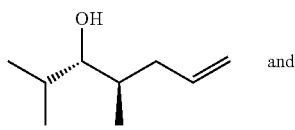
and

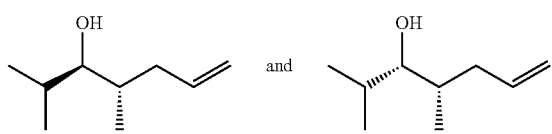
and

To a solution of 2-methylpent-4-enal (2.40 g, 24.4 mmol) in THF (10 mL) was added isopropylmagnesium chloride, 2.0 M in THF (24.4 mL, 48.9 mmol) at 0° C. The reaction mixture was allowed to warm to ambient temperature. After being stirred at ambient temperature for 12 h, the reaction mixture was quenched (sat. NH$_4$Cl), extracted (2×Et$_2$O), and washed (brine). The combined organic layers were dried (Na$_2$SO$_4$) and concentrated under reduced pressure. The residue was injected into a 40 g ISCO gold column and purified by Combi-Flash®, eluting with 0% to 20% EtOAc/hexanes to give the title compounds (550 mg, 3.85 mmol).

STEP 2

(3S,4R)—N,N-BIS(4-METHOXYBENZYL)-2,4-DIMETHYLHEPT-6-ENE-3-SULFONAMIDE AND (3S,4S)—N,N-BIS(4-METHOXYBENZYL)-2,4-DIMETHYLHEPT-6-ENE-3-SULFONAMIDE AND (3R,4R)—N,N-BIS(4-METHOXYBENZYL)-2,4-DIMETHYLHEPT-6-ENE-3-SULFONAMIDE AND (3R,4S)—N,N-BIS(4-METHOXYBENZYL)-2,4-DIMETHYLHEPT-6-ENE-3-SULFONAMIDE

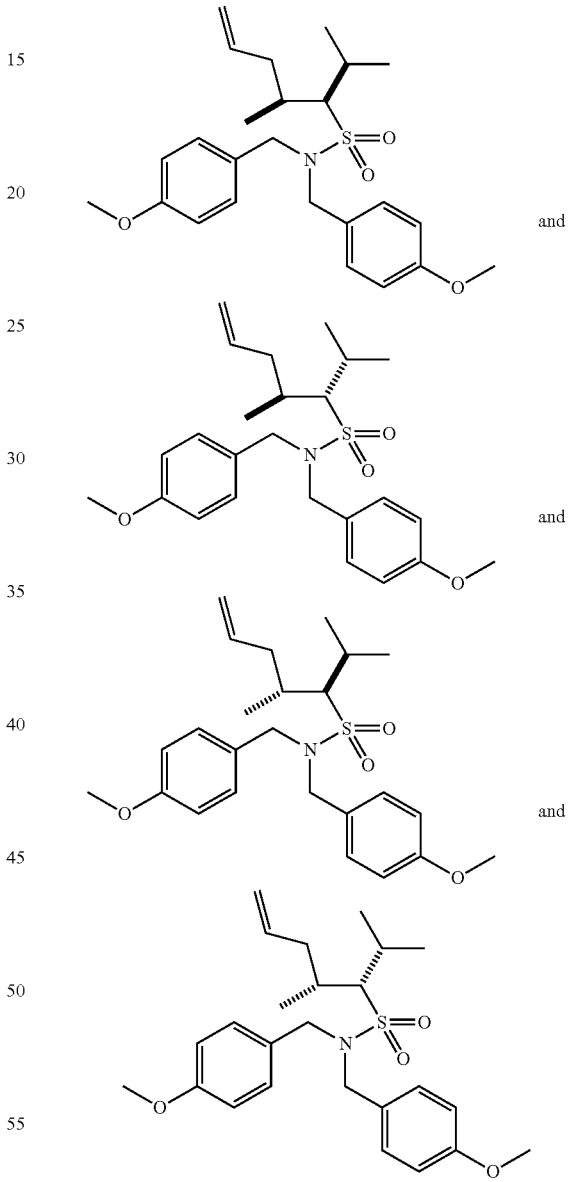

The title compound was prepared from a mixture of (3R,4R)-2,4-dimethylhept-6-en-3-ol, (3R,4S)-2,4-dimethylhept-6-en-3-ol, (3S,4R)-2,4-dimethylhept-6-en-3-ol, and (3S,4S)-2,4-dimethylhept-6-en-3-ol (from Step 1), following a similar procedure described in Intermediate EE22, Steps 3 through 6.

STEP 3: (3S,4R)-2,4-DIMETHYLHEPT-6-ENE-3-SULFONAMIDE AND (3S,4S)-2,4-DIMETHYLHEPT-6-ENE-3-SULFONAMIDE AND (3R,4R)-2,4-DIMETHYLHEPT-6-ENE-3-SULFONAMIDE AND (3R,4S)-2,4-DIMETHYLHEPT-6-ENE-3-SULFONAMIDE

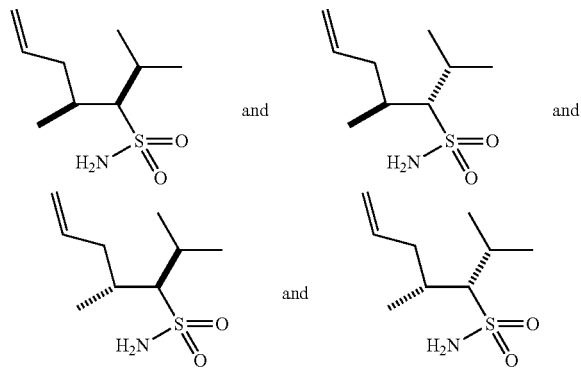

The title compounds were synthesized from a mixture of (3S,4R)—N,N-bis(4-methoxybenzyl)-2,4-dimethylhept-6-ene-3-sulfonamide, (3S,4S)—N,N-bis(4-methoxybenzyl)-2,4-dimethylhept-6-ene-3-sulfonamide, (3R,4R)—N,N-bis(4-methoxybenzyl)-2,4-dimethylhept-6-ene-3-sulfonamide, and (3R,4S)—N,N-bis(4-methoxybenzyl)-2,4-dimethylhept-6-ene-3-sulfonamide (from Step 2), following a similar procedure described for Example 26, Step 2.

STEP 4:
(1S,3'R,6'R,7'S,8'E,11'R,12'R)-6-CHLORO-7'-HYDROXY-11'-METHYL-12'-(1-METHYLETHYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'S,12'S)-6-CHLORO-7'-HYDROXY-11'-METHYL-12'-(1-METHYLETHYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'S,12'R)-6-CHLORO-7'-HYDROXY-11'-METHYL-12'-(1-METHYLETHYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'S)-6-CHLORO-7'-HYDROXY-11'-METHYL-12'-(1-METHYLETHYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE (ISOMER1)

The title compounds was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A) and a mixture of (3S,4R)-2,4-dimethylhept-6-ene-3-sulfonamide, (3S,4S)-2,4-dimethylhept-6-ene-3-sulfonamide, (3R,4R)-2,4-dimethylhept-6-ene-3-sulfonamide, and (3R,4S)-2,4-dimethylhept-6-ene-3-sulfonamide, following a similar procedure described in Example 2, Steps 1 and 2. The residue was injected into a 40 g ISCO gold column and purified by Combi-Flash®, eluting with 10% to 100% EtOAc (containing 0.5% AcOH)/hexanes to give a crude product as the faster eluting isomer. This crude product was purified by preparative reverse-phase HPLC (Gemini™ Prep C$_{18}$ 5 μm column; gradient elution of 50% to 90% MeCN in H$_2$O, where both solvents contain 0.1% TFA, 30 min method) to provide one of the title compounds as a white foam. $^1$H NMR (400 MHz, CD$_2$Cl$_2$) δ ppm 8.30 (s, 1H), 7.79-7.70 (m, 1H), 7.66 (d, J=8.4 Hz, 1H), 7.14 (m, 1H), 7.10 (m, 1H), 6.95-6.87 (m, 2H), 5.67 (dd, J=4.1, 15.8 Hz, 1H), 5.44-5.34 (m, 1H), 4.29-4.13 (m, 3H), 4.04 (m, 1H), 3.89-3.77 (m, 2H), 3.29 (d, J=14.3 Hz, 1H), 3.05 (dd, =3.5, 16.0 Hz, 1H), 2.78-2.69 (m, 2H), 2.62-2.53 (m, 1H), 2.48 (m, 1H), 2.31-2.19 (m, 1H), 2.05-1.70 (m, 9H), 1.61 (m, 1H), 1.37 (d, J=7.0 Hz, 3H), 1.35-1.26 (m, 4H), 1.17 (d, J=6.7 Hz, 3H); m/z (ESI, +ve ion) 627 (M+H)$^+$.

EXAMPLE 50

(1S,3'R,6'R,7'S,8'E,11'R,12'R)-6-CHLORO-7'-HYDROXY-11'-METHYL-12'-(1-METHYLETHYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'S,12'S)-6-CHLORO-7'-HYDROXY-11'-METHYL-12'-(1-METHYLETHYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'S,12'R)-6-CHLORO-7'-HYDROXY-11'-METHYL-12'-(1-METHYLETHYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'S)-6-CHLORO-7'-HYDROXY-11'-METHYL-12'-(1-METHYLETHYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

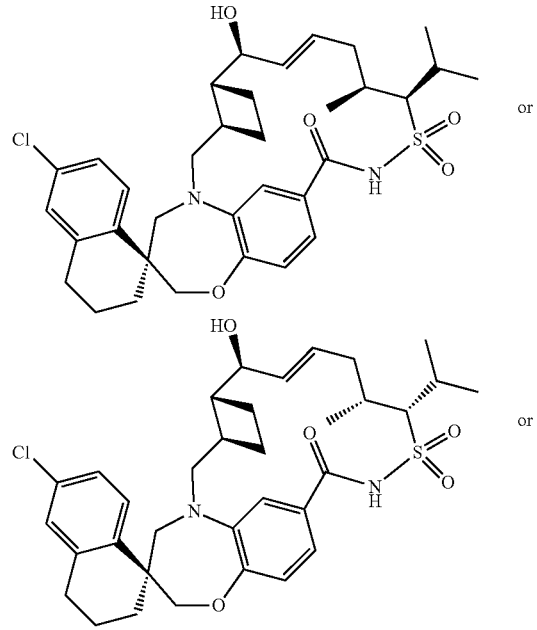

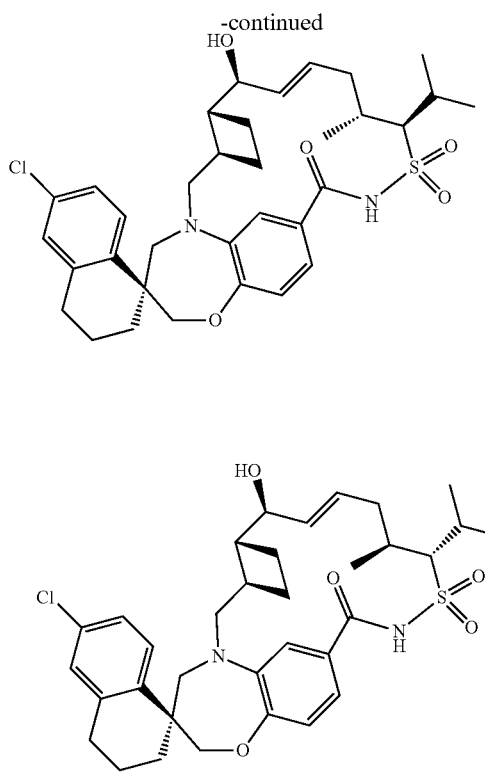

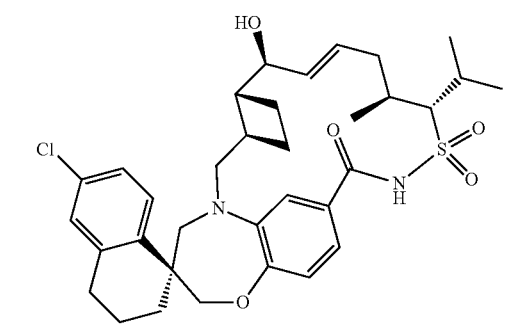

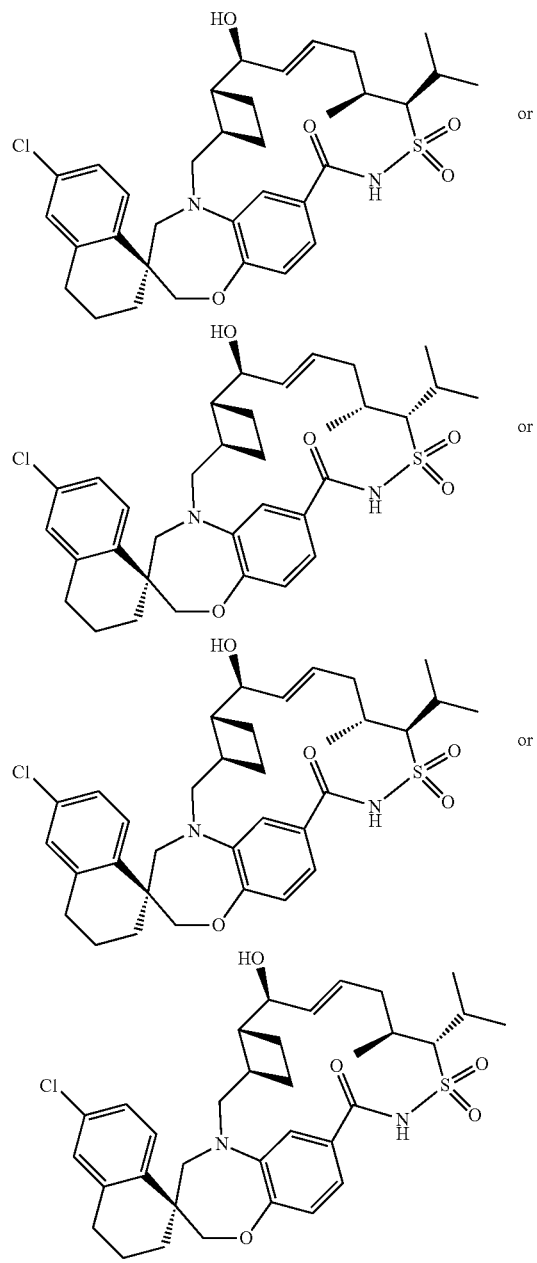

One of the title compounds was obtained as the second (slower) eluting isomer using Combi-Flash® separation as described in Example 54. $^1$H NMR (400 MHz, CD$_2$Cl$_2$) δ ppm 8.13 (s, 1H), 7.71 (d, J=8.4 Hz, 1H), 7.17 (dd, J=2.3, 8.4 Hz, 1H), 7.09 (d, J=2.3 Hz, 1H), 6.91 (m, 3H), 5.79-5.67 (m, 2H), 4.22-4.13 (m, 2H), 4.0) (s, 2H), 3.90-3.78 (m, 1H), 3.69 (d, J=14.3 Hz, 1H), 3.24 (d, J=14.3 Hz, 1H), 3.03 (dd, J=9.3, 15.4 Hz, 1H), 2.83-2.70 (m, 2H), 2.46-2.37 (m, 1H), 2.35-2.23 (m, 2H), 2.19-1.91 (m, 6H), 1.88-1.75 (m, 3H), 1.70-1.61 (m, 1H), 1.44-1.30 (m, 7H), 1.14 (d, J=6.7 Hz, 3H); m/z (ESI, +ve ion) 627 (M+H)$^+$.

EXAMPLE 51

(1S,3'R,6'R,7'S,8'E,11'R,12'R)-6-CHLORO-7'-HYDROXY-11'-METHYL-12'-(1-METHYLETHYL)-3,4-DIHYDRO-2H,15'H-SPIRO[NAPHTHALENE-1,22'-[20]OXA[13]THIA[1,14] DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'S,12'S)-6-CHLORO-7'-HYDROXY-11'-METHYL-12'-(1-METHYLETHYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'S,12'R)-6-CHLORO-7'-HYDROXY-11'-METHYL-12'-(1-METHYLETHYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'S)-6-CHLORO-7'-HYDROXY-11'-(1-METHYLETHYL)-3,4-DIHYDRO-2H,15'H-SPIRO[NAPHTHALENE-1,22'-[20]OXA[1,14]DIAZATETRACYCLO[14.7.2.0$^{3,6}$.0$^{19,24}$]PENTACOSA[8,16,18,24]TETRAEN]-15'-ONE 13',13'-DIOXIDE

One of the title compounds was obtained as the third (slower) eluting isomer using Combi-Flash® separation as described in Example 54. $^1$H NMR (400 MHz, CD$_2$Cl$_2$) δ ppm 8.11 (s, 1H), 7.77-7.69 (m, 1H), 7.16 (d, J=8.4 Hz, 1H), 7.13-7.06 (m, 1H), 7.00-6.88 (m, 3H), 5.85-5.60 (m, 2H), 4.24-4.06 (m, 4H), 3.95-3.80 (m, 1H), 3.69 (d, J=14.1 Hz, 1H), 3.51-3.34 (m, 2H), 2.83-2.70 (m, 2H), 2.46-2.24 (m, 3H), 2.18-1.90 (m, 6H), 1.87-1.70 (m, 4H), 1.35 (dd, J=7.0, 14.3 Hz, 7H), 1.22-1.07 (m, 3H); m/z (ESI, +ve ion) 627 (M+H)$^+$.

EXAMPLE 52

(1S,3'R,6'R,7'S,8'E,11'R,12'R)-6-CHLORO-7'-HYDROXY-11'-METHYL-12'-(1-METHYLETHYL)-3,4-DIHYDRO-2H,15'H-SPIRO[NAPHTHALENE-1,22'-[20]OXA[13]THIA[1,14] DIAZATETRACYCLO[14.7.2.0$^{3,6}$.0$^{19,24}$]

PENTACOSA[8,16,18,24]TETRAEN]-15'-ONE 13',13'-DIOXIDE OR (1S,3'R,6'R,7'S,8'E,11'S,12'S)-6-CHLORO-7'-HYDROXY-11'-METHYL-12'-(1-METHYLETHYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'S,12'R)-6-CHLORO-7'-HYDROXY-11'-METHYL-12'-(1-METHYLETHYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'S)-6-CHLORO-7'-HYDROXY-11'-METHYL-12'-(1-METHYLETHYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

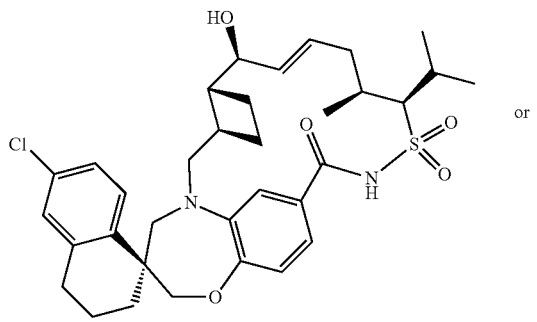

or

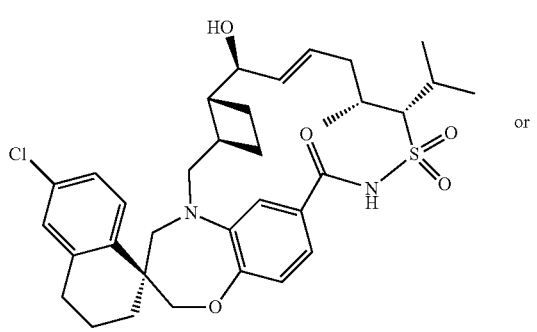

or

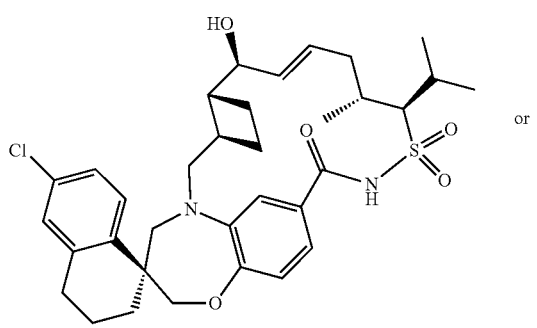

or

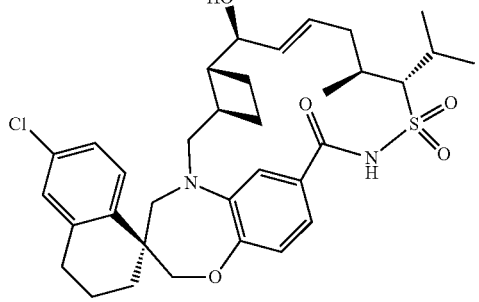

One of the title compounds was obtained as the fourth (slower) eluting isomer using Combi-Flash® separation as described in Example 54. $^1$H NMR (400 MHz, CD$_2$Cl$_2$) δ ppm 8.11 (br. s., 1H), 7.71 (t, J=6.9 Hz, 1H), 7.25-6.87 (m, 5H), 5.88-5.43 (m, 2H), 4.20-4.02 (m, 3H), 3.84 (m, 1H), 3.74-3.55 (m, 2H), 3.55-3.40 (m, 1H), 3.40-3.12 (m, 1H), 2.82-2.62 (m, 3H), 2.53 (d, J=5.3 Hz, 2H), 2.32 (m, 3H), 2.08-1.62 (m, 8H), 1.37-1.12 (m, 10H); m/z (ESI, +ve ion) 627 (M+H)$^+$.

EXAMPLE 53

(1S,3'R,6'R,7'S,8'E,11'R,12'R)-6-CHLORO-7'-METHOXY-11'-METHYL-12'-(1-METHYLETHYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'S,12'S)-6-CHLORO-7'-METHOXY-11'-METHYL-12'-(1-METHYLETHYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'S,12'R)-6-CHLORO-7'-METHOXY-11'-METHYL-12'-(1-METHYLETHYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'S)-6-CHLORO-7'-METHOXY-11'-METHYL-12'-(1-METHYLETHYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

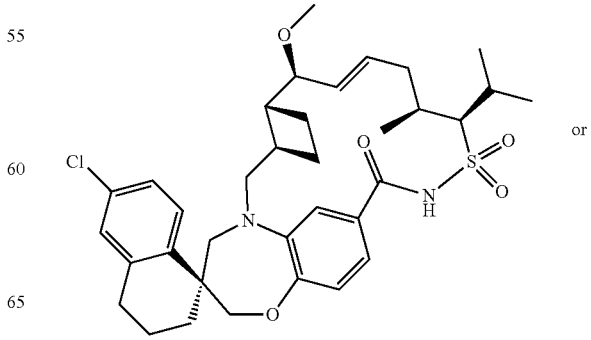

or

-continued

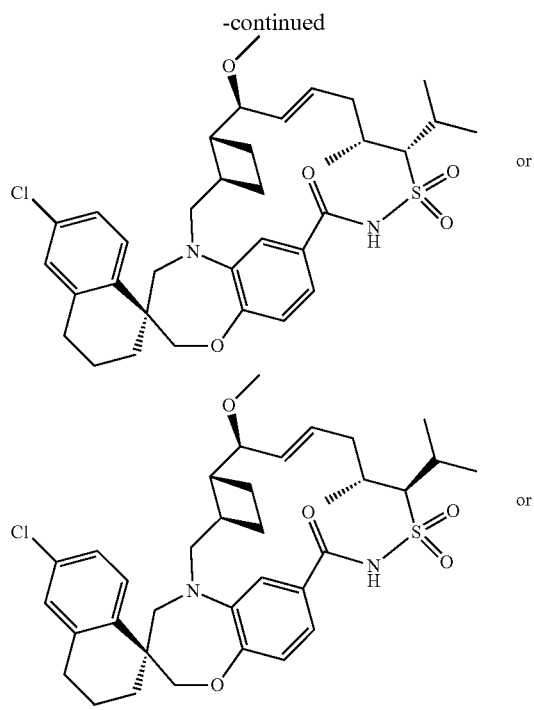
or

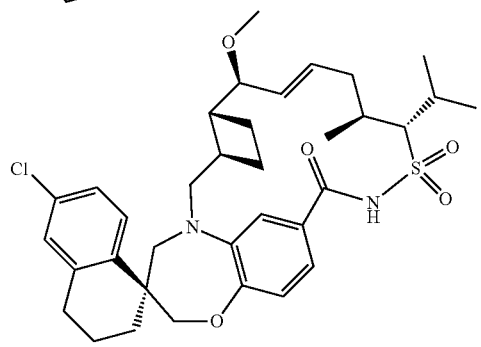

To a solution of the product (from Example 54; 9 mg, 0.014 mmol) in THF (1 mL) was added sodium hydride, 60% dispersion in mineral oil (1.43 mg, 0.036 mmol), followed by MeI (3.1 mg, 0.022 mmol). The solution was stirred at room temperature overnight. The reaction was then quenched with sat. NH$_4$Cl and brine, extracted (2×Et$_2$O), and washed (1× brine). The combined organic layers were dried (Na$_2$SO$_4$) and concentrated under the reduced pressure. The residue was injected into a 4 g ISCO gold column and purified by Combi-Flash®, eluting with 0% to 100% EtOAc (containing 0.5% AcOH)/hexanes to give one of the title compounds (7 mg, 10.9 μmol) as colorless oil. $^1$H NMR (400 MHz, CD$_2$Cl$_2$) δ ppm 8.15 (br. s., 1H), 7.71 (d, J=8.4 Hz, 1H), 7.17 (dd, J=2.3, 8.4 Hz, 1H), 7.09 (d, J=2.2 Hz, 1H), 6.90 (m, 2H), 6.84 (m, 1H), 5.73 (ddd, J=3.9, 8.7, 15.2 Hz, 1H), 5.52 (dd, J=8.8, 15.5 Hz, 1H), 4.23 (m, 1H), 4.12-4.04 (m, 2H), 3.82 (d, J=15.1 Hz, 1H), 3.72-3.62 (m, 2H), 3.25-3.17 (m, 4H), 3.02 (dd, J=10.0, 15.5 Hz, 1H), 2.83-2.69 (m, 2H), 2.47-2.38 (m, 1H), 2.35-2.23 (m, 3H), 2.21-2.02 (m, 3H), 1.97-1.72 (m, 5H), 1.68-1.60 (m, 1H), 1.40-1.30 (m, 7H), 1.13 (d, J=6.7 Hz, 3H); m/z (ESI, +ve ion) 641 (M+H)$^+$.

EXAMPLE 54

(1S,3'R,6'R,7'S,8'E,11'R,12'R)-6-CHLORO-7'-(2-METHOXYETHOXY)-11'-METHYL-12'-(1-METHYLETHYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'S,12'S)-6-CHLORO-7'-(2-METHOXYETHOXY)-11'-METHYL-12'-(1-METHYLETHYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'S,12'R)-6-CHLORO-7'-(2-METHOXYETHOXY)-11'-METHYL-12'-(1-METHYLETHYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13-DIOXIDE OR (1S,3'R,6'R,7'S,8'E,11'R,12'S)-6-CHLORO-7'-(2-METHOXYETHOXY)-11'-METHYL-12'-(1-METHYLETHYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

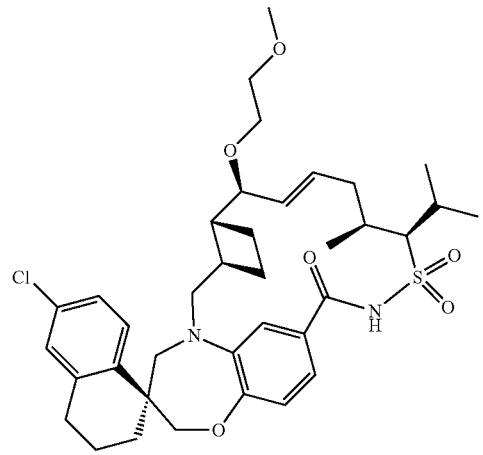
or

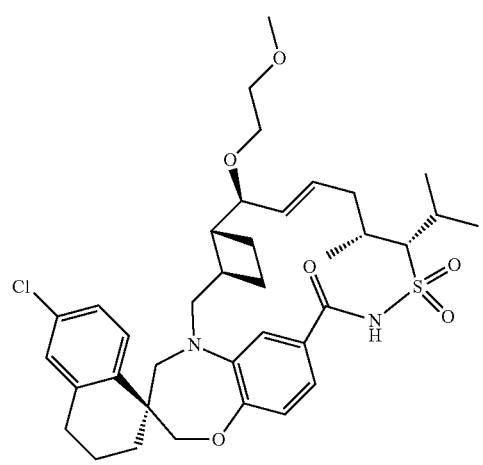
or

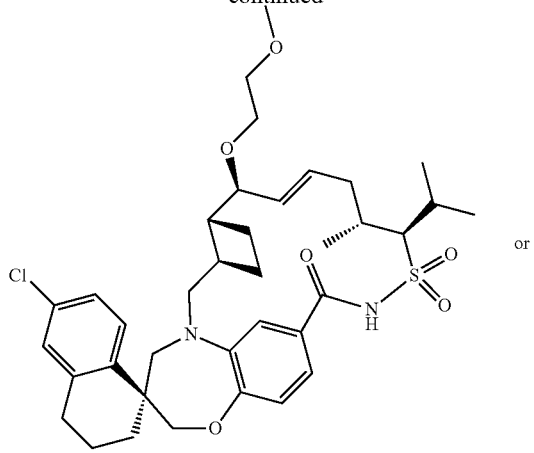

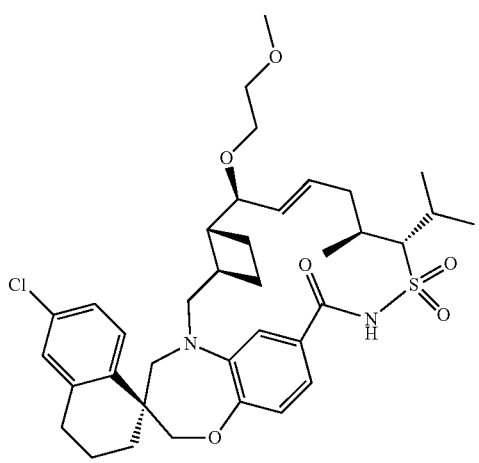

To a solution of the product from Example 54 (10 mg, 0.016 mmol) in THF (1 mL) was added sodium hydride, 60% dispersion in mineral oil (1.6 mg, 0.040 mmol), followed by 2-bromoethyl methyl ether (2.2 mg, 0.016 mmol). The solution was stirred at room temperature for ~48 h. The reaction was then quenched with sat. NH$_4$Cl and brine, extracted (2×Et$_2$O), and washed (1× brine). The combined organic layers were dried (Na$_2$SO$_4$) and concentrated under the reduced pressure. This crude product was purified by preparative reverse-phase HPLC (Gemini™ Prep C$_{18}$ 5 μm column, gradient elution of 50% to 90% MeCN in H$_2$O, where both solvents contain 0.1% TFA, 30 min method) to provide one of the title compounds (4 mg, 5.8 μmol) as a white amorphous solid. $^1$H NMR (400 MHz, CD$_2$Cl$_2$) δ ppm 8.09 (s, 1H), 7.70 (d, J=8.6 Hz, 1H), 7.16 (dd, J=2.2, 8.5 Hz, 1H), 7.09 (d, J=2.2 Hz, 1H), 6.94-6.87 (m, 2H), 6.84 (s, 1H), 5.71 (ddd, J=4.0, 8.5, 15.3 Hz, 1H), 5.60-5.48 (m, 1H), 4.21 (m, 1H), 4.08 (s, 2H), 3.86-3.74 (m, 2H), 3.68 (d, J=13.9 Hz, 1H), 3.53-3.36 (m, 4H), 3.32 (s, 3H), 3.23 (d, J=14.3 Hz, 1H), 3.01 (dd, J=10.1, 15.2 Hz, 1H), 2.83-2.69 (m, 2H), 2.48-2.39 (m, 1H), 2.34-2.12 (m, 4H), 2.12-2.01 (m, 2H), 1.99-1.75 (m, 5H), 1.72-1.63 (m, 1H), 1.45-1.30 (m, 7H), 1.13 (d, J=6.8 Hz 3H); m/z (ESI, +ve ion) 685 (M+H)$^+$.

EXAMPLE 55

(1S,3'R,6'R,7'S,8'E,11'S,12'S)-6-CHLORO-12'-CYCLOBUTYL-7'-HYDROXY-11'-METHYL-3,4-DIHYDRO-2H,15'H-SPIRO[NAPHTHALENE-1,22'-[20]OXA[13]THIA[1,14] DIAZATETRACYCLO[14.7.2.0$^{3,6}$.0$^{19,24}$]PENTACOSA[8,16,18,24] TETRAEN]-15'-ONE 13',13'-DIOXIDE OR (1S,3'R,6'R,7'S,8'E,11'R,12'R)-6-CHLORO-12'-CYCLOBUTYL-7'-HYDROXY-11'-METHYL-3,4-DIHYDRO-2H,15'H-SPIRO [NAPHTHALENE-1,22'-[20]OXA[13]THIA[1,14] DIAZATETRACYCLO[14.7.2.0$^{3,6}$.0$^{19,24}$] PENTACOSA [8,16,18,24]TETRAEN]-15'-ONE 13',13'-DIOXIDE OR (1S,3'R,6'R,7'S,8'E,11'R,12'S)-6-CHLORO-12'-CYCLOBUTYL-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$] PENTACOSA[8,16,18,24]TETRAEN]-15'-ONE 13',13'-DIOXIDE OR (1S,3'R,6'R,7'S,8'E,11'S,12'R)-6-CHLORO-12'-CYCLOBUTYL-7'-HYDROXY-11'-METHYL-3,4-DIHYDRO-2H,15'H-SPIRO [NAPHTHALENE-1,22'-[20]OXA[13]THIA[1,14] DIAZATETRACYCLO[14.7.2.0$^{3,6}$.0$^{19,24}$] PENTACOSA [8,16,18,24]TETRAEN]-15'-ONE 13',13'-DIOXIDE

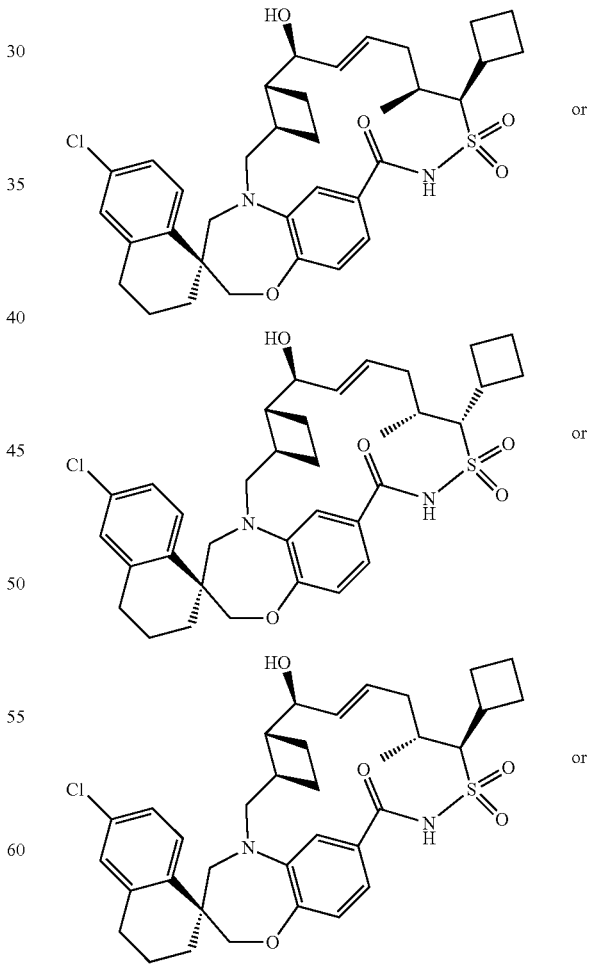

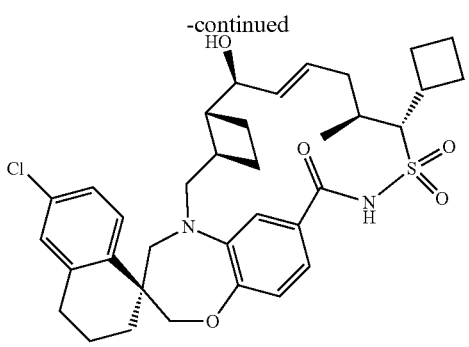

STEP 1: (R)-2-METHYLPENT-4-ENAL AND (S)-2-METHYLPENT-4-ENAL

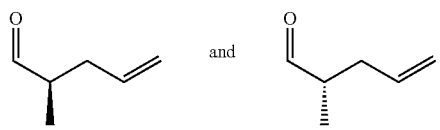

To a solution of oxalyl chloride (6.65 mL, 74.9 mmol) in DCM (30 mL) at −60° C. was added a solution of DMSO anhydrous (10.6 mL, 150 mmol) in DCM (20 mL) under $N_2$. After being stirred for 2 min, a solution of 2-methylpent-4-en-1-ol (5.00 g, 49.9 mmol) in DCM (20 mL) was added, and the resulting mixture was stirred for 15 min at −60° C. $Et_3N$ (34.7 mL, 250 mmol) was then added. After being stirred at ambient temperature for 20 min, the mixture was quenched with DCM and $H_2O$, extracted (2×$Et_2O$), and washed (1× brine). The combined organic layers were dried ($Na_2SO_4$) and concentrated under the reduced pressure to afford the title compound. The title compound was taken to the next step without further purification.

STEP 2: (1R,2R)-1-CYCLOBUTYL-2-METHYL-PENT-4-EN-1-OL AND (1R,2S)-1-CYCLOBUTYL-2-METHYLPENT-4-EN-1-OL AND (1S,2R)-1-CYCLOBUTYL-2-METHYLPENT-4-EN-1-OL AND (1S,2S)-1-CYCLOBUTYL-2-METHYLPENT-4-EN-1-OL

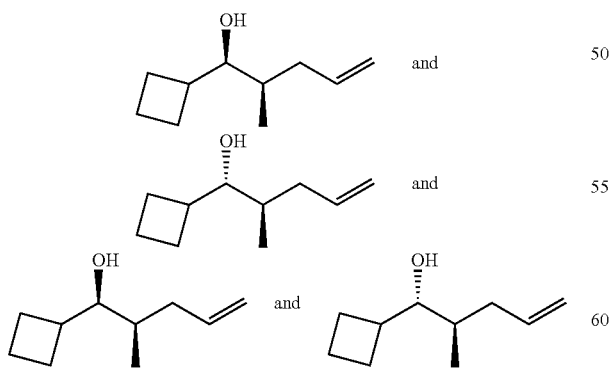

To a solution of (R)-2-methylpent-4-enal and (S)-2-methylpent-4-enal (5 g, 50.9 mmol) (Example 183, Step 1) in THF (30 mL) was added cyclobutylmagnesium bromide (17.8 g, 112 mmol) at −78° C. The reaction was allowed to warm to room temperature. After being stirred at room temperature for 3 h, the reaction was quenched (sat. $NH_4Cl$), extracted (2×$Et_2O$), and washed (1× brine). The combined organic layers were dried ($Na_2SO_4$) and concentrated under the reduced pressure. The residue was injected into a 40 g ISCO gold column and purified by Combi-Flash®, eluting with 0% to 30% EtOAc/hexanes to give the title compound (4.2 g, 27.2 mmol).

STEP 3

(1S,2R)-1-CYCLOBUTYL-N,N-BIS(4-METHOXYBEN-ZYL)-2-METHYLPENT-4-ENE-1-SULFONAMIDE AND (1R,2R)-1-CYCLOBUTYL-N,N-BIS(4-METHOXYBEN-ZYL)-2-METHYLPENT-4-ENE-1-SULFONAMIDE AND (1S,2S)-1-CYCLOBUTYL-N,N-BIS(4-METHOXYBEN-ZYL)-2-METHYLPENT-4-ENE-1-SULFONAMIDE AND (1R,2S)-1-CYCLOBUTYL-N,N-BIS(4-METHOXYBEN-ZYL)-2-METHYLPENT-4-ENE-1-SULFONAMIDE

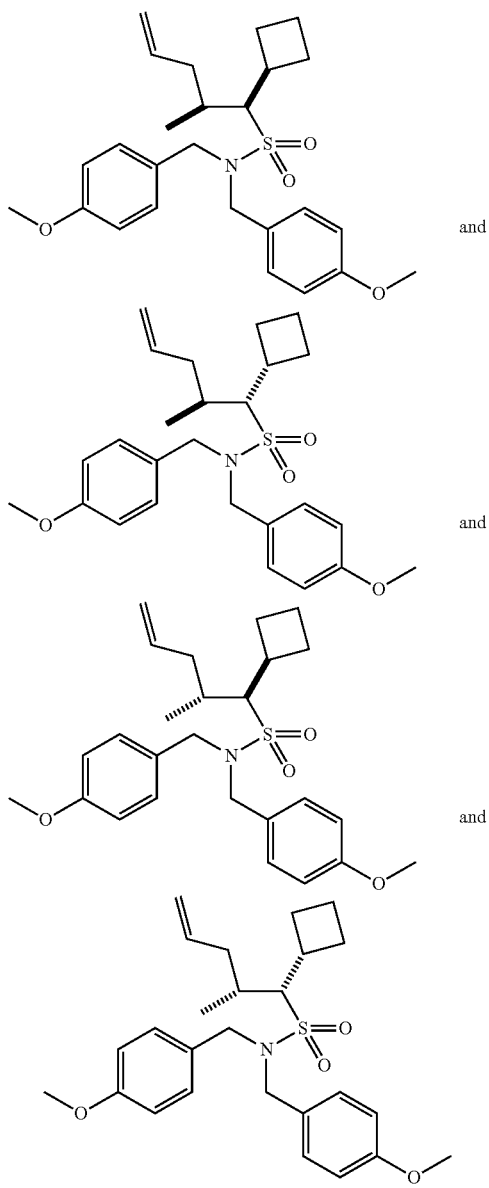

The title compound was prepared from a mixture of (1R,2R)-1-cyclobutyl-2-methylpent-4-en-1-ol, (1R,2S)-1-cyclobutyl-2-methylpent-4-en-1-ol, (1S,2R)-1-cyclobutyl-2-methylpent-4-en-1-ol, and (1S,2S)-1-cyclobutyl-2-methylpent-4-en-1-ol (from Step 2), following a similar procedure described in Intermediate EE22, Steps 3 through 6.

STEP 4

(1S,2R)-1-CYCLOBUTYL-2-METHYLPENT-4-ENE-1-SULFONAMIDE AND (1R,2R)-1-CYCLOBUTYL-2-METHYLPENT-4-ENE-1-SULFONAMIDE AND (1S,2S)-1-CYCLOBUTYL-2-METHYLPENT-4-ENE-1-SULFONAMIDE AND (1R,2S)-1-CYCLOBUTYL-2-METHYLPENT-4-ENE-1-SULFONAMIDE

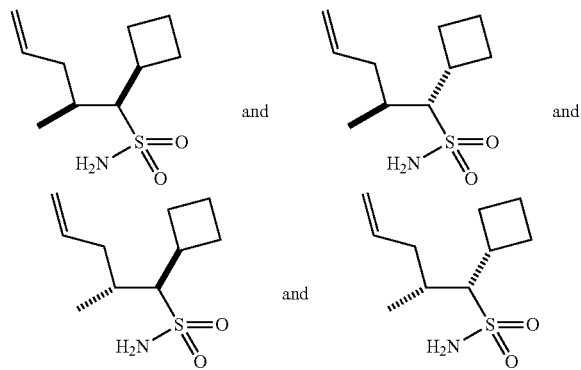

The title compounds were synthesized from a mixture of (1S,2R)-1-cyclobutyl-N,N-bis(4-methoxybenzyl)-2-methylpent-4-ene-1-sulfonamide, (1R,2R)-1-cyclobutyl-N,N-bis(4-methoxybenzyl)-2-methylpent-4-ene-1-sulfonamide, (1S,2S)-1-cyclobutyl-N,N-bis(4-methoxybenzyl)-2-methylpent-4-ene-1-sulfonamide, and (1R,2S)-1-cyclobutyl-N,N-bis(4-methoxybenzyl)-2-methylpent-4-ene-1-sulfonamide (from Step 2), following a similar procedure described in Example 26, Step 2.

STEP 5

(1S,3'R,6'R,7'S,8'E,11'S,12'S)-6-CHLORO-12'-CYCLOBUTYL-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'R)-6-CHLORO-12'-CYCLOBUTYL-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'S)-6-CHLORO-12'-CYCLOBUTYL-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

The title compounds was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12) and a mixture of (1S,2R)-1-cyclobutyl-2-methylpent-4-ene-1-sulfonamide, (1R,2R)-1-cyclobutyl-2-methylpent-4-ene-1-sulfonamide, (1S,2S)-1-cyclobutyl-2-methylpent-4-ene-1-sulfonamide, and (1R,2S)-1-cyclobutyl-2-methylpent-4-ene-1-sulfonamide (from Step 3), following a similar procedure described in Example 2, Steps 1 and 2. The residue was injected into a 40 g ISCO gold column and purified by Combi-Flash®, eluting with 10% to 100% EtOAc (containing 0.5% AcOH)/hexanes to give a crude product as the faster eluting isomer. This crude product was purified by preparative reverse-phase HPLC (Gemini™ Prep C$_{18}$ 5 μm column; gradient elution of 50% to 90% MeCN in H$_2$O, where both solvents contain 0.1% TFA, 30 min method) to provide one of the title compounds as a white foam. $^1$H NMR (400 MHz, CD$_2$Cl$_2$) δ ppm 8.26 (br. s., 1H), 7.71 (d, J=8.4 Hz, 1H), 7.16 (dd, J=2.3, 8.4 Hz, 1H), 7.09 (d, J=2.3 Hz, 1H), 6.95-6.89 (m, 3H), 5.91 (ddd, J=3.8, 8.9, 15.0 Hz, 1H), 5.70 (dd, J=8.1, 15.2 Hz, 1H), 4.25 (dd, J=3.8, 8.1 Hz, 1H), 4.12-4.05 (m, 3H), 3.84 (m, 1H), 3.68 (d, J=14.3 Hz, 1H), 3.25 (d, J=14.3 Hz, 1H), 3.09-3.02 (m, 1H), 3.00-2.89 (m, 1H), 2.82-2.70 (m, 2H), 2.47-2.38 (m, 1H), 2.36-2.12 (m, 5H), 2.06-1.94 (m, 6H), 1.88-1.77 (m, 4H), 1.73-1.62 (m, 1H), 1.49-1.32 (m, 2H), 1.08 (d, J=6.8 Hz, 3H); m/z (ESI, +ve ion) 639 (M+H)$^+$.

EXAMPLE 56

(1S,3'R,6'R,7'S,8'E,11'S,12'S)-6-CHLORO-12'-CYCLOBUTYL-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'R)-6-CHLORO-12'-CYCLOBUTYL-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'S)-6-CHLORO-12'-CYCLOBUTYL-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

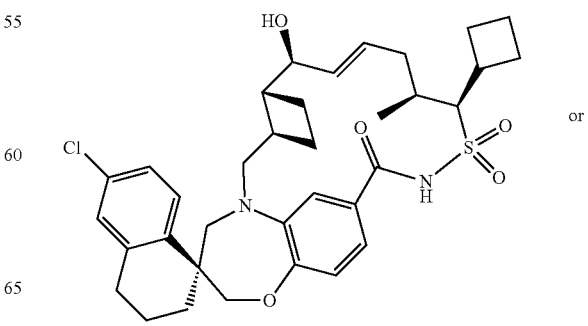

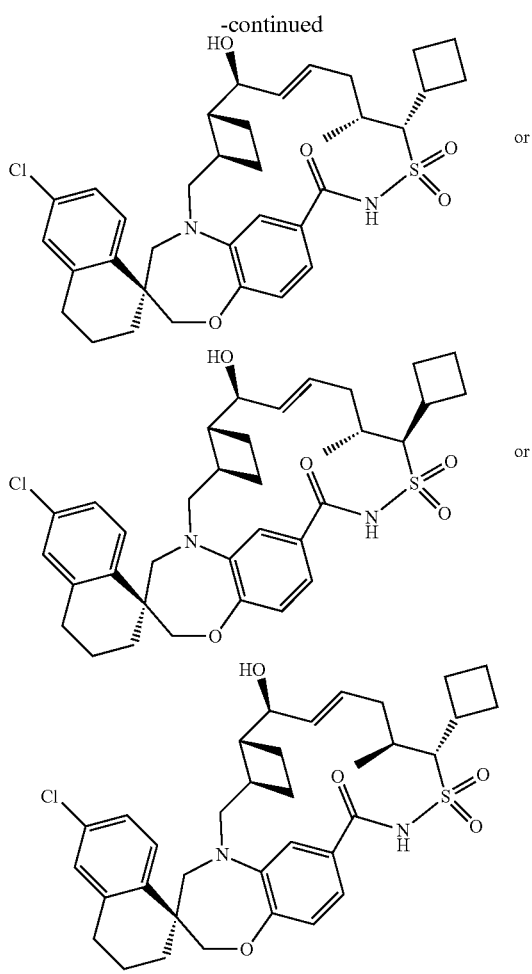

One of the title compounds was obtained as the second (slower) eluting isomer using Combi-Flash® separation as described in Example 55. ¹H NMR (400 MHz, CD₂Cl₂) δ ppm 8.10 (br. s., 1H), 7.73-7.67 (m, 1H), 7.17 (m, 1H), 7.11-7.05 (m, 2H), 6.97-6.89 (m, 2H), 6.01 (m, 1H), 5.65 (dd, J=6.1, 15.5 Hz 1H), 4.18 (m, 1H), 4.13-4.01 (m, 2H), 3.75 (m, 2H), 3.60 (m, 1H), 3.40 (m, 1H), 3.25 (m, 1H), 2.92 (m, 1H), 2.83-2.72 (m, 2H), 2.53 (m, 2H), 2.35-1.56 (m, 16H), 1.44 (m, 1H), 1.15-1.03 (m, 3H); m/z (ESI, +ve ion) 639 (M+H)⁺.

EXAMPLE 57

(1S,3'R,6'R,7'S,8'E,11'S,12'S)-6-CHLORO-12'-CYCLOBUTYL-7-HYDROXY-11'-METHYL-3,4-DIHYDRO-2H,15'H-SPIRO[NAPHTHALENE-1,22'-[20]OXA[13]THIA[1,14] DIAZATETRACYCLO[14.7.2.0³,⁶.0¹⁹,²⁴]PENTACOSA[8,16,18,24]TETRAEN]-15'-ONE 13',13'-DIOXIDE OR (1S,3'R,6'R,7'S,8'E,11'R,12'R)-6-CHLORO-12'-CYCLOBUTYL-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴] PENTACOSA[8,16,18,24]TETRAEN]-15'-ONE 13',13'-DIOXIDE OR (1S,3'R,6'R,7'S,8'E,11'R,12'S)-6-CHLORO-12'-CYCLOBUTYL-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0³,⁶.0¹⁹,²⁴]PENTACOSA[8,16,18,24]TETRAEN]-15'-ONE 13',13'-DIOXIDE OR (1S,3'R,6'R,7'S,8'E,11'S,12'R)-6-CHLORO-12'-CYCLOBUTYL-7'-HYDROXY-11'-METHYL-3,4-DIHYDRO-2H,15'H-SPIRO[NAPHTHALENE-1,22'-[20]OXA[13]THIA[1,14] DIAZATETRACYCLO[14.7.2.0³,⁶.0¹⁹,²⁴]PENTACOSA[8,16,18,24]TETRAEN]-15'-ONE 13',13'-DIOXIDE

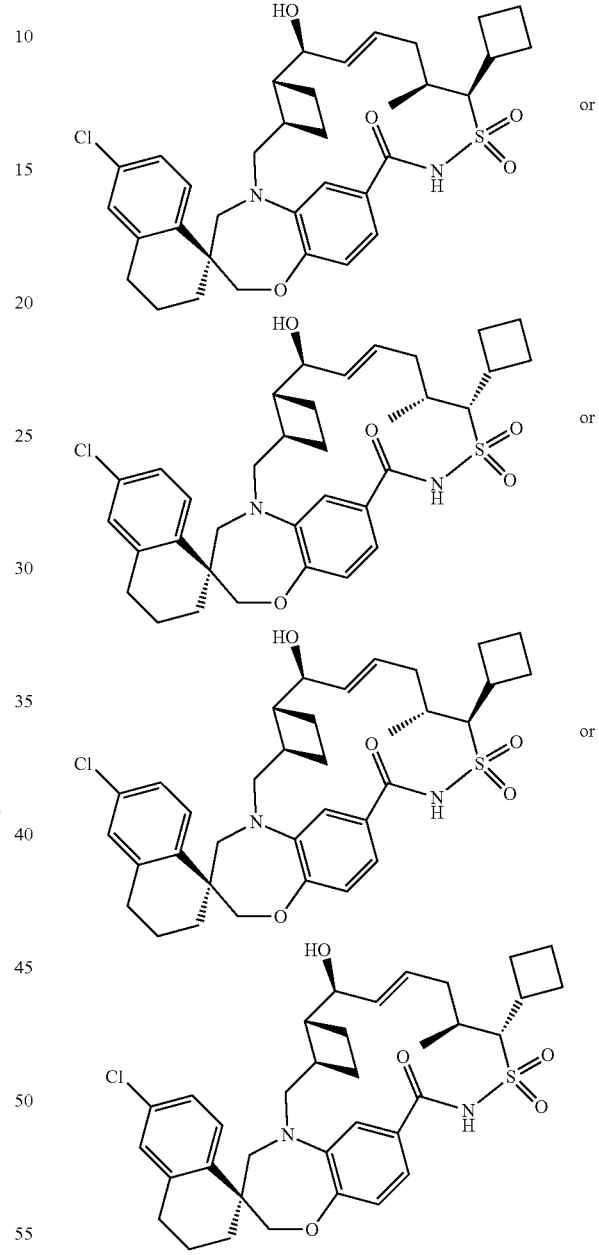

One of the title compounds was obtained as the third (slower) eluting isomer using Combi-Flash® separation as described in Example 55. ¹H NMR (400 MHz, CD₂Cl₂) δ ppm 8.22 (br. s., 1H), 7.67 (d, J=8.4 Hz, 1H), 7.58 (m, 1H), 7.15 (dd, J=2.3, 8.4 Hz, 1H), 7.10 (d, J=2.2 Hz, 1H), 6.94-6.88 (m, 2H), 5.78-5.61 (m, 2H), 4.26-4.18 (m, 2H), 4.07 (d, J=11.0 Hz, 1H), 4.02-3.87 (m, 2H), 3.72 (m, 1H), 3.36 (m, 1H), 3.14 (m, 11H), 3.00-1.60 (m, 21H), 1.55-1.40 (m, 1H), 1.10 (d, J=6.7 Hz, 3H); m/z (ESI, +ve ion) 639 (M+H)⁺.

EXAMPLE 58

(1S,3'R,6'R,7'S,8'E,11'S,12'R)-6-CHLORO-12'-(CYCLO-PROPYLMETHYL)-7'-HYDROXY-11'-METHYL-3,4-DI-HYDRO-2H,15'H-SPIRO[NAPHTHALENE-1,22'-[20] OXA[13]THIA[1,14] DIAZATETRACYCLO[14.7.2.0$^{3,6}$.0$^{19,24}$] PENTACOSA[8,16,18,24] TETRAEN]-15'-ONE 13',13'-DIOXIDE OR (1S,3'R,6'R,7'S,8'E,11'S,12'S)-6-CHLORO-12'-(CYCLOPROPYLMETHYL)-7'-HYDROXY-11'-METHYL-3,4-DIHYDRO-2H,15'H-SPIRO[NAPHTHALENE-1,22'-[20]OXA[13]THIA [1,14] DIAZATETRACYCLO [14.7.2.0$^{3,6}$.0$^{19,24}$]PENTACOSA [8,16,18,24]TETRAEN]-15'-ONE 13',13'-DIOXIDE OR (1S,3'R,6'R,7'S,8'E,11'R,12'R)-6-CHLORO-12'-(CYCLO-PROPYLMETHYL)-7'-HYDROXY-11'-METHYL-3,4-DI-HYDRO-2H,15'H-SPIRO[NAPHTHALENE-1,22'-[20] OXA[13]THIA [1,14]DIAZATETRACYCLO [14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'S)-6-CHLORO-12'-(CYCLOPROPYLMETHYL)-7'-HYDROXY-11'-METHYL-3,4-DIHYDRO-2H,15'H-SPIRO [NAPHTHALENE-1,22'-[20]OXA[13]THIA [1,14] DIAZATETRACYCLO[14.7.2.0$^{3,6}$.0$^{19,24}$] PENTACOSA [8,16,18,24]TETRAEN]-15'-ONE 13',13'-DIOXIDE

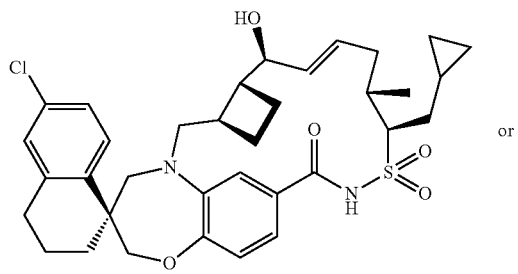 or

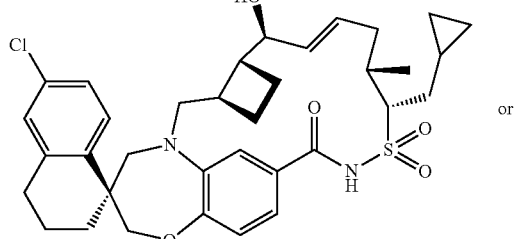 or

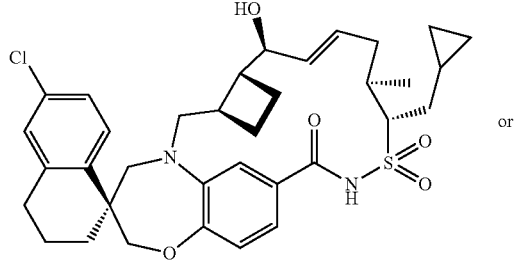 or

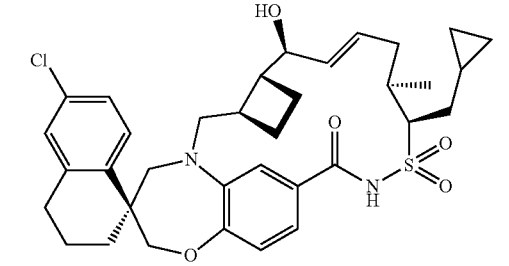

STEP 1: (2S)—N,N-BIS(4-METHOXYBENZYL)-2-METHYLPENT-4-ENE-1-SULFONAMIDE AND (2R)—N,N-BIS(4-METHOXYBENZYL)-2-METHYL-4-PENTENE-1-SULFONAMIDE

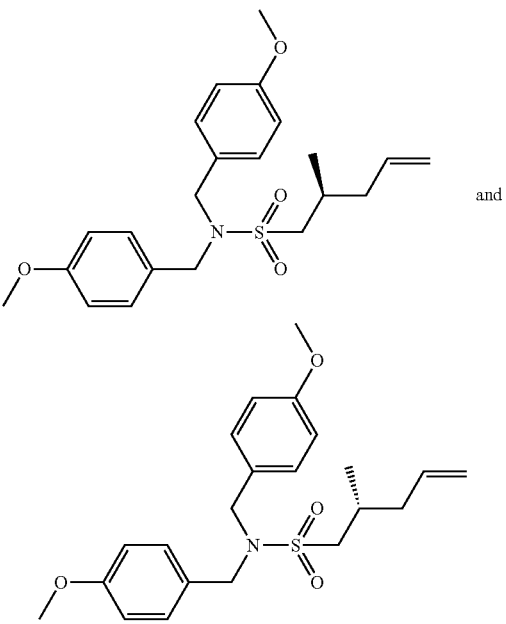

The title compound was prepared from Intermediate EE12 and pent-4-en-2-yl 4-methylbenzenesulfonate following a similar procedure described in Example 26, Step 1.

STEP 2

(2S,3R)-1-CYCLOPROPYL-N,N-BIS(4-METHOXYBEN-ZYL)-3-METHYL-5-HEXENE-2-SULFONAMIDE AND (2R,3S)-1-CYCLOPROPYL-N,N-BIS(4-METHOXYBEN-ZYL)-3-METHYL-5-HEXENE-2-SULFONAMIDE AND (2R,3R)-1-CYCLOPROPYL-N,N-BIS(4-METHOXY-BENZYL)-3-METHYL-5-HEXENE-2-SULFONAMIDE AND (2S,3S)-1-CYCLOPROPYL-N,N-BIS(4-METHOXYBENZYL)-3-METHYL-5-HEXENE-2-SULFONAMIDE

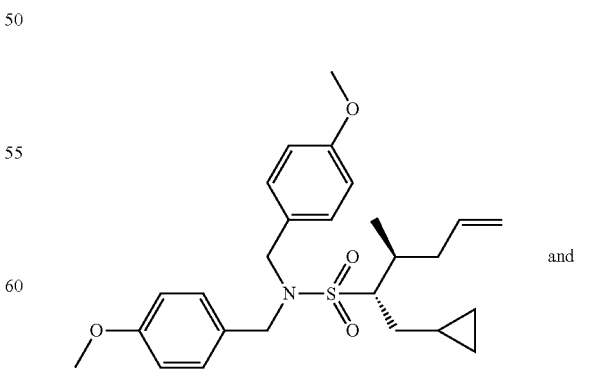

185
-continued

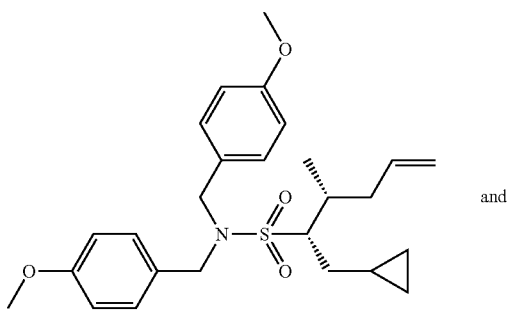

and

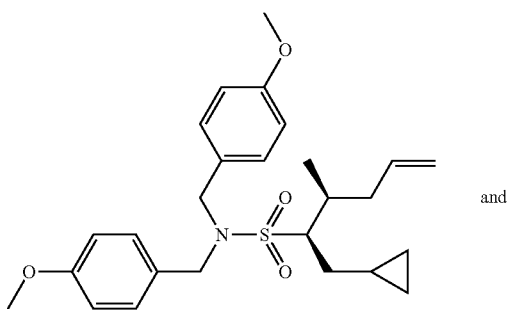

and

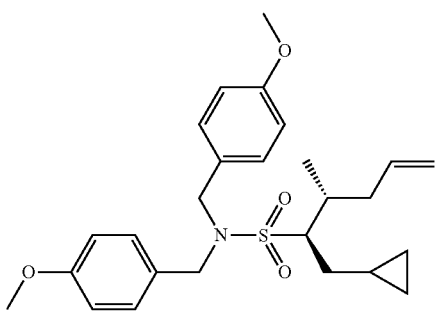

To a solution of (2S)—N,N-bis(4-methoxybenzyl)-2-methylpent-4-ene-1-sulfonamide and (2R)—N,N-bis(4-methoxybenzyl)-2-methylpent-4-ene-1-sulfonamide (600 mg, 1.49 mmol) in THF was added butyllithium solution, 2.5 N in hexanes (0.624 mL, 1.561 mmol) at −78° C. under N₂. After the reaction was stirred at −78° C. for 15 min, a solution of (bromomethyl)-cyclopropane (0.288 mL, 2.97 mmol) in THF (1 mL) was added. The reaction mixture was stirred at −78° C. for 1 h and then allowed to warm to ambient temperature. The mixture was quenched with H₂O and extracted with EtOAc. The organic layer was washed with H₂O and dried (Na₂SO₄). Solvent was evaporated, and the resulting residue was purified by chromatography (SiO₂ gel, 10 to 50%, EtOAc/Hexanes) to afford the title compounds as a colorless liquid.

186
STEP 3

(120637-9): (2S, 3S)-1-CYCLOPROPYL-3-METHYL-HEX-5-ENE-2-SULFONAMIDE AND (2S, 3R)-1-CYCLOPROPYL-3-METHYLHEX-5-ENE-2-SULFONAMIDE AND (2R, 3S)-1-CYCLOPROPYL-3-METHYLHEX-5-ENE-2-SULFONAMIDE AND (2R, 3R)-1-CYCLOPROPYL-3-METHYLHEX-5-ENE-2-SULFONAMIDE

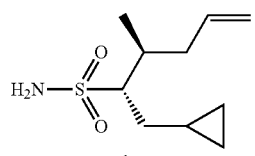

and

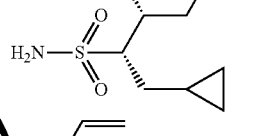

and

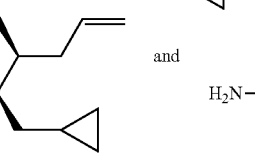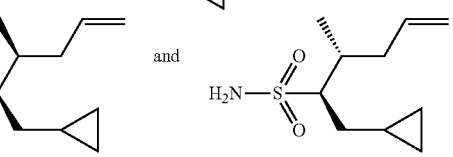

A mixture of (2S,3R)-1-Cyclopropyl-N,N-bis(4-methoxybenzyl)-3-methyl-5-hexene-2-sulfonamide, (2R,3S)-1-cyclopropyl-N,N-bis(4-methoxybenzyl)-3-methyl-5-hexene-2-sulfonamide, (2R,3R)-1-cyclopropyl-N,N-bis(4-methoxybenzyl)-3-methyl-5-hexene-2-sulfonamide, and (2S,3S)-1-cyclopropyl-N,N-bis(4-methoxybenzyl)-3-methyl-5-hexene-2-sulfonamide (510 mg, 1.11 mmol) was treated with anisole (1.81 g, 16.7 mmol) in TFA (3.81 g, 33.4 mmol). The mixture was stirred, heated at 40° C. for 18 h, and then concentrated. The resulting residue was purified by chromatography (SiO₂ gel, hexane/EtOAc, 9:1 to 1:1) to afford the title compounds as a light brown oil.

STEP 4

(3S)-6'-CHLORO-N-(((2R,3S)-1-CYCLOPROPYL-3-METHYL-5-HEXEN-2-YL)SULFONYL)-5-(((1R,2R)-2-((1S,2E)-1-HYDROXY-2-HEXEN-1-YL)CYCLOBUTYL)METHYL)-3',4,4',5-TETRAHYDRO-2'H-SPIRO[1,5-BENZOXAZEPINE-3,1'-NAPHTHALENE]-7-CARBOXAMIDE AND (3S)-6'-CHLORO-N-(((2R,3R)-1-CYCLOPROPYL-3-METHYL-5-HEXEN-2-YL)SULFONYL)-5-(((1R,2R)-2-((1S,2E)-1-HYDROXY-2-HEXEN-1-YL)CYCLOBUTYL)METHYL)-3',4,4',5-TETRAHYDRO-2'H-SPIRO[1,5-BENZOXAZEPINE-3,1'-NAPHTHALENE]-7-CARBOXAMIDE AND (3S)-6'-CHLORO-N-(((2S,3S)-1-CYCLOPROPYL-3-METHYL-5-HEXEN-2-YL)SULFONYL)-5-(((1R,2R)-2-((1S,2E)-1-HYDROXY-2-HEXEN-1-YL)CYCLOBUTYL)METHYL)-3',4,4',5-TETRAHYDRO-2'H-SPIRO[1,5-BENZOXAZEPINE-3,1'-NAPHTHALENE]-7-CARBOXAMIDE AND (3S)-6'-CHLORO-N-(((2S,3R)-1-CYCLOPROPYL-3-METHYL-5-HEXEN-2-YL)SULFONYL)-5-(((1R,2R)-2-((1S,2E)-1-HYDROXY-2-HEXEN-1-YL)CYCLOBUTYL)METHYL)-3',4,4',5-TETRAHYDRO-2'H-SPIRO[1,5-BENZOXAZEPINE-3,1'-NAPHTHALENE]-7-CARBOXAMIDE

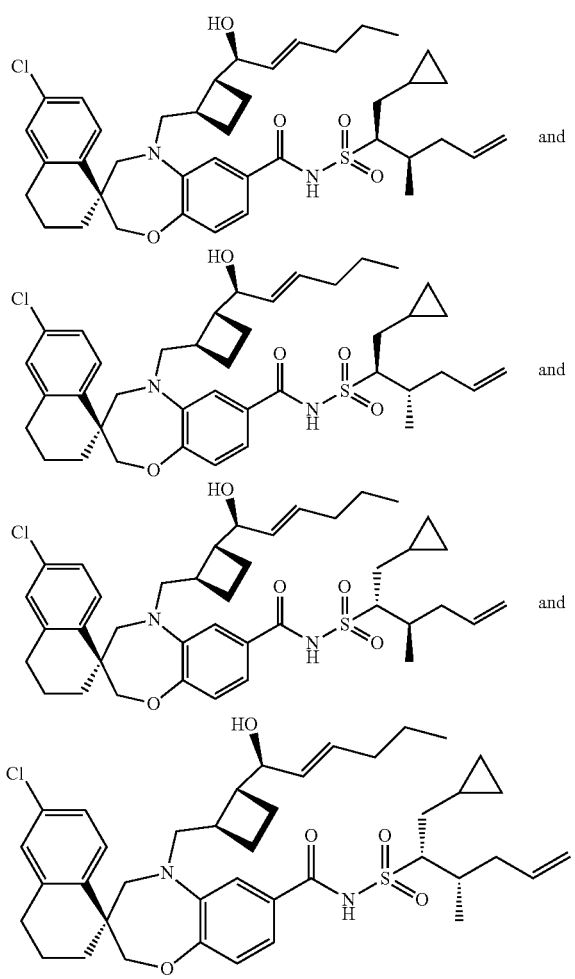

and and and

A mixture of (2S, 3S)-1-cyclopropyl-3-methylhex-5-ene-2-sulfonamide, (2S, 3R)-1-cyclopropyl-3-methylhex-5-ene-2-sulfonamide, (2R, 3S)-1-cyclopropyl-3-methylhex-5-ene-2-sulfonamide, and (2R, 3R)-1-cyclopropyl-3-methylhex-5-ene-2-sulfonamide (160 mg, 0.74 mmol) was added to (S)-6'-chloro-5-(((1R,2S)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A; 250 mg, 0.49 mmol), 1-(3-dimethylaminopropyl)-3-ethylcarbodiimide hydrochloride (141 mg, 0.74 mmol), DMAP (90 mg, 0.74 mmol) and Et$_3$N (0.20 mL, 1.47 mmol) in DCM (1 mL). The reaction mixture was stirred at ambient temperature for 3 days. The mixture was then diluted with DCM and H$_2$O was added. The organic layer was dried (MgSO$_4$) and concentrated. The resulting residue was chromatographed (SiO$_2$ gel, 1:0 to 1:1, hexane/EtOAc+0.5% HOAc) to afford the title compound.

STEP 5

(1S,3'R,6'R,7'S,8'E,11'S,12'R)-6-CHLORO-12'-(CYCLOPROPYL METHYL)-7'-HYDROXY-11'-METHYL-3,4-DIHYDRO-2H,15'H-SPIRO[NAPHTHALENE-1,22'-[20]OXA[13]THIA[1,14] DIAZATETRACYCLO [14.7.2.0$^{3,6}$.0$^{19,24}$]PENTACOSA 18,16,18,241 TETRAEN]-15'-ONE 13',13'-DIOXIDE OR (1S,3'R,6'R,7'S,8'E,11'S,12'S)-6-CHLORO-12'-(CYCLOPROPYLMETHYL)-7'-HYDROXY-11'-METHYL-3,4-DIHYDRO-2H,15'H-SPIRO[NAPHTHALENE-1,22'-[20]OXA[13]THIA [1,14] DIAZATETRACYCLO[14.7.2.0$^{3,6}$.0$^{19,24}$] PENTACOSA [8,16,18,24]TETRAEN]-15'-ONE 13',13'-DIOXIDE OR (1S,3'R,6'R,7'S,8'E, 11'R,12'R)-6-CHLORO-12'-(CYCLOPROPYLMETHYL)-7'-23 HYDROXY-11'-METHYL-3,4-DIHYDRO-2H,15'H-SPIRO[NAPHTHALENE-1,22'-[20]OXA[13]THIA [1,14]DIAZATETRACYCLO[14.7.2.0$^{3,6}$.0$^{19,24}$] PENTACOSA[8,16,18,24]TETRAEN]-15'-ONE 13',13'-DIOXIDE OR (1S,3'R,6'R,7'S,8'E,11'R,12'S)-6-CHLORO-12'-(CYCLOPROPYLMETHYL)-7'-HYDROXY-11'-METHYL-3,4-DIHYDRO-2H,15'H-SPIRO[NAPHTHALENE-1,22'-[20]OXA[13]THIA [1,14] DIAZATETRACYCLO [14.7.2.0$^{3,6}$.0$^{19,24}$]PENTACOSA[8,16,18,24]TETRAEN]-15'-ONE 13',13'-DIOXIDE

A RBF was charged with the above mixture of (3S)-6'-chloro-n-(((2R,3S)-1-cyclopropyl-3-methyl-5-hexen-2-yl)sulfonyl)-5-(((1R,2R)-2-((1S,2E)-1-hydroxy-2-hexen-1-yl)cyclobutyl)methyl)-3',4,4',5-tetrahydro-2'H-spiro[1,5-benzoxazepine-3,1'-naphthalene]-7-carboxamide, (3S)-6'-chloro-n-(((2R,3R)-1-cyclopropyl-3-methyl-5-hexen-2-yl)sulfonyl)-5-(((1R,2R)-2-((1S,2E)-1-hydroxy-2-hexen-1-yl)cyclobutyl)methyl)-3',4,4',5-tetrahydro-2'H-spiro[1,5-benzoxazepine-3,1'-naphthalene]-7-carboxamide, (3S)-6'-chloro-n-(((2S,3S)-1-cyclopropyl-3-methyl-5-hexen-2-yl)sulfonyl)-5-(((1R,2R)-2-((1S,2E)-1-hydroxy-2-hexen-1-yl)cyclobutyl)methyl)-3',4,4',5-tetrahydro-2'H-spiro[1,5-benzoxazepine-3,1'-naphthalene]-7-carboxamide and (3S)-6'-chloro-n-(((2S,3R)-1-cyclopropyl-3-methyl-5-hexen-2-yl)sulfonyl)-5-(((1R,2R)-2-((1S,2E)-1-hydroxy-2-hexen-1-yl)cyclobutyl)methyl)-3',4,4',5-tetrahydro-2'H-spiro[1,5-benzoxazepine-3,1'-naphthalene]-7-carboxamide (210 mg, 0.30 mmol) in DCE (100 mL). After bubbling into the flask with argon for 15 min, to the homogeneous solution was added Hoveyda-Grubbs II (65 mg, 0.35 mmol) and the contents of the flask was stirred at 50° C. for 18 h. The reaction mixture was cooled and air was introduced by bubbling into the flask for 2 min. Solvent was evaporated, and the crude residue was purified by preparative reverse-phase HPLC (Gemini™ Prep C$_{18}$ 5 µm column; gradient elution of 25% to 75% MeCN in H$_2$O, where both solvents contain 0.1% TFA, 30 min method) to afford the title compound as the first eluting isomer. $^1$H NMR (500 MHz, CDCl$_3$) δ ppm 8.08 (s, 1H), 7.70 (d, J=8.3 Hz, 1H), 7.19 (dd, J=2.2, 8.6 Hz, 1H), 7.10 (d, J=2.0 Hz, 1H), 6.99 (br s, 1H), 6.97-6.89 (m, 2H), 5.97-5.88 (m, 1H), 5.72 (dd, J=8.1, 15.2 Hz, 1H), 4.30-4.22 (m, 2H), 4.10 (s, 2H), 3.82 (d, J=14.9 Hz, 1H), 3.69 (d, J=14.2 Hz, 1H), 3.26 (d, J=14.2 Hz, 1H), 3.06 (br s, 1H), 2.85-2.71 (m, 2H), 2.53-2.39 (m, 1H), 2.33 (quin, J=8.7 Hz, 1H), 2.27-2.12 (m, 2H), 2.09-1.86 (m, 5H), 1.86-1.77 (m, 3H), 1.75-1.61 (m, 1H), 1.50-1.31 (m, 2H), 1.23-1.12 (m, 1H), 1.05 (d, J=6.8 Hz, 3H), 0.63 (d, J=7.8 Hz, 2H), 0.35-0.25 (m, 1H), 0.13-0.06 (m, 1H). m/z (ESI, +ve ion) 639.2 (M+H)$^+$.

EXAMPLE 59

(1S,3'R,6'R,7'S,8'E,11'S,12'R)-6-CHLORO-12'-(CYCLOPROPYL METHYL)-7'-HYDROXY-11'-METHYL-3,4-DIHYDRO-2H,15'H-SPIRO[NAPHTHALENE-1,22'-[20] OXA[13]THIA[1,14] DIAZATETRACYCLO [14.7.2.0$^{3,6}$.0$^{19,24}$]PENTACOSA [8,16,18,24] TETRAEN]-15'-ONE 13',13'-DIOXIDE OR (1S,3'R,6'R,7'S,8'E,11'S,12'S)-6-CHLORO-12'-(CYCLOPROPYLMETHYL)-7'-HYDROXY-11'-METHYL-3,4-DIHYDRO-2H,15'H-SPIRO[NAPHTHALENE-1,22'-[20]OXA[13]THIA [1,14] DIAZATETRACYCLO[14.7.2.0$^{3,6}$.0$^{19,24}$] PENTACOSA[8,16,18,24]TETRAEN]-15'-ONE 13',13'-DIOXIDE OR (1S,3'R,6'R,7'S,8'E,11'R,12'R)-6-CHLORO-12'-(CYCLO-PROPYLMETHYL)-7'-HYDROXY-11'-METHYL-3,4-DI-HYDRO-2H,15'H-SPIRO[NAPHTHALENE-1,22'-[20]OXA[13]THIA [1,14]DIAZATETRACYCLO[14.7.2.0³,⁶.0¹⁹,²⁴] PENTACOSA[8,16,18,24]TETRAEN]-15'-ONE 13',13'-DIOXIDE OR (1S,3'R,6'R,7'S,8'E,11'R,12'S)-6-CHLORO-12'-(CYCLOPROPYLMETHYL)-7'-HY-DROXY-11'-METHYL-3,4-DIHYDRO-2H,15'H-SPIRO[NAPHTHALENE-1,22'-[20]OXA[13]THIA [1,14] DIAZATETRACYCLO[14.7.2.0³,⁶.0¹⁹,²⁴] PENTACOSA [8,16,18,24]TETRAEN]-15'-ONE 13',13'-DIOXIDE

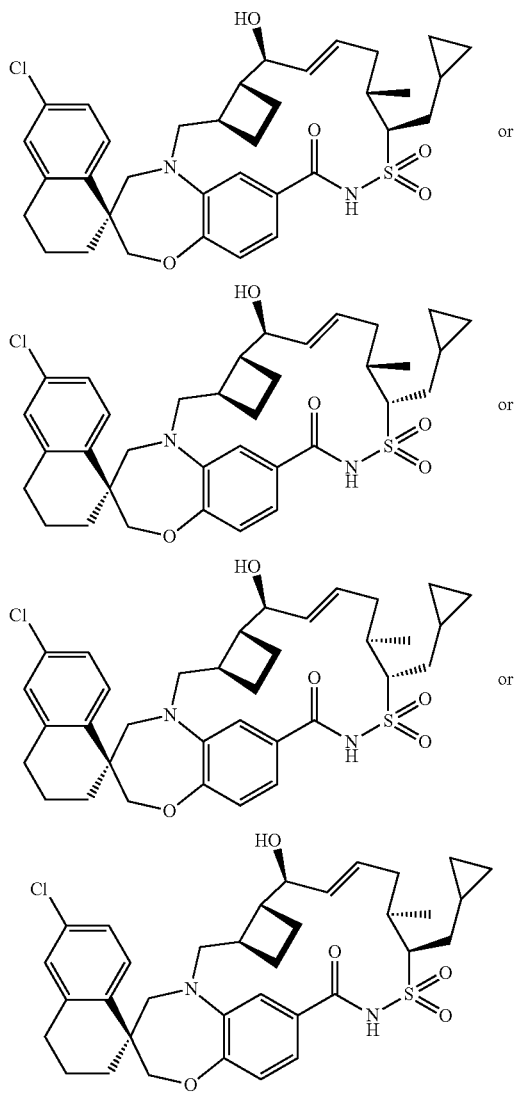

The title compound was obtained as a single isomer (second eluting peak) from the preparative reverse-phase HPLC separation in Example 58. ¹H NMR (500 MHz, CDCl₃) δ ppm 8.17 (br s, 1H), 7.79 (d, J=8.6 Hz, 1H), 7.24-7.15 (m, 2H), 7.10 (s, 1H), 6.98 (d, J=8.3 Hz, 1H), 6.67 (br s, 1H), 6.03 (m, 1H), 5.66 (dd, J=6.4, 15.2 Hz, 1H), 4.32-4.02 (m, 3H), 3.91-3.82 (m, 1H), 3.80-3.72 (m, 1H), 3.63 (m, 1H), 3.42-3.38 (m, 1H), 3.30-3.20 (m, 1H), 2.85-2.73 (m, 2H), 2.55-2.50 (m, 2H), 2.29 (br s, 1H), 2.20-2.15 (m, 1H), 2.10-1.60 (m, 9H), 1.55-1.43 (m, 2H), 1.42-1.35 (m, 1H), 1.13 (d, J=7.1 Hz, 3H), 0.61 (d, J=8.6 Hz, 2H), 0.30-0.25 (m, 1H), 0.15-0.11 (m, 1H). m/z (ESI, +ve ion) 639.2 (M+H)⁺.

EXAMPLE 60

(1S,3'R,6'R,7'S,8'E,11'S,12'R)-6-CHLORO-12'-(CYCLO-PROPYLMETHYL)-7'-HYDROXY-11'-METHYL-3,4-DI-HYDRO-2H,15'H-SPIRO[NAPHTHALENE-1,22'-[20]OXA[13]THIA[1,14]DIAZATETRACYCLO [14.7.2.0³,⁶.0¹⁹,²⁴]PENTACOSA[18,16,18,24]TETRAEN]-15'-ONE 13',13'-DIOXIDE OR (1S,3'R,6'R,7'S,8'E,11'S,12'S)-6-CHLORO-12'-(CYCLOPROPYLMETHYL)-7'-HY-DROXY-11'-METHYL-3,4-DIHYDRO-2H,15'H-SPIRO[NAPHTHALENE-1,22'-[20]OXA[13]THIA [1,14] DIAZATETRACYCLO[14.7.2.0³,⁶.0¹⁹,²⁴]PENTACOSA[8,16,18,24]TETRAEN]-15'-ONE 13',13'-DIOXIDE OR (1S,3'R,6'R,7'S,8'E,11'R,12'R)-6-CHLORO-12'-(CYCLOPRO-PYLMETHYL)-7'-HYDROXY-11'-METHYL-3,4-DIHYDRO-2H,15'H-SPIRO[NAPHTHALENE-1,22'-[20]OXA[13]THIA [1,14] DIAZATETRACYCLO[14.7.2.0³,⁶.0¹⁹,²⁴]PENTACOSA[8,16,18,24]TETRAEN]-15'-ONE 13',13'-DIOXIDE OR (1S,3'R,6'R,7'S,8'E,11'R,12'S)-6-CHLORO-12'-(CYCLOPROPYLMETHYL)-7'-HY-DROXY-11'-METHYL-3,4-DIHYDRO-2H,15'H-SPIRO[NAPHTHALENE-1,22'-[20]OXA[13]THIA [1,14] DIAZATETRACYCLO[14.7.2.0³,⁶.0¹⁹,²⁴]PENTACOSA[8,16,18,24] TETRAEN]-15'-ONE 13',13'-DIOXIDE

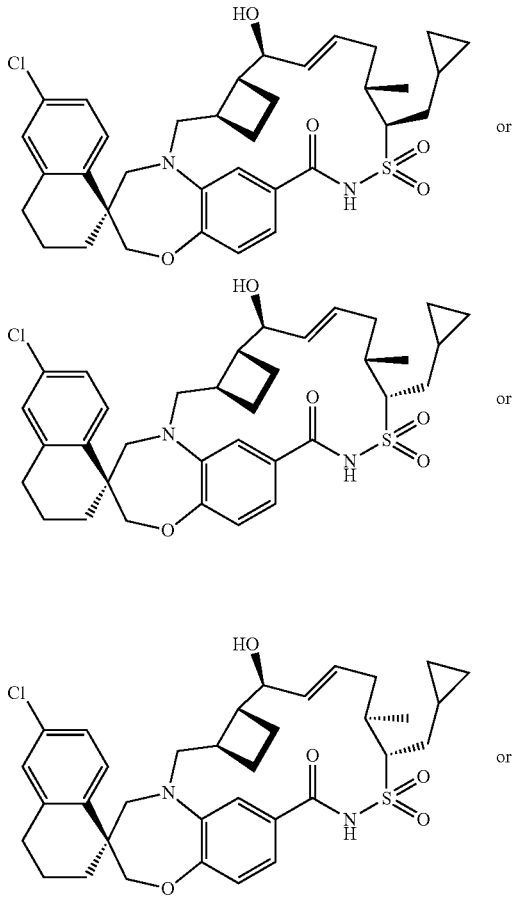

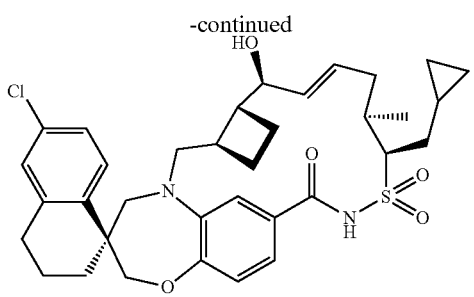

The title compound was obtained as a single isomer (third eluting peak) from the preparative reverse-phase HPLC separation in Example 58. $^1$H NMR (500 MHz, CDCl$_3$) δ ppm 8.19 (br s, 1H), 7.72 (br s, 1H), 7.65 (d, J=8.6 Hz, 1H), 7.17 (dd, J=2.2, 8.6 Hz, 1H), 7.11 (s, 1H), 6.92 (s, 2H), 5.72 (dd, J=3.7, 15.7 Hz, 1H), 5.55 (brs, 1H), 4.27-4.20 (m, 2H), 4.20-4.14 (m, 1H), 4.14-4.10 (m, 1H), 4.00-3.88 (m, 1H), 3.79 (d, J=12.7 Hz, 1H), 3.30 (d, J=13.9 Hz, 1H), 3.10 (d, J=15.7 Hz, 1H), 2.80-2.70 (m, 2H), 2.58-2.39 (m, 2H), 2.35-2.06 (m, 3H), 2.05-1.93 (m, 3H), 1.90-1.62 (m, 4H), 1.70-1.64 (m, 1H), 1.51-1.30 (m, 2H), 1.24-1.15 (m, 1H), 1.11 (d, J=5.1 Hz, 3H), 0.71-0.50 (m, 2H), 0.31 (qd, J=4.8, 9.4 Hz, 1H), 0.15 (qd, J=4.6, 9.3 Hz, 1H). m/z (ESI, +ve ion) 639.2 (M+H)$^+$.

EXAMPLE 61

(1S,3'R,6'R,7'S,8'E,11'S,12'R)-6-CHLORO-12'-(CYCLOPROPYL METHYL)-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[18,16,18,24]TETRAEN]-15'-ONE 13',13'-DIOXIDE OR (1S,3'R,6'R,7'S,8'E,11'S,12'S)-6-CHLORO-12'-(CYCLOPROPYLMETHYL)-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'R)-6-CHLORO-12'-(CYCLOPROPYLMETHYL)-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$] PENTACOSA[8,16,18,24]TETRAEN]-15'-ONE 13',13'-DIOXIDE OR (1S,3'R,6'R,7'S,8'E,11'R,12'S)-6-CHLORO-12'-(CYCLOPROPYLMETHYL)-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$] PENTACOSA[8,16,18,24]TETRAEN]-15'-ONE 13',13'-DIOXIDE OR (1S,3'R,6'R,7'S,8'Z,11'S,12'R)-6-CHLORO-12'-(CYCLOPROPYLMETHYL)-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$] PENTACOSA[8,16,18,24]TETRAEN]-15'-ONE 13',13'-DIOXIDE OR (1S,3'R,6'R,7'S,8'Z,11'S,12'S)-6-CHLORO-12'-(CYCLOPROPYLMETHYL)-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$] PENTACOSA[8,16,18,24]TETRAEN]-15'-ONE 13',13'-DIOXIDE OR (1S,3'R,6'R,7'S,8'Z,11'R,12'R)-6-CHLORO-12'-(CYCLOPROPYLMETHYL)-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$] PENTACOSA[8,16,18,24]TETRAEN]-15'-ONE 13',13'-DIOXIDE OR (1S,3'R,6'R,7'S,8'Z,11'R,12'S)-6-CHLORO-12'-(CYCLOPROPYLMETHYL)-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$] PENTACOSA[8,16,18,24]TETRAEN]-15'-ONE 13',13'-DIOXIDE

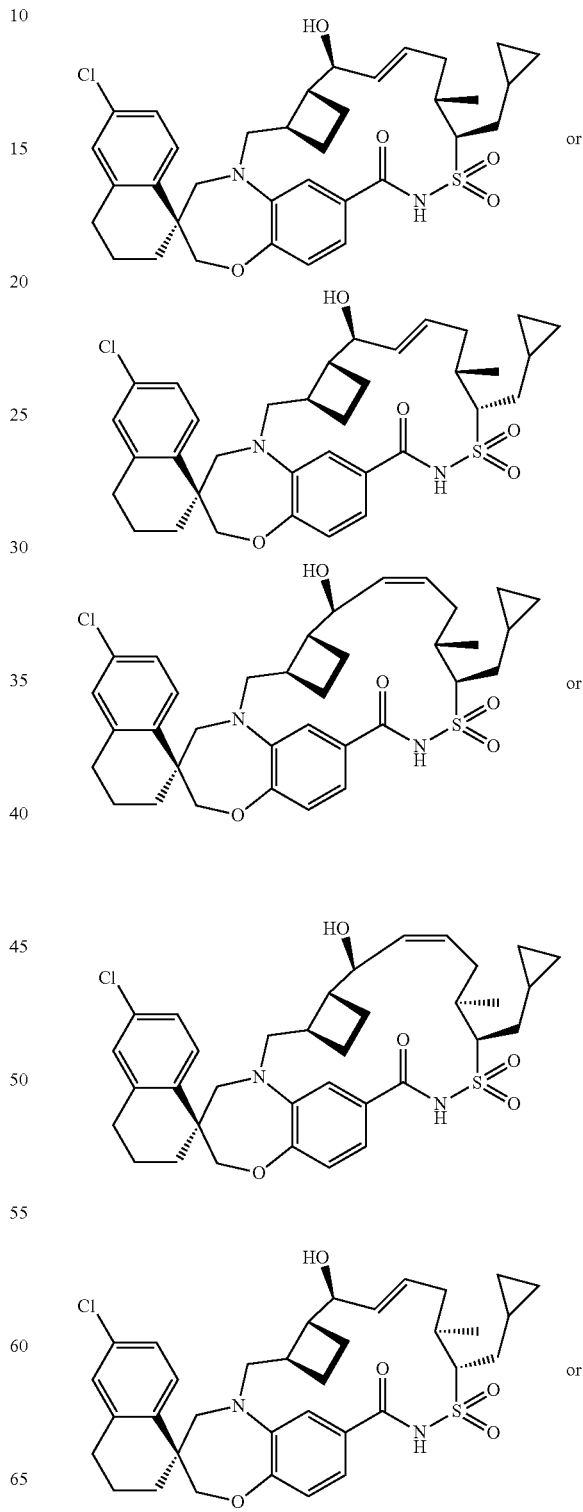

-continued

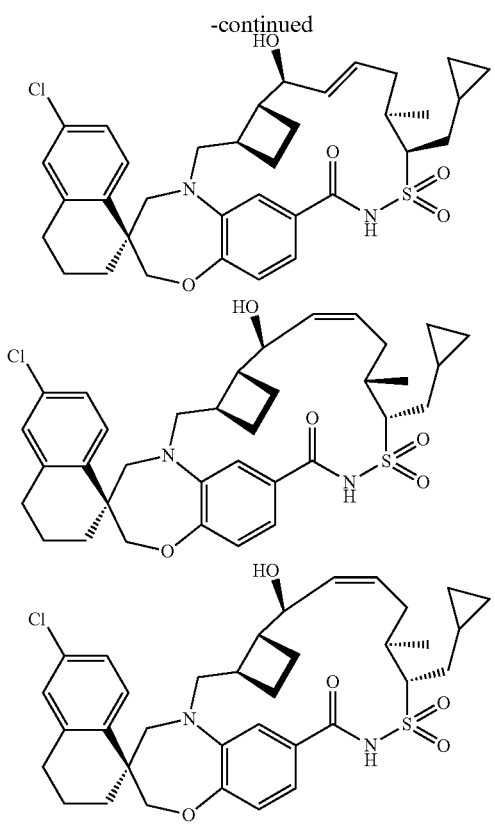

The title compound was obtained as a single isomer (fourth eluting peak) from the preparative reverse-phase HPLC separation in Example 58. $^1$H NMR (500 MHz, CDCl$_3$) δ ppm 7.72 (d, J=11 Hz, 1H), 7.50-7.44 (m, 1H), 7.21-7.16 (m, 1H), 7.15-7.05 (m, 2H), 7.00 (d, J=8.3 Hz, 1H), 5.75 (m, 1H), 5.54 (m, 1H), 4.42 (br s, 1H), 4.16-4.01 (m, 2H), 3.90 (d, J=15.2 Hz, 1H), 3.80-3.60 (m, 2H), 3.25-3.04 (m, 2H), 2.87-2.70 (m, 2H), 2.27-2.10 (m, 3H), 2.09-1.52 (m, 9H), 1.53-1.39 (m, 3H), 1.21-1.14 (m, 1H), 1.08 (d, J=6.8 Hz, 3H), 0.71-0.50 (m, 2H), 0.31-0.20 (m, 1H), 0.16-0.10 (m, 1H). m/z (ESI, +ve ion) 639.2 (M+H)$^+$.

EXAMPLE 62

(1S,3'R,6'R,7'S,8'E,11'S,12'R)-6-CHLORO-12'-(CYCLOPROPYLMETHYL)-7'-METHOXY-11'-METHYL-3,4-DIHYDRO-2H,15'H-SPIRO[NAPHTHALENE-1,22'-[20]OXA[13]THIA[1,14]DIAZATETRACYCLO [14.7.2.0$^{3,6}$.0$^{19,24}$]PENTACOSA[86,18,24]TETRAEN]-15'-ONE 13',13'-DIOXIDE OR (1S,3'R,6'R,7'S,8'E,11'S,12'S)-6-CHLORO-12'-(CYCLOPROPYLMETHYL)-7'-METHOXY-11'-METHYL-3,4-DIHYDRO-2H,15'H-SPIRO[NAPHTHALENE-1,22'-[20]OXA[13]THIA [1,14] DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'R)-6-CHLORO-12'-(CYCLOPROPYLMETHYL)-7'-METHOXY-11'-METHYL-3,4-DIHYDRO-2H,15'H-SPIRO[NAPHTHALENE-1,22'-[20]OXA[13]THIA [1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'S)-6-CHLORO-12'-(CYCLOPROPYLMETHYL)-7'-METHOXY-11'-METHYL-3,4-DIHYDRO-2H,15'H-SPIRO[NAPHTHALENE-1,22'-[20]OXA[13]THIA [1,14] DIAZATETRACYCLO[14.7.2.0$^{3,6}$.0$^{19,24}$]PENTACOSA[8,16,18,24]TETRAEN]-15'-ONE 13',13'-DIOXIDE

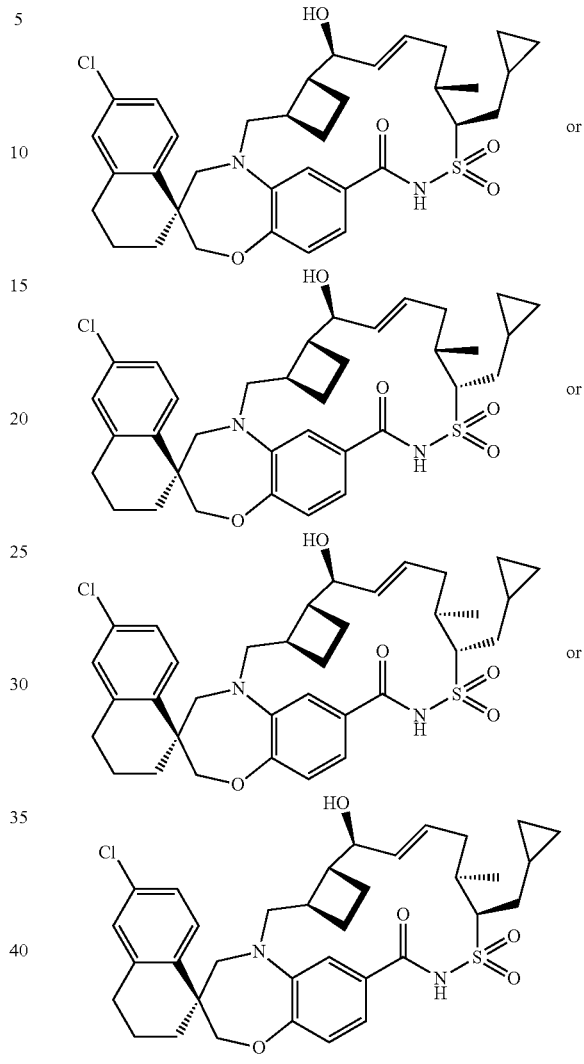

To a 15-mL RBF was added sodium hydride, 60% dispersion in mineral oil (8.3 mg, 0.203 mmol) and (1S,3'R,6'R,7'S,8'E,11'S,12'R)-6-chloro-12'-(cyclopropylmethyl)-7'-hydroxy-11'-methyl-3,4-dihydro-2h,15'h-spiro [naphthalene-1,22'-[20]oxa[13]thia[1,14] diazatetracyclo [14.7.2.0$^{3,6}$.0$^{19,24}$] pentacosa[8,16,18,24]tetraen]-15-one 13',13'-dioxide or (1S,3'R,6'R,7'S,8'E,11'S,12'S)-6-chloro-12'-(cyclopropylmethyl)-7'-hydroxy-11'-methyl-3,4-dihydro-2h,15'h-spiro[naphthalene-1,22'-[20]oxa[13]thia[1,14]diazatetracyclo[14.7.2.0$^{3,6}$.0$^{19,24}$] pentacosa[8,16,18,24]tetraen]-15'-one 13',13'-dioxide or (1S,3'R,6'R,7'S,8'E,11'R,12'R)-6-chloro-12'-(cyclopropylmethyl)-7'-hydroxy-11'-methyl-3,4-dihydro-2h,15'h-spiro[naphthalene-1,22'-[20] oxa[13]thia[1,14]diazatetracyclo[14.7.2.0$^{3,6}$.0$^{19,24}$] pentacosa[8,16,18,24]tetraen]-15'-one 13',13'-dioxide or (1S,3'R,6'R,7'S,8'E,11'R,12'S)-6-chloro-12'-(cyclopropylmethyl)-7'-hydroxy-11'-methyl-3,4-dihydro-2h,15'h-spiro [naphthalene-1,22'-[20]oxa[13]thia[1,14] diazatetracyclo [14.7.2.0$^{3,6}$.0$^{19,24}$]pentacosa[8,16,18,24]tetraen]-15'-one 13',13'-dioxide (13 mg, 0.020 mmol) in THF (1 mL) at 0° C. The reaction mixture was stirred at 0° C. for 30 min and MeI (6.32 μl, 0.102 mmol) was added. The mixture was stirred and allowed to warm from 0° C. to ambient temperature for 18 h, quenched with aqueous 1.0 N HCl, and extracted with EtOAc. The organic layer was dried (MgSO$_4$) and concentrated. The residue was chromatographed (SiO$_2$ gel, 10-40%, EtOAc+10% methanol/hexane) to afford the title compound as a white solid. $^1$H NMR (400 MHz, CDCl$_3$) δ ppm 8.08 (s, 1H), 7.70 (d, J=8.4 Hz, 1H), 7.19 (dd, J=2.2, 8.5 Hz, 1H), 7.10 (d, J=2.2 Hz, 1H), 6.96-6.90 (m, 3H), 5.90-5.70 (m, 1H), 5.53 (dd, J=9.8, 14.5 Hz, 1H), 4.32 (dd, J=4.7, 7.0 Hz, 1H), 4.10 (s, 2H), 3.83 (d, J=15.1 Hz, 1H), 3.74-3.66 (m, 2H), 3.28-3.20 (m, 4H), 3.02 (dd, J=10.2, 15.3 Hz, 1H), 2.84-2.71 (m, 2H), 2.51-2.43 (m, 1H), 2.39-2.18 (m, 3H), 2.14-1.92 (m, 4H), 1.90-1.75 (m, 3H), 1.65-1.50 (m, 2H), 1.47-1.35 (m, 2H), 1.25-1.18 (m, 1H), 1.05 (d, J=6.8 Hz, 3H), 0.67-0.58 (m, 2H), 0.34-0.26 (m, 1H), 0.12-0.04 (m, 1H). m/z (ESI, +ve ion) 653.2 (M+H)$^+$.

EXAMPLE 63

(1S,3'R,6'R,7'S,8'E,11'R,12'S)-6-CHLORO-12'-(CYCLOBUTYLMETHYL)-7'-HYDROXY-11'-METHYL-3,4-DIHYDRO-2H,15'H-SPIRO[NAPHTHALENE-1,22'-[20]OXA[13]THIA[1,14] DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'S,12'R)-6-CHLORO-12'-(CYCLOBUTYLMETHYL)-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$] PENTACOSA[8,16,18,24]TETRAEN]-15'-ONE 13',13'-DIOXIDE OR (1S,3'R,6'R,7'S,8'E,11'R,12'R)-6-CHLORO-12'-(CYCLOBUTYLMETHYL)-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$] PENTACOSA[8,16,18,24]TETRAEN]-15'-ONE 13',13'-DIOXIDE OR (1S,3'R,6'R,7'S,8'E,11'S,12'S)-6-CHLORO-12'-(CYCLOBUTYLMETHYL)-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$] PENTACOSA[8,16,18,24]TETRAEN]-15'-ONE 13',13'-DIOXIDE

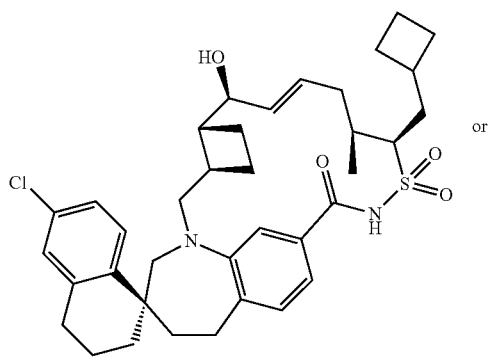

or

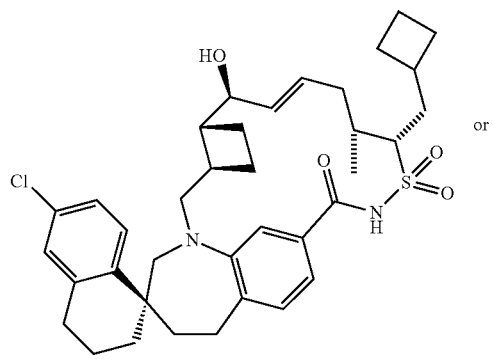

or

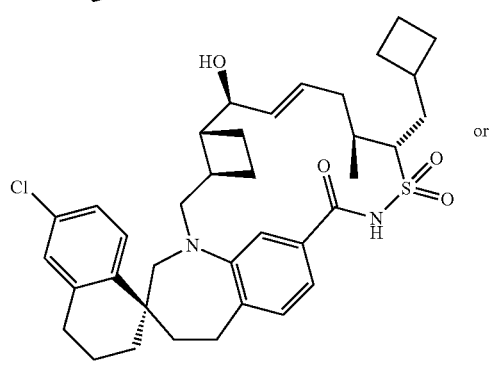

or

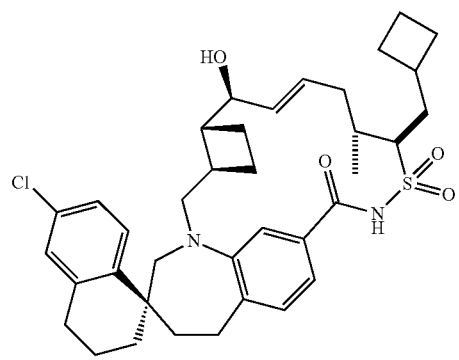

STEP 1

(2R,3R)-1-CYCLOBUTYL-3-METHYLHEX-5-ENE-2-SULFONAMIDE AND (2S,3S)-1-CYCLOBUTYL-3-METHYLHEX-5-ENE-2-SULFONAMIDE AND (2R,3S)-1-CYCLOBUTYL-3-METHYLHEX-5-ENE-2-SULFONAMIDE AND (2S,3R)-1-CYCLOBUTYL-3-METHYLHEX-5-ENE-2-SULFONAMIDE

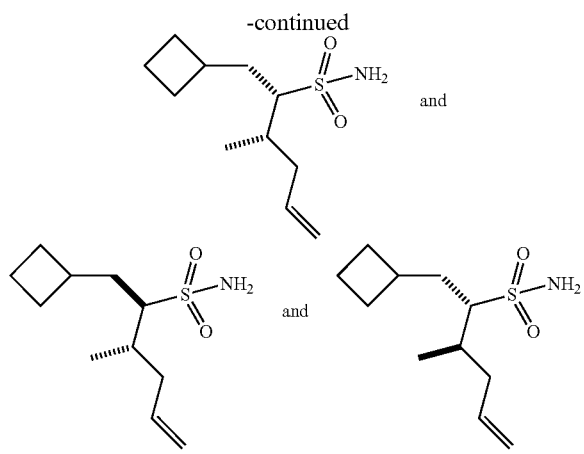

The title compound was prepared from (R)—N,N-bis(4-methoxybenzyl)-2-methylpent-4-ene-1-sulfonamide and (S)—N,N-bis(4-methoxybenzyl)-2-methylpent-4-ene-1-sulfonamide and (bromomethyl)cyclobutane by a procedure analogous to that described in Example 58, Steps 2 through 3.

STEP 2

(1S,3'R,6'R,7'S,8'E,11'R,12'S)-6-CHLORO-12'-(CYCLOBUTYLMETHYL)-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'S,12'R)-6-CHLORO-12'-(CYCLOBUTYLMETHYL)-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$] PENTACOSA[8,16,18,24]TETRAEN]-15'-ONE 13',13'-DIOXIDE OR (1S,3'R,6'R,7'S,8'E,11'R,12'R)-6-CHLORO-12'-(CYCLOBUTYLMETHYL)-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$] PENTACOSA[8,16,18,24]TETRAEN]-15'-ONE 13',13'-DIOXIDE OR (1S,3'R,6'R,7'S,8'E,11'S,12'S)-6-CHLORO-12'-(CYCLOBUTYLMETHYL)-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19-24}$] PENTACOSA[8,16,18,24]TETRAEN]-15'-ONE 13',13'-DIOXIDE

The title compound was prepared from (S)-6'-chloro-5-(((1R,2R)-2-((S,E)-1-hydroxyhex-2-en-1-v)cyclobutyl)methyl)-3',4,4',5-tetrahydro-2H,2'H-spiro[benzo[b][1,4]oxazepine-3,1'-naphthalene]-7-carboxylic acid (Intermediate AA12) and a mixture of (2R,3R)-1-cyclobutyl-3-methylhex-5-ene-2-sulfonamide, (2S,3S)-1-cyclobutyl-3-methylhex-5-ene-2-sulfonamide, (2R,3S)-1-cyclobutyl-3-methylhex-5-ene-2-sulfonamide, and (2S,3R)-1-cyclobutyl-3-methylhex-5-ene-2-sulfonamide (from Step 1) by a procedure analogous to that described in Example 58, Steps 4 through 5. The residue was purified by preparative reverse-phase HPLC (Gemini™ Prep Cia 5 μm column; gradient elution of 50% to 95% MeCN in H$_2$O, where both solvents contain 0.1% TFA, 30 min method) to provide one of the title compounds as the faster eluting isomer as a white foam. $^1$H NMR (400 MHz, CD$_2$Cl$_2$) δ ppm 8.09 (s, 1H), 7.70 (d, J=8.4 Hz, 1H), 7.16 (dd, J=2.2, 8.5 Hz, 1H), 7.09 (d, J=2.2 Hz, 1H), 6.95-6.88 (m, 3H), 5.82-5.68 (m, 2H), 4.19 (dd, J=4.1, 7.6 Hz, 1H), 4.08 (s, 2H), 3.93 (dd, J=2.5, 8.8 Hz, 1H), 3.82 (m, 1H), 3.68 (d, J=14.3 Hz, 1H), 3.25 (d, J=14.3 Hz, 1H), 3.05 (dd, J=9.4, 15.3 Hz, 1H), 2.83-2.68 (m, 3H), 2.41 (m, 1H), 2.31 (m, 1H), 2.23-2.10 (m, 4H), 2.08-2.00 (m, 2H), 1.98-1.52 (m, 12H), 1.48-1.33 (m, 1H), 1.01 (d, J=6.8 Hz, 3H); m/z (ESI, +ve ion) 653 (M+H)$^+$.

EXAMPLE 64

(1S,3'R,6'R,7'S,8'E,11'R,12'S)-6-CHLORO-12'-(CYCLOBUTYLMETHYL)-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'S,12'R)-6-CHLORO-12'-(CYCLOBUTYLMETHYL)-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$] PENTACOSA[8,16,18,24]TETRAEN]-15'-ONE 13',13'-DIOXIDE OR (1S,3'R,6'R,7'S,8'E,11'R,12'R)-6-CHLORO-12'-(CYCLOBUTYLMETHYL)-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$] PENTACOSA[8,16,18,24]TETRAEN]-15'-ONE 13',13'-DIOXIDE OR (1S,3'R,6'R,7'S,8'E,11'S,12'S)-6-CHLORO-12'-(CYCLOBUTYLMETHYL)-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$] PENTACOSA[8,16,18,24]TETRAEN]-15'-ONE 13',13'-DIOXIDE

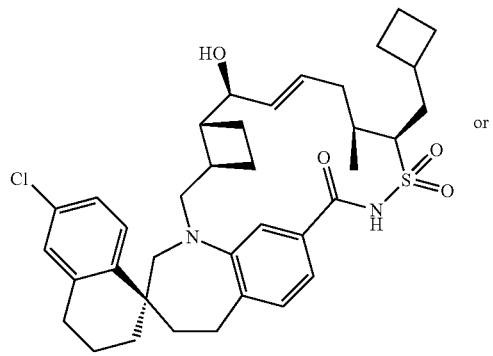

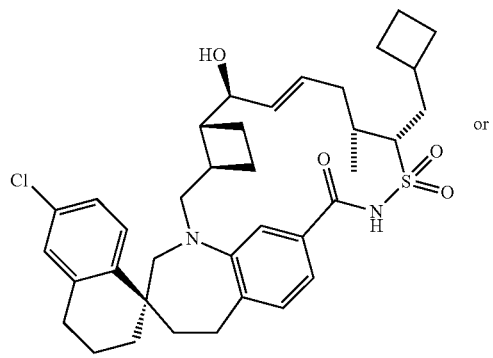

-continued

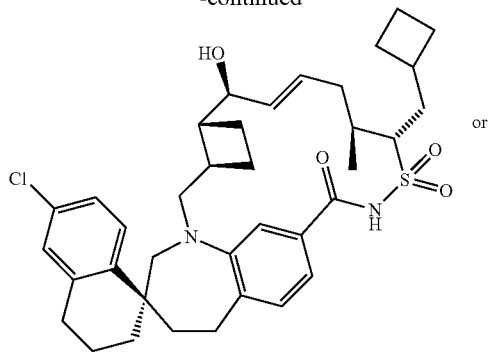

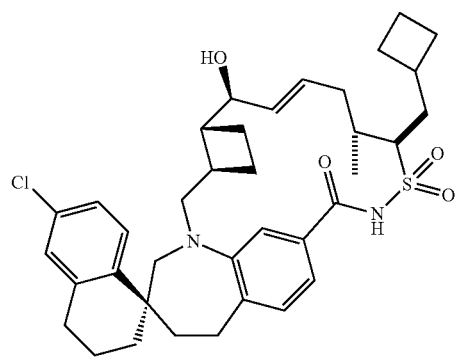

One of the title compounds was obtained as the second (slower) eluting isomer using preparative reverse-phase HPLC as described in Example 63. ¹H NMR (400 MHz, CD$_2$Cl$_2$) δ ppm 8.05 (s, J=7.4, 7.4 Hz, 1H), 7.70 (d, J=8.4 Hz, 1H), 7.17 (dd, J=2.2, 8.5 Hz, 1H), 7.14-7.08 (m, 2H), 6.97-6.90 (m, 1H), 6.65 (m, 1H), 6.00 (m, 1H), 5.65 (dd, J=6.1, 15.1 Hz, 1H), 4.19-4.02 (m, 3H), 3.76 (m, 1H), 3.61 (m, 1H), 3.52 (m, 1H), 3.43 (d, J=14.5 Hz, 1H), 3.24 (m, 1H), 2.83-2.73 (m, 2H), 2.73-2.62 (m, 1H), 2.55-2.46 (m, 1H), 2.35-2.10 (m, 5H), 2.08-1.96 (m, 3H), 1.95-1.81 (m, 6H), 1.79-1.65 (m, 5H), 1.47 (d, J=15.3 Hz, 1H), 1.16-1.07 (m, 3H); m/z (ESI, +ve ion) 653 (M+H)⁺.

EXAMPLE 65

(1S,3'R,6'R,7'S,8'E,11'S,12'R)-6-CHLORO-7'-HYDROXY-11'-METHYL-12'-(2-METHYLPROPYL)-3,4-DIHYDRO-2H,15'H-SPIRO[NAPHTHALENE-1,22'-[20]OXA[13]THIA[1,14] DIAZATETRACYCLO[14.7.2.0$^{3,6}$.0$^{19,24}$] PENTACOSA[8,16,18,24]TETRAEN]-15'-ONE 13',13'-DIOXIDE OR (1S,3'R,6'R,7'S,8'E,11'R,12'S)-6-CHLORO-7'-HYDROXY-11'-METHYL-12'-(2-METHYLPROPYL)-3,4-DIHYDRO-2H,15'H-SPIRO[NAPHTHALENE-1,22'-[20]OXA[13]THIA[1,14] DIAZATETRACYCLO [14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'S,12'S)-6-CHLORO-7'-HYDROXY-11'-METHYL-12'-(2-METHYLPROPYL)-3,4-DIHYDRO-2H,15'H-SPIRO [NAPHTHALENE-1,22'-[20]OXA[13]THIA[1,14] DIAZATETRACYCLO[14.7.2.0$^{3,6}$.0$^{19,24}$] PENTACOSA [8,16,18,24]TETRAEN]-15'-ONE 13',13'-DIOXIDE OR (1S,3'R,6'R,7'S,8'E,11'R,12'R)-6-CHLORO-7'-HYDROXY-11'-METHYL-12'-(2-METHYLPROPYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$] PENTACOSA[8,16,18,24]TETRAEN]-15'-ONE 13',13'-DIOXIDE

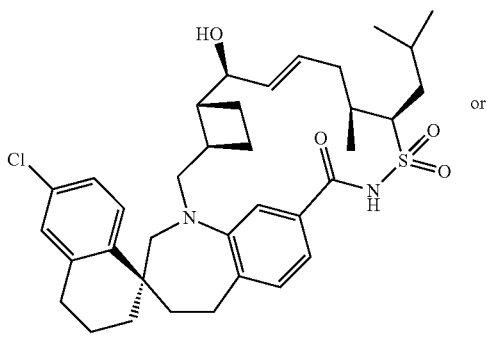

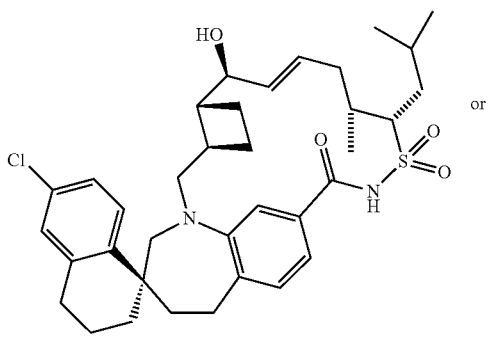

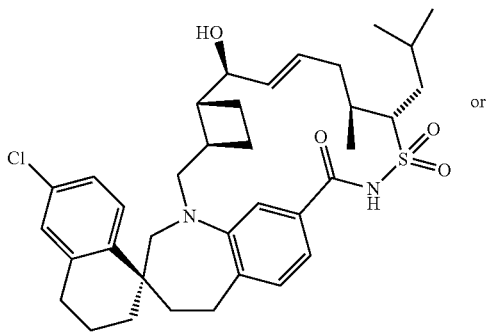

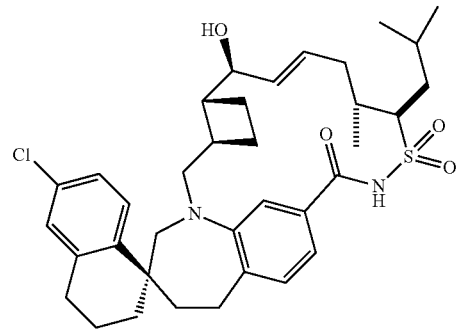

STEP 1: (4R,5R)-2,5-DIMETHYLOCT-7-ENE-4-SULFONAMIDE AND (4S,5S)-2,5-DIMETHYLOCT-7-ENE-4-SULFONAMIDE AND (4R,5S)-2,5-DIMETHYLOCT-7-ENE-4-SULFONAMIDE AND (4S,5R)-2,5-DIMETHYLOCT-7-ENE-4-SULFONAMIDE

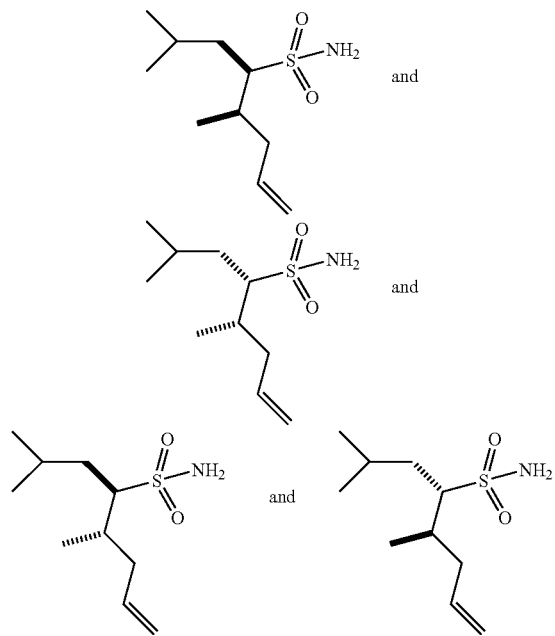

The title compound was prepared from (R)—N,N-bis(4-methoxybenzyl)-2-methylpent-4-ene-1-sulfonamide and (S)—N,N-bis(4-methoxybenzyl)-2-methylpent-4-ene-1-sulfonamide (Example 58, Step 1) and isobutyl bromide by a procedure analogous to that described in Example 58, Steps 2 through 3.

STEP 2

(1S,3'R,6'R,7'S,8'E,11'S,12'R)-6-CHLORO-7'-HYDROXY-11'-METHYL-12'-(2-METHYLPROPYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'S)-6-CHLORO-7'-HYDROXY-11'-METHYL-12'-(2-METHYLPROPYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E, 11'S, 12'S)-6-CHLORO-7'-HYDROXY-11'-METHYL-12'-(2-METHYLPROPYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$] PENTACOSA[8,16,18,24]TETRAEN]-15'-ONE 13',13'-DIOXIDE OR (1S,3'R,6'R,7'S,8'E,11'R,12'R)-6-CHLORO-7'-HYDROXY-11'-METHYL-12'-(2-METHYLPROPYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

The title compound was prepared from (S)-6'-chloro-5-(((1R,2R)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12) and a mixture of (4R,5R)-2,5-dimethyloct-7-ene-4-sulfonamide, (4S,5S)-2,5-dimethyloct-7-ene-4-sulfonamide, (4R,5S)-2,5-dimethyloct-7-ene-4-sulfonamide, and (4S,5R)-2,5-dimethyloct-7-ene-4-sulfonamide (from Step 1) by a procedure analogous to that described in Example 58, Steps 4 through 5. The residue was purified by preparative reverse-phase HPLC (Gemini™ Prep C$_{18}$ 5 μm column; gradient elution of 50% to 95% MeCN in H$_2$O, where both solvents contain 0.1% TFA, 30 min method) to provide one of the title compounds as the faster eluting isomer as a white foam. $^1$H NMR (400 MHz, CD$_2$Cl$_2$) δ ppm 8.09 (s, 1H), 7.71 (d, J=8.5 Hz, 1H), 7.17 (dd, J=2.3, 8.6 Hz, 1H), 7.09 (d, J=2.3 Hz, 1H), 6.96-6.90 (m, 3H), 5.86-5.78 (m, 1H), 5.76-5.68 (m, 1H), 4.22-4.12 (m, 2H), 4.09 (s, 2H), 3.84 (m, 1H), 3.69 (d, J=14.3 Hz, 1H), 3.26 (d, J=14.3 Hz, 1H), 3.05 (dd, J=9.4, 15.3 Hz, 1H), 2.83-2.70 (m, 2H), 2.46-2.28 (m, 2H), 2.18-1.91 (m, 8H), 1.88-1.76 (m, 3H), 1.76-1.66 (m, 1H), 1.46-1.31 (m, 2H), 1.04-0.98 (m, 9H); m/z (ESI, +ve ion) 641 (M+H)$^+$.

EXAMPLE 66

(1S,3'R,6'R,7'S,8'E,11'S,12'R)-6-CHLORO-7'-HYDROXY-11'-METHYL-12'-(2-METHYLPROPYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'S)-6-CHLORO-7'-HYDROXY-11'-METHYL-12'-(2-METHYLPROPYL)-3,4-DIHYDRO-2H,15'H-SPIRO[NAPHTHALENE-1,22'-[20]OXA[13]THIA[1,14]DIAZATETRACYCLO [14.7.2.0$^{3,6}$.0$^{19,24}$] PENTACOSA[8,16,18,24]TETRAEN]-15'-ONE 13',13'-DIOXIDE OR (1S,3'R,6'R,7'S,8'E,11'S,12'S)-6-CHLORO-7'-HYDROXY-11'-METHYL-12'-(2-METHYLPROPYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'R)-6-CHLORO-7'-HYDROXY-11'-METHYL-12'-(2-METHYLPROPYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$] PENTACOSA[8,16,18,24]TETRAEN]-15'-ONE 13',13'-DIOXIDE

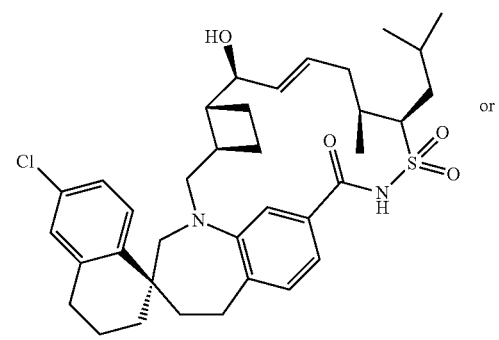

203

-continued

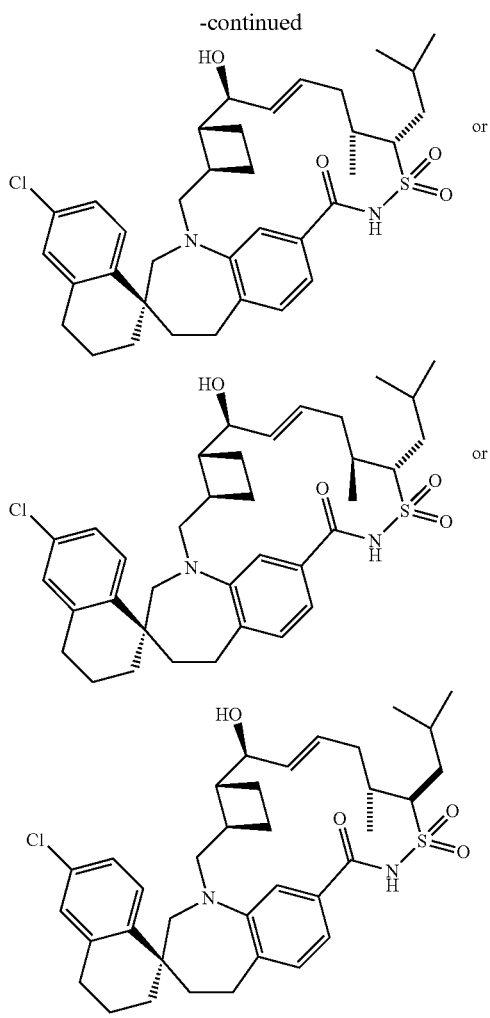

One of the title compounds was obtained as a single isomer (second, slower, eluting peak) using preparative reverse-phase HPLC as described in Example 65. $^1$H NMR (400 MHz, $CD_2Cl_2$) δ ppm 8.11-8.04 (m, 1H), 7.71 (d, J=8.4 Hz, 1H), 7.18 (dd, J=2.2, 8.4 Hz, 1H), 7.15-7.09 (m, 2H), 6.97-6.90 (m, 1H), 6.65 (m, 1H), 6.04 (m, 1H), 5.65 (dd, J=6.4, 15.4 Hz, 1H), 4.17 (m, 1H), 4.07 (q, J=12.2 Hz, 2H), 3.81-3.69 (m, 2H), 3.63 (m, 1H), 3.43 (d, J=14.3 Hz, 1H), 3.24 (m, 1H), 2.82-2.71 (m, 2H), 2.56-2.48 (m, 1H), 2.29-2.18 (m, 1H), 2.07-1.82 (m, 9H), 1.81-1.65 (m, 2H), 1.51-1.38 (m, 3H), 1.09 (d, J=7.0 Hz 3H), 1.05-0.93 (m, 6H); m/z (ESI, +ve ion) 641 (M+H)+.

EXAMPLE 67

(1S,3'R,6'R,7'S,8'E,11'S,12'R)-6-CHLORO-7'-HYDROXY-11'-METHYL-12'-(2-METHYLPROPYL)-3,4-DIHYDRO-2H,15'H-SPIRO[NAPHTHALENE-1,22'-[20]OXA[13]THIA[1,14] DIAZATETRACYCLO[14.7.2.0$^{3,6}$.0$^{19,24}$] PENTACOSA[8,16,18,24]TETRAEN]-15'-ONE 13',13'-DIOXIDE OR (1S,3'R,6'R,7'S,8'E,11'R,12'S)-6-CHLORO-7'-HYDROXY-11'-METHYL-12'-(2-METHYLPROPYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'S,12'S)-6-CHLORO-7'-HYDROXY-11'-METHYL-12'-(2-

204

METHYLPROPYL)-3,4-DIHYDRO-2H,15'H-SPIRO[NAPHTHALENE-1,22'-[20]OXA[13]THIA[1,14] DIAZATETRACYCLO[14.7.2.0$^{3,6}$.0$^{19,24}$] PENTACOSA[8,16,18,24]TETRAEN]-15'-ONE 13',13'-DIOXIDE OR (1S,3'R,6'R,7'S,8'E,11'R,12'R)-6-CHLORO-7'-HYDROXY-11'-METHYL-12'-(2-METHYLPROPYL)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$] PENTACOSA[8,16,18,24]TETRAEN]-15'-ONE 13',13'-DIOXIDE

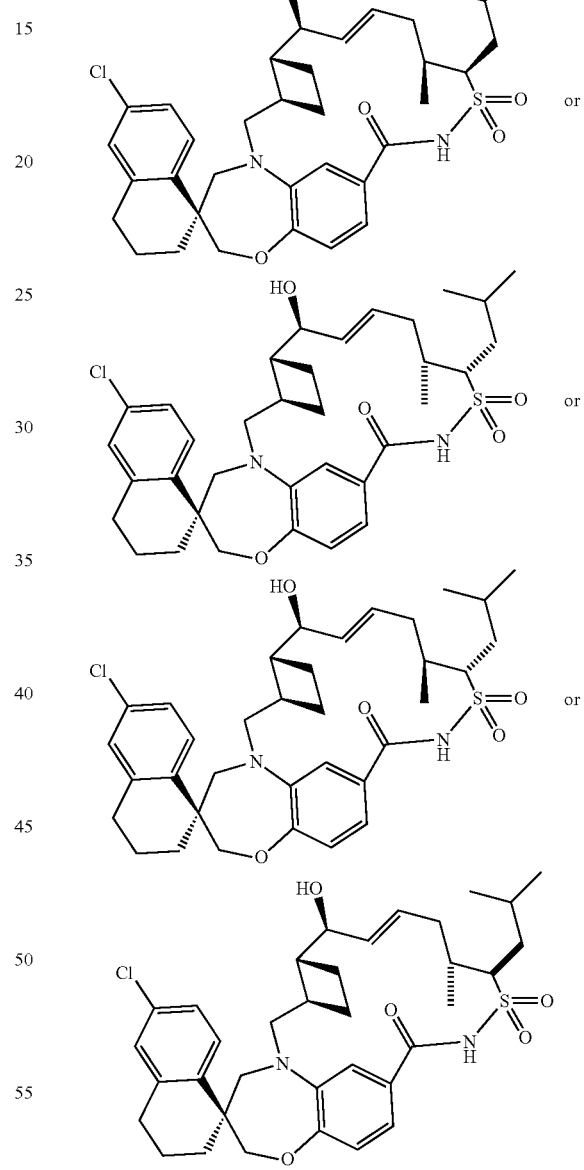

One of the title compounds was obtained as single isomer (third eluting peak) using preparative reverse-phase HPLC as described in Example 65. $^1$H NMR (400 MHz, $CD_2Cl_2$) δ ppm 8.17 (br. s., 1H), 7.74 (d, J=8.6 Hz, 1H), 7.66 (d, J=8.8 Hz, 1H), 7.16 (s, 1H), 7.10 (d, J=3.1 Hz, 1H), 6.98 (d, J=8.2 Hz, 1H), 6.91 (s, 1H), 5.73-5.66 (m, 2H), 4.43 (br. s., 1H), 4.23 (s, 2H), 4.15-4.04 (m, 4H), 3.90 (d, J=15.1 Hz, 1H), 3.70 (d, J=14.3 Hz, 1H), 3.33 (d, J=12.9 Hz, 1H), 3.22 (d, J=14.5 Hz, 1H), 3.11 (d, J=15.1 Hz, 2H), 2.75 (d, J=5.7 Hz, 3H), 2.51 (d, J=6.5 Hz, 1H), 2.07-1.88 (m, 10H), 1.06-1.00 (m, 9H) m/z (ESI, +ve ion) 641 (M+H)+.

EXAMPLE 68

(1S,3'R,6'R,7'S,8'E,11'S,12'R)-6-CHLORO-7'-HYDROXY-11'-METHYL-12'-PROPYL-3,4-DIHYDRO-2H,15'H-SPIRO[NAPHTHALENE-1,22'-[20]OXA[13]THIA [1,14] DIAZATETRACYCLO[14.7.2.0³,⁶.0¹⁹,²⁴] PENTACOSA [8,16,18,24]TETRAEN]-15'-ONE 13',13'-DIOXIDE OR (1S,3'R,6'R,7'S,8'E,11'R,12'R)-6-CHLORO-7'-HYDROXY-11'-METHYL-12'-PROPYL-3,4-DIHYDRO-2H,15'H-SPIRO[NAPHTHALENE-1,22'-[20]OXA[13]THIA[1,14] DIAZATETRACYCLO [14.7.2.0³,⁶.0¹⁹,²⁴]PENTACOSA [8,16,18,24]TETRAEN]-15'-ONE 13',13'-DIOXIDE OR (1S,3'R,6'R,7'S,8'E,11'S,12'S)-6-CHLORO-7'-HYDROXY-11'-METHYL-12'-PROPYL-3,4-DIHYDRO-2H,15'H-SPIRO[NAPHTHALENE-1,22'-[20]OXA[13]THIA[1,14] DIAZATETRACYCLO [14.7.2.0³,⁶.0¹⁹,²⁴]PENTACOSA [8,16,18,24]TETRAEN]-15'-ONE 13',13'-DIOXIDE OR (1S,3'R,6'R,7'S,8'E,11'R,12'S)-6-CHLORO-7'-HYDROXY-11'-METHYL-12'-PROPYL-3,4-DIHYDRO-2H,15'H-SPIRO[NAPHTHALENE-1,22'-[20]OXA[13]THIA[1,14] DIAZATETRACYCLO [14.7.2.0³,⁶.0¹⁹,²⁴]PENTACOSA [8,16,18,24]TETRAEN]-15'-ONE 13',13'-DIOXIDE

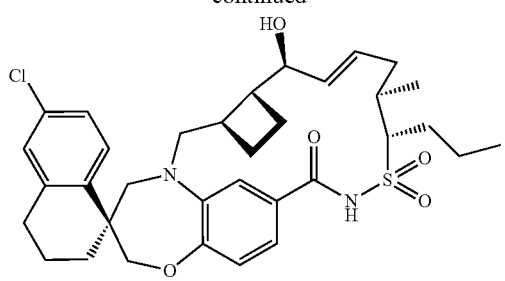

or

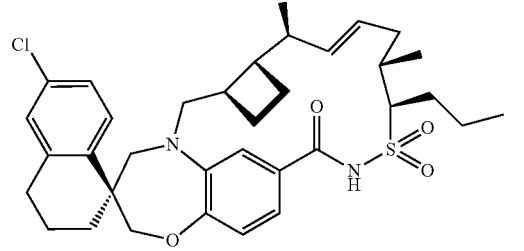

or

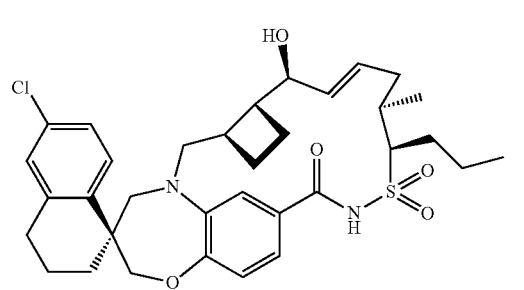

or

STEP 1

(4R,5S)—N,N-BIS(4-METHOXYBENZYL)-5-METHYL-7-OCTENE-4-SULFONAMIDE AND (4S,5S)—N,N-BIS(4-METHOXYBENZYL)-5-METHYL-7-OCTENE-4-SULFONAMIDE AND (4S,5R)—N,N-BIS(4-METHOXYBENZYL)-5-METHYL-7-OCTENE-4-SULFONAMIDE AND (4R,5R)—N,N-BIS(4-METHOXYBENZYL)-5-METHYL-7-OCTENE-4-SULFONAMIDE AND

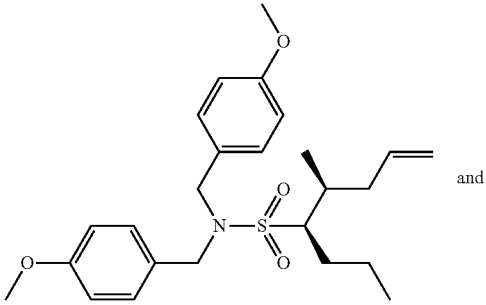

and

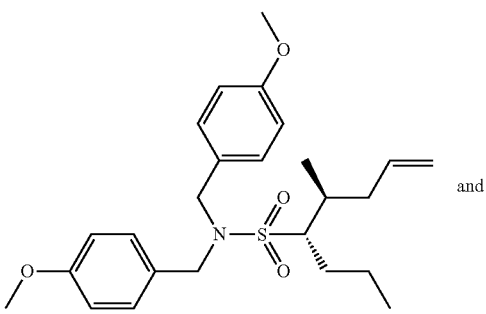

and

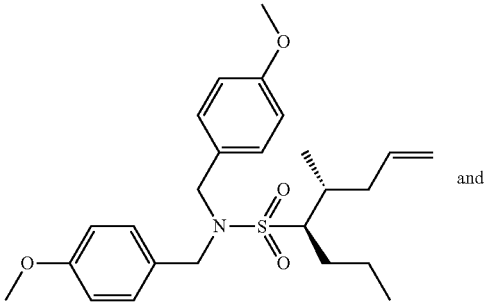

and

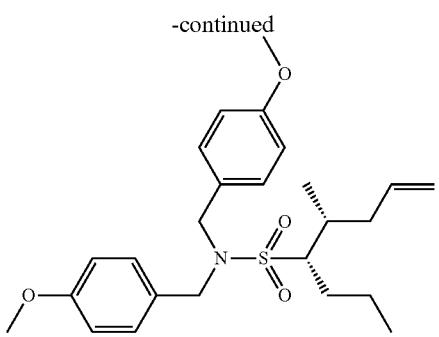

The title compounds were prepared from (2S)—N, N-bis (4-methoxybenzyl)-2-methylpent-4-ene-1-sulfonamide and (2R)—N, N-bis(4-methoxybenzyl)-2-methylpent-4-ene-1-sulfonamide (from Example 58, Step 1) with 1-bromopropane, following a similar procedure described in Example 58, Step 2.

STEP 2: (4R,5S)-5-METHYL-7-OCTENE-4-SULFONAMIDE AND (4R,5R)-5-METHYL-7-OCTENE-4-SULFONAMIDE AND (4S,5S)-5-METHYL-7-OCTENE-4-SULFONAMIDE AND (4S,5R)-5-METHYL-7-OCTENE-4-SULFONAMIDE

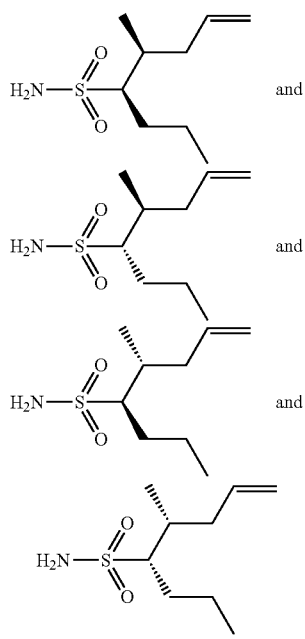

The title compounds was prepared from a mixture of (4R,5S)—N,N-bis(4-methoxybenzyl)-5-methyl-7-octene-4-sulfonamide, (4S,5S)—N,N-bis(4-methoxybenzyl)-5-methyl-7-octene-4-sulfonamide, (4S,5R)—N,N-bis(4-methoxybenzyl)-5-methyl-7-octene-4-sulfonamide and (4R,5R)—N,N-bis(4-methoxybenzyl)-5-methyl-7-octene-4-sulfonamide by a similar procedure described in Example 58, Step 3.

STEP 3

(3S)-6'-CHLORO-5-(((1R,2R)-2-((1S,2E,5R,6S)-1-HYDROXY-5-METHYL-6-SULFAMOYL-2-NONEN-1-YL) CYCLOBUTYL)METHYL)-3',4,4',5-TETRAHYDRO-2'H-SPIRO[1,5-BENZOXAZEPINE-3,1'-NAPHTHALENE]-7-CARBOXYLIC ACID AND (3S)-6'-CHLORO-5-(((1R,2R)-2-((1S,2E,5R,6R)-1-HYDROXY-5-METHYL-6-SULFAMOYL-2-NONEN-1-YL) CYCLOBUTYL)METHYL)-3',4,4',5-TETRAHYDRO-2'H-SPIRO[1,5-BENZOXAZEPINE-3,1'-NAPHTHALENE]-7-CARBOXYLIC ACID AND (3S)-6'-CHLORO-5-(((1R,2R)-2-((1S,2E,5S,6S)-1-HYDROXY-5-METHYL-6-SULFAMOYL-2-NONEN-1-YL) CYCLOBUTYL)METHYL)-3',4,4',5-TETRAHYDRO-2'H-SPIRO[1,5-BENZOXAZEPINE-3,1'-NAPHTHALENE]-7-CARBOXYLIC ACID AND (3S)-6'-CHLORO-5-(((1R,2R)-2-((1S,2E,5S,6R)-1-HYDROXY-5-METHYL-6-SULFAMOYL-2-NONEN-1-YL) CYCLOBUTYL)METHYL)-3',4,4',5-TETRAHYDRO-2'H-SPIRO[1,5-BENZOXAZEPINE-3,1'-NAPHTHALENE]-7-CARBOXYLIC ACID

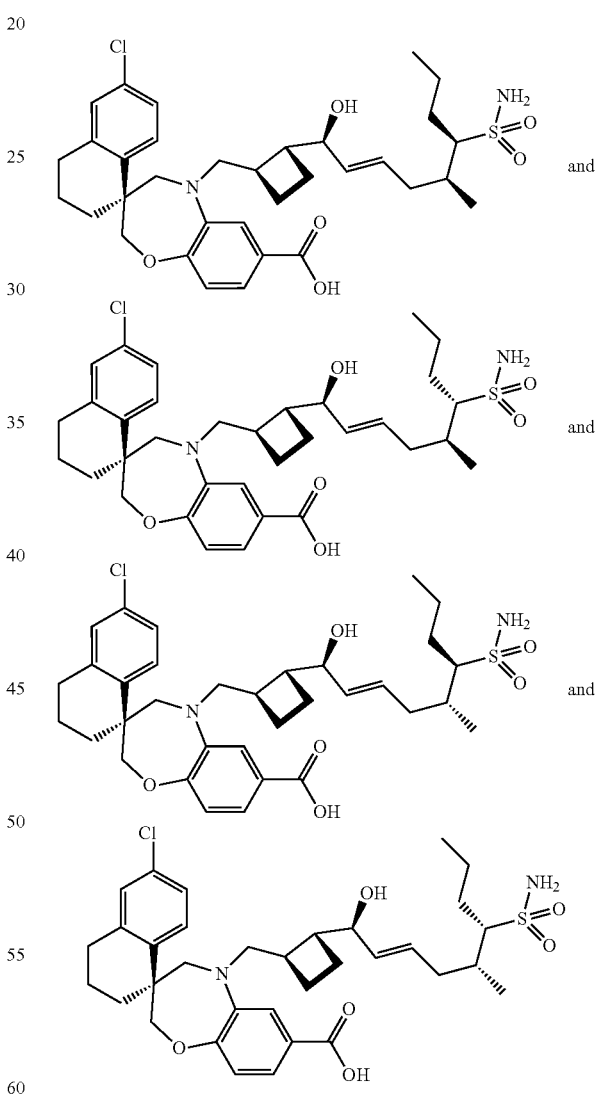

A mixture of (S)-6'-chloro-5-(((1R,2S)-2-((S,E)-1-hydroxyhex-2-en-1-yl)cyclobutyl) methyl)-3',4,4',5-tetrahydro-2H,2'H-spiro[benzo[b][1,4]oxazepine-3,1'-naphthalene]-7-carboxylic acid (Intermediate AA12A, 120 mg, 0.24 mmol), a mixture of (4R,5S)-5-methyl-7-octene-4-sulfonamide, (4R,5R)-5-methyl-7-octene-4-sulfonamide, (4S,5S)-

5-methyl-7-octene-4-sulfonamide, and (4S,5R)-5-methyl-7-octene-4-sulfonamide (from Step 2,121 mg; 0.59 mmol) in 1,2 dichloroethane (2 mL) was introduced to argon by bubbling argon into the reaction flask for 20 min. Hoveyda-Grubbs II was then added. The mixture was stirred at ambient temperature for 2 h, concentrated, and the residue was chromatographed (SiO$_2$ gel, 9:1 to 0:1, hexane/0.3% AcOH+EtOAc) to afford a grey oil as the title compounds.

STEP 4

(1S,3'R,6'R,7'S,8'E,11'S,12'R)-6-CHLORO-7'-HYDROXY-11'-METHYL-12'-PROPYL-3,4-DIHYDRO-2H,15'H-SPIRO[NAPHTHALENE-1,22'-[20]OXA[13]THIA [1,14] DIAZATETRACYCLO[14.7.2.0$^{3,6}$.0$^{19,24}$] PENTACOSA [8,16,18,24]TETRAEN]-15'-ONE 13',13'-DIOXIDE OR (1S,3'R,6'R,7'S,8'E,11'R,12'R)-6-CHLORO-7'-HYDROXY-11'-METHYL-12'-PROPYL-3,4-DIHYDRO-2H,15'H-SPIRO[NAPHTHALENE-1,22'-[20]OXA[13]THIA[1,14] DIAZATETRACYCLO [14.7.2.0$^{3,6}$.0$^{19,24}$]PENTACOSA [8,16,18,24]TETRAEN]-15'-ONE 13',13'-DIOXIDE OR (1S,3'R,6'R,7'S,8'E,11'S,12'S)-6-CHLORO-7'-HYDROXY-11'-METHYL-12'-PROPYL-3,4-DIHYDRO-2H,15'H-SPIRO[NAPHTHALENE-1,22'-[20]OXA[13]THIA[1,14] DIAZATETRACYCLO [14.7.2.0$^{3,6}$.0$^{19,24}$]PENTACOSA [8,16,18,24]TETRAEN]-15'-ONE 13',13'-DIOXIDE OR (1S,3'R,6'R,7'S,8'E,11'R,12'S)-6-CHLORO-7'-HYDROXY-11'-METHYL-12'-PROPYL-3,4-DIHYDRO-2H,15'H-SPIRO[NAPHTHALENE-1,22'-[20]OXA[13]THIA[1,14] DIAZATETRACYCLO [14.7.2.0$^{3,6}$.0$^{19,24}$]PENTACOSA [8,16,18,24]TETRAEN]-15'-ONE 13',13'-DIOXIDE

A mixture of (3S)-6'-chloro-5-(((1R,2R)-2-((1S,2E,5R,6S)-1-hydroxy-5-methyl-6-sulfamoyl-2-nonen-1-yl)cyclobutyl)methyl)-3',4,4',5-tetrahydro-2'H-spiro[1,5-benzoxazepine-3,1'-naphthalene]-7-carboxylic acid, (3S)-6'-chloro-5-(((1R,2R)-2-((1S,2E,5R,6R)-1-hydroxy-5-methyl-6-sulfamoyl-2-nonen-1-yl)cyclobutyl)methyl)-3',4,4',5-tetrahydro-2'H-spiro[1,5-benzoxazepine-3,1'-naphthalene]-7-carboxylic acid, (3S)-6'-chloro-5-(((1R,2R)-2-((1S,2E,5S,6S)-1-hydroxy-5-methyl-6-sulfamoyl-2-nonen-1-yl)cyclobutyl)methyl)-3',4,4',5-tetrahydro-2'H-spiro[1,5-benzoxazepine-3,1'-naphthalene]-7-carboxylic acid, and (3S)-6'-chloro-5-(((1R,2R)-2-((1S,2E,5S,6R)-1-hydroxy-5-methyl-6-sulfamoyl-2-nonen-1-yl)cyclobutyl) methyl)-3',4,4',5-tetrahydro-2'H-spiro[1,5-benzoxazepine-3,1'-naphthalene]-7-carboxylic acid (110 mg, 0.170 mmol) was added to 1-(3-dimethylaminopropyl)-3-ethylcarbodiimide, HCl (98 mg, 0.51 mmol), and DMAP (41.7 mg, 0.341 mmol) in DCM (80 mL) at 0° C. The reaction mixture was then allowed to warm to ambient temperature and stirred for 18 h. Solvent was evaporated, and the crude residue was chromatographed (SiO$_2$ gel, 9:1 to 0:1, hexane/EtOAc+0.3% AcOH) to afford a grey oil (65 mg). Further purification of the oil by preparative reverse-phase HPLC (Gemini™ Prep C$_{18}$ 5 μm column; gradient elution of 25% to 75% MeCN in H$_2$O, where both solvents contain 0.1% TFA, 30 min method) afforded the first eluting isomer as the title compound as a white solid. $^1$H NMR (500 MHz, CDCl$_3$) δ ppm 8.07 (s, 1H), 7.70 (d, J=8.3 Hz, 1H), 7.19 (dd, J=2.0, 8.6 Hz, 1H), 7.10 (s, 1H), 6.98-6.88 (m, 3H), 5.93-5.85 (m, 1H), 5.72 (dd, J=7.9, 15.3 Hz, 1H), 4.26 (dd, J=4.0, 8.2 Hz, 1H), 4.16-4.06 (m, 3H), 3.83 (d, J=14.9 Hz, 1H), 3.70 (d, J=14.4 Hz, 1H), 3.24 (d, J=14.2 Hz, 1H), 3.03 (dd, J=9.8, 15.2 Hz, 1H), 2.83-2.72 (m, 2H), 2.45 (dd, J=3.7, 8.6 Hz, 1H), 2.32 (t, J=9.0 Hz, 1H), 2.16-1.94 (m, 7H), 1.91-1.74 (m, 5H), 1.74-1.62 (m, 2H), 1.40 (t, J=12.8 Hz, 1H), 1.10-0.98 (m, 6H). m/z (ESI, +ve ion) 627.2 (M+H)$^+$.

EXAMPLE 69

(1S,3'R,6'R,7'S,8'E,11'S,12'R)-6-CHLORO-7'-HYDROXY-11'-METHYL-12'-PROPYL-3,4-DIHYDRO-2H,15'H-SPIRO[NAPHTHALENE-1,22'-[20]OXA[13]THIA[1,14] DIAZATETRACYCLO[14.7.2.0$^{3,6}$.0$^{19,24}$]PENTACOSA [8,16,18,24]TETRAEN]-15'-ONE 13',13'-DIOXIDE OR (1S,3'R,6'R,7'S,8'E,11'R,12'R)-6-CHLORO-7'-HYDROXY-11'-METHYL-12'-PROPYL-3,4-DIHYDRO-2H,15'H-SPIRO[NAPHTHALENE-1,22'-[20]OXA[13]THIA[1,14] DIAZATETRACYCLO [14.7.2.0$^{3,6}$.0$^{19,24}$]PENTACOSA [8,16,18,24]TETRAEN]-15'-ONE 13',13'-DIOXIDE OR (1S,3'R,6'R,7'S,8'E,11'S,12'S)-6-CHLORO-7'-HYDROXY-11'-METHYL-12'-PROPYL-3,4-DIHYDRO-2H,15'H-SPIRO[NAPHTHALENE-1,22'-[20]OXA[13]THIA[1,14] DIAZATETRACYCLO [14.7.2.0$^{3,6}$.0$^{19,24}$]PENTACOSA [8,16,18,24]TETRAEN]-15'-ONE 13',13'-DIOXIDE OR (1S,3'R,6'R,7'S,8'E,11'R,12'S)-6-CHLORO-7'-HYDROXY-11'-METHYL-12'-PROPYL-3,4-DIHYDRO-2H,15'H-SPIRO[NAPHTHALENE-1,22'-[20]OXA[13]THIA[1,14] DIAZATETRACYCLO [14.7.2.0$^{3,6}$.0$^{19,24}$]PENTACOSA [8,16,18,24]TETRAEN]-15'-ONE 13',13'-DIOXIDE OR (1S,3'R,6'R,7'S,8'E,11'S,12'R)-6-CHLORO-7'-HYDROXY-11'-METHYL-12'-PROPYL-3,4-DIHYDRO-2H,15H-SPIRO[NAPHTHALENE-1,22'-[20]OXA[13]THIA[1,14] DIAZATETRACYCLO [14.7.2.0$^{3,6}$.0$^{19,24}$]PENTACOSA [8,16,18,24]TETRAEN]-15'-ONE 13',13'-DIOXIDE OR (1S,3'R,6'R,7'S,8'Z,11'R,12'R)-6-CHLORO-7'-HYDROXY-11'-METHYL-12'-PROPYL-3,4-DIHYDRO-2H,15'H-SPIRO[NAPHTHALENE-1,22'-[20]OXA[ 13]THIA[1,14] DIAZATETRACYCLO [14.7.2.0$^{3,6}$.0$^{19,24}$]PENTACOSA [8,16,18,24]TETRAEN]-15'-ONE 13',13'-DIOXIDE OR (1S,3'R,6'R,7'S,8'Z,11'S,12'S)-6-CHLORO-7'-HYDROXY-11'-METHYL-12'-PROPYL-3,4-DIHYDRO-2H,15'H-SPIRO[NAPHTHALENE-1,22'-[20]OXA[13]THIA[1,14] DIAZATETRACYCLO [14.7.2.0$^{3,6}$.0$^{19,24}$]PENTACOSA [8,16,18,24]TETRAEN]-15'-ONE 13',13'-DIOXIDE OR (1S,3'R,6'R,7'S,8'Z,11'R,12'S)-6-CHLORO-7'-HYDROXY-11'-METHYL-12'-PROPYL-3,4-DIHYDRO-2H,15'H-SPIRO[NAPHTHALENE-1,22'-[20]OXA[13]THIA[1,14] DIAZATETRACYCLO [14.7.2.0$^{3,6}$.0$^{19,24}$]PENTACOSA [8,16,18,24]TETRAEN]-15'-ONE 13',13'-DIOXIDE

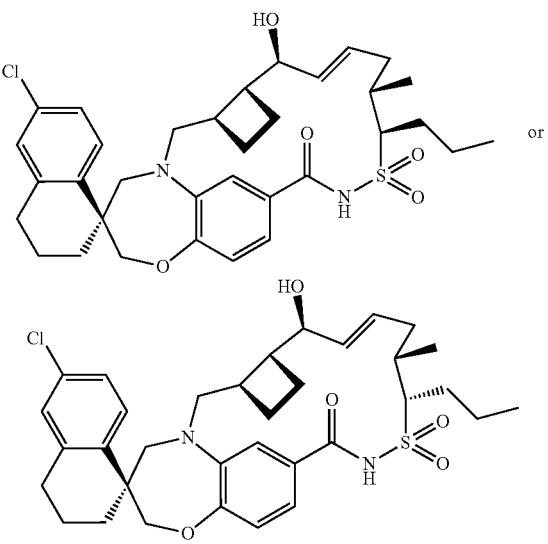

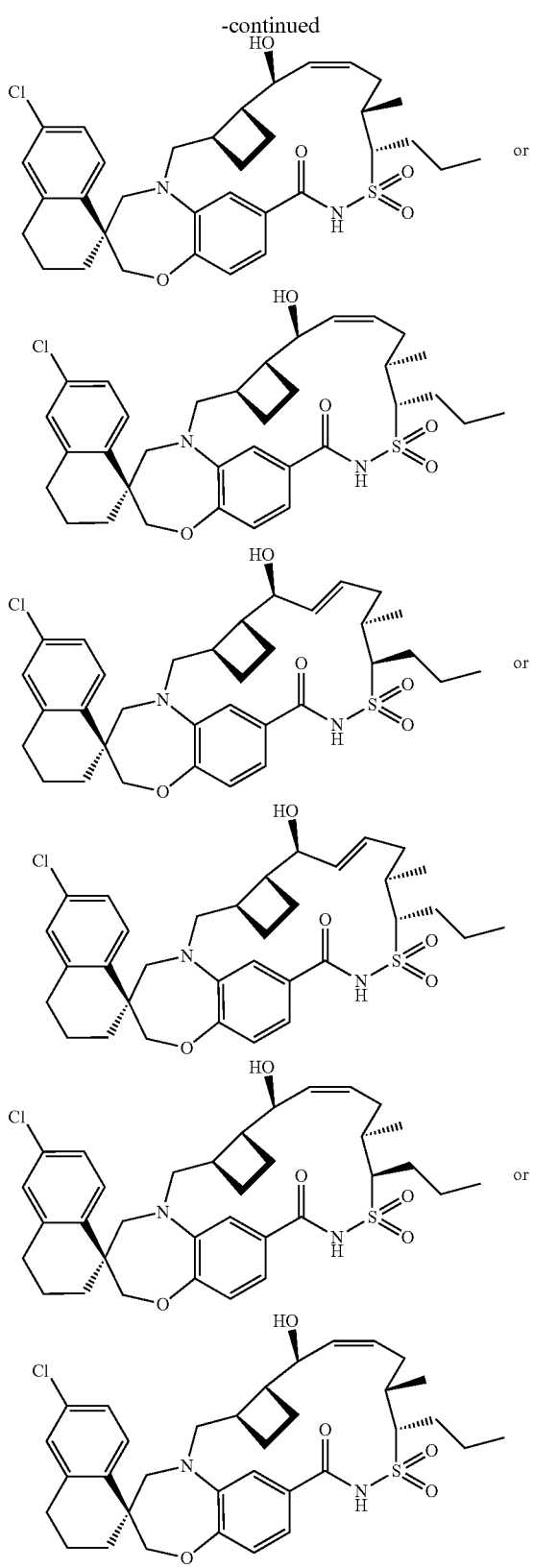

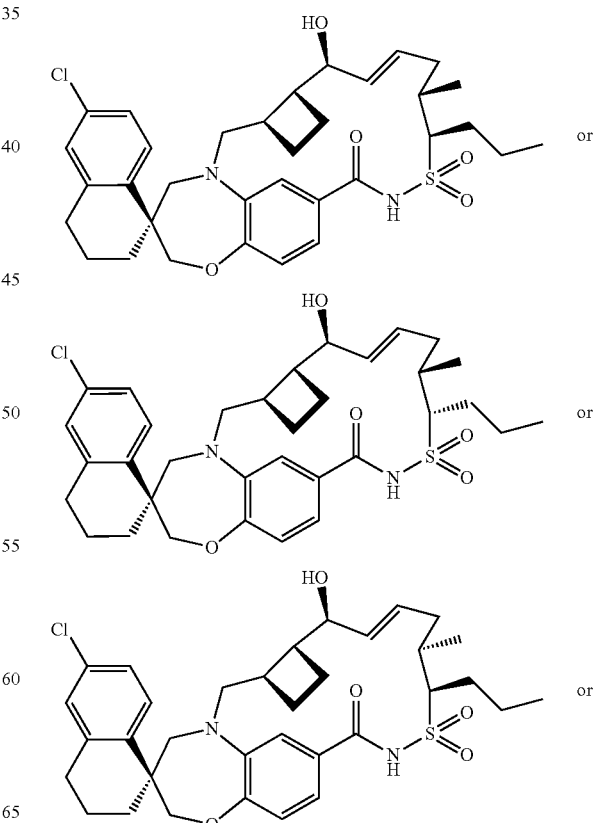

(br s, 1H), 6.14 (br s, 1H), 5.81 (br s, 1H), 4.23 (br s, 1H), 4.19-4.04 (m, 3H), 3.69 (d, J=14.4 Hz, 2H), 3.58 (br s, 1H), 3.40-3.18 (br, 2H), 3.15-3.00 (br s, 1H), 2.85-2.70 (m, 2H), 2.44 (br s, 1H), 2.35 (br s, 2H), 2.18 (br s, 1H), 2.10-1.90 (m, 3H), 1.80-1.63 (m, 6H), 1.63-1.54 (m, 1H), 1.48 (br s, 1H), 1.11 (br s, 3H), 1.05-0.99 (m, 3H). m/z (ESI, +ve ion) 627.2 (M+H)$^+$.

EXAMPLE 70

(1S,3'R,6'R,7'S,8'E,11'S,12'R)-6-CHLORO-7'-HYDROXY-11'-METHYL-12'-PROPYL-3,4-DIHYDRO-2H,15'H-SPIRO[NAPHTHALENE-1,22'-[20]OXA[13]THIA[1,14] DIAZATETRACYCLO [14.7.2.0$^{3,6}$.0$^{19,24}$]PENTACOSA [18,16,18,24]TETRAEN]-15'-ONE 13',13'-DIOXIDE OR (1S,3'R,6'R,7'S,8'E,11'R,12'R)-6-CHLORO-7'-HYDROXY-11'-METHYL-12'-PROPYL-3,4-DIHYDRO-2H,15'H-SPIRO[NAPHTHALENE-1,22'-[20]OXA[13]THIA[1,14] DIAZATETRACYCLO [14.7.2.0$^{3,6}$.0$^{19,24}$] PENTACOSA [8,16,18,24]TETRAEN]-15'-ONE 13',13'-DIOXIDE OR (1S,3'R,6'R,7'S,8'E,11'S,12'S)-6-CHLORO-7'-HYDROXY-11'-METHYL-12'-PROPYL-3,4-DIHYDRO-2H,15'H-SPIRO[NAPHTHALENE-1,22'-[20]OXA[[13]THIA[1,14] DIAZATETRACYCLO[14.7.2.0$^{3,6}$.0$^{19,24}$] PENTACOSA [8,16,18,24]TETRAEN]-15'-ONE 13',13'-DIOXIDE OR (1S,3'R,6'R,7'S,8'E,11'R,12'S)-6-CHLORO-7'-HYDROXY-11'-METHYL-12'-PROPYL-3,4-DIHYDRO-2H,15'H-SPIRO[NAPHTHALENE-1,22'-[20]OXA[13]THIA[1,14] DIAZATETRACYCLO [14.7.2.0$^{3,6}$.0$^{19,24}$] PENTACOSA [8,16,18,24]TETRAEN]-15'-ONE 13',13'-DIOXIDE

The title compounds were obtained as the second eluting isomer from the preparative reverse-phase HPLC separation in Example 68. $^1$H NMR (500 MHz, CDCl$_3$) δ ppm 7.71 (d, J=8.3 Hz, 1H), 7.11-7.08 (m, 1H), 7.00-6.87 (m, 2H), 6.84

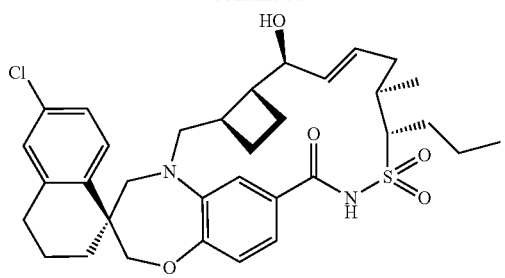

The title compounds were obtained as the third eluting isomer from the preparative reverse-phase HPLC separation in Example 68. $^1$H NMR (500 MHz, CDCl$_3$) δ ppm 8.32 (br s, 1H), 7.70 (d, J=8.6 Hz, 1H), 7.23-7.16 (m, 2H), 7.10 (s, 1H), 6.97 (d, J=8.3 Hz, 1H), 6.66 (br s, 1H), 6.08 (br s, 1H), 5.66 (dd, J=6.2, 15.3 Hz, 1H), 4.21 (br s, 1H), 4.15-4.00 (m, 2H), 3.83-3.60 (m, 3H), 3.42 (d, J=14.7 Hz, 1H), 3.25 (br s, 1H), 2.85-2.74 (m, 2H), 2.60-2.47 (m, 2H), 2.38-2.18 (m, 2H), 2.15-2.00 (m, 3H), 2.00-1.58 (m, 9H), 1.46 (brs, 1H), 1.17-1.08 (m, 3H), 1.07-0.96 (m, 3H). m/z (ESI, +ve ion) 627.2 (M+H)$^+$.

EXAMPLE 71

(1S,3'R,6'R,7'S,8'E,11'S,12'R)-12'-BUTYL-6-CHLORO-7'-HYDROXY-11'-METHYL-3,4-DIHYDRO-2H,15'H-SPIRO[NAPHTHALENE-1,22'-[20]OXA[13]THIA[1,14] DIAZATETRACYCLO [14.7.2.0$^{3,6}$.0$^{19,24}$]PENTACOSA [18,16,18,24]TETRAEN]-15'-ONE 13',13'-DIOXIDE OR (1S,3'R,6'R,7'S,8'E,11'S,12'S)-12'-BUTYL-6-CHLORO-7'-HYDROXY-11'-METHYL-3,4-DIHYDRO-2H,15'H-SPIRO[NAPHTHALENE-1,22'-[20]OXA[13]THIA[1,14] DIAZATETRACYCLO[14.7.2.0$^{3,6}$.0$^{19,24}$] PENTACOSA [8,16,18,24]TETRAEN]-15'-ONE 13',13'-DIOXIDE OR (1S,3'R,6'R,7'S,8'E,11'R,12'R)-12'-BUTYL-6-CHLORO-7'-HYDROXY-11'-METHYL-3,4-DIHYDRO-2H,15'H-SPIRO[NAPHTHALENE-1,22'-[20]OXA[13]THIA[1,14] DIAZATETRACYCLO[14.7.2.0$^{3,6}$.0$^{19,24}$] PENTACOSA [8,16,18,24]TETRAEN]-15'-ONE 13',13'-DIOXIDE OR (1S,3'R,6'R,7'S,8'E,11'R,12'S)-12'-BUTYL-6-CHLORO-7'-HYDROXY-11'-METHYL-3,4-DIHYDRO-2H,15'H-SPIRO[NAPHTHALENE-1,22'-[20]OXA[13]THIA[1,14] DIAZATETRACYCLO[14.7.2.0$^{3,6}$.0$^{19,24}$] PENTACOSA [8,16,18,24]TETRAEN]-15'-ONE 13',13'-DIOXIDE

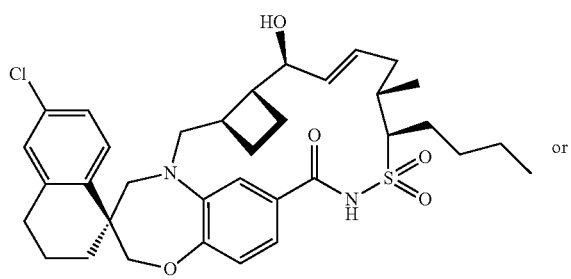
or

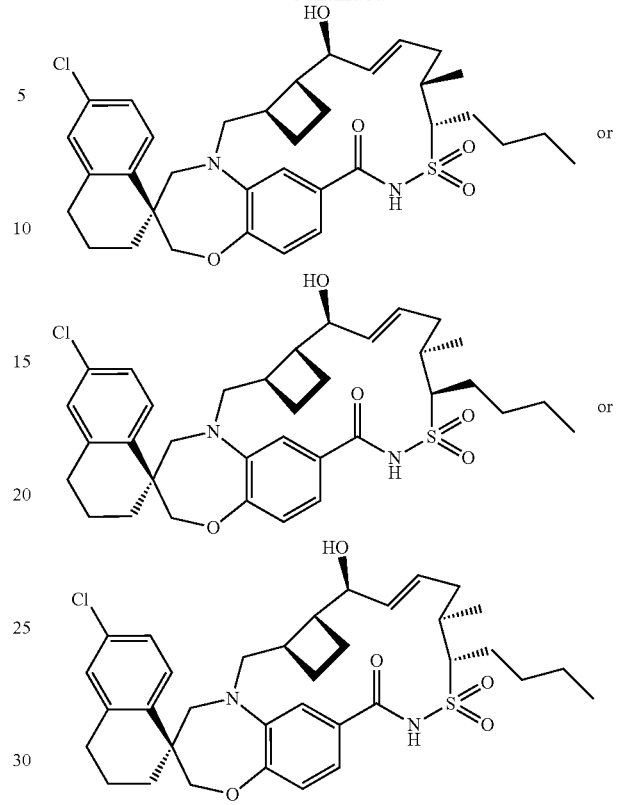

STEP 1

(4S,5R)—N,N-BIS(4-METHOXYBENZYL)-4-METHYL-1-NONENE-5-SULFONAMIDE AND (4R,5R)—N,N-BIS(4-METHOXYBENZYL)-4-METHYL-1-NONENE-5-SULFONAMIDE AND (4S,5S)—N,N-BIS(4-METHOXYBENZYL)-4-METHYL-1-NONENE-5-SULFONAMIDE AND (4R,5S)—N,N-BIS(4-METHOXYBENZYL)-4-METHYL-1-NONENE-5-SULFONAMIDE

The title compounds were prepared from (2S)—N,N-bis(4-methoxybenzyl)-2-methylpent-4-ene-1-sulfonamide and (2R)—N,N-bis(4-methoxybenzyl)-2-methylpent-4-ene-1-sulfonamide (from Example 58, Step 1) with 1-bromobutane following a similar procedure described in Example 58, Step 2.

Step 2: (4S,5R)-4-METHYL-1-NONENE-5-SULFONAMIDE AND (4S,5R)-4-METHYL-1-NONENE-5-SULFONAMIDE AND (4S,5R)-4-METHYL-1-NONENE-5-SULFONAMIDE AND (4S,5R)-4-METHYL-1-NONENE-5-SULFONAMIDE

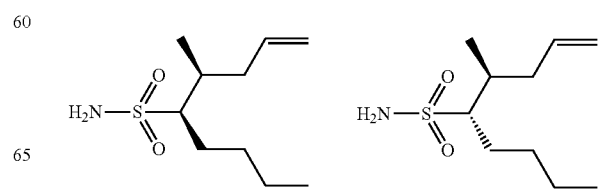

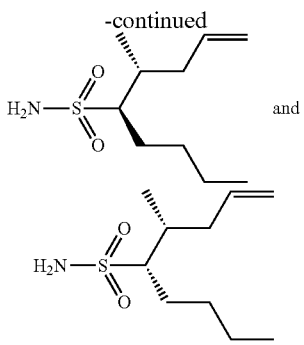

The title compounds were prepared from a mixture of (4S,5R)—N,N-bis(4-methoxybenzyl)-4-methyl-1-nonene-5-sulfonamide, (4R,5R)—N,N-bis(4-methoxybenzyl)-4-methyl-1-nonene-5-sulfonamide, (4S,5S)—N,N-bis(4-methoxybenzyl)-4-methyl-1-nonene-5-sulfonamide, (4R,5S)—N,N-bis(4-methoxybenzyl)-4-methyl-1-nonene-5-sulfonamide by a similar procedure described in Example 58, Step 3.

STEP 3

(3S)-6'-CHLORO-5-(((1R,2R)-2-((1S,2E)-1-HYDROXY-2-HEXEN-1-YL)CYCLOBUTYL)METHYL)-N-(((2R,3S)-3-(2-PROPEN-1-YL)-2-HEPTANYL) SULFONYL)-3',4,4',5-TETRAHYDRO-2'H-SPIRO[1,5-BENZOXAZEPINE-3,1'-NAPHTHALENE]-7-CARBOXAMIDE AND (3S)-6'-CHLORO-5-(((1R,2R)-2-((1S,2E)-1-HYDROXY-2-HEXEN-1-YL)CYCLOBUTYL)METHYL)-N-(((2R,3S)-3-(2-PROPEN-1-YL)-2-HEPTANYL)SULFONYL)-3',4,4',5-TETRAHYDRO-2'H-SPIRO[1,5-BENZOXAZEPINE-3,1'-NAPHTHALENE]-7-CARBOXAMIDE AND (3S)-6'-CHLORO-5-(((1R,2R)-2-((1S,2E)-1-HYDROXY-2-HEXEN-1-YL)CYCLOBUTYL)METHYL)-N-(((2R,3S)-3-(2-PROPEN-1-YL)-2-HEPTANYL)SULFONYL)-3',4,4',5-TETRAHYDRO-2'H-SPIRO[1,5-BENZOXAZEPINE-3,1'-NAPHTHALENE]-7-CARBOXAMIDE AND (3S)-6'-CHLORO-5-(((1R,2R)-2-((1S,2E)-1-HYDROXY-2-HEXEN-1-YL)CYCLOBUTYL)METHYL)-N-(((2R,3S)-3-(2-PROPEN-1-YL)-2-HEPTANYL)SULFONYL)-3',4,4',5-TETRAHYDRO-2'H-SPIRO[1,5-BENZOXAZEPINE-3,1'-NAPHTHALENE]-7-CARBOXAMIDE

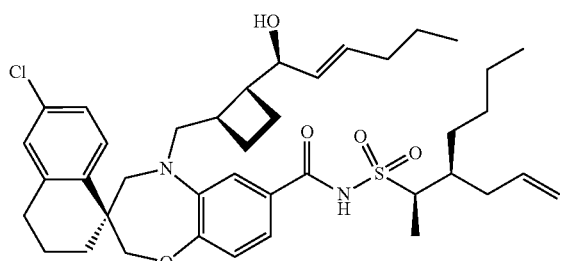

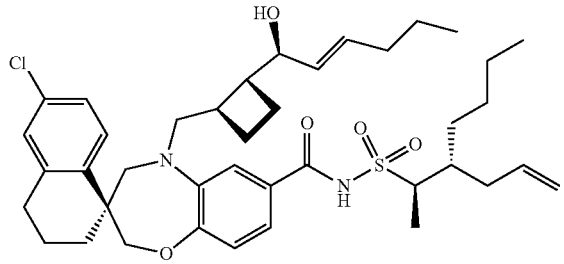

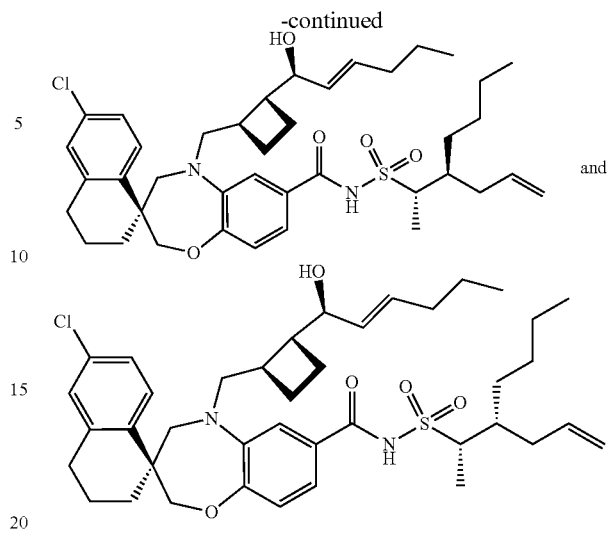

The title compounds were prepared from a mixture of (4S,5R)-4-methyl-1-nonene-5-sulfonamide, (4R,5R)-4-methyl-1-nonene-5-sulfonamide, (4S,5S)-4-methyl-1-nonene-5-sulfonamide and (4R,5R)-4-methyl-1-nonene-5-sulfonamide (Step 2) and (S)-6'-chloro-5-(((1R,2S)-2-((S,E)-1-hydroxyhex-2-en-1-yl)cyclobutyl)methyl)-3',4,4',5-tetrahydro-2H,2'H-spiro[benzo[b][1,4]oxazepine-3,1'-naphthalene]-7-carboxylic acid (Intermediate AA12A) using a similar procedure described in Example 58, Step 4.

STEP 4

(1S,3'R,6'R,7'S,8'E,11'S,12'R)-12'-BUTYL-6-CHLORO-7'-HYDROXY-11'-METHYL-3,4-DIHYDRO-2H,15'H-SPIRO[NAPHTHALENE-1,22'-[20]OXA[13] THIA[1,14] DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'S,12'S)-12'-BUTYL-6-CHLORO-7'-HYDROXY-11'-METHYL-3,4-DIHYDRO-2H,15'H-SPIRO[NAPHTHALENE-1,22'-[20]OXA[13]THIA[1,14]DIAZATETRACYCLO [14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'R)-12'-BUTYL-6-CHLORO-7'-HYDROXY-11'-METHYL-3,4-DIHYDRO-2H,15'H-SPIRO[NAPHTHALENE-1,22'-[20]OXA[13]THIA[1,14]DIAZATETRACYCLO [14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'S)-12'-BUTYL-6-CHLORO-7'-HYDROXY-11'-METHYL-3,4-DIHYDRO-2H,15'H-SPIRO[NAPHTHALENE-1,22'-[20]OXA[13]THIA[1,14]DIAZATETRACYCLO [14.7.2.0$^{3,6}$.0$^{19,24}$]PENTACOSA[8,16,18,24]TETRAEN]-15'-ONE 13',13'-DIOXIDE

The title compounds were prepared from the above mixture (3S)-6'-chloro-5-(((1R,2R)-2-((1S,2E)-1-hydroxy-2-hexen-1-yl)cyclobutyl)methyl)-N-(((2R,3S)-3-(2-propen-1-yl)-2-heptanyl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S,2E)-1-hydroxy-2-hexen-1-yl)cyclobutyl)methyl)-N-(((2R,3S)-3-(2-propen-1-yl)-2-heptanyl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1s,2e)-1-hydroxy-2-hexen-1-yl)cyclobutyl)methyl)-N—(((1R,3S)-3-(2-propen-1-yl)-2-heptanyl)sulfonyl)-3',4,4',5-tetrahydro-2'H-spiro[1,5-benzoxazepine-3,1'-naphthalene]-7-carboxamide and (3S)-6'-chloro-5-(((1R,2R)-2-((1S,2E)-1-hydroxy-2-hexen-1-yl)

cyclobutyl)methyl)-N-(((2R,3S)-3-(2-propen-1-yl)-2-heptanyl)sulfonyl)-3',4,4',5-tetrahydro-2'H-spiro[1,5-benzoxazepine-3,1'-naphthalene]-7-carboxamide using a similar procedure described in Example 58, Step 5. $^1$H NMR (500 MHz, CDCl$_3$) δ ppm 8.07 (br s, 1H), 7.70 (d, J=8.6 Hz, 1H), 7.19 (d, J=8.3 Hz, 1H), 7.11-7.09 (m, 1H), 6.99-6.87 (m, 3H), 5.93-5.86 (m, 1H), 5.72 (dd, J=8.2, 15.3 Hz, 1H), 4.26 (dd, J=3.9, 8.3 Hz, 1H), 4.13-4.07 (m, 3H), 3.83 (d, J=15.4 Hz, 1H), 3.70 (d, J=14.4 Hz, 1H), 3.24 (d, J=14.2 Hz, 1H), 3.03 (dd, J=9.5, 15.2 Hz, 1H), 2.83-2.72 (m, 2H), 2.51-2.39 (m, 1H), 2.32 (t, J=9.4 Hz, 1H), 2.20-1.64 (m, 6H), 1.63-1.63 (m, 7H), 1.63-1.53 (m, 1H), 1.50-1.33 (m, 3H), 1.06 (d, J=6.8 Hz, 3H), 0.97 (t, J=7.3 Hz, 3H). m/z (ESI, +ve ion) 641.2 (M+H)$^+$.

EXAMPLE 72

(1S,3'R,6'R,7'S,8'Z,11'R,12'R)-12'-BUTYL-6-CHLORO-7'-HYDROXY-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'Z,11'R,12'S)-12'-BUTYL-6-CHLORO-7'-HYDROXY-11'-METHYL-3,4-DIHYDRO-2H,15'H-SPIRO[NAPHTHALENE-1,22'-[20]OXA[13]THIA[1,14]DIAZATETRACYCLO [14.7.2.0$^{3,6}$.0$^{19,24}$]PENTACOSA[8,16,18,24]TETRAEN]-15'-ONE 13',13'-DIOXIDE OR (1S,3'R,6'R,7'S,8'Z,11'S,12'R)-12'-BUTYL-6-CHLORO-7'-HYDROXY-11'-METHYL-3,4-DIHYDRO-2H,15'H-SPIRO[NAPHTHALENE-1,22'-[20]OXA[13]THIA[1,14]DIAZATETRACYCLO [14.7.2.0$^{3,6}$.0$^{19,24}$]PENTACOSA[8,16,18,24]TETRAEN]-15'-ONE 13',13'-DIOXIDE OR (1S,3'R,6'R,7'S,8'Z,11'S,12'S)-12'-BUTYL-6-CHLORO-7'-HYDROXY-11'-METHYL-3,4-DIHYDRO-2H,15'H-SPIRO[NAPHTHALENE-1,22'-[20]OXA[13]THIA[1,14]DIAZATETRACYCLO [14.7.2.0$^{3,6}$.0$^{19,24}$]PENTACOSA[8,16,18,24]TETRAEN]-15'-ONE 13',13'-DIOXIDE

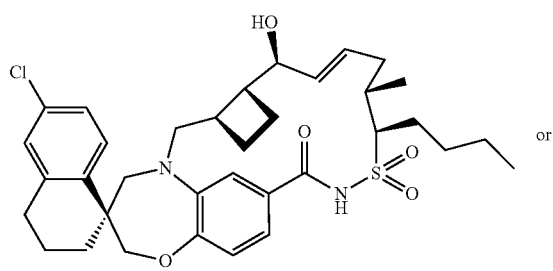 or

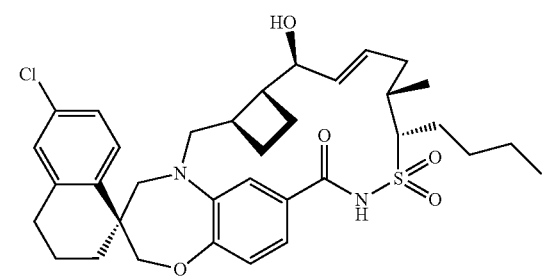

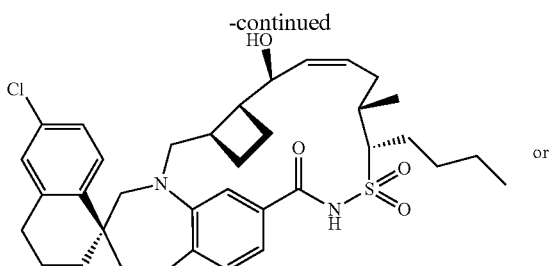 or

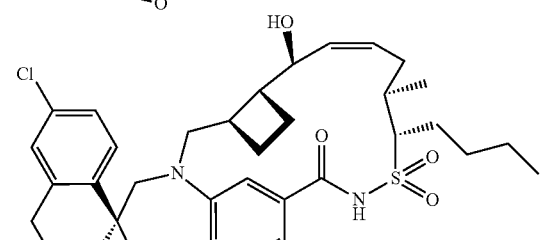

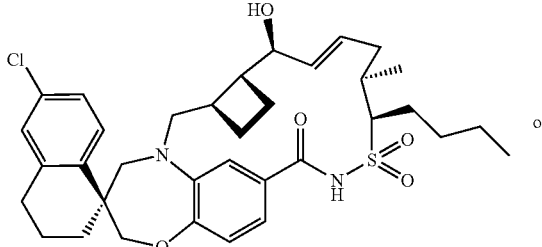 or

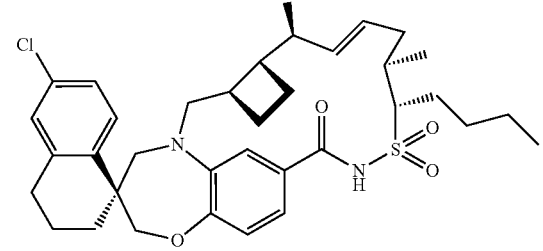

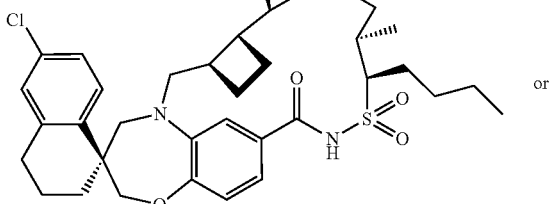 or

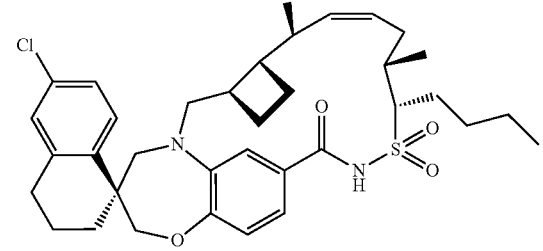

The title compounds were obtained as single isomer (second eluting peak) from the preparative reverse-phase HPLC separation in Example 71. $^1$H NMR (500 MHz, CDCl$_3$) δ=9.92 (br s, 1H), 7.71 (d, J=8.6 Hz, 1H), 7.47 (d, J=8.1 Hz, 1H), 7.20-7.12 (m, 1H), 7.12-7.06 (m, 2H), 6.98 (d, J=8.3 Hz, 1H), 5.75 (br s, 1H), 5.53 (td, J=2.4, 2.4, 11.8

Hz, 1H), 4.41 (br s, 1H), 4.13-4.01 (m, 2H), 3.88 (d, J=15.4 Hz, 1H), 3.64 (d, J=14.4 Hz, 1H), 3.57 (br s, 1H), 3.19-2.99 (m, 2H), 2.83-2.71 (m, 2H), 2.29-2.15 (m, 2H), 2.13-2.02 (m, 2H), 2.02-1.87 (m, 4H), 1.77-1.63 (m, 7H), 1.62-1.50 (m, 1H), 1.49-1.31 (m, 3H), 1.12-1.03 (m, 3H), 1.02-0.88 (m, 3H). m/z (ESI, +ve ion) 641.2 (M+H)$^+$.

EXAMPLE 73. (1S,3'R,6'R,7'S,8'E,11'S,12'R)-7'-BUTOXY-6-CHLORO-11',12'-DIMETHYL-3,4-DIHYDRO-2H,15'H-SPIRO[NAPHTHALENE-1, 22' [20]OXA[13]THIA[1,14] DIAZATETRACYCLO[14.7.2.0$^{3,6}$.0$^{19,24}$] PENTACOSA[8,16,18,24]TETRAEN]-15'-ONE 13',13'-DIOXIDE

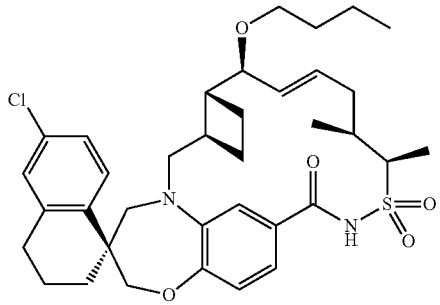 [SMILES: CCCCO[C@H]1/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]

To a solution of (1S,3'R,6'R,7'S,8'E,11'S,12'R)-6-chloro-7'-hydroxy-11',12'-dimethyl-3,4-dihydro-2h,15'h-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 2; 60 mg, 0.1 mmol) in THF (2 mL) was added 60% sodium hydride in mineral oil (20 mg, 0.5 mmol) at 0° C. The mixture was stirred at 0° C. for 30 min. 1-Iodobutane (92 mg, 54 uL, 0.5 mmol) was added and the mixture thus obtained was stirred at 0° C. for 4 h and HPLC-MS analysis indicated completion of the reaction. The reaction was quenched with sat. NH$_4$Cl and extracted with EtOAc. The combined organic layers were washed with brine and dried over MgSO$_4$. The solvent was evaporated under reduced pressure and the residue was purified by flash chromatography on SiO$_2$ gel (24 g, HP SiO$_2$, Teledyne ISCO) eluting with 15% to 65% EtOAc in hexane to provide (1S,3'R,6'R,7',8'E,11'S,12'R)-7'-butoxy-6-chloro-11',12'-dimethyl-3,4-dihydro-2h,15'h-spiro[naphthalene-1,22' [20]oxa[13]thia[1,14]diazatetracyclo[14.7.2.0$^{3,6}$.0$^{19,24}$]pentacosa[8,16,18,24]tetraen]-15'-one 13',13'-dioxide as a white solid (15 mg, 23% yield). $^1$H NMR (500 MHz, CDCl$_3$) δ ppm 8.13 (s, 1H), 7.70 (d, J=8.4, 2.3 Hz, 1H), 7.09 (d, J=2.2 Hz, 1H), 6.92-6.95 (m, 2H), 6.89 (s, 1H), 5.80 (ddd, J=15.1, 9.6, 3.2 Hz, 1H), 5.54 (dd, J=15.1, 9.6 Hz, 1H), 4.31-4.36 (m, 1H), 4.07-4.11 (m, 2H), 3.84 (d, J=15.4 Hz, 1H), 3.68-3.74 (m, 2H), 3.39 (dt, J=9.3, 6.7 Hz, 1H), 3.22-3.27 (m, 2H), 3.00 (dd, J=15.2, 10.3 Hz, 1H), 2.75-2.83 (m, 2H), 2.41-2.47 (m, 1H), 2.30-2.36 (m, 1H), 2.14-2.21 (m, 1H), 1.94-2.12 (m, 2H), 1.73-1.88 (m, 4H), 1.58-1.62 (m, 1H), 1.48-1.55 (m, 4H), 1.20-1.42 (m, 4H), 1.05 (d, J=10.0 Hz, 3H), 0.92 (t, J=10.0 Hz, 3H); MS m/z (ESI, +ve ion) 656.0 (M+H)$^+$.

EXAMPLE 74

(1S,3'R,6'R,7'S,8'E,11'S,12'R)-6-CHLORO-7'-(2-METHOXYETHOXY)-11',12'-DIMETHYL-3,4-DIHYDRO-2H,15'H-SPIRO[NAPHTHALENE-1,22'-[20] OXA[13] THIA[1,14]DIAZATETRACYCLO[14.7.2.0$^{3,6}$.0$^{19,24}$]PENTACOSA[8,16,18,24] TETRAEN]-15'-ONE-13',13'-DIOXIDE

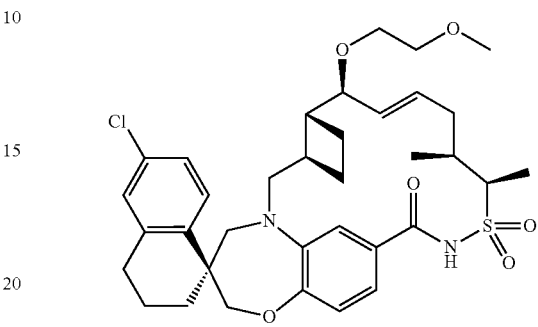

To a solution of (1S,3'R,6'R,7'S,8'E,11'S,12'R)-6-chloro-7'-hydroxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$] pentacosa[8,16,18,24]tetraen]-15-one 13',13'-dioxide (Example 2, 100 mg, 0.167 mmol) in DMF (3.34 mL) cooled to 0° C. was added sodium hydride, 60% dispersion in mineral oil (66.8 mg, 1.67 mmol). The reaction mixture was stirred at 0° C. for 15 min, and then 2-bromoethyl methyl ether (Alfa Aesar, 0.078 mL, 0.834 mmol) was added. The reaction mixture was stirred at ambient temperature. After 48 h, the mixture was quenched with aq. NH$_4$Cl and diluted with water, then extracted with EtOAc. The organic layer was dried over MgSO$_4$ and concentrated. The crude material was purified by chromatography through a Redi-Sep pre-packed silica gel column (12 g), eluting with 10-40% EtOAc (containing 0.3% AcOH)/heptanes to provide the title compound (61 mg, 0.093 mmol, 55.6% yield). $^1$H NMR (500 MHz, CD$_2$Cl$_2$) δ 8.02 (s, 1H), 7.70 (d, J=8.6 Hz, 1H), 7.17 (dd, J=2.2, 8.6 Hz, 1H), 7.09 (d, J=2.2 Hz, 1H), 6.91 (s, 2H), 6.86 (s, 1H), 5.79 (ddd, J=3.3, 9.6, 15.2 Hz, 1H), 5.54 (dd, J=9.8, 14.4 Hz, 1H), 4.26 (ddd, J=1.0, 7.3, 14.4 Hz, 1H), 4.12-4.04 (m, 2H), 3.82 (d, J=15.2 Hz, 1H), 3.75 (dd, J=3.3, 9.2 Hz, 1H), 3.69 (d, J=14.7 Hz, 1H), 3.53-3.49 (m, 1H), 3.48-3.41 (m, 2H), 3.39-3.34 (m, 1H), 3.32 (s, 3H), 3.25 (d, J=14.2 Hz, 1H), 3.02 (dd, J=10.3, 15.4 Hz, 1H), 2.83-2.70 (m, 2H), 2.49-2.41 (m, 1H), 2.36-2.28 (m, 1H), 2.21-2.13 (m, 1H), 2.13-2.07 (m, 1H), 2.05 (d, J=13.7 Hz, 1H), 1.99-1.91 (m, 3H), 1.89-1.77 (m, 3H), 1.71-1.59 (m, 1H), 1.44 (d, J=7.3 Hz, 3H), 1.39 (t, J=13.1 Hz, 1H), 1.02 (d, J=6.8 Hz, 3H). MS (ESI, +ve ion) m/z 657.1 (M+H)$^+$.

EXAMPLE 75

(1S,3'R,6'R,7'S,8'E,12'R)-6-CHLORO-12'-ETHYL-7'-(2-METHOXYETHOXY)-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$] PENTACOSA[8,16,18,24]TETRAEN]-15'-ONE 13',13'-DIOXIDE

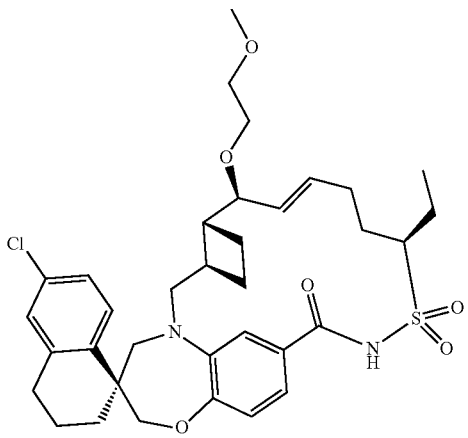 [SMILES: CC[C@@H]1CC/C=C/[C@H](OCCOC)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 74 using (1S,3'R,6'R,7'S,8'E,12'R)-6-chloro-12'-ethyl-7'-hydroxy-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 17) and 1-bromo-2-methoxyethane (Aldrich). $^{1}$H NMR (400 MHz, CD$_3$OD) δ 7.75 (d, J=8.6 Hz, 1H), 7.19 (dd, J=2.2, 8.8 Hz, 1H), 7.12 (d, J=2.2 Hz, 1H), 7.01 (dd, J=1.6, 8.2 Hz, 1H), 6.94 (d, J=8.2 Hz, 1H), 6.88 (d, J=1.6 Hz, 1H), 5.89 (ddd, J=6.1, 13.1, 21.5 Hz, 1H), 5.60 (dd, J=9.0, 15.1 Hz, 1H), 4.09 (dd, J=12.7, 15.3 Hz, 2H), 4.05-3.99 (m, 1H), 3.91-3.82 (m, 2H), 3.69 (d, J=14.5 Hz, 1H), 3.62-3.57 (m, 11H), 3.53 (dd, J=4.1, 8.0 Hz, 2H), 3.50-3.45 (m, 1H), 3.38 (s, 3H), 3.08 (dd, J=10.3, 15.2 Hz, 1H), 2.87-2.73 (m, 2H), 2.55-2.40 (m, 2H), 2.40-2.26 (m, 2H), 2.11 (dd, J=7.4, 15.1 Hz, 2H), 1.98-1.65 (m, 10H), 1.46 (t, J=10.9 Hz, 1H), 1.20 (t, J=7.4 Hz, 3H). m/z (ESI, +ve ion) 657.2 (M+H)$^{+}$.

EXAMPLE 76

(1S,3'R,6'R,7'S,8'E,12'R)-6-CHLORO-7'-(2-METHOXYETHOXY)-12'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

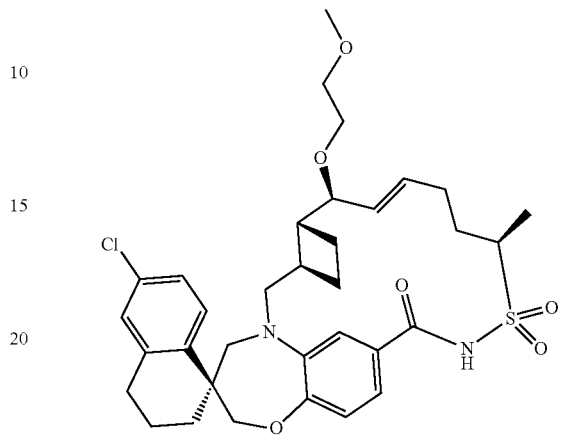

The title compound was prepared in an analogous manner to that described in Example 74 using (1S,3'R,6'R,7'S,8'E,12'R)-6-chloro-T-hydroxy-12'-methyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (Example 11) and 1-bromo-2-methoxyethane (Aldrich). $^{1}$H NMR (400 MHz, CD$_3$OD) δ 7.72 (d, J=8.6 Hz, 1H), 7.16 (dd, J=8.5, 2.2 Hz, 1H), 7.10 (d, J=2.2 Hz, 1H), 6.98 (d, J=8.3 Hz, 1H), 6.91 (d, J=8.2 Hz, 1H), 6.85 (d, J=1.8 Hz, 1H), 5.80-5.87 (m, 1H), 5.58 (dd, J=15.5, 8.8 Hz, 1H), 4.03-4.18 (m, 3H), 3.80-3.86 (m, 2H), 3.41-3.68 (m, 5H), 3.35 (s, 3H), 3.06 (dd, J=15.3, 10.4 Hz, 1H), 2.70-2.81 (m, 2H), 2.24-2.53 (m, 4H), 2.09 (d, J=13.7 Hz, 1H), 1.68-1.96 (m, 7H), 1.50 (d, J=7.0 Hz, 3H), 1.39-1.47 (m, 2H). m/z (ESI, +ve ion) 643.2 (M+H)$^{+}$.

EXAMPLE 77

(1S,3'R,6'R,7'S,8'E,11'R)-6-CHLORO-7'-(2-METHOXYETHOXY)-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$]PENTACOSA [8,16,18,24]TETRAEN]-15'-ONE 13',13'-DIOXIDE OR (1S,3'R,6'R,7'S,8'E,11'S)-6-CHLORO-7'-(2-METHOXYETHOXY)-11'-METHYL-3,4-DIHYDRO-2H,15'H-SPIRO[NAPHTHALENE-1,22'-[20]OXA[13]THIA[1,14] DIAZATETRACYCLO [14.7.2.0$^{3,6}$.0$^{19,24}$] PENTACOSA[8,16,18,24]TETRAEN]-15'-ONE 13',13'-DIOXIDE

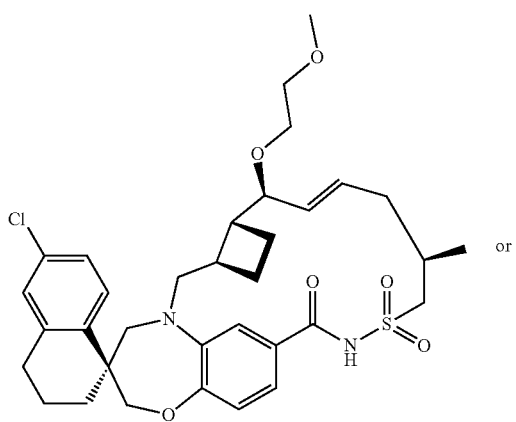

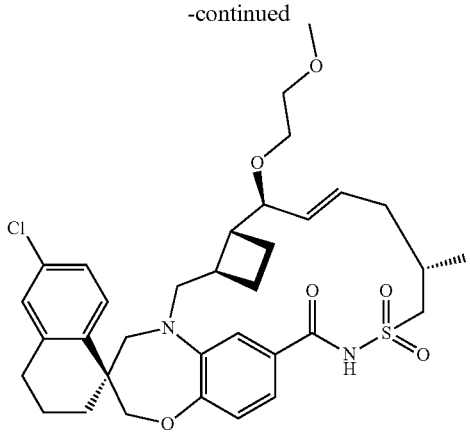

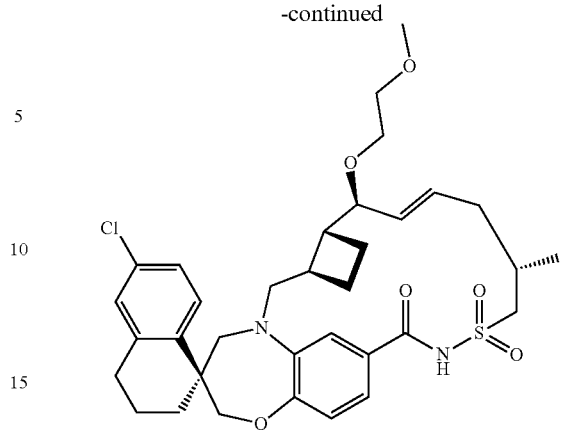

The title compound was prepared in an analogous manner to that described in Example 74 using (1S,3'R,6'R,7'S,8'E, 11'R)-6-chloro-7'-hydroxy-11'-methyl-3,4-dihydro-2H, 15'H-spiro[naphthalene-1,22'-[20]oxa[13]thia[1,14]diaza-tetracyclo[14.7.2.0$^{3,6}$.0$^{19,24}$]pentacosa[8,16,18,24]tetraen]-15'-one 13',13'-dioxide or (1S,3'R,6'R,7'S,8'E,11'S)-6-chloro-7'-hydroxy-11'-methyl-3,4-dihydro-2H,15'H-spiro [naphthalene-1,22'-[20]oxa[13]thia[1,14]diazatetracyclo [14.7.2.0$^{3,6}$.0$^{19,24}$]pentacosa[8,16,18,24]tetraen]-15'-one 13',13'-dioxide (Example 30) and 1-bromo-2-methoxy-ethane (Aldrich). $^1$H NMR (500 MHz, CDCl$_3$) δ ppm 8.32 (s, 1H), 7.68 (d, J=8.6 Hz, 1H), 7.17 (dd, J=2.2, 8.6 Hz, 1H), 7.09 (d, J=2.0 Hz, 1H), 7.05-6.97 (m, 1H), 6.92 (d, J=8.1 Hz, 1H), 5.94-5.85 (m, 1H), 5.51 (dd, J=7.0, 15.3 Hz, 1H), 4.17-4.04 (m, 2H), 3.75-3.68 (m, 2H), 3.66-3.46 (m, 7H), 3.44-3.34 (m, 4H), 2.80-2.72 (m 2H), 2.45-2.40 (m, 2H), 2.22-2.10 (m, 3H), 2.00-1.75 (m, 6H), 1.75-1.55 (m, 2H), 1.53-1.48 (m, 1H), 1.18 (d, J=6.4 Hz, 3H). m/z (ESI, +ve ion) 643.2 (M+H)$^+$.

EXAMPLE 78

(1S,3'R,6'R,7'S,8'E,11'S)-6-CHLORO-7'-(2-METHOXY-ETHOXY)-11'-METHYL-3,4-DIHYDRO-2H,15'H-SPIRO [NAPHTHALENE-1,22'-[20]OXA[13]THIA[1,14]DIAZA-TETRACYCLO[14.7.2.0$^{3,6}$.0$^{19,24}$]PENTACOSA [8,16,18,24]TETRAEN]-15'-ONE 13',13'-DIOXIDE OR (1S,3'R, 6'R,7'S,8'E,11'R)-6-CHLORO-7'-(2-METHOXYETHOXY)-11'-METHYL-3,4-DIHYDRO-2H, 15'H-SPIRO[NAPHTHALENE-1,22'-[20]OXA[13]THIA [1,14] DIAZATETRACYCLO[14.7.2.0$^{3,6}$.0$^{19,24}$] PENTACOSA[8,16,18,24] TETRAEN]-15'-ONE 13',13'-DIOXIDE

The title compound was prepared in an analogous manner to that described in Example 74 using (1S,3'R,6'R,7'S,8'E, 11'S)-6-chloro-7'-methoxy-11'-methyl-3,4-dihydro-2H, 15'H-spiro[naphthalene-1,22'-[20]oxa[13]thia[1,14]diaza-tetracyclo[14.7.2.0$^{3,6}$.0$^{19,24}$]pentacosa[8,16,18,24]tetraen]-15'-one 13',13'-dioxide or (1S,3'R,6'R,7'S,8'E,11'R)-6-chloro-7'-methoxy-11'-methyl-3,4-dihydro-2H,15'H-spiro [naphthalene-1,22'-[20]oxa[13]thia[1,14]diazatetracyclo [14.7.2.0$^{3,6}$.0$^{19,24}$]pentacosa[8,16,18,24]tetraen]-15'-one 13',13'-dioxide (Example 31) and 1-bromo-2-methoxy-ethane (Aldrich). $^1$H NMR (500 MHz, CDCl$_3$) δ ppm 8.22 (s, 1H), 7.70 (d, J=8.6 Hz, 1H), 7.18 (dd, J=2.1, 8.4 Hz, 1H), 7.09 (d, J=2.0 Hz, 1H), 6.95-6.88 (m, 2H), 6.83 (s, 1H), 5.88-5.80 (m, 1H), 5.56 (dd, J=9.0, 15.2 Hz, 1H), 4.36 (dd, J=4.8, 15.3 Hz, 1H), 4.14-4.04 (m, 2H), 3.85-3.78 (m, 2H), 3.71 (d, J=14.2 Hz, 1H), 3.60-3.48 (m, 3H), 3.45-3.34 (m, 4H), 3.23 (d, J=14.4 Hz, 1H), 3.09-2.91 (m, 2H), 2.84-2.71 (m, 2H), 2.53-2.44 (m, 1H), 2.36-2.23 (m, 2H), 2.13-1.92 (m, 5H), 1.89-1.74 (m, 3H), 1.69-1.54 (m, 1H), 1.39 (t, J=12.6 Hz, 1H), 1.16 (d, J=6.6 Hz, 3H). m/z (ESI, +ve ion) 643.2 (M+H)$^+$.

EXAMPLE 79

(1S,3'R,6'R,7'S,8'E,11'S,12'R)-6-CHLORO-7'-(2-(2-METHOXYETHOXY)ETHOXY)-11',12'-DIMETHYL-3, 4-DIHYDRO-2H,15'H-SPIRO[NAPHTHALENE-1,22'-[20]OXA[13]THIA[1,14]DIAZATETRACYCLO [14.7.2.0$^{3,6}$.0$^{19,24}$]PENTACOSA[8,16,18,24]TETRAEN]-15'-ONE 13',13'-DIOXIDE

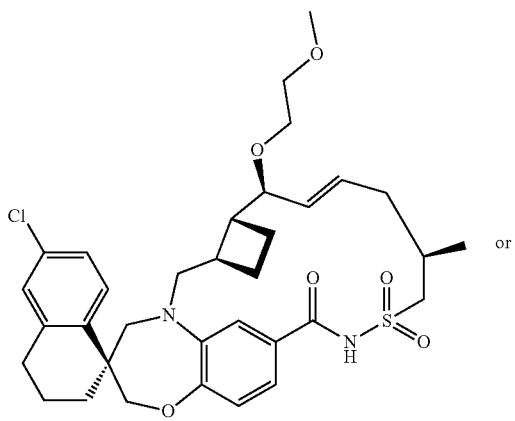

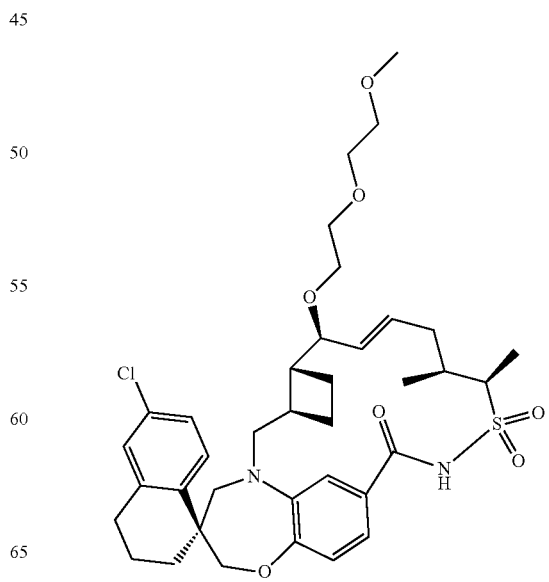

A mixture of dr (1S,3'R,6'R,7'S,8'E,11'S,12'R)-6-chloro-7'-hydroxy-11',12'-dimethyl-3,4-dihydro-2H,15'H-spiro[naphthalene-1,22'[20]oxa[13]thia[1,14]diazatetracyclo [14.7.2.0$^{3,6}$.0$^{19,24}$] pentacosa[8,16,18,24]tetraen]-15'-one 13',13'-dioxide (15 mg, 0.025 mmol) (Examples 2) and sodium hydride, 60% dispersion in mineral oil (9.9 mg, 0.43 mmol) in DMF was stirred under argon for 10 min. 1-(2-bromoethoxy)-2-methoxyethane (22.6 mg, 0.124 mmol) was added at ambient temperature. The reaction mixture was stirred for 18 h, quenched with saturated aqueous NH$_4$Cl, and extracted with EtOAc (×3). The combined organic layers were dried (MgSO$_4$) and concentrated. The residue was chromatographed (silica gel, 0-50%, EtOAc+0.3% HOAc/hexane) to afford the title compound as a white solid. $^1$H NMR (400 MHz, CDCl$_3$) δ ppm 8.09 (s, 1H), 7.70 (d, J=8.6 Hz, 1H), 7.18 (dd, J=2.2, 8.5 Hz, 1H), 7.09 (d, J=2.2 Hz, 1H), 6.95-6.87 (m, 3H), 5.82 (ddd, J=3.2, 9.4, 15.1 Hz, 1H), 5.54 (dd, J=9.1, 15.2 Hz, 1H), 4.35-4.24 (m, 1H), 4.16-4.05 (m, 2H), 3.87-3.74 (m, 2H), 3.70-3.54 (m, 8H), 3.45-3.44 (m, 1H), 3.40 (s, 3H), 3.23 (d, J=14.3 Hz, 1H), 2.99 (dd, J=10.2, 15.3 Hz, 1H), 2.84-2.71 (m, 2H), 2.53-2.42 (m, 1H), 2.38-2.24 (m, 1H), 2.15-1.93 (m, 4H), 1.90-1.72 (m, 3H), 1.72-1.57 (m, 3H), 1.49 (d, J=7.2 Hz, 3H), 1.42-1.35 (m, 1H), 1.05 (d, J=6.8 Hz, 3H). m/z (ESI, +ve ion) 701.2 (M+H)$^+$.

EXAMPLE 80

(1S,3'R,6'R,7'S,8'E,11'S,12'R)-6-CHLORO-7'-(2-(2-(2-METHOXYETHOXY)ETHOXY)ETHOXY)-11',12'-DIMETHYL-3,4-DIHYDRO-2H,15'H-SPIRO[NAPHTHALENE-1,22'-[20]OXA[13]THIA[1,14]DIAZATETRACYCLO [14.7.2.0$^{3,6}$.0$^{19,24}$]PENTACOSA[8,16,18,24]TETRAEN-15'-ONE 13',13'-DIOXIDE

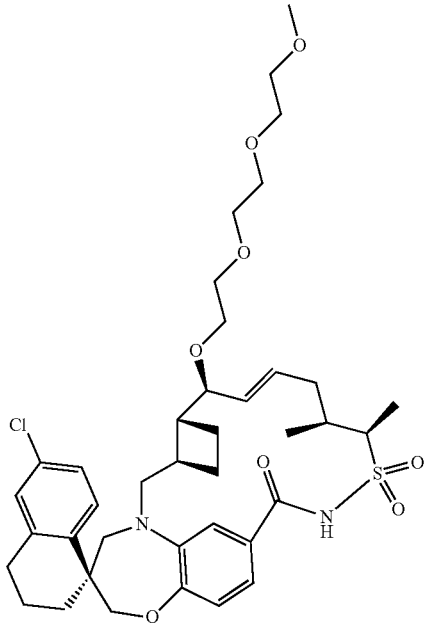 [SMILES: COCCOCCOCCO[C@H]1/C=C/C[C@H](C)[C@@H](C)S(=O)(=O)NC(=O)c2ccc3c(c2)N(C[C@@H]2CC[C@H]21)C[C@@]1(CCCc2cc(Cl)ccc21)CO3]

The title compound was prepared from (1S,3'R,6'R,7'S,8'E, 11'S,12'R)-6-chloro-7'-hydroxy-11',12'-dimethyl-3,4-dihydro-2H,15'H-spiro[naphthalene-1,22'[20]oxa 13]thia[1,14] diazatetracyclo[14.7.2.0$^{3,6}$.0$^{19,24}$] pentacosa[8,16,18,24]tetraen]-15'-one 13',13'-dioxide (Example 2) using a similar procedure described in Example 79 replacing 1-(2-bromoethoxy)-2-methoxyethane with 1-bromo-2-[2-(2-methoxyethoxy)ethoxy]ethane. $^1$H NMR (400 MHz, CDCl$_3$) δ ppm 7.97 (s, 1H), 7.70 (d, J=8.4 Hz, 1H), 7.19 (dd, J=2.2, 8.4 Hz, 1H), 7.10 (d, J=2.0 Hz, 1H), 6.95-6.87 (m, 3H), 5.86-5.75 (m, 1H), 5.54 (dd, J=9.0, 15.1 Hz, 1H), 4.35-4.22 (m, 1H), 4.13-4.05 (m, 2H), 3.86-3.76 (m, 2H), 3.72-3.63 (m, 7H), 3.63-3.54 (m, 5H), 3.44-3.42 (m, 1H), 3.40 (s, 3H), 3.23 (d, J=14.3 Hz, 1H), 2.99 (dd, J=10.1, 15.4 Hz, 1H), 2.84-2.71 (m, 2H), 2.48 (d, J=10.6 Hz, 1H), 2.38-2.26 (m, 1H),2.21-1.90 (m, 4H), 1.89-1.72 (m, 3H), 1.70-1.58 (m, 3H), 1.50 (d, J=7.2 Hz, 3H), 1.45-1.32 (m, 1H), 1.06 (d, J=6.8 Hz, 3H). m/z (ESI, +ve ion) 745.2 (M+H)$^+$.

EXAMPLE 81

(1S,3'R,6'R,7'S,8'E,11'S,12'R)-6-CHLORO-11',12'-DIMETHYL-7'-(3,6,9,12-TETRAOXATRIDEC-1-YLOXY)-3,4-DIHYDRO-2H,15'H-SPIRO[NAPHTHALENE-1,22'-[20]OXA[13]THIA[1,14]DIAZATETRACYCLO [14.7.2.0$^{3,6}$.0$^{19,24}$]PENTACOSA[8,16,18,24] TETRAEN]-15'-ONE 13',13'-DIOXIDE

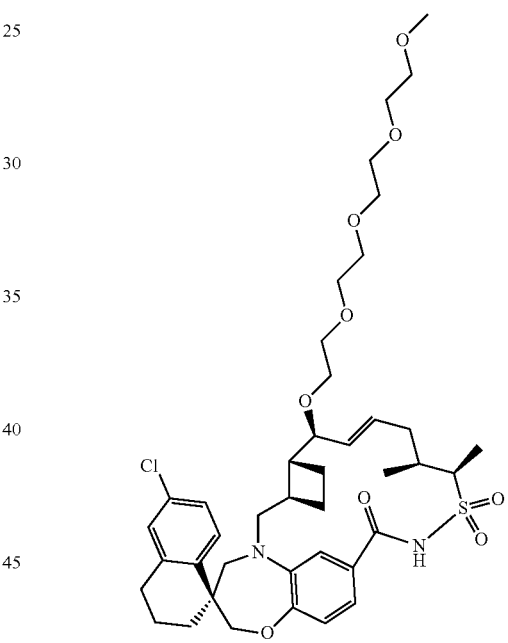

The title compound was prepared from (1S,3'R,6'R,7'S,8'E,11'S,12'R)-6-chloro-7'-hydroxy-11',12'-dimethyl-3,4-dihydro-2H,15'H-spiro[naphthalene-1,22'[20]oxa[13]thia[1,14] diazatetracyclo[14.7.2.0$^{3,6}$.0$^{19,24}$] pentacosa[8,16,18,24]tetraen]-15-one 13',13'-dioxide (Example 2) using a similar procedure described in Example 79, replacing 1-(2-bromoethoxy)-2-methoxyethane with triethylene glycol 2-bromoethyl methyl ether. $^1$H NMR (400 MHz, CDCl$_3$) δ ppm 8.02 (s, 1H), 7.70 (d, J=8.6 Hz, 1H), 7.19 (dd, J=2.2, 8.4 Hz, 1H), 7.09 (d, J=2.2 Hz, 1H), 6.94-6.88 (m, 3H), 5.85-5.77 (m, 1H), 5.54 (dd, J=8.5, 15.4 Hz, 1H), 4.31 (q, J=7.4 Hz, 1H), 4.09 (s, 2H), 3.85-3.75 (m, 2H), 3.74-3.62 (m, 11H), 3.62-3.50 (m, 5H), 3.45-3.42 (m, 1H), 3.39 (s, 3H), 3.23 (d, J=14.3 Hz, 1H), 3.03-2.95 (m, 1H), 2.83-2.72 (m, 2H), 2.52-2.43 (m, 1H), 2.32 (t, J=9.5 Hz, 1H), 2.21-1.92 (m, 4H), 1.90-1.74 (m, 3H), 1.68-1.56 (m, 3H), 1.50 (d, J=7.2 Hz, 3H), 1.40 (t, J=13.2 Hz, 1H), 1.06 (d, J=6.8 Hz, 3H). m/z (ESI, +ve ion) 789.2 (M+H)$^+$.

EXAMPLE 82

(1S,3'R,6'R,7'S,8'E,11'S,12'R)-6-CHLORO-12'-(CYCLO-PROPYLMETHYL)-7'-(2-METHOXYETHOXY)-11'-METHYL-3,4-DIHYDRO-2H,15'H-SPIRO[NAPHTHA-LENE-1,22'-[20]OXA[13]THIA[1,14]DIAZATETRACYCLO [14.7.2.0$^{3,6}$.0$^{19,24}$] PENTACOSA [8,16,18,24]TETRAEN]-15'-ONE 13',13'-DIOXIDE OR (1S,3'R,6'R,7'S,8'E,11'S,12'S)-6-CHLORO-12'-(CYCLO-PROPYLMETHYL)-7'-(2-METHOXYETHOXY)-11'-METHYL-3,4-DIHYDRO-2H,15'H-SPIRO[NAPHTHA-LENE-1,22'-[20]OXA[13]THIA[1,14]DIAZATETRACYCLO[14.7.2.0$^{3,6}$.0$^{19,24}$]PENTACOSA[18,16,18,24]TETRAEN]-15'-ONE 13',13'-DIOXIDE OR (1S,3'R,6'R,7'S,8'E,11'R,12'R)-6-CHLORO-12'-(CYCLO-PROPYLMETHYL)-7'-(2-METHOXYETHOXY)-11'-METHYL-3,4-DIHYDRO-2H,15'H-SPIRO[NAPHTHA-LENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE OR (1S,3'R,6'R,7'S,8'E,11'R,12'S)-6-CHLORO-12'-(CYCLO-PROPYLMETHYL)-7'-23 (2-METHOXYETHOXY)-11'-METHYL-3,4-DIHYDRO-2H,15'H-SPIRO[NAPHTHA-LENE-1,22'-[20]OXA[13]THIA[1,14]DIAZATETRACYCLO[14.7.2.0$^{3,6}$.0$^{19,24}$]PENTACOSA[8,16,18,24]TETRAEN]-15'-ONE 13',13'-DIOXIDE

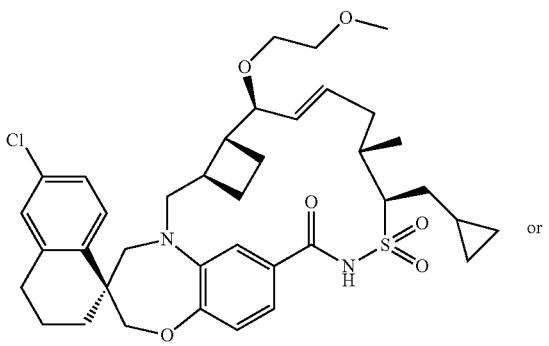

or

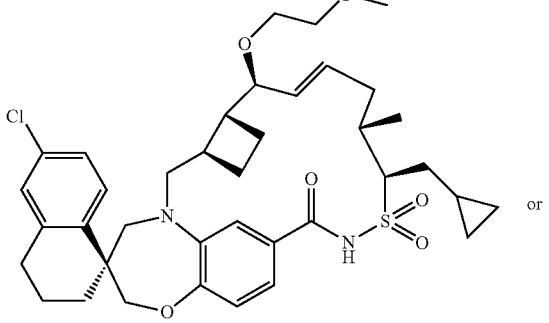

or

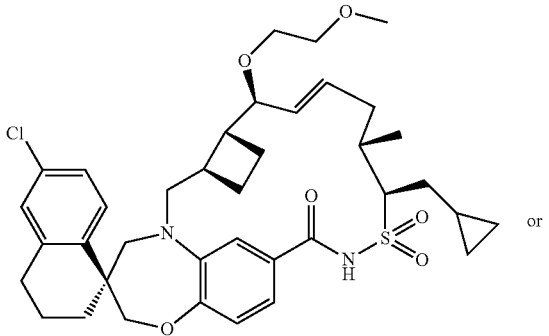

or

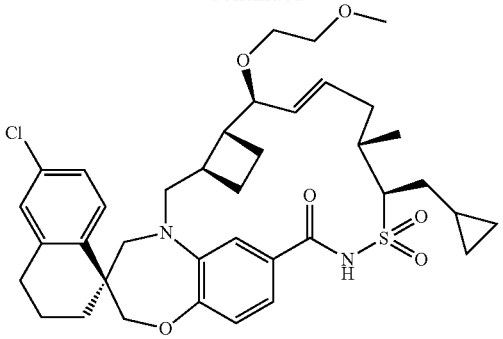

The title compound was prepared in an analogous manner to that described in Example 74 using (1S,3'R,6'R,7'S,8'E,11'S,12'R)-6-chloro-12'-(cyclopropylmethyl)-7'-hydroxy-11'-methyl-3,4-dihydro-2h,15'h-spiro[naphthalene-1,22'-[20]oxa[13]thia[1,14]diazatetracyclo [14.7.2.0$^{3,6}$.0$^{19,24}$] pentacosa[8,16,18,24]tetraen]-15'-one 13',13'-dioxide or (1S,3'R,6'R,7'S,8'E,11'S,12'S)-6-chloro-12'-(cyclopropylmethyl)-7'-hydroxy-11'-methyl-3,4-dihydro-2h,15'h-spiro[naphthalene-1,22'-[20]oxa[13]thia[1,14] diazatetracyclo [14.7.2.0$^{3,6}$.0$^{19,24}$]pentacosa[8,16,18,24]tetraen]-15'-one 13',13'-dioxide or (1S,3'R,6'R,7'S,8'E,11'R,12'R)-6-chloro-12'-(cyclopropylmethyl)-7'-hydroxy-11'-methyl-3,4-dihydro-2h,15'h-spiro[naphthalene-1,22'-[20]oxa[13]thia[1,14]diazatetracyclo[14.7.2.0$^{3,6}$.0$^{19,24}$] pentacosa[8,16,18,24] tetraen]-15'-one 13',13'-dioxide or (1S,3'R,6'R,7'S,8'E,11'R,12'S)-6-chloro-12'-(cyclopropylmethyl)-7'-hydroxy-11'-methyl-3,4-dihydro-2h,15'h-spiro[naphthalene-1,22'-[20]oxa[13]thia[1,14]diazatetracyclo[14.7.2.0$^{3,6}$.0$^{19,24}$] pentacosa[8,16,18,24]tetraen]-15'-one 13',13'-dioxide (Example 59), and 1-bromo-2-methoxyethane (Aldrich). $^1$H NMR (400 MHz, CDCl$_3$) δ ppm 8.05 (s, 1H), 7.70 (d, J=8.6 Hz, 1H), 7.18 (dd, J=2.2, 8.5 Hz, 1H), 7.09 (d, J=2.2 Hz, 1H), 6.96-6.90 (m, 3H), 5.91-5.83 (m, 1H), 5.56 (dd, J=9.0, 15.1 Hz, 1H), 4.30 (dd, J=4.5, 7.2 Hz, 1H), 4.09 (s, 2H), 3.87-3.79 (m, 2H), 3.74-3.67 (m, 1H), 3.59-3.50 (m, 3H), 3.48-3.41 (m, 1H), 3.41-3.35 (s, 3H), 3.23 (d, J=14.5 Hz, 1H), 3.00 (dd, J=10.2, 15.3 Hz, 1H), 2.84-2.71 (m, 2H), 2.50 (d, J=10.6 Hz, 1H), 2.37-2.16 (m, 3H), 2.13-1.92 (m, 4H), 1.91-1.73 (m, 3H), 1.71-1.52 (m, 2H), 1.51-1.34 (m, 2H), 1.23-1.14 (m, 1H), 1.05 (d, J=6.8 Hz, 3H), 0.67-0.58 (m, 2H), 0.29 (dd, J=4.4, 9.1 Hz, 1H), 0.08 (dd, J=4.1, 9.0 Hz, 1H). m/z (ESI, +ve ion) 697.3 (M+H)$^+$.

EXAMPLE 83

(1S,3'R,6'R,7'S,8'E,11'S,12'R)-6-CHLORO-12'-ETHYL-7-(2-METHOXYETHOXY)-11'-METHYL-3,4-DIHYDRO-2H,15'H-SPIRO[NAPHTHALENE-1,22'-[20]OXA[13]THIA[1,14]DIAZATETRACYCLO[14.7.2.0$^{3,6}$.0$^{19,24}$] PENTACOSA [8,16,18,24]TETRAEN]-ONE-13',13'-DIOXIDE

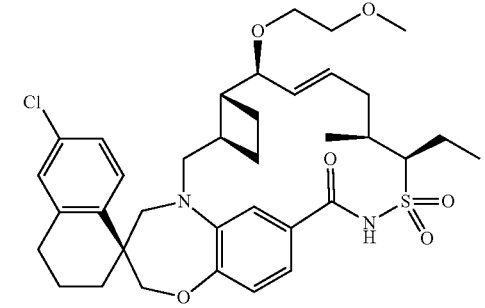 [SMILES: CC[C@@H]1[C@@H](C)C/C=C/[C@H](OCCOC)[C@@H]2CC[C@H]2CN2C[C@@]3(CCCc4cc(Cl)ccc43)COc3ccc(cc32)C(=O)NS1(=O)=O]

The title compound was prepared in an analogous manner to that described in Example 74 using (1S,3'R,6'R,7'S,8'E,11'S,12'R)-6-chloro-12'-ethyl-7'-hydroxy-11'-methyl-3,4-dihydro-2H,15'H-spiro[naphthalene-1,22'-[20]oxa[13]thia[1,14]diazatetracyclo [14.7.2.0$^{3,6}$.0$^{19,24}$]pentacosa[8,16,18,24]tetraen]-15'-one 13',13'-dioxide (Example 24), and 1-bromo-2-methoxyethane (Aldrich). $^1$H NMR (500 MHz, CD$_2$Cl$_2$) δ 8.08 (s, 1H), 7.71 (d, J=8.6 Hz, 1H), 7.17 (dd, J=2.4, 8.6 Hz, 1H), 7.09 (d, J=2.2 Hz, 1H), 6.91 (d, J=0.7 Hz, 2H), 6.87 (s, 1H), 5.82 (ddd, J=3.4, 9.4, 15.3 Hz, 1H), 5.54 (dd, J=9.4, 15.8 Hz, 1H), 4.11-4.05 (m, 2H), 4.00 (dd, J=2.8, 9.4 Hz, 1H), 3.82 (d, J=14.9 Hz, 1H), 3.78 (dd, J=3.2, 9.0 Hz, 1H), 3.69 (d, J=14.4 Hz, 1H), 3.53 (ddd, J=3.4, 5.4, 9.3 Hz, 1H), 3.45 (dt, J=3.7, 5.0 Hz, 2H), 3.38 (ddd, J=3.4, 5.9, 9.5 Hz, 1H), 3.32 (s, 3H), 3.25 (d, J=14.4 Hz, 1H), 3.02 (dd, J=10.3, 15.4 Hz, 1H), 2.84-2.70 (m, 2H), 2.45 (ddd, J=3.7, 10.0, 19.1 Hz, 1H), 2.37-2.29 (m, 1H), 2.29-2.19 (in, 1H), 2.13-2.08 (m, 1H), 2.08-2.01 (m, 2H), 2.00-1.89 (m, 3H), 1.89-1.77 (m, 4H), 1.66 (quin, J=8.6 Hz, 1H), 1.44-1.35 (m, 1H), 1.28 (t, J=7.3 Hz, 3H), 1.02 (d, J=6.8 Hz, 3H). MS (ESI, +ve ion) m/z 671.1 (M+H)$^+$; 693.1 (M+Na)$^+$.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:

1. A compound, wherein the compound has the following formula:

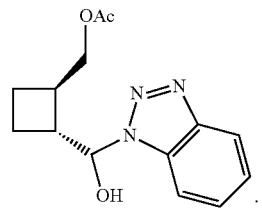 [SMILES: CC(=O)OC[C@@H]1CC[C@H]1C(O)n1nnc2ccccc21]

* * * * *